(12) United States Patent  
Luna et al.

(10) Patent No.: US 11,336,804 B2  
(45) Date of Patent: May 17, 2022

(54) STEREOSCOPIC VISUALIZATION CAMERA AND INTEGRATED ROBOTICS PLATFORM

(71) Applicant: ALCON INC., Fribourg (CH)

(72) Inventors: Maximiliano Ramirez Luna, Santa Barbara, CA (US); Michael Weissman, Santa Barbara, CA (US); Thomas Paul Riederer, Santa Barbara, CA (US); George Charles Polchin, Santa Barbara, CA (US); Ashok Burton Tripathi, Santa Barbara, CA (US); Patrick Terry, Santa Barbara, CA (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 17/141,661

(22) Filed: Jan. 5, 2021

(65) Prior Publication Data

US 2021/0297560 A1 Sep. 23, 2021

Related U.S. Application Data

(60) Division of application No. 16/398,014, filed on Apr. 29, 2019, now Pat. No. 10,917,543, which is a (Continued)

(51) Int. Cl.
*H04N 5/225* (2006.01)
*H04N 5/232* (2006.01)
(Continued)

(52) U.S. Cl.
CPC .......... *H04N 5/2252* (2013.01); *A61B 34/32* (2016.02); *A61B 34/77* (2016.02); *B25J 9/0009* (2013.01);
(Continued)

(58) Field of Classification Search
CPC ............ H04N 5/2252; H04N 5/23299; H04N 13/204; A61B 34/77; A61B 34/32; B25J 9/0009; B25J 9/04; B25J 9/1607
See application file for complete search history.

(56) References Cited

U.S. PATENT DOCUMENTS 4,418,993 A 12/1983 Lipton
5,662,584 A 9/1997 Hori et al.
(Continued)

FOREIGN PATENT DOCUMENTS

CN 105050527 A 11/2015
CN 106068175 A 11/2016
(Continued)

*Primary Examiner* — Tat C Chio
(74) *Attorney, Agent, or Firm* — Quinn IP Law

(57) ABSTRACT

A robotic imaging apparatus is disclosed. A robotic imaging apparatus includes a robotic arm, a stereoscopic camera, and a sensor positioned between the robotic arm and the stereoscopic camera. The sensor transmits output data that is indicative of translational and/or rotational force imparted on the stereoscopic camera by an operator. The robotic imaging apparatus also includes a processor that is configured to determine a movement sequence for the robotic arm based on a current position of the robotic arm and the output data from the sensor and to cause at least one of the joints of the robotic arm to rotate based on the determined movement sequence via one or more motor control signals provided to the at least one joint. The rotation of the at least one joint provides power-assisted movement of the robotic arm based on the detected translational and/or rotational forces imparted by the operator.

20 Claims, 59 Drawing Sheets

Related U.S. Application Data continuation-in-part of application No. 15/814,127, filed on Nov. 15, 2017, now Pat. No. 10,299,880.

(60) Provisional application No. 62/663,689, filed on Apr. 27, 2018, provisional application No. 62/489,289, filed on Apr. 24, 2017, provisional application No. 62/489,876, filed on Apr. 25, 2017.

(51) Int. Cl.
| | |
|---|---|
| *H04N 13/204* | (2018.01) |
| *B25J 9/00* | (2006.01) |
| *A61B 34/00* | (2016.01) |
| *B25J 9/04* | (2006.01) |
| *B25J 9/16* | (2006.01) |
| *A61B 34/32* | (2016.01) |

(52) U.S. Cl.
CPC ............... *B25J 9/04* (2013.01); *B25J 9/1607* (2013.01); *H04N 5/23299* (2018.08); *H04N 13/204* (2018.05)

(56) References Cited

U.S. PATENT DOCUMENTS

| | | |
|---|---|---|
| 10,561,469 B2 * | 2/2020 | Kasai .................... A61B 90/06 |
| 2007/0140673 A1 | 6/2007 | Butler-Smith et al. |
| 2010/0026787 A1 | 2/2010 | Yasuda et al. |
| 2010/0277627 A1 | 11/2010 | Jacques et al. |
| 2011/0279653 A1 | 11/2011 | Hoshino |
| 2013/0100257 A1 | 4/2013 | Sawachi |
| 2015/0212294 A1 | 7/2015 | Imamura et al. |
| 2015/0335480 A1 | 11/2015 | Alvarez et al. |
| 2016/0246041 A1 | 8/2016 | Rappel |
| 2016/0353079 A1 | 12/2016 | Sawada |
| 2017/0143442 A1 | 5/2017 | Tesar et al. |
| 2018/0129018 A1 | 5/2018 | Cheng et al. |

FOREIGN PATENT DOCUMENTS

| | | | |
|---|---|---|---|
| EP | 0146476 A2 | 6/1985 | |
| EP | 3120979 A1 | 1/2017 | |
| EP | 3175810 A1 | 6/2017 | |
| WO | 2014139023 A1 | 9/2014 | |
| WO | WO-2014139023 A1 * | 9/2014 | ......... A61B 17/3421 |

* cited by examiner

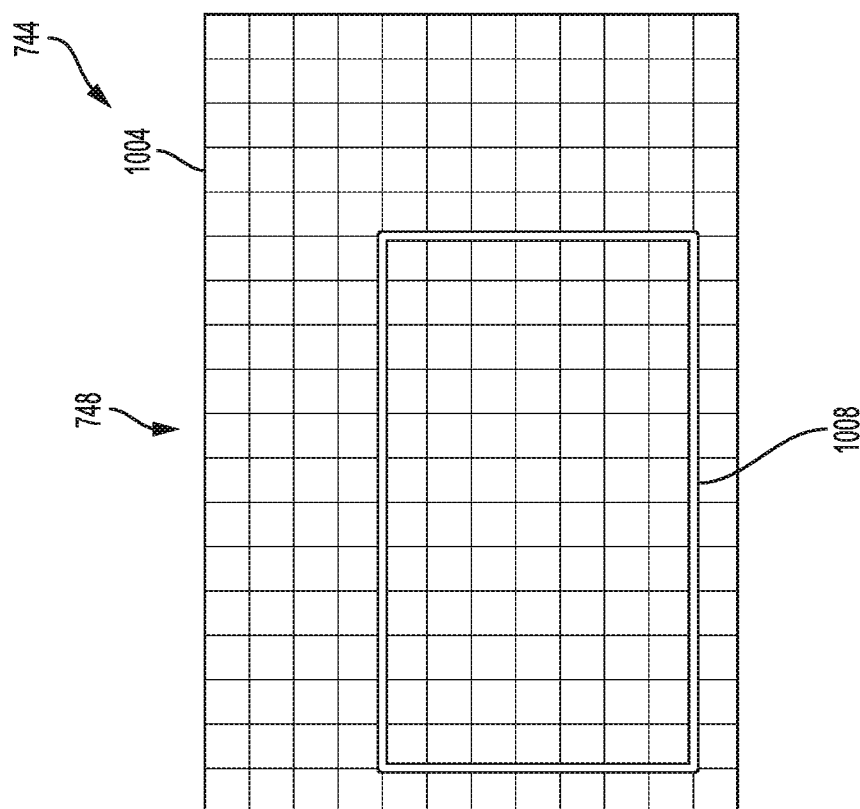
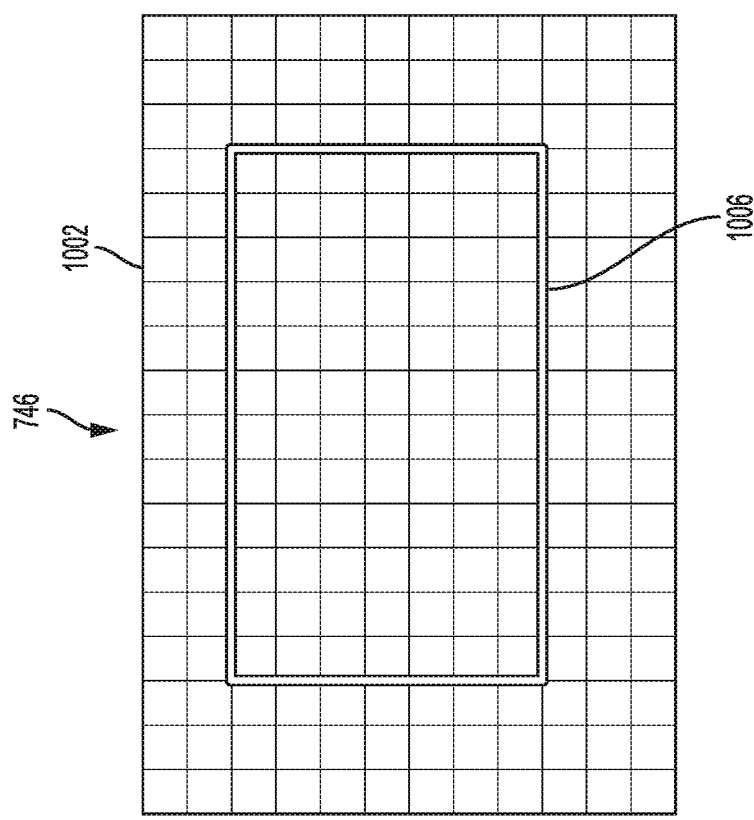
FIG. 10

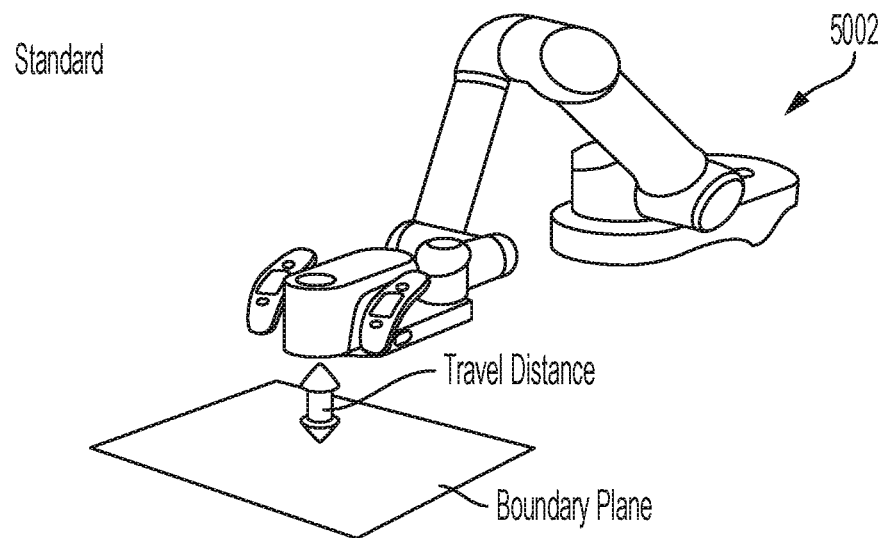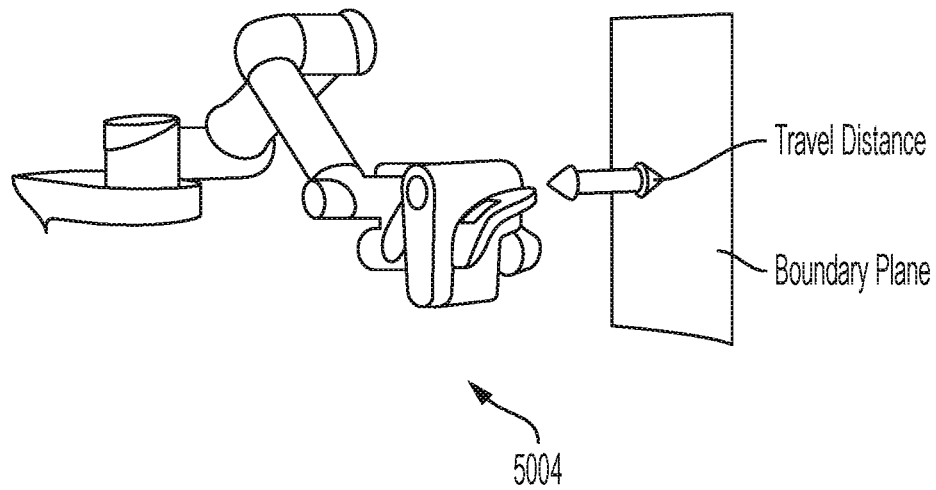
FIG. 50

SEC. A-A

STEREOSCOPIC VISUALIZATION CAMERA AND INTEGRATED ROBOTICS PLATFORM

PRIORITY CLAIM

The present application claims priority to and the benefit as a divisional application of U.S. patent application Ser. No. 16/398,014, filed on Apr. 29, 2019, which claims priority to and the benefit of U.S. Provisional Patent Application No. 62/663,689, filed on Apr. 27, 2018, and which is a continuation-in-part of U.S. patent application Ser. No. 15/814,127, filed Nov. 15, 2017, now U.S. Pat. No. 10,299,880, which claims priority to and the benefit of U.S. Provisional Patent Application No. 62/489,289 filed on Apr. 24, 2017 and U.S. Provisional Patent Application No. 62/489,876 filed on Apr. 25, 2017, the entirety of which are incorporated herein by reference.

BACKGROUND

Surgery is art. Accomplished artists create works of art that far exceed the capabilities of a normal person. Artists use a brush to turn canisters of paint into vivid images that provoke strong and unique emotions from viewers. Artists take ordinary words written on paper and turn them into dramatic and awe-inspiring performances. Artists grasp instruments causing them to emit beautiful music. Similarly, surgeons take seemingly ordinary scalpels, tweezers, and probes and produce life-altering biological miracles.

Like artists, surgeons have their own methods and preferences. Aspiring artists are taught the fundamentals of their craft. Beginners often follow prescribed methods. As they gain experience, confidence, and knowledge, they develop their own unique artistry reflective of themselves and their personal environment. Similarly, medical students are taught the fundamentals of surgical procedures. They are rigorously tested on these methods. As the students progress through residency and professional practice, they develop derivations of the fundamentals (still within medical standards) based on how they believe the surgery should best be completed. For instance, consider the same medical procedure performed by different renowned surgeons. The order of events, pacing, placement of staff, placement of tools, and use of imaging equipment varies between each of the surgeons based on their preferences. Even incision sizes and shapes can be unique to the surgeon.

The artistic-like uniqueness and accomplishment of surgeons make them weary of surgical tools that change or alter their methods. The tool should be an extension of the surgeon, operating simultaneously and/or in harmonious synchronization. Surgical tools that dictate the flow of a procedure or change the rhythm of a surgeon are often discarded or modified to conform.

In an example, consider microsurgery visualization where certain surgical procedures involve patient structures that are too small for a human to visualize easily with the naked eye. For these microsurgery procedures, magnification is required to adequately view the micro-structures. Surgeons generally want visualization tools that are natural extensions of their eyes. Indeed, early efforts at microsurgery visualization comprised attaching magnifying lens to head-mounted optical eyepieces (called surgical loupes). The first pair was developed in 1876. Vastly improved versions of surgical loupes (some including optical zooms and integrated light sources) are still being used by surgeons today. FIG. 1 shows a diagram of a pair of surgical loupes 100 with a light source 102 and magnification lenses 104. The 150-year staying power of surgical loupes can be attributed to the fact that they are literally an extension of a surgeon's eyes.

Despite their longevity, surgical loupes are not perfect. Loupes with magnifying lenses and light sources, such as the loupes 100 of FIG. 1, have much greater weight. Placing even a minor amount of weight on the front of a surgeon's face can increase discomfort and fatigue, especially during prolonged surgeries. The surgical loupes 100 also include a cable 106 that is connected to a remote power supply. The cable effectively acts as a chain, thereby limiting the mobility of the surgeon during their surgical performance.

Another microsurgery visualization tool is the surgical microscope, also referred to as the operating microscope. Widespread commercial development of surgical microscopes began in the 1950s with the intention of replacing surgical loupes. Surgical microscopes include optical paths, lenses, and focusing elements that provide greater magnification compared to surgical loupes. The large array of optical elements (and resulting weight) meant that surgical microscopes had to be detached from the surgeon. While this detachment gave the surgeon more room to maneuver, the bulkiness of the surgical microscope caused it to consume considerable operating space above a patient, thereby reducing the size of the surgical stage.

FIG. 2 shows a diagram of a prior art surgical microscope 200. As one can imagine, the size and presence of the surgical microscope in the operating area made it prone to bumping. To provide stability and rigidity at the scope head 201, the microscope is connected to relatively large boom arms 202 and 204 or other similar support structure. The large boom arms 202 and 204 consume additional surgical space and reduce the maneuverability of the surgeon and staff. In total, the surgical microscope 200 shown in FIG. 2 could weigh as much as 350 kilograms ("kg").

To view a target surgical site using the surgical microscope 200, a surgeon looks directly though oculars 206. To reduce stress on a surgeon's back, the oculars 206 are generally positioned along a surgeon's natural line of sight using the arm 202 to adjust height. However, surgeons do not perform by only looking at a target surgical site. The oculars 206 have to be positioned such that the surgeon is within arm's length of a working distance to the patient. Such precise positioning is critical to ensure the surgical microscope 200 becomes an extension rather than a hindrance to the surgeon, especially when being used for extended periods of time.

Like any complex instrument, it takes surgeons tens to hundreds of hours to feel comfortable using a surgical microscope. As shown in FIG. 2, the design of the surgical microscope 200 requires a substantially 90° angle optical path from the surgeon to the target surgical site. For instance, a perfectly vertical optical path is required from the target surgical site to the scope head 201. This means that the scope head 201 has to be positioned directly above the patient for every microsurgical procedure. In addition, the surgeon has to look almost horizontally (or some slight angle downward) into the oculars 206. A surgeon's natural inclination is to direct his vision to his hands at the surgical site. Some surgeons even want to move their heads closer to the surgical site to have more precise control of their hand movements. Unfortunately, the surgical microscopes 200 do not give surgeons this flexibility. Instead, surgical microscopes 200 ruthlessly dictate that the surgeon is to place their eyes on the oculars 206 and hold their head at arm's length during their surgical performance, all while consuming valuable surgical space above the patient. A surgeon cannot even simply look down at a patient because the scope head 201 blocks the surgeon's view.

To make matters worse, some surgical microscopes 200 include a second pair of oculars 208 for co-performers (e.g., assistant surgeons, nurses, or other clinical staff). The second pair of oculars 208 is usually positioned at a right angle from the first oculars 206. The closeness between the oculars 206 and 208 dictates that the assistant must stand (or sit) in close proximity to the surgeon, further restricting movement. This can be annoying to some surgeons who like to perform with some space. Despite their magnification benefits surgical microscopes 200 are not natural extensions of a surgeon. Instead, they are overbearing directors in the surgical room.

SUMMARY

The present disclosure is directed to a stereoscopic robotic system that includes a stereoscopic visualization camera and robotic arm. The example stereoscopic robotic system is configured to acquire stereoscopic images of a target surgical site while enabling an operator to position the stereoscopic visualization camera using the robotic arm. As disclosed herein, the robotic arm includes electro-mechanically operated joints that provide structurally stability to enable the stereoscopic visualization camera to record high-resolution images without jitter or other artifacts that can arise from unintended camera movement. The robotic arm also provides structural flexibility that permits an operator to position the stereoscopic visualization camera at different positions and/or orientations to obtain desired views of a target surgical site. The example stereoscopic robotic system accordingly enables a surgeon to complete life-altering microsurgeries comfortably in whatever position suits the surgeon.

The stereoscopic robotic system of the present disclosure can be positioned about any number of orientations relative to the surgical field that best suits the needs of the surgeon or patient, rather than the physical and mechanical limitations of the visualization apparatus. The stereoscopic robotic system is configured to provide motorized joint movement assistance that enables a surgeon or other operator to effortlessly position the stereoscopic visualization camera. In some embodiments, the stereoscopic robotic system is configured to provide motorized assisted movement of a robotic arm based on forces detected from an operator positioning the stereoscopic camera. The stereoscopic robotic system may also enable an operator to select a visual lock on a target surgical site while enabling the operator to change an orientation and/or position of the stereoscopic visualization camera. Additionally or alternatively, the stereoscopic robotic system is configured with one or more boundaries that prevent the stereoscopic visualization camera and/or the robotic arm from contacting a patient, surgical staff, and/or surgical instruments. Altogether, the stereoscopic robotic system operates as an extension of a surgeon's eyes while giving the surgeon the freedom to conduct a microsurgery procedure generally without restrictions or impediments.

Aspects of the subject matter described herein may be useful alone or in combination with one or more other aspect described herein. Without limiting the foregoing description, in a first aspect of the present disclosure, a robotic imaging apparatus includes a base section configured for connection to a secure structure or a cart and a robotic arm having a first end connected to the base section, a second end including a coupling interface, and a plurality of joints and links connecting the first end to the second end. Each joint includes a motor configured to rotate the joint around an axis and a joint sensor configured to transmit a position of the respective joint. The robotic imaging apparatus also includes a stereoscopic camera connected to the robotic arm at the coupling interface. The stereoscopic camera is configured to record left and right images of a target surgical site for producing a stream of stereoscopic images of the target surgical site. The robotic imaging apparatus further includes a sensor positioned at the coupling interface and configured to detect and transmit output data that is indicative of translational and rotational force imparted on the stereoscopic camera by an operator. The robotic imaging apparatus additionally includes a memory storing at least one algorithm defined by one or more instructions and/or data structures that specify a rotation direction, speed, and duration for each of the joints of the robotic arm based at least on a current position of the robotic arm and detected translational and rotational forces. Moreover, the robotic imaging apparatus includes at least one processor communicatively coupled to the sensor and the robotic arm. The at least one processor configured to receive the output data from the sensor that is indicative of the translational and rotational forces and determine, using the at least one algorithm in the memory, a movement sequence for the robotic arm based on a current position of the robotic arm and the output data from the sensor. The at least one processor is also configured to cause at least one of the joints of the robotic arm to rotate based on the determined movement sequence via one or more motor control signals provided to the at least one joint. The rotation of the at least one joint provides power-assisted movement of the robotic arm based on the detected translational and rotational forces imparted on the stereoscopic camera by the operator.

In accordance with a second aspect of the present disclosure, which may be used in combination with any other aspect listed herein unless stated otherwise, the at least one processor is configured to determine the current position of the robotic arm based on output data from the joint sensors of the plurality of joints.

In accordance with a third aspect of the present disclosure, which may be used in combination with any other aspect listed herein unless stated otherwise, the sensor includes at least one of a six-degrees-of-freedom haptic force-sensing device or a torque sensor.

In accordance with a fourth aspect of the present disclosure, which may be used in combination with any other aspect listed herein unless stated otherwise, the stereoscopic camera includes at least one control arm having a release button to enable the power-assisted movement, and the at least one processor is configured to receive an input message indicative that the release button was selected, and determine the movement sequence using the output data from the sensor after receiving the input message related to the release button.

In accordance with a fifth aspect of the present disclosure, which may be used in combination with any other aspect listed herein unless stated otherwise, the apparatus further includes a coupling plate with a first end configured to connect to the coupling interface of the robotic arm and a second end including a second coupling interface configured to connect to the stereoscopic camera. The coupling plate includes at least one joint including a joint sensor configured to transmit a position of the respective joint and a motor that is controllable by the at least one processor according to the movement sequence.

In accordance with a sixth aspect of the present disclosure, which may be used in combination with any other aspect listed herein unless stated otherwise, the sensor is located at the coupling interface or the second coupling interface.

In accordance with a seventh aspect of the present disclosure, which may be used in combination with any other aspect listed herein unless stated otherwise, the coupling plate includes a second joint that enables the stereoscopic camera to be manually rotated by an operator between a horizontal orientation and a vertical orientation. The second joint includes a joint sensor configured to transmit a position of the second joint.

In accordance with an eighth aspect of the present disclosure, which may be used in combination with any other aspect listed herein unless stated otherwise, the stereoscopic camera includes a housing including a bottom side that is configured to connect to the robotic arm at the coupling interface.

In accordance with a ninth aspect of the present disclosure, which may be used in combination with any other aspect listed herein unless stated otherwise, a robotic imaging apparatus includes a robotic arm comprising a first end for connection to a secure structure, a second end including a coupling interface, and a plurality of joints and links connecting the first end to the second end, each joint including a motor configured to rotate the joint around an axis and a joint sensor configured to transmit a position of the respective joint. The robotic imaging apparatus also includes an imaging device connected to the robotic arm at the coupling interface, the imaging device configured to record images of a target surgical site, and a sensor positioned at the coupling interface and configured to detect and transmit force and/or torque output data that is indicative of force and/or torque imparted on the imaging device by an operator. The robotic imaging apparatus further includes at least one processor communicatively coupled to the sensor and the robotic arm. The at least one processor is configured to receive the force and/or torque output data from the sensor, convert the force and/or torque output data into translational and rotational vectors, determine, using kinematics, a movement sequence for the robotic arm based on a current position of the robotic arm and the translational and rotational vectors, the movement sequence specifying a rotation direction, a speed, and a duration of movement for at least some of the joints of the robotic arm, and cause at least one of the joints of the robotic arm to rotate based on the determined movement sequence via one or more motor control signals provided to the at least one joint.

In accordance with a tenth aspect of the present disclosure, which may be used in combination with any other aspect listed herein unless stated otherwise, the processor is configured to determine a least one scale factor based on at least one of the current position of the robotic arm or a future position of the robotic arm based on the movement sequence, and apply the scale factor to at least one joint speed of the movement sequence.

In accordance with an eleventh aspect of the present disclosure, which may be used in combination with any other aspect listed herein unless stated otherwise, the at least one scale factor is configured based on a distance of the robotic arm or the imaging device from a virtual boundary. The at least one scale factor decreases to a value of '0' as the virtual boundary is approached.

In accordance with a twelfth aspect of the present disclosure, which may be used in combination with any other aspect listed herein unless stated otherwise, the virtual boundary corresponds to at least one of a patient, a medical instrument, or operating room staff.

In accordance with a thirteenth aspect of the present disclosure, which may be used in combination with any other aspect listed herein unless stated otherwise, the processor is configured to cause a display device to display an icon indicative that the at least one scale factor has been applied to the movement sequence.

In accordance with a fourteenth aspect of the present disclosure, which may be used in combination with any other aspect listed herein unless stated otherwise, the processor is configured to determine a least one scale factor based on joint angles between joints of the robotic arm or joint limits, and apply the scale factor to at least one joint speed of the movement sequence.

In accordance with a fifteenth aspect of the present disclosure, which may be used in combination with any other aspect listed herein unless stated otherwise, the processor is configured to provide gravity compensation for the force and/or torque output data, and provide force-application compensation for the force and/or torque output data to compensate for an offset between a location of the sensor and a location of the imaging device upon which the force and/or torque is imparted by the operator.

In accordance with a sixteenth aspect of the present disclosure, which may be used in combination with any other aspect listed herein unless stated otherwise, the processor is configured to determine or identify joint singularities for the plurality of joints of the robotic arm for control of hysteresis and backlash, and determine the movement sequence based on the kinematics while avoiding robotic arm movement through the joint singularities.

In accordance with a seventeenth aspect of the present disclosure, which may be used in combination with any other aspect listed herein unless stated otherwise, the robotic imaging apparatus further includes a coupling plate with a first end configured to connect to the coupling interface of the robotic arm and a second end including a second coupling interface configured to connect to the stereoscopic camera. The coupling plate includes at least one joint including a joint sensor configured to transmit a position of the respective joint and a motor that is controllable by the at least one processor according to the movement sequence. The sensor is located at the coupling interface or the second coupling interface.

In accordance with an eighteenth aspect of the present disclosure, which may be used in combination with any other aspect listed herein unless stated otherwise, the robotic arm includes at least four joints and the coupling plate includes at least two joints.

In accordance with a nineteenth aspect of the present disclosure, which may be used in combination with any other aspect listed herein unless stated otherwise, the processor is configured to cause at least one of the joints of the robotic arm to rotate by transmitting one or more command signals to the motor of the respective joint indicative of the rotation direction, the speed, and the duration of movement as specified by the movement sequence.

In accordance with a twentieth aspect of the present disclosure, which may be used in combination with any other aspect listed herein unless stated otherwise, the processor is configured to compare images recorded by the imaging device as the robotic arm is being moved during the movement sequence to confirm the robotic arm is being moved as specified during the movement sequence.

In accordance with a twenty-first aspect of the present disclosure, which may be used in combination with any other aspect listed herein unless stated otherwise, the kinematics includes at least one of inverse kinematics or Jacobean kinematics.

In accordance with a twenty-second aspect of the present disclosure, any of the structure and functionality illustrated and described in connection with FIGS. 3 to 65 may be used in combination with any of the structure and functionality illustrated and described in connection with any of the other of FIGS. 3 to 65 and with any one or more of the preceding aspects.

In light of the aspects above and the disclosure herein, it is accordingly an advantage of the present disclosure to provide a stereoscopic robotic system that provides seamless coordination between a stereoscopic camera and a robotic arm.

It is another advantage of the present disclosure to provide a stereoscopic robotic system that uses a robotic arm to increase a focal range, working distance, and/or magnification of a stereoscopic robotic system.

It is a further another advantage of the present disclosure to provide a stereoscopic robotic system that provides powered assisted movement of the robotic arm based on forces/torques imparted on a stereoscopic camera by an operator.

The advantages discussed herein may be found in one, or some, and perhaps not all of the embodiments disclosed herein. Additional features and advantages are described herein, and will be apparent from the following Detailed Description and the figures.

BRIEF DESCRIPTION OF THE FIGURES

FIG. 10 shows a diagram of an example of a right optical image sensor and a left optical image sensor of the example stereoscopic visualization camera of FIGS. 7 and 8, according to an example embodiment of the present disclosure.

FIG. 50 shows a diagram illustrative of horizontal and vertical boundary planes for restricting movement of the stereoscopic visualization camera and/or the robotic arm, according to an example embodiment of the present disclosure.

DETAILED DESCRIPTION

Figure 1:
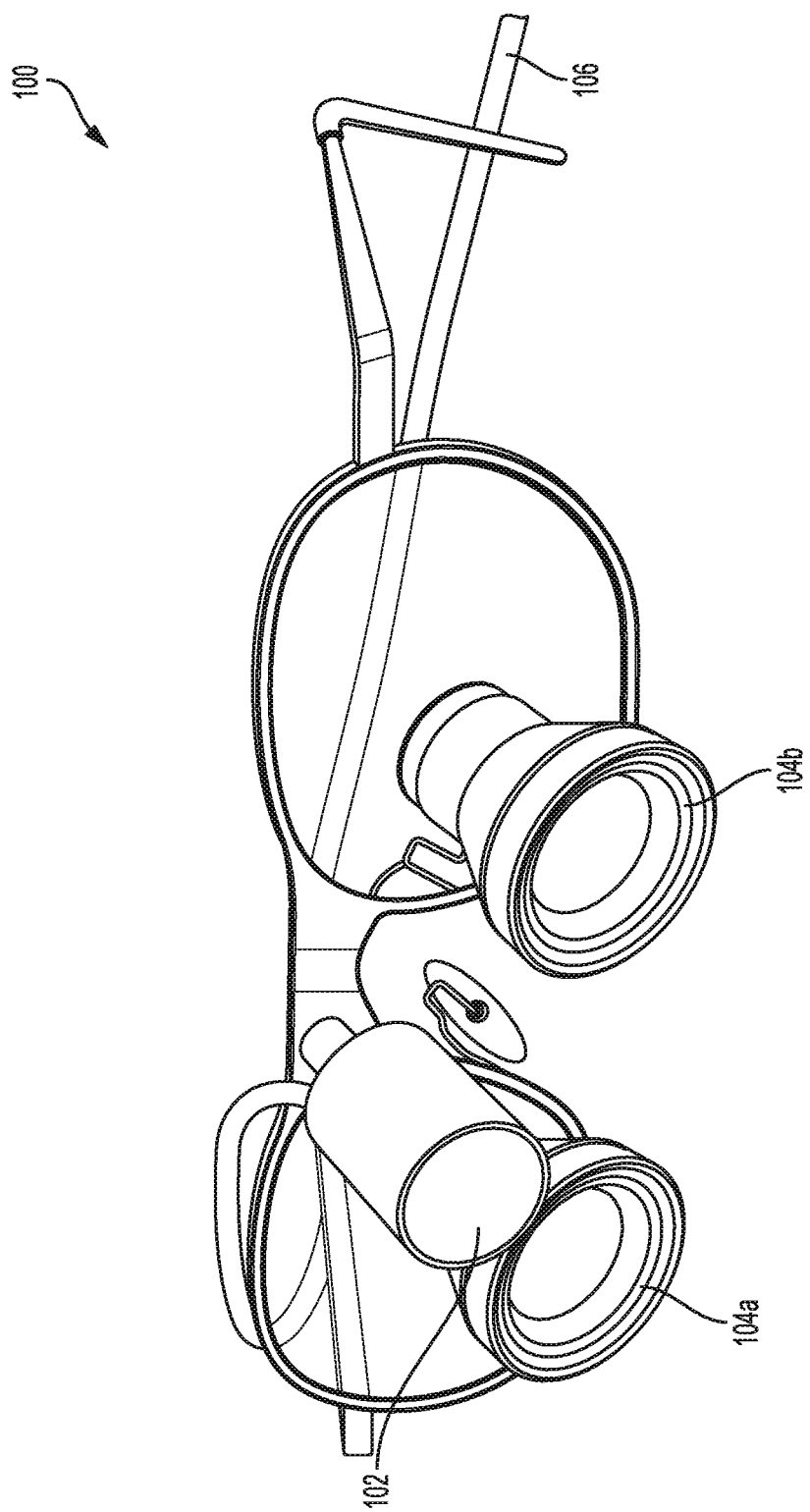
FIG. 1 shows a diagram of a pair of prior art surgical loupes.

The present disclosure relates in general to a stereoscopic visualization camera and platform. The stereoscopic visualization camera may be referred to as a digital stereoscopic microscope ("DSM"). The example camera and platform are configured to integrate microscope optical elements and video sensors into a self-contained head unit that is significantly smaller, lighter, and more maneuverable than prior art microscopes (such as the surgical loupes 100 of FIG. 1 and the surgical microscope 200 of FIG. 2). The example camera is configured to transmit a stereoscopic video signal to one or more television monitors, projectors, holographic devices, smartglasses, virtual reality devices, or other visual display devices within a surgical environment.

The monitors or other visual display devices may be positioned within the surgical environment to be easily within a surgeon's line of sight while performing surgery on a patient. This flexibility enables the surgeon to place display monitors based on personal preferences or habits. In addition, the flexibility and slim profile of the stereoscopic visualization camera disclosed herein reduces area consumed over a patient. Altogether, the stereoscopic visualization camera and monitors (e.g., the stereoscopic visualization platform) enables a surgeon and surgical team to perform complex microsurgical surgical procedures on a patient without being dictated or restricted in movement compared to the surgical microscope 200 discussed above. The example stereoscopic visualization platform accordingly operates as an extension of the surgeon's eyes, enabling the surgeon to perform masterpiece microsurgeries without dealing with the stress, restrictions, and limitations induced by previous known visualization systems.

The disclosure herein generally refers to microsurgery. The example stereoscopic visualization camera may be used in virtually any microsurgical procedure including, for example, cranial surgery, brain surgery, neurosurgery, spinal surgery, ophthalmologic surgery, corneal transplants, orthopedic surgery, ear, nose and throat surgery, dental surgery, plastics and reconstructive surgery, or general surgery.

The disclosure also refers herein to target site, scene, or field-of-view. As used herein, target site or field-of-view includes an object (or portion of an object) that is being recorded or otherwise imaged by the example stereoscopic visualization camera. Generally the target site, scene, or field-of-view is a working distance away from a main objective assembly of the example stereoscopic visualization camera and is aligned with the example stereoscopic visualization camera. The target site may include a patient's biological tissue, bone, muscle, skin or combinations thereof. In these instances, the target site may be three dimensional by having a depth component corresponding to a progression of a patient's anatomy. The target site may also include one or more templates used for calibration or verification of the example stereoscopic visualization camera. The templates may be two-dimensional, such as a graphic design on paper (or plastic sheet) or three dimensional, such as to approximate a patient's anatomy in a certain region.

Reference is also made throughout to an x-direction, a y-direction, a z-direction, and a tilt-direction. The z-direction is along an axis from the example stereoscopic visualization camera to the target site and generally refers to depth. The x-direction and y-direction are in a plane incident to the z-direction and comprise a plane of the target site. The x-direction is along an axis that is 90° from an axis of the y-direction. Movement along the x-direction and/or the y-direction refer to in-plane movement and may refer to movement of the example stereoscopic visualization camera, movement of optical elements within the example stereoscopic visualization camera, and/or movement of the target site.

The tilt-direction corresponds to movement along Euler angles (e.g., a yaw axis, a pitch axis, and a roll axis) with respect to the x-direction, the y-direction, and/or the z-direction. For example, a perfectly aligned lens has substantially a 0° tilt with respect to the x-direction, the y-direction, and/or the z-direction. In other words, a face of the lens is 90° or perpendicular to light along the z-direction. In addition, edges of the lens (if the lens has a rectangular shape) are parallel along the x-direction and the y-direction. Lens and/or optical image sensors can be titled through yaw movement, pitch movement, and/or roll movement. For example, a lens and/or optical image sensor may be titled along a pitch axis, with respect to the z-direction, to face upwards or downwards. Light along the z-direction contacts a face of a lens (that is pitched upwards or downwards) at non-perpendicular angle. Tilting of a lens and/or optical image sensor along a yaw axis, pitch axis, or roll axis enables, for example, a focal point or ZRP to be adjusted.

I. Example Stereoscopic Visualization Camera

Figure 3:
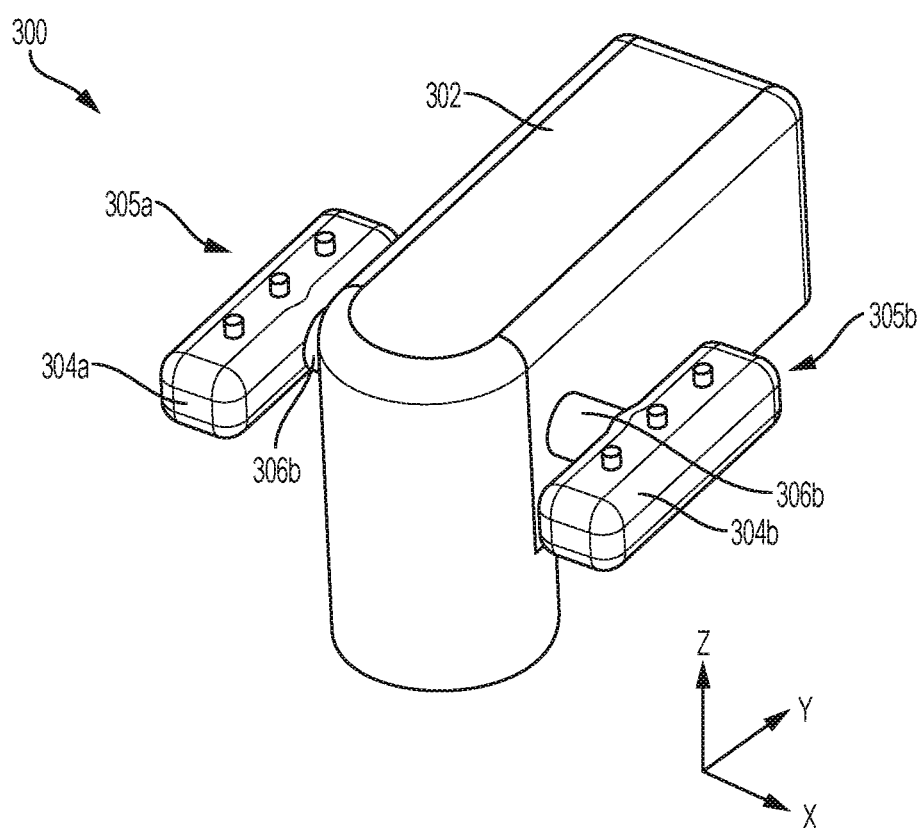
FIGS. 3 and 4 show diagrams of perspective views of a stereoscopic visualization camera, according to an example embodiment of the present disclosure.
Figure 4:
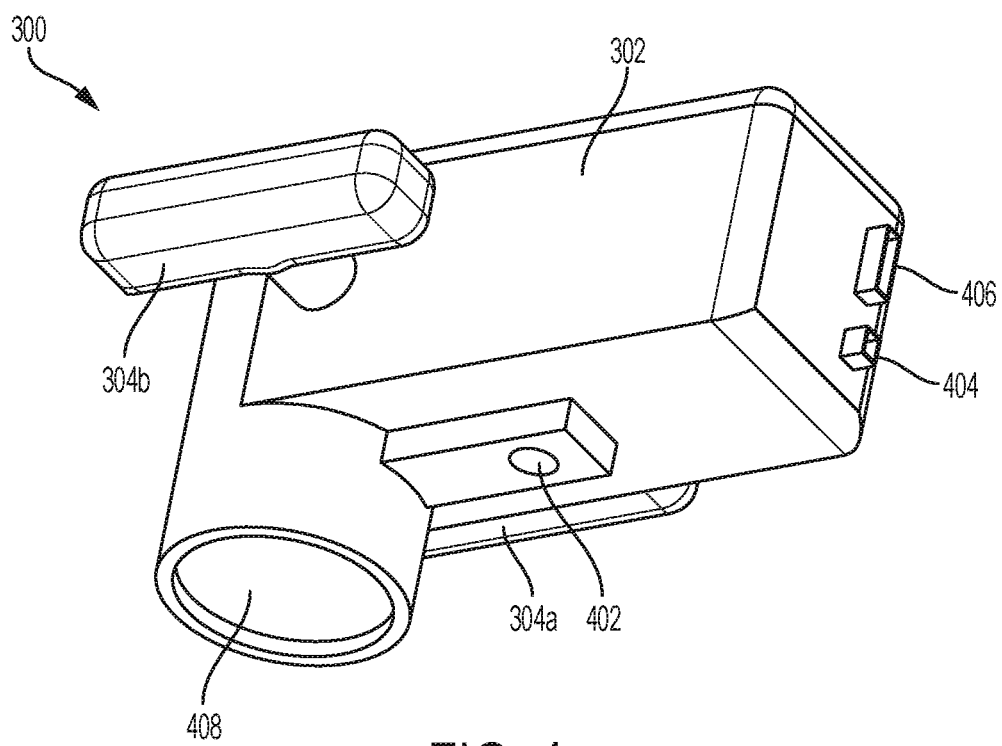

FIGS. 3 and 4 show diagrams of perspective views of a stereoscopic visualization camera 300, according to an example embodiment of the present disclosure. The example camera 300 includes a housing 302 configured to enclose optical elements, lens motors (e.g., actuators), and signal processing circuitry. The camera 300 has a width (along an x-axis) between 15 to 28 centimeters (cm), preferably around 22 cm. In addition, the camera 300 has a length (along a y-axis) between 15 to 32 cm, preferably around 25 cm. Further, the camera 300 has a height (along a z-axis) between 10 to 20 cm, preferably around 15 cm. The weight of the camera 300 is between 3 to 7 kg, preferably around 3.5 kg.

The camera 300 also includes control arms 304a and 304b (e.g., operating handles), which are configured to control magnification level, focus, and other microscope features. The control arms 304a and 304b may include respective controls 305a and 305b for activating or selecting certain features. For example, the control arms 304a and 304b may include controls 305a and 305b for selecting a fluorescence mode, adjusting an amount/type of light projected onto a target site, and controlling a display output signal (e.g., selection between 1080p or 4K and/or stereoscopic). In addition, the controls 305a and/or 305b may be used to initiate and/or perform a calibration procedure and/or move a robotic arm connected to the stereoscopic visualization camera 300. In some instances, the controls 305a and 305b may include the same buttons and/or features. In other instances the controls 305a and 305b may include different features. Further, the control arms 304a and 304b may also be configured as grips to enable an operator to position the stereoscopic visualization camera 300.

Each control arm 304 is connected to the housing 302 via a rotatable post 306, as shown in FIG. 3. This connection enables the control arms 304 to be rotated with respect to the housing 302. This rotation provides flexibility to a surgeon to arrange the control arms 304 as desired, further enhancing the adaptability of the stereoscopic visualization camera 300 to be in synchronization with a surgical performance.

While the example camera 300 shown in FIGS. 3 and 4 includes two control arms 304a and 304b, it should be appreciated that the camera 300 may only include one control arm or zero control arms. In instances where the stereoscopic visualization camera 300 does not include a control arm, controls may be integrated with the housing 302 and/or provided via a remote control.

FIG. 4 shows a bottom-up perspective view of a rear-side of the stereoscopic visualization camera 300, according to an example embodiment of the present disclosure. The stereoscopic visualization camera 300 includes a mounting bracket 402 configured to connect to a support. As described in more detail in FIGS. 5 and 6, the support may include an arm with one or more joints to provide significant maneuverability. The arm may be connected to a movable cart or secured to a wall or ceiling.

The stereoscopic visualization camera 300 also includes a power port 404 configured to receive a power adapter. Power may be received from an AC outlet and/or a battery on a cart. In some instances, the stereoscopic visualization camera 300 may include an internal battery to facilitate operation without cords. In these instances, the power port 404 may be used to charge the battery. In alternative embodiments, the power port 404 may be integrated with the mounting bracket 402 such that the stereoscopic visualization camera 300 receives power via wires (or other conductive routing materials) within the support.

FIG. 4 also shows that the stereoscopic visualization camera 300 may include a data port 406. The example data port 406 may include any type of port including, for example, an Ethernet interface, a high-definition multimedia interface ("HDMI") interface, a universal serial bus ("USB") interface, a Serial Digital Interface ("SDI"), a digital optical interface, an RS-232 serial communication interface etc. The data port 406 is configured to provide a communicative connection between the stereoscopic visualization camera 300 and cords routed to one or more computing devices, servers, recording devices, and/or display devices. The communicative connection may transmit stereoscopic video signals or two-dimensional video signals for further processing, storage, and/or display. The data port 406 may also enable control signals to be sent to the stereoscopic visualization camera 300. For instance, an operator at a connected computer (e.g., a laptop computer, desktop computer, and/or tablet computer) may transmit control signals to the stereoscopic visualization camera 300 to direct operation, perform calibration, or change an output display setting.

In some embodiments, the data port 406 may be replaced (and/or supplemented) with a wireless interface. For example, the stereoscopic visualization camera 300 may transmit stereoscopic display signals via Wi-Fi to one or more display devices. A use of a wireless interface, combined with an internal battery, enables the stereoscopic visualization camera 300 to be wire-free, thereby further improving maneuverability within a surgical environment.

The stereoscopic visualization camera 300 shown in FIG. 4 also includes a front working distance main objective lens 408 of a main objective assembly. The example lens 408 is the start of the optical path within the stereoscopic visualization camera 300. Light from a light source internal to the stereoscopic visualization camera 300 is transmitted through the lens 408 to a target site. Additionally, light reflected from the target site is received in the lens and passed to downstream optical elements.

II. Exemplary Maneuverability of the Stereoscopic Visualization Camera

Figure 5:
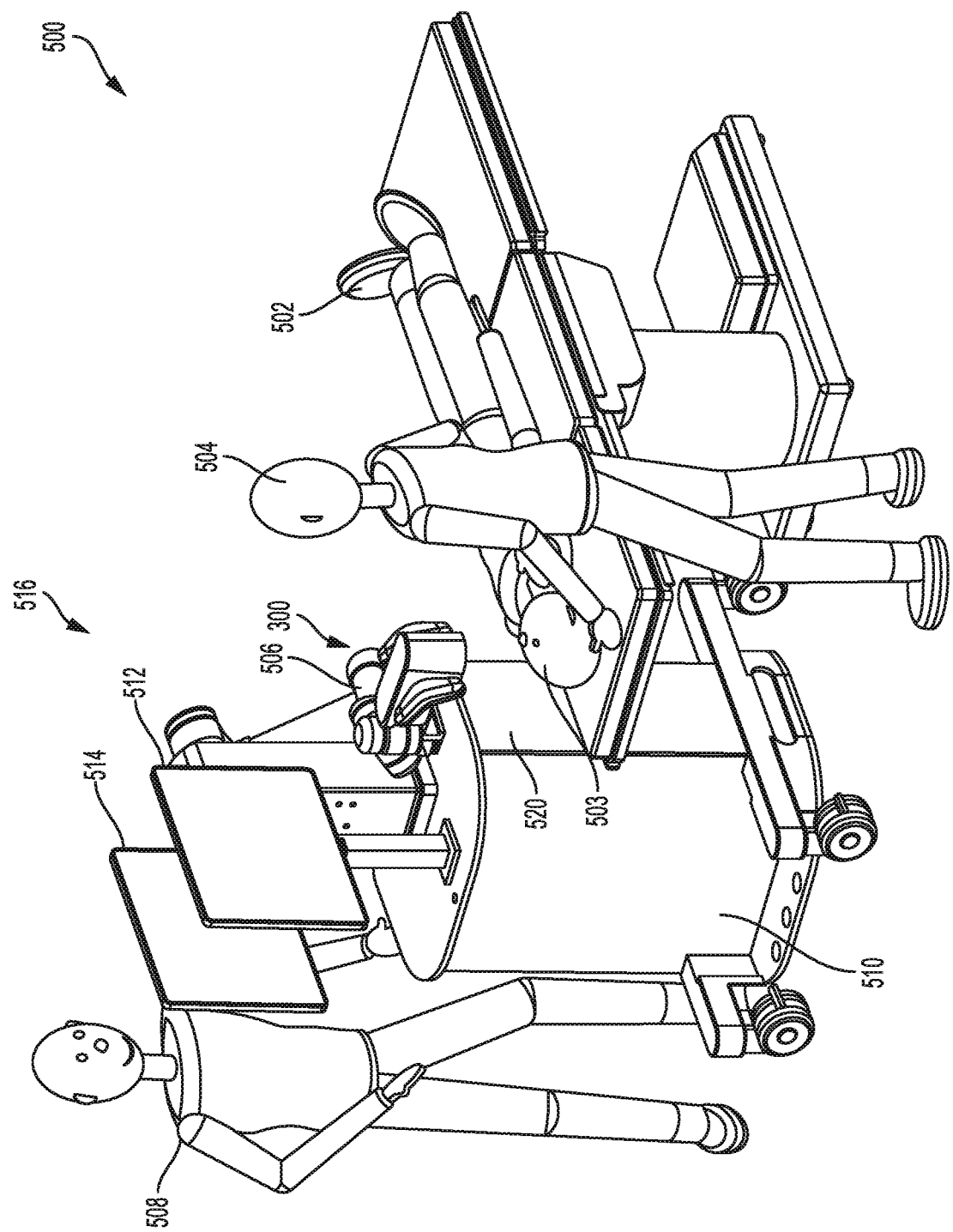
FIGS. 5 and 6 show diagrams of a microsurgical environment including the stereoscopic visualization camera of FIGS. 3 and 4, according to example embodiments of the present disclosure.
Figure 6:
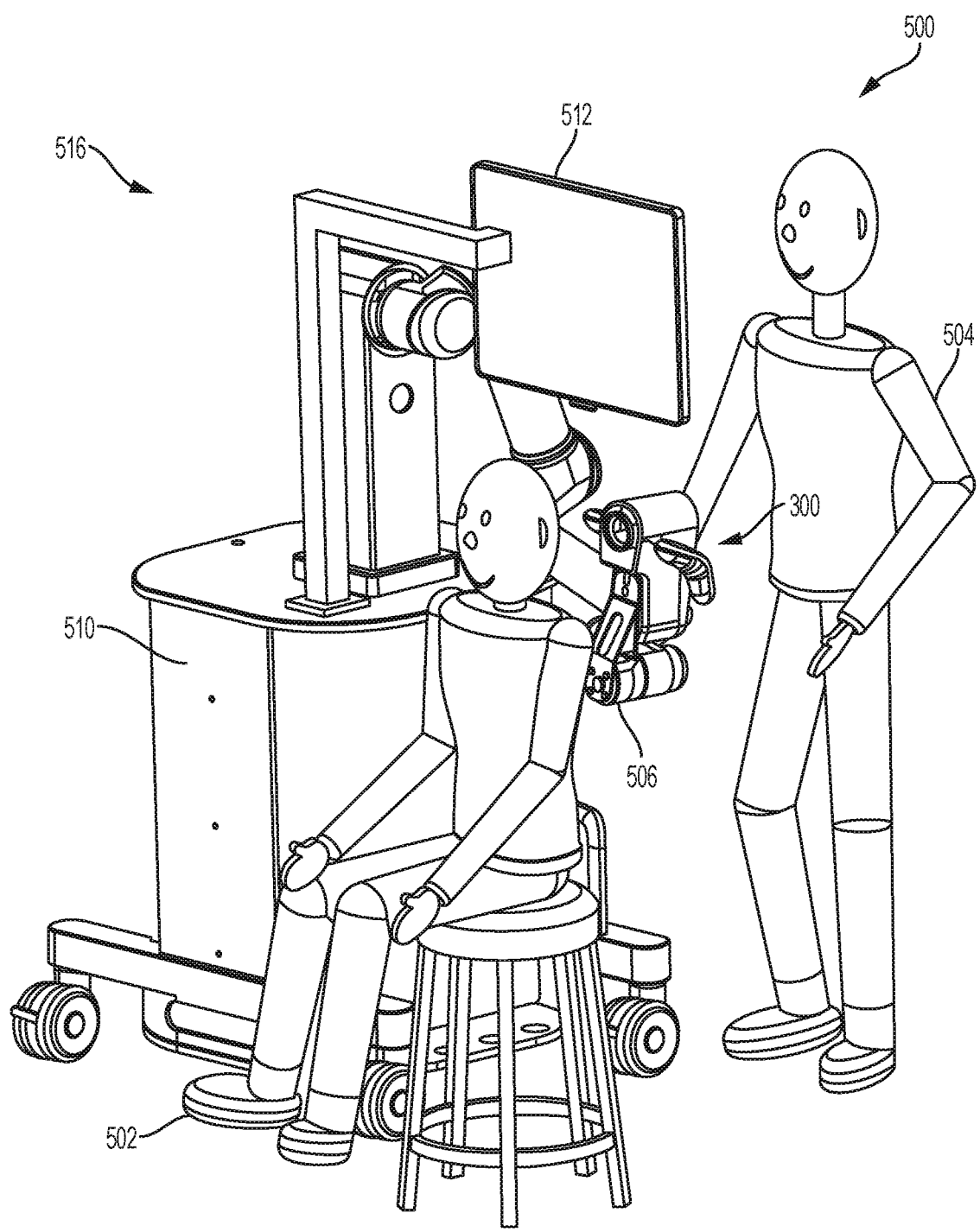

FIGS. 5 and 6 show diagrams of the stereoscopic visualization camera 300 used within a microsurgical environment 500, according to example embodiments of the present disclosure. As illustrated, the small footprint and maneuverability of the stereoscopic visualization camera 300 (especially when used in conjunction with a multiple-degree of freedom arm) enables flexible positioning with respect to a patient 502. A portion of the patient 502 in view of the stereoscopic visualization camera 300 includes a target site 503. A surgeon 504 can position the stereoscopic visualization camera 300 in virtually any orientation while leaving more than sufficient surgical space above the patient 502 (lying in the supine position). The stereoscopic visualization camera 300 accordingly is minimally intrusive (or not intrusive) to enable the surgeon 504 to perform a life-altering microsurgical procedure without distraction or hindrance.

In FIG. 5, the stereoscopic visualization camera 300 is connected to a mechanical arm 506 via mounting bracket 402. The arm 506 may include one or more rotational or extendable joints with electromechanical brakes to facilitate easy repositioning of the stereoscopic visualization camera 300. To move the stereoscopic visualization camera 300, the surgeon 504, or the assistant 508, actuates brake releases on one or more joints of the arm 506. After the stereoscopic visualization camera 300 is moved into a desired position, the brakes may be engaged to lock the joints of the arm 506 in place.

A significant feature of the stereoscopic visualization camera 300 is that it does not include oculars. This means that the stereoscopic visualization camera 300 does not have to be aligned with the eyes of the surgeon 504. This freedom enables the stereoscopic visualization camera 300 to be positioned and orientated in desirable positions that were not practical or possible with prior known surgical microscopes. In other words, the surgeon 504 can perform microsurgery with the most optimal view for conducting the procedure rather than being restricted to merely adequate view dictated by oculars of a surgical microscope.

Returning to FIG. 5, the stereoscopic visualization camera 300, via the mechanical arm 506, is connected to a cart 510 with display monitors 512 and 514 (collectively a stereoscopic visualization platform or stereoscopic robotic platform 516). In the illustrated configuration, the stereoscopic visualization platform 516 is self-contained and may be moved to any desired location in the microsurgical environment 500 including between surgical rooms. The integrated platform 516 enables the stereoscopic visualization camera 300 to be moved and used on-demand without time needed to configure the system by connecting the display monitors 512 and 514.

The display monitors 512 and 514 may include any type of display including a high-definition television, an ultra-high definition television, smart-eyewear, projectors, one or more computer screens, laptop computers, tablet computers, and/or smartphones. The display monitors 512 and 514 may be connected to mechanical arms to enable flexible positioning similar to the stereoscopic visualization camera 300. In some instances, the display monitors 512 and 514 may include a touchscreen to enable an operator to send commands to the stereoscopic visualization camera 300 and/or adjust a setting of a display.

In some embodiments, the cart 516 may include a computer 520. In these embodiments, the computer 520 may control a robotic mechanical arm connected to the stereoscopic visualization camera 300. Additionally or alternatively, the computer 520 may process video (or stereoscopic video) signals (e.g., an image or frame stream) from the stereoscopic visualization camera 300 for display on the display monitors 512 and 514. For example, the computer 520 may combine or interleave left and right video signals from the stereoscopic visualization camera 300 to create a stereoscopic signal for displaying a stereoscopic image of a target site. The computer 520 may also be used to store video and/or stereoscopic video signals into a video file (stored to a memory) so the surgical performance can be documented and played back. Further, the computer 520 may also send control signals to the stereoscopic visualization camera 300 to select settings and/or perform calibration.

In some embodiments, the microsurgical environment 500 of FIG. 5 includes an ophthalmic surgery procedure. In this embodiment, the mechanical arm 506 may be programmed to perform an orbiting sweep of a patient's eye. Such a sweep enables the surgeon to examine a peripheral retina during vitreo-retinal procedures. In contrast, with conventional optical microscopes, the only way a surgeon can view the peripheral retina is to push the side of the eye into the field of view using a technique known as scleral depression.

FIG. 6 shows a diagram of the microsurgical environment 500 with the patient 502 in a sitting position for a posterior-approach skull base neurosurgery. In the illustrated embodiment, the stereoscopic visualization camera 300 is placed into a horizontal position to face the back of the head of the patient 502. The mechanical arm 506 includes joints that enable the stereoscopic visualization camera 300 to be positioned as shown. In addition, the cart 510 includes the monitor 512, which may be aligned with the surgeon's natural view direction.

The absence of oculars enables the stereoscopic visualization camera 300 to be positioned horizontally and lower than the eye-level view of the surgeon 504. Further, the relatively low weight and flexibility enables the stereoscopic visualization camera 300 to be positioned in ways unimaginable for other known surgical microscopes. The stereoscopic visualization camera 300 thereby provides a microsurgical view for any desired position and/or orientation of the patient 502 and/or the surgeon 504.

While FIGS. 5 and 6 show two example embodiments for positioning the stereoscopic visualization camera 300, it should be appreciated that the stereoscopic visualization camera 300 may be positioned in any number of positions depending on the number of degrees of freedom of the mechanical arm 506. It is entirely possible in some embodiments to position the stereoscopic visualization camera 300 to face upwards (e.g., upside down).

III. Comparison of the Example Stereoscopic Visualization Platform to Known Surgical Microscopes In comparing the stereoscopic visualization camera 300 of FIGS. 3 to 6 to the surgical microscope 200 of FIG. 2, the differences are readily apparent. The inclusion of oculars 206 with the surgical microscope requires that the surgeon constantly orient his/her eyes to eyepieces, which are in a fixed location relative to the scope head 201 and patient. Further, the bulkiness and weight of the surgical microscope restricts it to being positioned only in a generally vertical orientation with respect to a patient. In contrast, the example stereoscopic visualization camera 300 does not include oculars and may be positioned in any orientation or position with respect to a patient, thereby freeing the surgeon to move during surgery.

To enable other clinician staff to view a microsurgical target site, the surgical microscope 200 requires the addition of second oculars 208. Generally, most known surgical microscopes 200 do not allow adding third oculars. In contrast, the example stereoscopic visualization camera 300 may be communicatively coupled to an unlimited number of display monitors. While FIGS. 5 and 6 above showed display monitors 512 and 514 connected to cart 510, a surgical room may be surrounded in display monitors that all show the microsurgical view recorded by the stereoscopic visualization camera 300. Thus, instead of limiting a view to one or two people (or requiring sharing an ocular), an entire surgical team can view a magnified view of a target surgical site. Moreover, people in other rooms, such as training and observation rooms, can be presented with the same magnified view displayed to the surgeon.

Compared to the stereoscopic visualization camera 300, the two-ocular surgical microscope 200 is more prone to being bumped or inadvertently moved. Since surgeons place their heads on oculars 206 and 208 during surgery to look through eyepieces, the scope head 201 receives constant force and periodic bumps. Adding the second oculars 208 doubles the force from a second angle. Altogether, the constant force and periodic bumping by the surgeons may cause the scope head 201 to move, thereby requiring the scope head 201 to be repositioned. This repositioning delays the surgical procedure and annoys the surgeon.

The example stereoscopic visualization camera 300 does not include oculars and is not intended to receive contact from a surgeon once it is locked into place. This corresponds to a significantly lower chance of the stereoscopic visualization camera 300 being accidentally moved or bumped during the surgeon's performance.

To facilitate the second oculars 208, the surgical microscope 200 has to be outfitted with a beamsplitter 210, which may include glass lenses and mirrors housed in precision metallic tubes. The use of a beamsplitter 210 reduces light received at the first oculars because some of the light is reflected to the second oculars 208. Further, addition of the second oculars 208 and the beamsplitter 210 increases the weight and bulkiness of the scope head 201.

In contrast to the surgical microscope 200, the stereoscopic visualization camera 300 only contains optical paths for sensors, thereby reducing weight and bulkiness. In addition, the optical sensors receive the full incident light since beamsplitters are not needed to redirect a portion of the light. This means the image received by optical sensors of the example stereoscopic visualization camera 300 is as bright and clear as possible.

Some models of surgical microscopes may enable a video camera to be attached. For instance, the surgical microscope 200 of FIG. 2 includes a monoscopic video camera 212 connected to an optical path via beamsplitter 214. The video camera 212 may be monoscopic or stereoscopic, such as the Leica® TrueVision® 3D Visualization System Ophthalmology camera. The video camera 212 records an image received from the beamsplitter 214 for display on a display monitor. The addition of the video camera 212 and beamsplitter 214 further add to the weight of the scope head 201. In addition, the beamsplitter 214 consumes additional light destined for the oculars 206 and/or 208.

Each beamsplitter 210 and 214 divides the incident light fractionally into three paths, removing light from the surgeon's view. The surgeon's eye has limited low-light sensitivity such that light from the operative site presented to him/her must be sufficient to allow the surgeon to perform the procedure. However, a surgeon cannot always increase the intensity of light applied to a target site on a patient, especially in ophthalmological procedures. A patient's eye has limited high-light sensitivity before it develops light toxicity. Hence, there is a limitation to the number and fraction of beamsplitters and to the amount of light which can be split off from the first oculars 206 to enable the use of ancillary devices 208 and 212.

The example stereoscopic visualization camera 300 of FIGS. 3 to 6 does not include beamsplitters such that optical imaging sensors receive the full amount of light from a main objective assembly. This enables the use of sensors with low-light sensitivity or even optical sensors with sensitivity outside the wavelengths of visible light to be used since post-processing can make the images sufficiently bright and visible (and adjustable) for display on the monitors.

Further, since the optical elements that define the optical paths are self-contained within the stereoscopic visualization camera 300, the optical elements may be controlled through the camera. This control allows placement and adjustment of the optical elements to be optimized for a three-dimensional stereoscopic display rather than for microscope oculars. This configuration of the camera permits control to be provided electronically from camera controls or from a remote computer. In addition, the control may be provided automatically through one or more programs onboard the camera 300 configured to adjust optical elements for retaining focus while zooming or to adjust for optical defects and/or spurious parallax. In contrast, optical elements of the surgical microscope 200 are external to the video camera 212 and controlled only via operator input, which is generally optimized for viewing a target site through the oculars 206.

In a final comparison, the surgical microscope 200 includes an X-Y panning device 220 for moving a field-of-view or target scene. The X-Y panning device 220 is typically a large, heavy, and expensive electromechanical module since it must rigidly support and move the surgical scope head 201. In addition, moving the scope head 201 changes the positioning of the surgeon to the new location of the oculars 206.

In contrast, the example stereoscopic visualization camera 300 includes a memory including instructions, which when executed, cause a processor to select pixel data of optical sensors to enable X-Y panning across a wide pixel grid. In addition, the example stereoscopic visualization camera 300 may include a small motor or actuator that controls a main objective optical element to change a working distance to a target site without moving the camera 300.

IV. Example Optical Elements of the Stereoscopic Visualization Camera

Figure 7:
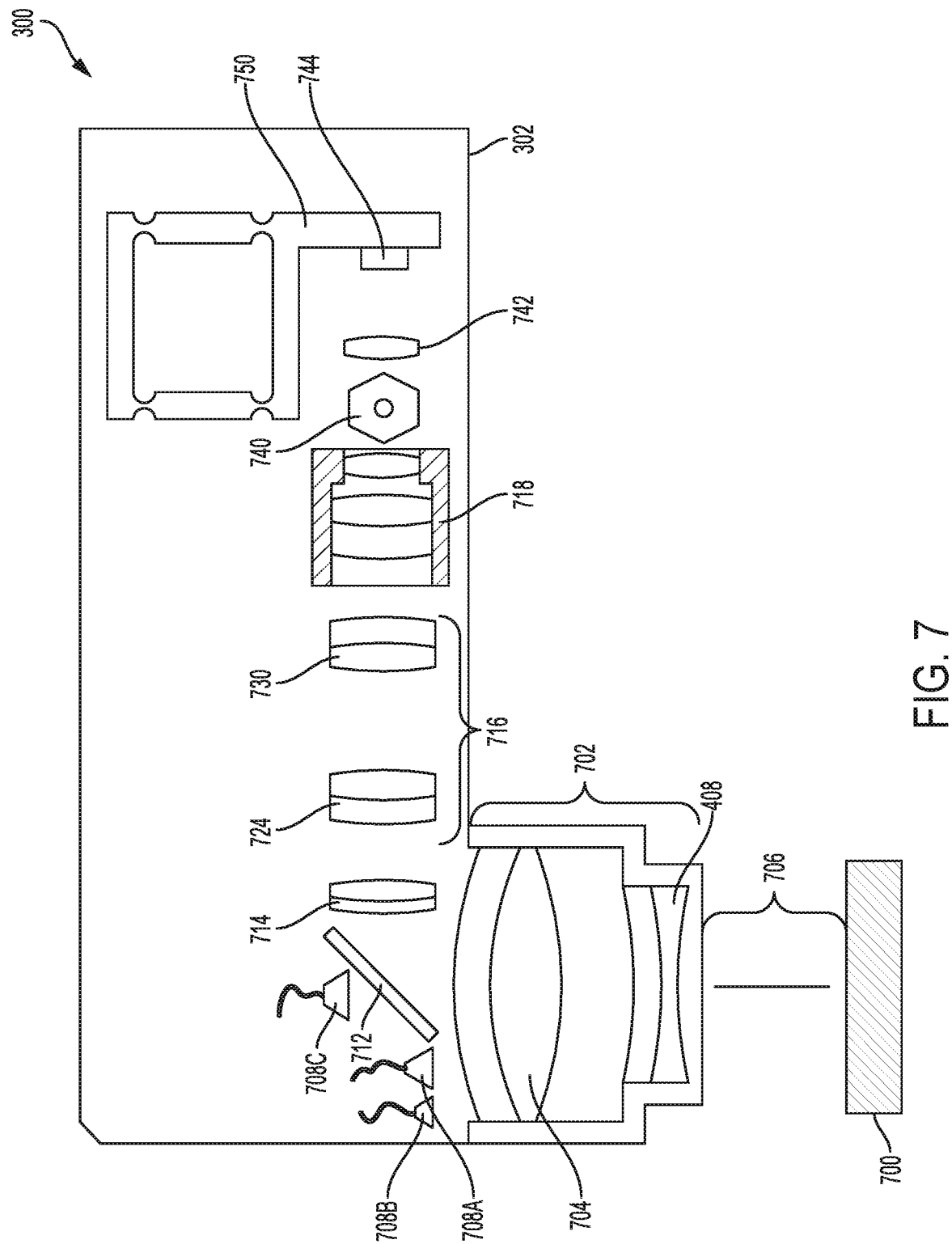
FIGS. 7 and 8 show diagrams illustrative of optical elements within the example stereoscopic visualization camera of FIGS. 3 to 6, according to an example embodiment of the present disclosure.
Figure 8:
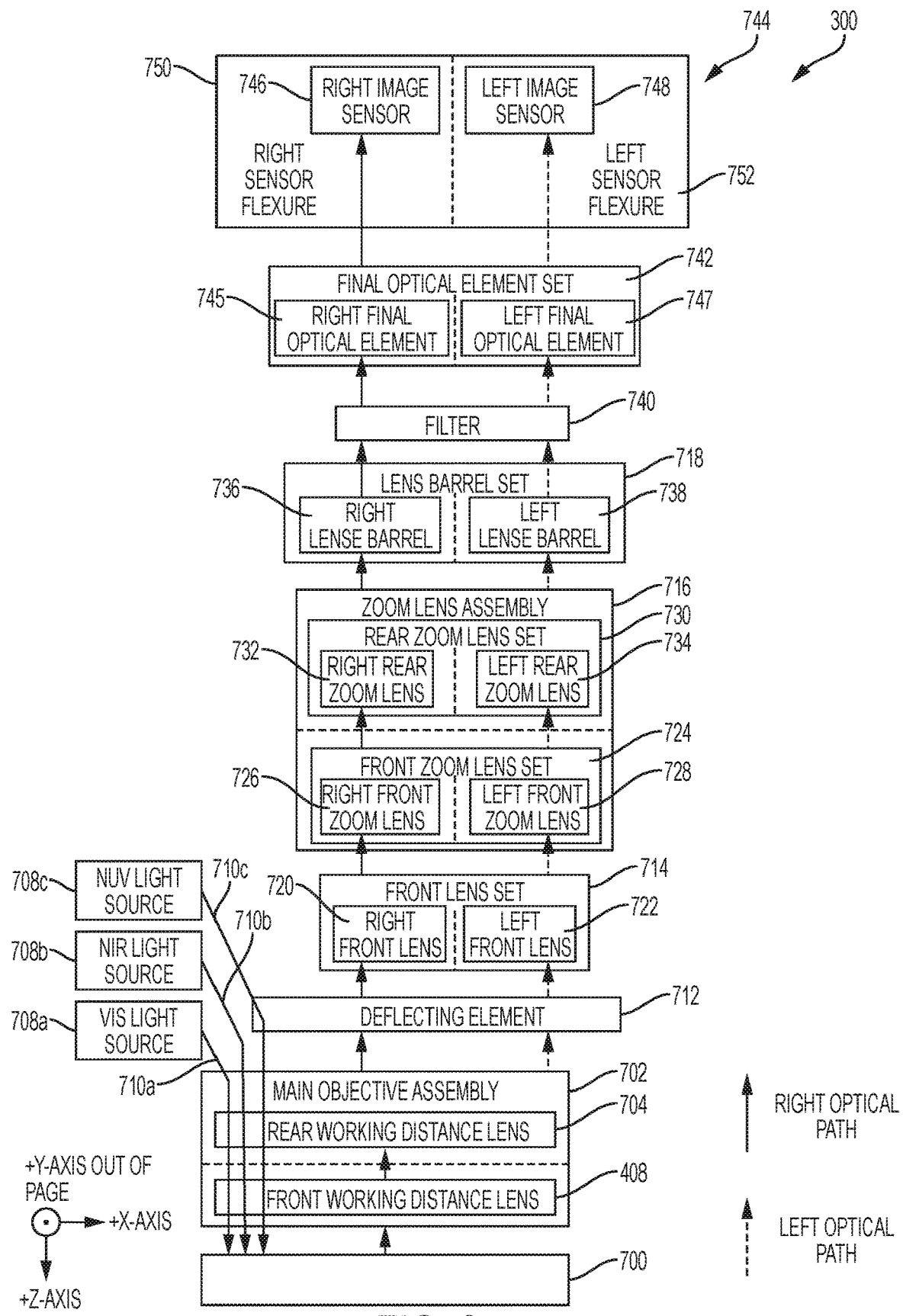

FIGS. 7 and 8 show diagrams illustrative of optical elements within the example stereoscopic visualization camera 300 of FIGS. 3 to 6, according to an example embodiment of the present disclosure. It may seem relatively simple to acquire left and right views of a target site to construct a stereoscopic image. However, without careful design and compensation, many stereoscopic images have alignment issues between the left and right views. When viewed for a prolonged period of time, alignment issues can create confusion in an observer's brain as a result of differences between the left and right views. This confusion can lead to headaches, fatigue, vertigo, and even nausea.

The example stereoscopic visualization camera 300 reduces (or eliminates) alignment issues by having a right optical path and left optical path with independent control and/or adjustment of some optical elements while other left and right optical elements are fixed in a common carrier. In an example embodiment, some left and right zoom lenses may be fixed to a common carrier to ensure left and right magnification is substantially the same. However, front or rear lenses may be independently adjustable radially, rotationally, axially, and/or tilted to compensate for small differences in zoom magnification, visual defects, and/or spurious parallax such as movement of a zoom repeat point. Compensation provided by adjustable lenses results in almost perfectly aligned optical paths throughout a complete zoom magnification range.

Additionally or alternatively, alignment issues may be reduced (or eliminated) using pixel readout and/or rendering techniques. For example, a right image (recorded by a right optical sensor) may be adjusted upwards or downwards with respect to a left image (recorded by a left optical sensor) to correct vertical misalignment between the images. Similarly, a right image may be adjusted left or right with respect to a left image to correct horizontal misalignment between the images.

FIGS. 7 and 8 below show an example arrangement and positioning of optical elements that provide for almost artifact, spurious parallax, and distortion-free aligned optical paths. As discussed later, certain of the optical elements may be moved during calibration and/or use to further align the optical paths and remove any remaining distortions, spurious parallax, and/or defects. In the illustrated embodiment, the optical elements are positioned in two parallel paths to generate a left view and a right view. Alternative embodiments may include optical paths that are folded, deflected or otherwise not parallel.

The illustrated paths correspond to a human's visual system such that the left view and right view, as displayed on a stereoscopic display, appear to be separated by a distance that creates a convergence angle of roughly 6 degrees, which is comparable to the convergence angle for an adult human's eyes viewing an object at approximately 4 feet away, thereby resulting in stereopsis. In some embodiments, image data generated from the left view and right view are combined together on the display monitor(s) 512 and 514 to generate a stereoscopic image of a target site or scene. Alternative embodiments comprise other stereoscopic displays where the left view is presented to only the left eye of a viewer and the corresponding right view is presented to only the right eye. In exemplary embodiments used to adjust and verify proper alignment and calibration, both views are displayed overlaid to both eyes.

A stereoscopic view is superior to a monoscopic view because it mimics the human visual system much more closely. A stereoscopic view provides depth perception, distance perception, and relative size perception to provide a realistic view of a target surgical site to a surgeon. For procedures such as retinal surgery, stereoscopic views are vital because surgical movements and forces are so small that the surgeon cannot feel them. Providing a stereoscopic view helps a surgeon's brain magnify tactile feel when the brain senses even minor movements while perceiving depth.

FIG. 7 shows a side view of the example stereoscopic visualization camera 300 with the housing 302 being transparent to expose the optical elements. FIG. 8 shows a diagram illustrative of an optical path provided by the optical elements shown in FIG. 7. As shown in FIG. 8, the optical path includes a right optical path and a left optical path. The optical paths in FIG. 8 are shown from a perspective of facing a forward direction and looking down at the stereoscopic visualization camera 300. From this view, the left optical path appear on the right side of FIG. 8 while the right optical path is shown on the left side.

The optical elements shown in FIG. 7 are part of the left optical path. It should be appreciated that the right optical path in FIG. 7 is generally identical to the left optical path regarding relation location and arrangement of optical elements. As mentioned above, the interpupillary distance between a center of the optical paths is between 58 to 70 mm, which may be scaled to 10 to 25 mm. Each of the optical elements comprise lenses having certain diameters (e.g., between 2 mm and 29 mm). Accordingly, a distance between the optical elements themselves is between 1 to 23 mm, preferably around 10 mm.

The example stereoscopic visualization camera 300 is configured to acquire images of a target site 700 (also referred to as a scene or field-of-view ("FOV") or target surgical site). The target site 700 includes an anatomical location on a patient. The target site 700 may also include laboratory biological samples, calibration slides/templates, etc. Images from the target site 700 are received at the stereoscopic visualization camera 300 via a main objective assembly 702, which includes the front working distance lens 408 (shown in FIG. 4) and a rear working distance lens 704.

A. Example Main Objective Assembly

The example main objective assembly 702 may include any type of refractive assembly or reflective assembly. FIG. 7 shows the objective assembly 702 as an achromatic refractive assembly with the front working distance lens 408 being stationary and the rear working distance lens 704 being movable along the z-axis. The front working distance lens 408 may comprise a plano convex ("PCX") lens and/or a meniscus lens. The rear working distance lens 704 may comprise an achromatic lens. In examples where the main objective assembly 702 includes an achromatic refractive assembly, the front working distance lens 408 may include a hemispherical lens and/or a meniscus lens. In addition, the rear working distance lens 704 may include an achromatic doublet lens, an achromatic doublet group of lenses, and/or an achromatic triplet lens.

The magnification of the main objective assembly 702 is between 6× to 20×. In some instances, the magnification of the main objective assembly 702 may vary slightly based on a working distance. For example, the main objective assembly 702 may have a magnification of 8.9× for a 200 mm working distance and a magnification of 8.75× for a 450 mm working distance.

The example rear working distance lens 704 is configured to be movable with respect to the front working distance lens 408 to change a spacing therebetween. The spacing between the lenses 408 and 704 determines the overall front focal length of the main objective assembly 702, and accordingly the location of a focal plane. In some embodiments, the focal length is the distance between the lenses 408 and 704 plus one-half the thickness of the front working distance lens 408.

Together, the front working distance lens 408 and the rear working distance lens 704 are configured to provide an infinite conjugate image for providing an optimal focus for downstream optical image sensors. In other words, an object located exactly at the focal plane of the target site 700 will have its image projected at a distance of infinity, thereby being infinity-coupled at a provided working distance. Generally, the object appears in focus for a certain distance along the optical path from the focal plane. However, past the certain threshold distance, the object begins to appear fuzzy or out of focus.

FIG. 7 shows working distance 706, which is the distance between an outer surface of the front working distance lens 408 and to the focal plane of the target site 700. The working distance 706 may correspond to an angular field-of-view, where a longer working distance results in a wider field-of-view or larger viewable area. The working distance 706 accordingly sets a plane of the target site or scene that is in focus. In the illustrated example, the working distance 706 is adjustable from 200 to 450 mm by moving the rear working distance lens 704. In an example, the field-of-view can be adjusted between 20 mm×14 mm to 200 mm×140 mm using upstream zooming lenses when the working distance is 450 mm.

The main objective assembly 702 shown in FIGS. 7 and 8 provides an image of the target site 700 for both the left and right optical paths. This means that the width of the lenses 408 and 704 should be at least as wide as the left and right optical paths. In alternative embodiments, the main objective assembly 702 may include separate left and right front working distance lenses 408 and separate left and right rear working distance lens 704. The width of each pair of the separate working distance lenses may be between ¼ to ½ of the width of the lenses 408 and 704 shown in FIGS. 7 and 8. Further, each of the rear working distance lenses 704 may be independently adjustable.

In some embodiments, the main objective assembly 702 may be replaceable. For example, different main objective assemblies may be added to change a working distance range, a magnification, a numerical aperture, and/or refraction/reflection type. In these embodiments, the stereoscopic visualization camera 300 may change positioning of downstream optical elements, properties of optical image sensors, and/or parameters of image processing based on which main objective assembly is installed. An operator may specify which main objective assembly is installed in the stereoscopic visualization camera 300 using one of the controls 305 of FIG. 3 and/or a user input device.

B. Example Lighting Sources

To illuminate the target site 700, the example stereoscopic visualization camera 300 includes one or more lighting sources. FIGS. 7 and 8 show three lighting sources including a visible light source 708a, a near-infrared ("NIR") light source 708b, and a near-ultraviolet ("NUV") light source 708c. In other examples, the stereoscopic visualization camera 300 may include additional or fewer (or no) light sources. For instance, the NIR and NUV light sources may be omitted. The example light sources 708 are configured to generate light, which is projected to the target scene 700. The generated light interacts and reflects off the target scene, with some of the light being reflected to the main objective assembly 702. Other examples may include external light sources or ambient light from the environment.

The example visible light source 708a is configured to output light in the human-visible part of the light spectrum in addition to some light with wavelengths outside the visible region. The NIR light source 708b is configured to output light that is primarily at wavelengths slightly past the red part of the visible spectrum, which is also referred to as "near-infrared." The NUV light source 708c is configured to output light that is primarily at wavelengths in the blue part of the visible spectrum, which is referred to as "near-ultraviolet." The light spectra output by the light sources 708 is controlled by respective controllers, described below. A brightness of light emitted by the light sources 708 may be controlled by a switching rate and/or applied voltage waveform.

FIGS. 7 and 8 illustrate that the visible light source 708a and the NIR light source 708b are provided directly through the main objective assembly 702 to the target site 700. As shown in FIG. 8, visible light from the visible light source 708a propagates along visible path 710a. Additionally, NIR light from the NIR light source 708b propagates along NIR path 710b. While the light sources 708a and 708b are shown as being behind the main objective assembly 702 (with respect to the target site 700), in other examples the light sources 708a and 708b may be provided before the main objective assembly 702. In one embodiment, the light sources 708a and 708b may be provided on an outside of the housing 302 and face toward the target site 700. In yet other embodiments, the light sources 708 may be provided separate from the stereoscopic visualization camera 300 using, for example, a Koeher illumination setup and/or a darkfield illumination setup.

In contrast to the light sources 708a and 708b, NUV light from the NUV light source 708c is reflected by a deflecting element 712 (e.g., a beamsplitter) to the main objective assembly 702 using an epi-illumination setup. The deflecting element 712 may be coated or otherwise configured to reflect only light beyond the NUV wavelength range, thereby filtering NUV light. NUV light from the NUV light source 708c propagates along NUV path 710c.

In some embodiments, the NIR and NUV light sources 708b and 708c may be used with excitation filters to further filter light that may not be blocked by filters (e.g., filter 740). The filters may be placed in front of the light sources 708b and 708c before the main objective assembly 702 and/or after the main objective assembly. The light from the NUV and NIR light sources 708b and 708c, after being filtered, comprises wavelengths that excite fluorescence in fluorescent sites 914 (shown in FIG. 9) of an anatomical object. Further, the light from the NUV and NIR light sources 708b and 708c, after being filtered, may comprise wavelengths that are not in the same range as those being emitted by the fluorescent sites 914.

The projection of the light from light sources 708 through the main objective assembly provides the benefit of changing the lighted field-of-view based on the working distance 706 and/or focal plane. Since the light passes through the main objective assembly 702, the angle at which light is projected changes based on the working distance 706 and corresponds to the angular field-of-view. This configuration accordingly ensures the field-of-view is properly illuminated by the light sources 708, regardless of working distance or magnification.

C. Example Deflecting Element

The example deflecting element 712 illustrated in FIGS. 7 and 8 is configured to transmit a certain wavelength of light from the NUV light source 708c to the target site 700 through the main objective assembly 702. The deflecting element 712 is also configured to reflect light received from the target site 700 to downstream optical elements, including a front lens set 714 for zooming and recording. In some embodiments, the deflecting element 712 may filter light received from the target site 700 through the main objective assembly 702 so that light of certain wavelengths reaches the front lens set 714.

The deflecting element 712 may include any type of mirror or lens to reflect light in a specified direction. In an example, the deflecting element 712 includes a dichroic mirror or filter, which has different reflection and transmission characteristics at different wavelengths. The stereoscopic visualization camera 300 of FIGS. 7 and 8 includes a single deflecting element 712, which provides light for both the right and left optical paths. In other examples, the camera 300 may include separate deflecting elements for each of the right and left optical paths. Further, a separate deflecting element may be provided for the NUV light source 708c.

Figure 9:
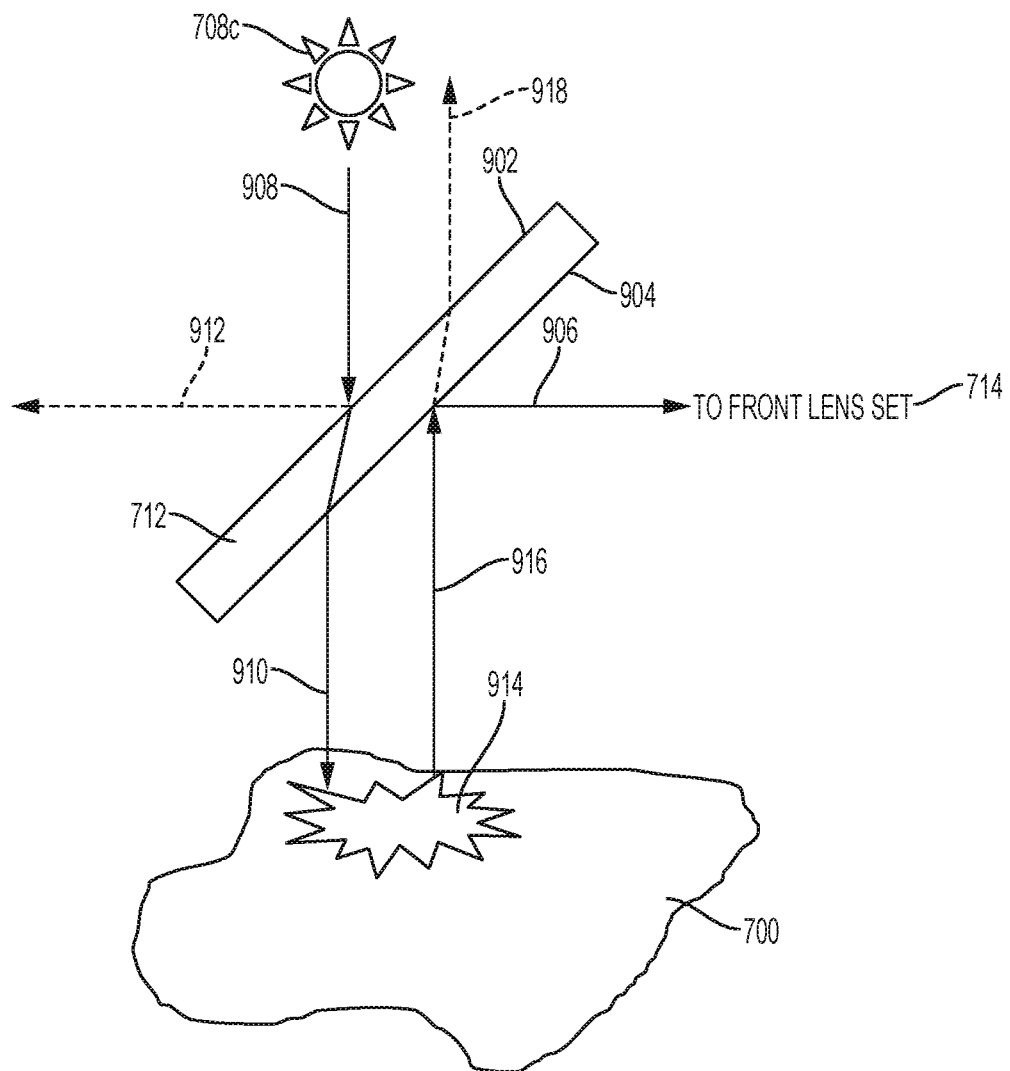
FIG. 9 shows a diagram of a deflecting element of the example stereoscopic visualization camera of FIGS. 7 and 8, according to an example embodiment of the present disclosure.

FIG. 9 shows a diagram of the deflecting element 712 of FIGS. 7 and 8, according to an example embodiment of the present disclosure. For brevity, the main objective assembly 702 is not shown. In this example, the deflecting element 712 includes two parallel faces 902 and 904 for transmitting and reflecting light of certain wavelengths. The parallel faces 902 and 904 are set at a 45° angle with respect to the left and right optical paths (represented as path 906). The 45° angle is selected since this angle causes reflected light to propagate at a 90° angle from the transmitted light, thereby providing optimal separation without causing the separated light to be detected in the downstream front lens set 714. In other embodiments, the angle of the deflecting element 712 could be between 10 degrees and 80 degrees without unintentionally propagating light of unwanted wavelengths.

The example NUV light source 708c is located behind the deflecting element 712 (with respect to the target site 700). Light from the light source 708c propagates along path 908 and contacts the deflecting element 712. NUV light around the primary wavelength range of the NUV light source 708c is transmitted through the deflecting element 712 along path 910 to the target site 700. Light from the NUV light source 708c that has a wavelength above (and below) the primary wavelength range of the NUV light source 708c is reflected along path 912 to a light sink or unused region of the housing 302.

When the NUV light reaches the target site 700, it is absorbed by one or more fluorescent sites 914 of an anatomical object. In some instances, the anatomical object may have been injected with a contrast agent configured to absorb NUV light and emit light with a different primary wavelength. In other instances, the anatomical object may naturally absorb NUV light and emit light with a different primary wavelength. At least some of the light reflected or emitted by the fluorescent site 914 propagates along path 916 until it contacts the deflecting element 712. Most of the light reflects off the surface 904 along path 906 to the front lens set 714. A portion of the light, including NUV light around the primary wavelength range of the NUV light source 708c is transmitted through the deflecting element 712 along path 918 to a light sink or unused region of the housing 302. The deflecting element 712 shown in FIG. 9 accordingly enables optical stimulation of a fluorescent agent at the target site 700 with one region of the spectrum while blocking much of the stimulating light from travelling to the downstream front lens set 714.

It should be appreciated that the reflectivity and transmissivity characteristics of the deflecting element 712 can be changed to meet other light spectrum requirements. In some instances, the housing 302 may include a slot that enables the deflecting element 712 and/or the NUV light source 708c to be replaced based on the desired light reflectivity and transmissivity characteristics. It should also be appreciated that a first path internal to the deflecting element 712 between path 908 and path 910 and a second path internal to the deflecting element 712 between path 916 and path 918 are each angled to represent schematically the refraction of the light as it travels between air and the interior of the deflecting element 712. The angles shown are not meant to represent actual reflection angles.

D. Example Zoom Lenses

The example stereoscopic visualization camera 300 of FIGS. 7 and 8 includes one or more zoom lens to change a focal length and angle of view of the target site 700 to provide zoom magnification. In the illustrated example, the zoom lens includes the front lens set 714, a zoom lens assembly 716, and a lens barrel set 718. It should be appreciated that in other embodiments, the front lens set 714 and/or the lens barrel set 718 may be omitted. Alternatively, the zoom lens may include additional lens to provide further magnification and/or image resolution.

The front lens set 714 includes a right front lens 720 for the right optical path and a left front lens 722 for the left optical path. The lenses 720 and 722 may each include a positive converging lens to direct light from the deflecting element 712 to respective lenses in the zoom lens assembly 716. A lateral position of the lenses 720 and 722 accordingly defines a beam from the main objective assembly 702 and the deflecting element 712 that is propagated to the zoom lens assembly 716.

One or both of the lenses 720 and 722 may be adjustable radially to match optical axes of the left and right optical paths. In other words, one or both of the lenses 720 and 722 may be moved left-right and/or up-down in a plane incident to the optical path. In some embodiments, one or more of the lenses 720 and 722 may be rotated or tilted to reduce or eliminate image optical defects and/or spurious parallax. Moving either or both of the lenses 720 and 722 during zooming may cause the zoom repeat point ("ZRP") for each optical path to appear to remain stationary to a user. In addition to radial movement, one or both of the front lenses 720 and 722 may be moved axially (along the respective optical path) to match magnifications of the optical paths.

The example zoom lens assembly 716 forms an afocal zoom system for changing the size of a field-of-view (e.g., a linear field-of-view) by changing a size of the light beam propagated to the lens barrel set 718. The zoom lens assembly 716 includes a front zoom lens set 724 with a right front zoom lens 726 and a left front zoom lens 728. The zoom lens assembly 716 also includes a rear zoom lens set 730 with a right rear zoom lens 732 and a left rear zoom lens 734. The front zoom lenses 726 and 728 may be positive converging lenses while the rear zoom lenses 732 and 734 include negative diverging lenses.

The size of an image beam for each of the left and right optical paths is determined based on a distance between the front zoom lenses 726 and 728, the rear zoom lenses 732 and 734 and the lens barrel set 718. Generally, the size of the optical paths reduces as the rear zoom lenses 732 and 734 move toward the lens barrel set 718 (along the respective optical paths), thereby decreasing magnification. In addition, the front zoom lenses 726 and 728 may also move toward (or away from) the lens barrel set 718 (such as in a parabolic arc), as the rear zoom lenses 732 and 734 move toward the lens barrel set 718, to maintain the location of the focal plane on the target site 700, thereby maintaining focus.

The front zoom lenses 726 and 728 may be included within a first carrier (e.g., the front zoom set 724) while the rear zoom lenses 732 and 724 are included within a second carrier (e.g., the rear zoom set 730). Each of the carriers 724 and 730 may be moved on tracks (or rails) along the optical paths such that left and right magnification changes concurrently. In this embodiment, any slight differences in magnification between the left and right optical paths may be corrected by moving the right front lens 720 and/or the left front lens 722. Additionally or alternatively, a right lens barrel 736 and/or a left lens barrel 738 of the lens barrel set 718 may be moved axially.

In alternative embodiments, the right front zoom lens 726 may be moved axially separately from the left front zoom lens 728. In addition, the right rear zoom lens 732 may be moved axially separately from the left rear zoom lens 734.

Separate movement may enable small magnification differences to be corrected by the zoom lens assembly 716, especially when the front lens set 714 and the lens barrel set 718 are stationary along the optical paths. Further, in some embodiments, the right front zoom lens 726 and/or the left front zoom lens 728 may be radially and/or rotationally adjustable (and/or tilted) to maintain an apparent location of a ZRP in the optical path. Additionally or alternatively, the right rear zoom lens 732 and/or the left rear zoom lens 734 may be radially and/or rotationally adjustable (and/or tilted) to maintain an apparent location of a ZRP in the optical path.

The example lens barrel set 718 includes the right lens barrel 736 and the left lens barrel 738, which are part of the afocal zoom system in addition with the zoom lens assembly 716. The lenses 736 and 738 may include positive converging lenses configured to straighten or focus a light beam from the zoom lens assembly 716. In other words, the lenses 736 and 738 focus the infinity-coupled output of the zoom lens assembly 716.

In some examples, the lens barrel set 718 is fixed radially and axially within the housing 302. In other examples, the lens barrel set 718 may be movable axially along the optical path to provide increased magnification. Additionally or alternatively, each of the lenses 736 and 738 may be radially and/or rotationally adjustable (and/or tilted) to, for example, correct for differences in optical properties (from manufacturing or natural glass deviations) between the left and right lenses of the front lens set 714, the front zoom lens set 724, and/or the rear zoom lens set 730.

Altogether, the example front lens set 714, the zoom lens assembly 716, and the lens barrel set 718 are configured to achieve an optical zoom between 5× to about 20×, preferably at a zoom level that has diffraction-limited resolution. In some embodiments, the front lens set 714, the zoom lens assembly 716, and the lens barrel set 718 may provide higher zoom ranges (e.g., 25× to 100×) if image quality can be compromised. In these embodiments, the stereoscopic visualization camera 300 may output a message to an operator indicative that a selected optical range is outside of an optical range and subject to a reduction in image quality.

In some embodiments, the lenses of the front lens set 714, the zoom lens assembly 716, the lens barrel set 718, and/or the main objective assembly 702 may each be constructed as a doublet from multiple optical sub-elements using materials that balance each other's optical distortion parameters. The doublet construction reduces chromatic aberrations and optical aberrations. For example, the front working distance lens 408 and the rear working distance lens 702 may each be constructed as a doublet. In another example, the front lenses 720 and 722, the front zoom lenses 726 and 728, the rear zoom lenses 732 and 734, and the lens barrels 736 and 738 may each comprise a doublet lens.

In yet further embodiments, the lenses of the front lens set 714, the zoom lens assembly 716, the lens barrel set 718, and/or the main objective assembly 702 may be tuned differently and/or have different properties to provide two parallel optical paths with different capabilities. For example, right lenses in zoom lens assembly 716 may be selected to provide 5× to 10× optical zoom for the right optical path while left lenses in the zoom lens assembly 716 are selected to provide 15× to 20× optical zoom for the left optical path. Such a configuration may enable two different magnifications to be shown at the same time and/or on the same screen, though in a monoscopic view.

E. Example Filter

The example stereoscopic visualization camera 300 of FIGS. 7 and 8 includes one or more optical filters 740 (or filter assemblies) to selectively transmit desired wavelengths of light. FIG. 8 shows that a single filter 740 may be applied to the right and left optical paths. In other examples, each of the optical paths may have a separate filter. The inclusion of separate filters enables, for example, different wavelengths of light to be filtered from the left and right optical paths at the same time, which enables, for example, fluorescent images to be displayed in conjunction with visible light images.

FIG. 7 shows that the filter 740 includes a wheel that is rotated about its axis of rotation. In the illustrated embodiment, the filter 740 can accommodate three different optical filter pairs. However, in other embodiments, the filter 740 may include additional or fewer filter pairs. Generally, light received at the filter 740 from the target site 700 includes a broad spectrum of wavelengths. The lenses of the main objective assembly 702, the front lens set 714, the zoom lens assembly 716, and the lens barrel set 718 are configured to pass a relatively wide bandwidth of light including wavelengths of interest to an operator and undesirable wavelengths. In addition, downstream optical image sensors are sensitive to certain wavelengths. The example filter 740 accordingly passes and blocks certain portions of the light spectrum to achieve different desirable features.

As a wheel, the filter 740 comprises a mechanical device capable of changing positions at about four times per second. In other embodiments, the filter 740 may include a digital micro-mirror, which can change a light path's direction at video frame rates such as 60 times per second. In these other embodiments, each of the left and right optical paths would include a micro-mirror. The left and right micro-mirror may have synchronized or simultaneous switching.

In some embodiments, the filter 740 may be synchronized to the light sources 708 to realize "time-interleaved" multispectral imaging. For example, the filter 740 may include an infrared cut filter, near-infrared bandpass filter, and near-ultraviolet cut filter. The different filter types are selected to work with different spectra of the light sources 708 and the reflectivity and transmissivity characteristics of the deflecting element 712 to pass certain desired wavelengths of light at predetermined times.

In one mode, the filter 740 and the light sources 708 are configured to provide a visible light mode. In this mode, the visible light source 708a transmits light from the visible region onto the target site 700, some of which is reflected to the main objective assembly 702. The reflected light may include some light beyond the visible spectrum, which may affect optical image sensors. The visible light is reflected by the deflecting element 712 and passes through the front lens set 714, the zoom lens assembly 716, and the lens barrel set 718. In this example, the filter 740 is configured to apply the infrared-cut filter or the near-ultraviolet cut filter to the optical paths to remove light outside the visible spectrum such that light only in the visible spectrum passes through to a final optical set 742 and an optical image sensor 744.

In another mode, filter 740 and the light sources 708 are configured to provide fluorescence light of a narrow wavelength to the optical sensor 744. In this mode, the NUV light source 708c transmits light from the deep-blue region of the spectrum to the target site 700. The deflecting element 712 allows the desired light of the deep-blue region to pass through while reflecting undesired light. The deep-blue light interacts with the target site 700 such that fluorescence light is emitted. In some examples, δ-Aminolaevulinic acid ("5ala") and/or Protoporphyrin IX is applied to the target site 700 to cause fluorescence light to be emitted when deep-blue light is received. The main objective assembly 702 receives the fluorescence light in addition to reflected deep-blue light and some visible light. The deep-blue light passes through the deflecting element 712 out of the right and left optical paths. Thus, only the visible light and fluorescence light pass through the front lens set 714, the zoom lens assembly 716, and the lens barrel set 718. In this example, the filter 740 is configured to apply the near-ultraviolet cut filter to the optical paths to remove light outside the desired fluorescence spectrum including visible light and any remaining NUV deep-blue light. Accordingly, only fluorescence light of a narrow wavelength reaches the optical image sensor 744, which enables the fluorescence light to be more easily detected and distinguished based on relative intensity.

In yet another mode, the filter 740 and the light sources 708 are configured to provide indocyanine green ("ICG") fluorescence light to the optical sensor 744. In this mode, the NIV light source 708b transmits light in the far-red region (which is also considered near-infrared) of the visible spectrum to the target site 700. In addition, the visible light source 708a transmits visible light to the target scene 700. The visible light and far-red light are absorbed by material with ICG at the target site, which then emits a highly stimulated fluorescence light in the further-red region. The main objective assembly 702 receives the fluorescence light in addition to reflected NIR light and visible light. The light is reflected by the deflecting element 712 to the front lens set 714, the zoom lens assembly 716, and the lens barrel set 718. In this example, the filter 740 is configured to apply the near-infrared bandpass filter to the optical paths to remove light outside the desired fluorescence spectrum including visible light and at least some of the NIR light. Accordingly, only fluorescence light in the further-red region reaches the optical image sensor 744, which enables the fluorescence light to be more easily detected and distinguished based on relatively intensity.

TABLE 1

| Light Source | Filter | Light Transmitted to Image Sensors |
|---|---|---|
| Visible | Infrared Cut Filter, Near-Ultraviolet Cut Filter | Visible Light |
| NUV | Near-Ultraviolet Cut Filter | Blue Visible and NIR Light |
| NIR and Visible | Near-Infrared Bandpass Filter | Further-Red Fluorescence |

Table 1 above shows a summary of the different possible combinations of lights sources and filters for causing light of a certain desired wavelength to reach the optical light sensor 744. It should be appreciated that other types of filters and/or light sources may be used to further increase the different types of light received at the image sensor 744. For instance, bandpass filters configured to pass light of a narrow wavelength may be used to correspond to certain biological stains or contrasts applied to the target site 700. In some examples, the filter 740 may include a cascade or more than one filter to enable light from two different ranges to be filtered. For example, a first filter 740 may apply an infrared cut filter and a near-ultraviolet cut filter such that only visible light of a desired wavelength range passes to the optical sensor 744.

In other embodiments, separate filters 740 may be used for the left and right optical paths. For example, a right filter may include an infrared cut filter while a left filter includes a near-infrared pass filter. Such a configuration enables viewing of the target site 700 in visible wavelengths simultaneously with IGC green fluorescence wavelengths. In another example, a right filter may include an infrared cut filter while a left filter includes a near-ultraviolet cut filter. In this configuration, the target site 700 may be shown in visible light simultaneously with SALA fluorescence light. In these other embodiments, the right and left image streams may still be combined into a stereoscopic view that provides a fluorescence view of certain anatomical structures combined with a view of the target site 700 in visible light.

F. Example Final Optical Element Set

The example stereoscopic visualization camera 300 of FIGS. 7 and 8 includes the final optical element set 742 to focus light received from the filter 740 onto the optical image sensor 744. The final optical element set 742 includes a right final optical element 745 and a left final optical element 747, which may each comprise a positive converging lens. In addition to focusing light, the optical elements 745 and 747 may be configured to correct minor aberrations in the right and left optical paths prior to the light reaching the optical image sensor 744. In some examples, the lenses 745 and 747 may be movable radially and/or axially to correct magnification and/or focusing aberrations caused by the front lens set 714, the zoom lens assembly 716, and the lens barrel set 718. In an example, the left final optical element 747 may be moved radially while the right final optical element 745 is fixed to remove ZRP movement during magnification changes.

G. Example Image Sensors

The example stereoscopic visualization camera 300 of FIGS. 7 and 8 includes the image sensor 744 to acquire and/or record incident light that is received from the final optical element set 742. The images sensor 744 includes a right optical image sensor 746 to acquire and/or record light propagating along the right optical path and a left optical image sensor 748 to acquire and/or record light propagating along the left optical path. Each of the left and right optical image sensors 746 and 748 include, for example, complementary metal-oxide-semiconductor ("CMOS") sensing elements, N-type metal-oxide-semiconductor ("NMOS"), and/or semiconductor charge-coupled device ("CCD") sensing elements. In some embodiments, the left and right optical sensors 746 and 748 are identical and/or have the same properties. In other embodiments, the left and right optical sensors 746 and 748 include different sensing elements and/or properties to provide varying capability. For example, the right optical image sensor 746 (using a first color filter array) may be configured to be more sensitive to blue fluorescence light while the left optical image sensor 748 (using a second color filter array) is configured to be more sensitive to visible light.

FIG. 10 shows an example of the right optical image sensor 746 and the left optical image sensor 748 of the image sensor 744, according to an example embodiment of the present disclosure. The right optical image sensor 746 includes a first two-dimensional grid or matrix 1002 of light-sensing elements (e.g., pixels). In addition, the left optical image sensor 748 includes a second two-dimensional pixel grid 1004 of light-sensing elements. Each of the pixels includes a filter that enables only light of a certain wavelength to pass, thereby contacting an underlying light detector. Filters for different colors are spread across the sensors 746 and 748 to provide light detection for all wavelengths across grids. The light detector may be sensitive to visible light, as well as additional ranges that are above and below the visible spectrum.

The light-sensing elements of the grids 1002 and 1004 are configured to record a range of wavelengths of light as a representation of the target site 700 that is in the field-of-view. Light incident on a light-sensing element causes an electrical change to accumulate. The electrical charge is read to determine an amount of light being received at the sensing element. In addition, since the filter characteristics of the sensing element are known to within manufacturing tolerances, the range of wavelengths of the received light is known. The representation of the target site 700 is directed onto the light-sensing elements such that the grids 1002 and 1004 for the respective optical image sensors 746 and 748 sample the target site 700 spatially. The resolution of the spatial sampling is a parameter that affects image quality and parity.

The number of pixels shown in the pixel grids 1002 and 1004 in FIG. 10 is not representative of the number of actual pixels in the optical image sensors 746 and 748. Instead, the sensors typically have a resolution between 1280×720 pixels and 8500×4500 pixels, preferably around 2048×1560 pixels. However, not all pixels of the grids 1002 and 1004 are selected for image transmission. Instead, a subset or pixel set of the grids 1002 and 1004 are selected for transmission. For example, in FIG. 10, pixel set 1006 is selected from the pixel grid 1002 for transmission as a right image and pixel set 1008 is selected from pixel grid 1004 for transmission as a left image. As illustrated, the pixel set 1006 does not need to be located in the same location as the pixel set 1008 in relation to respective pixel grids 1002 and 1004. The separate control of the pixel sets 1006 and 1008 enables left and right images to be aligned and/or corrected for image defects and/or spurious parallax such as moving ZRPs.

Selection of a pixel set from a pixel grid enables a portion of the pixel grid to be selected to compensate for image defects/spurious parallax and/or to more align the right and left optical images. In other words, the pixel set may be moved or adjusted (in real-time) with respect to the pixel grid to improve image quality by reducing or eliminating spurious parallax. Alternatively, either or both of the left and right views of the stereoscopic image can be moved virtually in the image processing pipeline (for example during rendering of the views for display) to accomplish the same effect. Rotational misalignment of the sensors can also be corrected virtually. A pixel set may also be moved across a pixel grid during use to provide an appearance of panning the field-of-view. In an example, a pixel set or window of 1920×1080 pixels may be selected from a pixel grid having 2048×1560 pixels. The location of the pixel window or set may be controlled by software/firmware and be moved during setup and/or use. The resolution of the optical image sensors 746 and 748 is accordingly specified based on a number of pixels in the length and width directions of the pixel set or window.

1. Color Sensing with the Example Image Sensors

As mentioned above, the optical sensing elements 746 and 748 include pixels with different filters to detect certain colors of light. For instance, some pixels are covered with filters that pass predominantly red light, some are covered with filters that pass predominantly green light, and some are covered with filters that pass predominantly blue light. In some embodiments, a Bayer pattern is applied to the pixel grids 1002 and 1004. However, it should be appreciated that in other embodiments, a different color pattern may be used that is optimized for certain wavelengths of light. For example, a green filter in each sensing region may be replaced with a broadband filter or a near-infrared filter, thereby extending the sensing spectrum.

The Bayer pattern is implemented by grouping two rows by two columns of pixels and covering one with a red filter, one with a blue filter, and two with a green filter, each in a checkerboard pattern. Thus the resolution of red and blue are each one quarter of the whole sensing region of interest while green resolution is half that of the whole sensing region of interest.

Green may be assigned to half the sensing region to cause the optical image sensors 746 and 748 to operate as a luminance sensor and mimic the human visual system. In addition, red and blue mimic chrominance sensors of the human visual system, but are not as critical as green sensing. Once an amount of red, green, and blue are determined for a certain region, other colors in the visible spectrum are determined by averaging the red, green, and blue values, as discussed in conjunction with de-Bayer program 1580a of FIG. 16 discussed below.

In some embodiments, the optical image sensors 746 and 748 may use stacked components to sense color rather than filters. For example, sensing elements may include red, green and blue sensing components stacked vertically inside a pixel's area. In another example, prisms split incident light into components using specially coated beamsplitters one or more times (typically at least two times resulting in three component colors, known as "3-chip") with sensing elements placed in each of the split beams' paths. Other sensor types use a different pattern such as replacing one of the green filters with a broadband filter or a near-infrared filter, thereby extending the sensing possibilities of the digital surgical microscope.

2. Sensing Light Outside the Visible Range with the Example Image Sensors

The example sensing element filters of the optical image sensors 746 and 748 are configured to also pass near-infrared light in a range that the sensing element can detect. This enables the optical image sensors 746 and 748 to detect at least some light outside of the visible range. Such sensitivity may decrease image quality in the visible part of the spectrum because it "washes out" the image, reducing contrast in many types of scenes and negatively affecting the color quality. As a result, the filter 740 may use the infrared cut filter to block near infrared wavelengths while passing the visible wavelengths to the optical image sensors 746 and 748.

However, such near-infrared sensitivity may be desirable. For example, a fluorescent agent, such ICG, can be introduced to the target site 700. ICG becomes excited or activated with visible or other wavelengths or light and emits fluorescence light in the near infrared range. As mentioned above, the NIR light source 708b provides NIR light and the visible light source 708a provides visible light to excite agents with ICG. Emitted light is further along the red spectrum, which may be passed through the filter 740 using a near-infrared bandpass or high-pass filter. The light from the red spectrum then is detected by the optical image sensors 746 and 748. By matching the spectral characteristics of the filter 740 to the expected behaviors of the light source 708 and the fluorescent agent, the agent and the biological structures, such as blood that contain the agent, can be differentiated at the target site 700 from other structures that do not contain the agent.

Note that in this example, the NIR light source 708b has a different primary wavelength from the near-infrared filter in the filter 740. Specifically, the NIR light source 708b has a primary wavelength around 780 nanometers ("nm") (around which the majority of the light's output spectrum exists). In contrast, the near-infrared filter of the filter 740 transmits light at wavelengths in a range of approximately 810 nm to 910 nm. The light from the NIR light source 708b and light passed through the filter 740 are both "near-infrared" wavelengths. However, the light wavelengths are separated so that the example stereoscopic visualization camera 300 can stimulate with the light source 708 and detect with the optical image sensor 744 while filtering the stimulation light. This configuration accordingly enables the use of fluorescent agents.

In another embodiment, agents can be excited in the blue, violet, and near-ultraviolet region and fluoresce light in the red region. An example of such an agent includes porphyrin accumulation in malignant gliomas caused by the introduction of SALA. In this example, it is necessary to filter out the blue light while passing the remainder of the spectrum. A near-ultraviolet cut filter is used for this situation. As in the case with "near-infrared" discussed above, the NUV light source 708c has a different primary wavelength from the near-ultraviolet cut filter in the filter 740.

H. Example Lens Carrier

Section IV(D) above mentions that at least some of the lenses of the front lens set 714, the zoom lens assembly 716, and/or the lens barrel set 718 may move in one or more carriers along rails. For example, the front zoom lens set 724 may comprise a carrier that moves front zoom lens 726 and 728 together axially.

Figure 11:
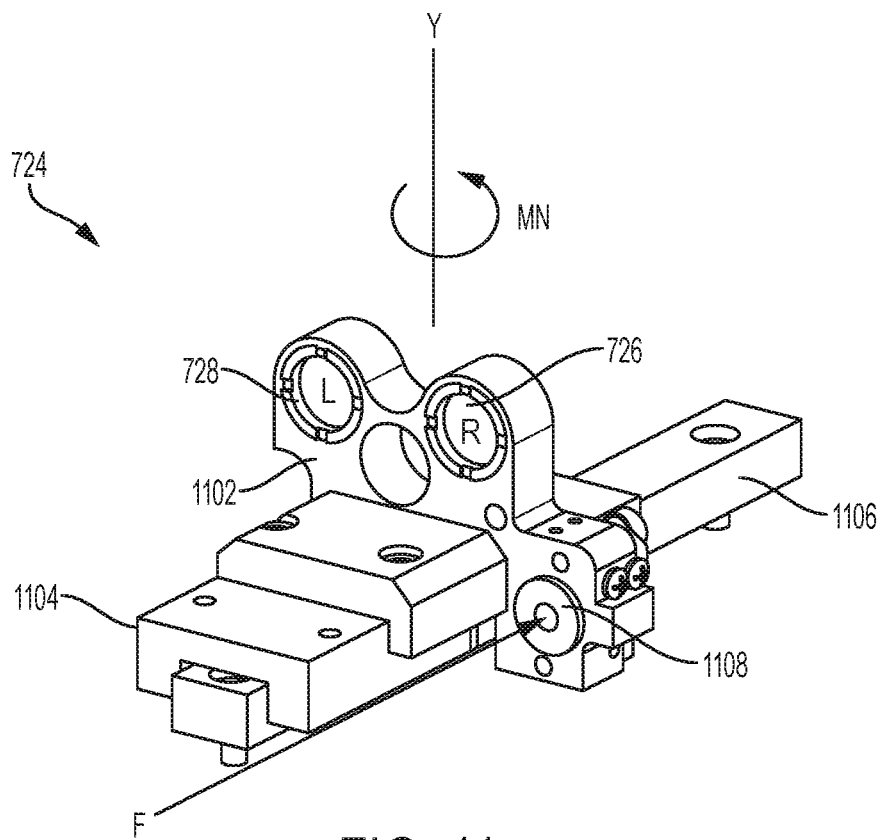
FIGS. 11 and 12 show diagrams of example carriers for optical elements of the example stereoscopic visualization camera of FIGS. 7 and 8, according to example embodiments of the present disclosure.
Figure 12:
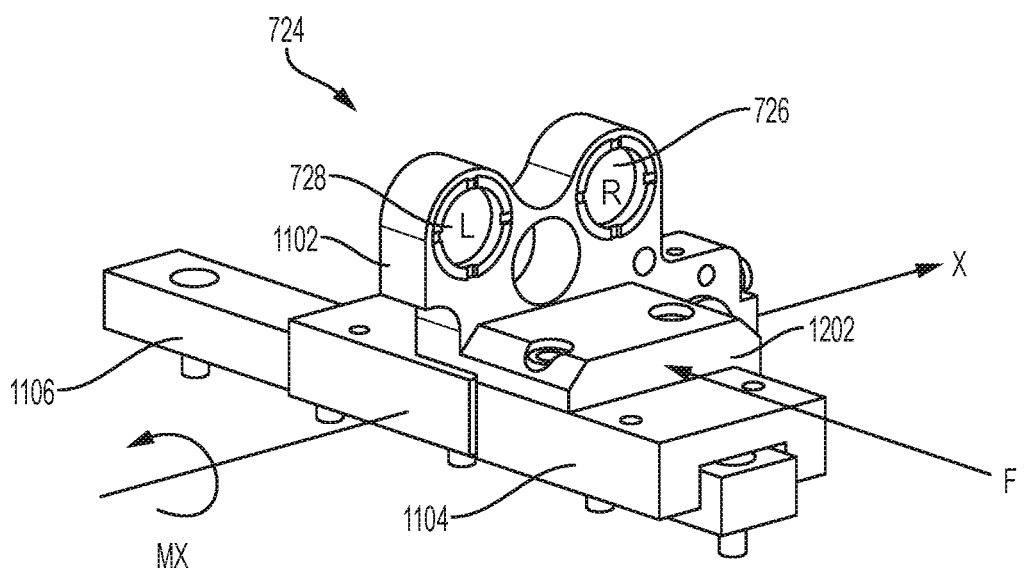

FIGS. 11 and 12 show diagrams of example carriers, according to example embodiments of the present disclosure. In FIG. 11, carrier 724 includes the right front zoom lens 726 and the left front zoom lens 728 within a support structure 1102. The carrier 724 includes a rail holder 1104 configured to moveably connect to rail 1106. A force 'F' is applied to an actuation section 1108 to cause the carrier 724 to move along the rail 1106. The force 'F' may be applied by a leadscrew or other linear actuation device. As illustrated in FIG. 11, the force 'F' is applied at an offset of the carrier 724. Friction between the rail 1106 and the carrier 724 generates a moment $M_y$ that causes the support structure 1102 to move slightly around the Y-axis shown in FIG. 11. This slight movement may cause the right front zoom lens 726 and the left front zoom lens 728 to shift slightly in opposite directions causing spurious parallax, which is an error in a parallax between views of a stereoscopic image.

FIG. 12 shows another example of the carrier 724. In this example, force 'F' is applied symmetrically at center structure 1202, which is connected to the rail holder 1104 and the support structure 1102. The force 'F' generates a moment $M_x$ that causes the carrier 724 to rotate or move slightly around the X-axis shown in FIG. 12. The rotational movement causes the right front zoom lens 726 and the left front zoom lens 728 to shift in the same direction by the same degree of movement, thereby reducing (or eliminating) the onset of spurious parallax.

While FIGS. 11 and 12 show lenses 726 and 728 within one carrier, in other embodiments the lenses 726 and 728 may each be within a carrier. In these examples, each lens would be on a separate track or rail. Separate leadscrews may be provided for each of the lenses to provide independent axial movement along the respective optical path.

I. Example Flexure

Section IV(D) above mentions that at least some of the lenses of the front lens set 714, the zoom lens assembly 716, and/or the lens barrel set 718 may be moved radially, rotated, and/or tilted. Additionally or alternatively, the optical image sensors 746 and 748 may be moved axially and/or tilted with respect to their respective incident optical path. The axial and/or tilt movement may be provided by one or more flexures. In some examples, the flexures may be cascaded such that a first flexure provides motion in a first direction and separate flexure provides independent motion in a second direction. In another example, a first flexure provides tilt along a pitch axis and separate flexure provides tilt along a yaw axis.

Figure 13:
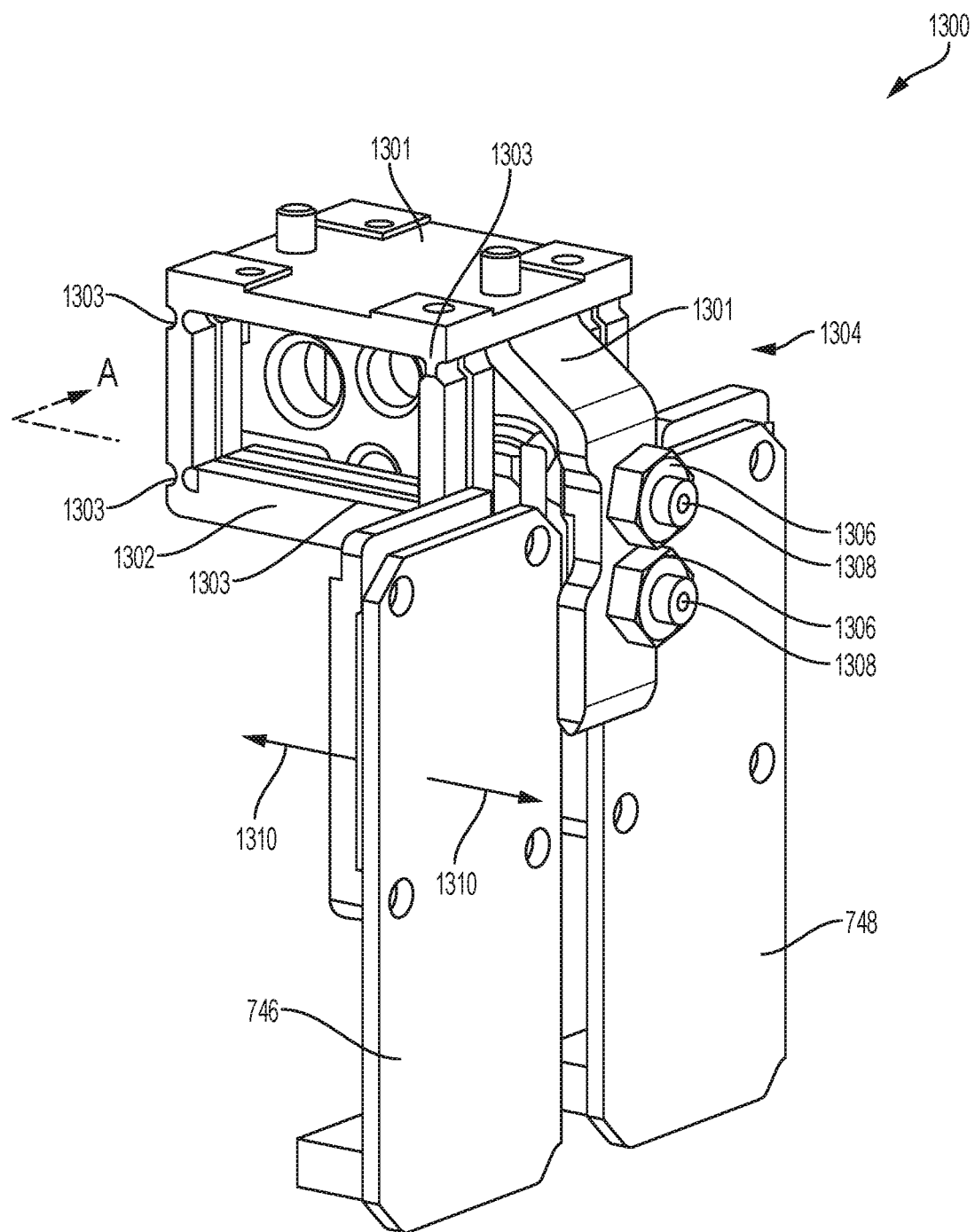
FIG. 13 shows a diagram of an example flexure of the example stereoscopic visualization camera of FIGS. 7 and 8, according to an example embodiment of the present disclosure.

FIG. 13 shows a diagram of an example dual flexure 1300, according to an example embodiment of the present disclosure. The flexure 1300 illustrated in FIG. 13 is for the optical image sensor 744 and is configured to independently move the right optical image sensor 746 and the left optical image sensor 748 along their respective optical axis for purposes of final focusing. The flexure 1300 includes a support beam 1301 for connection to the housing 302 of the example stereoscopic visualization camera 300 and to provide a rigid base for actuation. The flexure 1300 also includes a beam 1302 for each channel (e.g., sensor 746 and 748) that is rigid in all directions except for the direction of motion 1310. The beam 1302 is connected to flexing hinges 1303 that enable the beam 1302 to move in a direction of motion 1310, a parallelogram translation in this example.

An actuator device 1304 flexes the beam 1302 in the desired direction for a desired distance. The actuator device 1304 includes a push-screw 1306 and a pull screw 1308, for each channel, which apply opposite forces to the beam 1302 causing the flexing hinges 1303 to move. The beam 1302 may be moved inward, for example, by turning the push-screw 1306 to push on the beam 1302. The flexure 1300 illustrated in FIG. 13 is configured to independently move the right optical image sensor 746 and the left optical image sensor 748 axially along their optical axis.

After the beam 1302 is flexed into a desired position, a locking mechanism is engaged to prevent further movement, thereby creating a rigid column. The locking mechanism includes the push-screw 1306 and its respective concentric pull screw 1308, that when tightened, create large opposing forces that result in the rigid column of the beam 1302.

While the optical image sensors 746 and 748 are shown as being connected to the same flexure 1300, in other examples, the sensors may be connected to separate flexures. For example, returning to FIG. 8, the right optical image sensor 746 is connected to flexure 750 and the left optical image sensor 748 is connected to flexure 752. The use of the separate flexures 750 and 752 enables the optical image sensors 746 and 748 to be separately adjusted to, for example, align the left and right optical views and/or reduce or eliminate spurious parallax.

In addition, while FIG. 13 shows image sensors 746 and 748 connected to the flexure 1300, in other examples, the lenses of the front lens set 714, the zoom lens assembly 716, the lens barrel set 718, and/or the final optical element set 742 may be connected to alternative or additional flexures instead. In some instances, each of the right and left lenses of the front lens set 714, the zoom lens assembly 716, the lens barrel set 718, and/or the final optical element set 742 may be connected to a separate flexure 1300 to provide independent radial, rotational, and/or tilt adjustment.

The flexure 1300 may provide motion resolution of less than a micron. As a result of the very fine motion adjustment, images from the right and left optical paths may have an alignment accuracy of several or even one pixel for a 4K display monitor. Such accuracy is viewed on each display 512, 514 by overlaying the left and right views and observing both views with both eyes, rather than stereoscopically.

In some embodiments, the flexure 1300 can include the flexure disclosed in U.S. Pat. No. 5,359,474, titled "SYSTEM FOR THE SUB-MICRON POSITIONING OF A READ/WRITE TRANSDUCER," the entirety of which is incorporated herein by reference. In yet other embodiments, the lenses of the front lens set 714, the zoom lens assembly 716, the lens barrel set 718, and/or the final optical element set 742 may be stationary in a radial direction. Instead, a deflecting element (e.g., a mirror) with an adjustable deflection direction in an optical path may be used to steer the right and/or left optical paths to adjust alignment and/or spurious parallax. Additionally or alternatively, a tilt/shift lens may be provided in the optical path. For instance, a tilt of an optical axis may be controlled with an adjustable wedge lens. In further embodiments, lenses of the front lens set 714, the zoom lens assembly 716, the lens barrel set 718, and/or the final optical element set 742 may include dynamic lenses with parameters that can be changed electronically. For example, the lenses may include Varioptic liquid lenses produced by Invenios France SAS.

V. Example Processors of the Stereoscopic Visualization Camera

Figure 14:
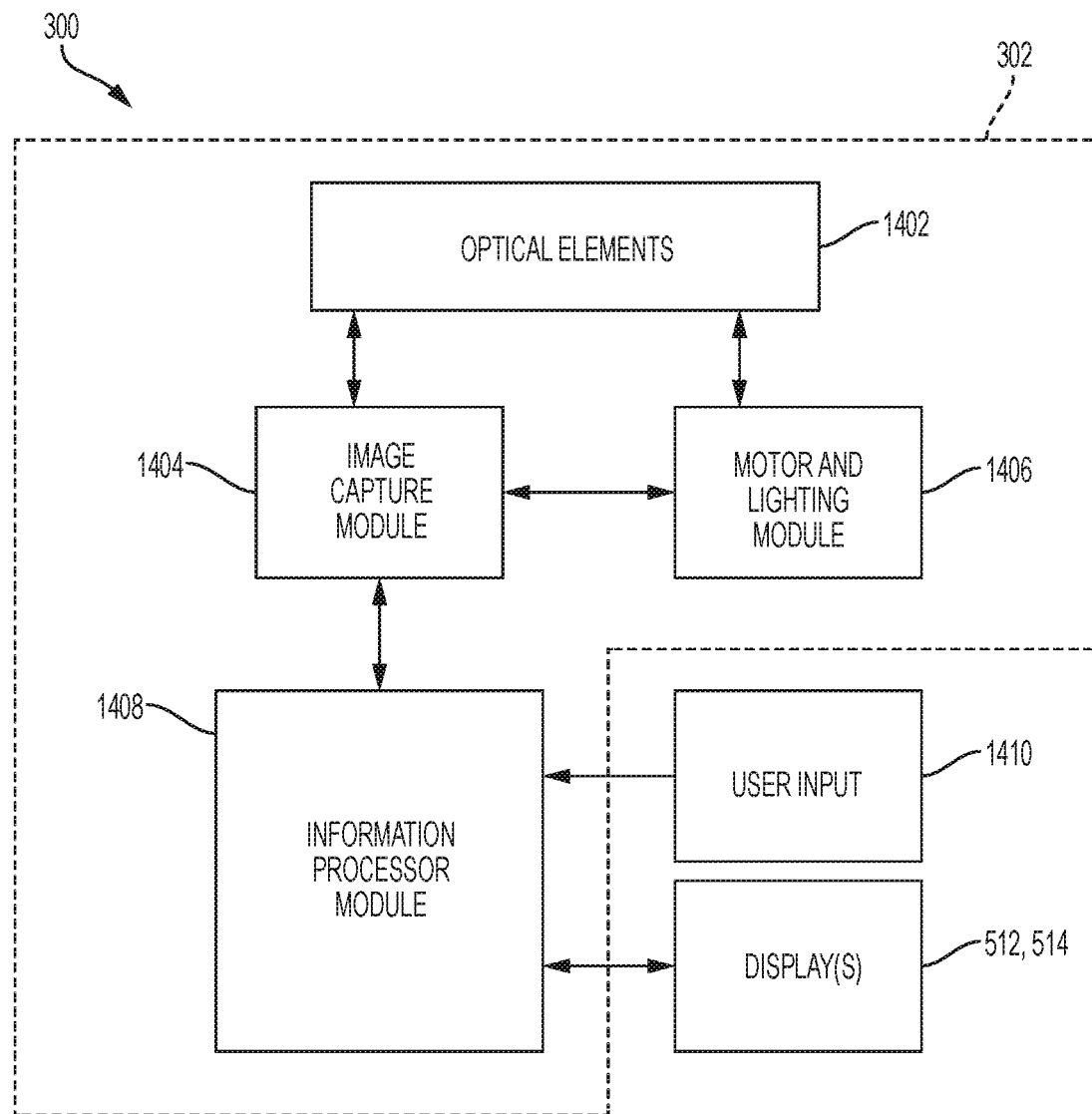
FIG. 14 shows a diagram of modules of the example stereoscopic visualization camera for acquiring and processing image data, according to an example embodiment of the present disclosure.

The example stereoscopic visualization camera 300 is configured to record image data from the right and left optical paths and output the image data to the monitor(s) 512 and/or 514 for display as a stereoscopic image. FIG. 14 shows a diagram of modules of the example stereoscopic visualization camera 300 for acquiring and processing image data, according to an example embodiment of the present disclosure. It should be appreciated that the modules are illustrative of operations, methods, algorithms, routines, and/or steps performed by certain hardware, controllers, processors, drivers, and/or interfaces. In other embodiments, the modules may be combined, further partitioned, and/or removed. Further, one or more of the modules (or portions of a module) may be provided external to the stereoscopic visualization camera 300 such as in a remote server, computer, and/or distributed computing environment.

In the illustrated embodiment of FIG. 14, the components 408, 702 to 750, and 1300 in FIGS. 7 to 13 are collectively referred to as optical elements 1402. The optical elements 1402 (specifically the optical image sensors 746 and 748) are communicatively coupled to an image capture module 1404 and a motor and lighting module 1406. The image capture module 1404 is communicatively coupled to an information processor module 1408, which may be communicatively coupled to an externally located user input device 1410 and one or more display monitors 512 and/or 514.

The example image capture module 1404 is configured to receive image data from the optical image sensors 746 and 748. In addition, the image capture module 1404 may define the pixel sets 1006 and 1008 within the respective pixel grids 1002 and 1004. The image capture module 1404 may also specify image recording properties, such as frame rate and exposure time.

The example motor and lighting module 1406 is configured to control one or more motors (or actuators) to change a radial, axial, and/or tilt position of one or more of the optical elements 1402. For instance, a motor or actuator may turn a drive screw to move the carrier 724 along the track 1106, as shown in FIGS. 11 and 12. A motor or actuator may also turn the push-screw 1306 and/or the pull screw 1308 of the flexure 1300 of FIG. 13 to adjust a radial, axial, or tilt position of a lens and/or optical image sensor. The motor and lighting module 1406 may also include drivers for controlling the light sources 708.

The example information processor module 1408 is configured to process image data for display. For instance, the information processor module 1408 may provide color correction to image data, filter defects from the image data, and/or render image data for stereoscopic display. The information processor module 1408 may also perform one or more calibration routines to calibrate the stereoscopic visualization camera 300 by providing instructions to the image capture module 1404 and/or the motor and lighting module 1406 to perform specified adjustments to the optical elements. The information processor module 1408 may further determine and provide in real-time instructions to the image capture module 1404 and/or the motor and lighting module 1406 to improve image alignment and/or reduce spurious parallax.

The example user input device 1410 may include a computer to provide instructions for changing operation of the stereoscopic visualization camera 300. The user input device 1410 may also include controls for selecting parameters and/or features of the stereoscopic visualization camera 300. In an embodiment, the user input device 1410 includes the control arms 304 of FIG. 3. The user input device 1410 may be hardwired to the information processor module 1408. Additionally or alternatively, the user input device 1410 is wirelessly or optically communicatively coupled to the information processor module 1408.

The example display monitors 512 and 514 include, for example, televisions and/or computer monitors configured to provide a three-dimensional viewing experience. For example, the display monitors may include the LG® 55LW5600 television. Alternatively, the display monitors 512 and 514 may include a laptop screen, tablet screen, a smartphone screen, smart-eyewear, a projector, a holographic display, etc.

The sections that follow describe the image capture module 1404, the motor and lighting module 1406, and the information processor module 1408 in more detail.

A. Example Image Capture Module

Figure 15:
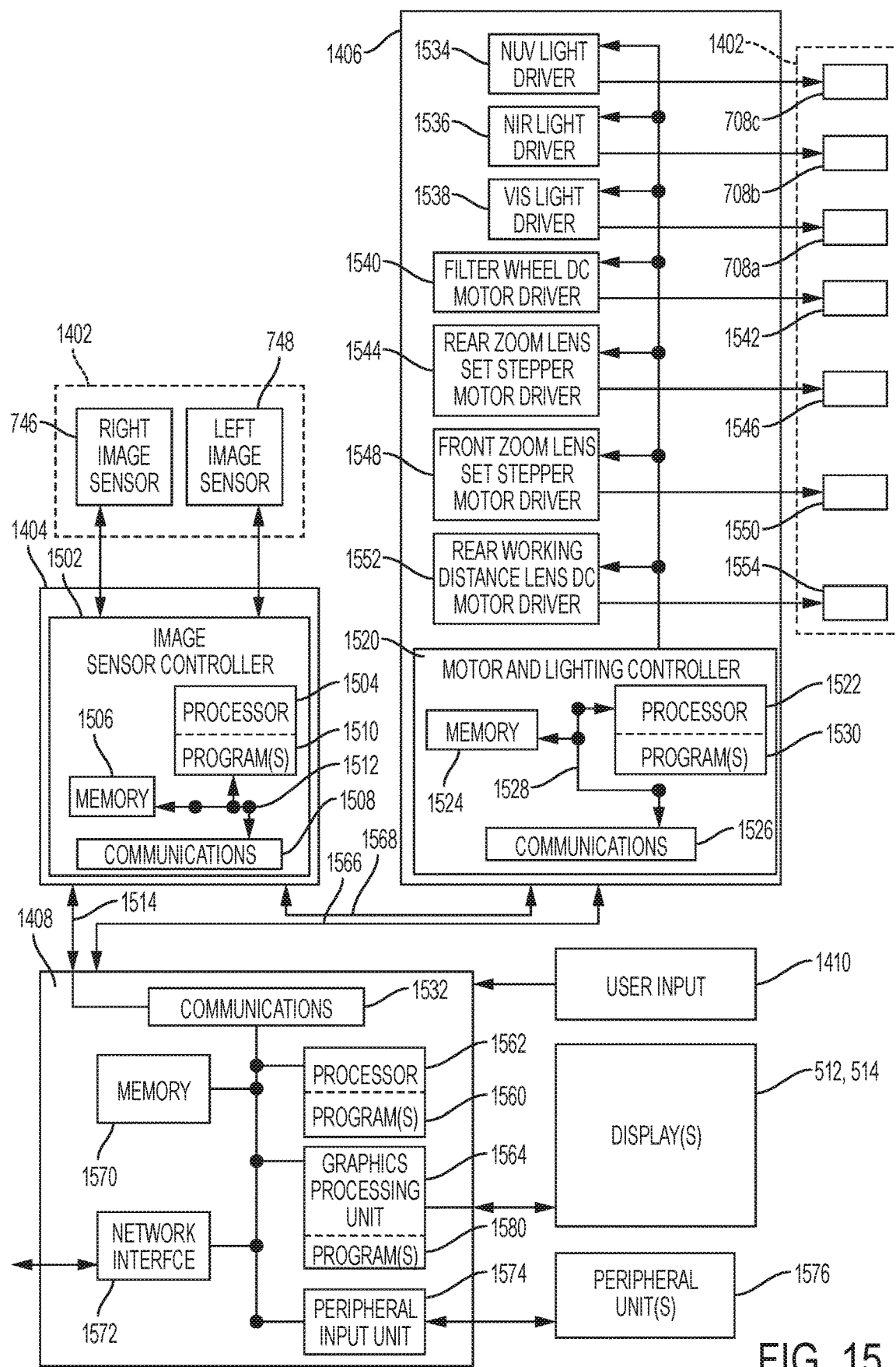
FIG. 15 shows a diagram of internal components of the modules of FIG. 14, according to an example embodiment of the present disclosure.

FIG. 15 shows a diagram of the image capture module 1404, according to an example embodiment of the present disclosure. The example image capture module 1404 includes an image sensor controller 1502, which includes a processor 1504, a memory 1506, and a communications interface 1508. The processor 1504, the memory 1506, and the communications interface 1508 may be communicatively coupled together via an image sensor controller bus 1512.

The processor 1504 is programmable with one or more programs 1510 that are persistently stored within the memory 1506. The programs 1510 include machine readable instructions, which when executed, cause the processor 1504 to perform one or more steps, routines, algorithms, etc. In some embodiments, the programs 1510 may be transmitted to the memory 1506 from the information processor module 1408 and/or from the user input device 1410. In other examples, the programs 1510 may be transmitted to the processor 1504 directly from the information processor module 1408 and/or from the user input device 1410.

The example image sensor controller 1502 is communicatively coupled to the right optical image sensor 746 and the left optical image sensor 748 of the optical elements 1402. The image sensor controller 1502 is configured to provide power to the optical image sensors 746 and 748 in addition to sending timing control data and/or programming data. In addition, the image sensor controller 1502 is configured to receive image and/or diagnostic data from the optical image sensors 746 and 748.

Each of the optical image sensors 746 and 748 contains programmable registers to control certain parameters and/or characteristics. One or more of the registers may specify a location of the pixel sets 1006 and 1008 within the respective pixel grids 1002 and 1004 of FIG. 10. The registers may store a value of a starting location with respect to an origin point or edge point of the pixel grids 1002 and 1004. The registers may also specify a width and height of the pixel sets 1006 and 1008 to define a rectangular region of interest. The image sensor controller 1502 is configured to read pixel data for pixels that are within the specified pixel sets 1006 and 1008. In some embodiments, the registers of the optical image sensors 746 and 748 may facilitate the designation of pixel sets of other shapes, such as circles, ovals, triangles, etc. Additionally or alternatively, the registers of the optical image sensors 746 and 748 may enable multiple pixel sets to be specified simultaneously for each of the pixel grids 1002 and 1004.

A light-sensing portion of the pixels of the pixel grids 1002 and 1004 is controlled by embedded circuitry, which specifies different modes of light-sensing. The modes include a reset mode, an integration mode, and a readout mode. During the reset mode, a charge storage component of a pixel is reset to a known voltage level. During the integration mode, the pixel is switched to an "on" state. Light that reaches a sensing area or element of the pixel causes a charge to accumulate in a charge storage component (e.g., a capacitor). The amount of stored electrical charge corresponds to the amount of light incident on the sensing element during the integration mode. During the readout mode, the amount of electrical charge is converted into a digital value and read out of the optical image sensors 746 and 748 via the embedded circuitry and transmitted to the image sensor controller 1502. To read every pixel, the charge storage component of each pixel in a given region is connected sequentially by switched internal circuitry to a readout circuit, which performs the conversion of the electrical charge from an analog value to digital data. In some embodiments, the pixel analog data is converted to 12-bit digital data. However, it should be appreciated that the resolution may be less or greater based on allowances for noise, settling time, frame rate, and data transmission speed. The digital pixel data of each pixel may be stored to a register.

The example processor 1504 of the image sensor controller 1502 of FIG. 15 is configured to receive pixel data (e.g., digital data indicative of an electrical charge stored in the pixel corresponding to an amount of incident light on an element of the pixel) from each of the pixels within the pixel sets 1006 and 1008. The processor 1504 forms a right image from the pixel data received from the right optical image sensor 746. In addition, the processor 1504 forms a left image from the pixel data received from the left optical image sensor 748. Alternatively, the processor 1504 forms only a portion (for example, one row or several rows) of each the left and right images before transmitting the data downstream. In some embodiments, the processor 1504 uses a register location to determine a location of each pixel within an image.

After the right and left images are created, the processor 1504 synchronizes the right and left images. The processor 1504 then transmits both of the right and left images to the communications interface 1508, which processes the images into a format for transmission to the information processor module 1408 via a communications channel 1514. In some embodiments, the communications channel 1514 conforms to the USB 2.0 or 3.0 standard and may comprise a copper or fiber optical cable. The communications channel 1514 may enable up to approximately 60 pairs (or more) of left and right images (having a stereoscopic resolution of 1920× 1080 and a data conversion resolution of 12-bits) per second to be transmitted per second. The use of a copper USB cable enables power to be provided from the information processor module 1408 to the image capture module 1404.

The sections below further describe features provided by the processor 1504 of the image sensor controller 1502 executing certain programs 1510 to acquire and/or process image data from the optical image sensors 746 and 748.

1. Exposure Example

The example processor 1504 may control or program an amount of time the optical image sensors 746 and 748 are in the integration mode, discussed above. The integration mode occurs for a time period referred to as an exposure time. The processor 1504 may set the exposure time by writing a value to an exposure register of the optical image sensors 746 and 748. Additionally or alternatively, the processor 1504 may transmit instructions to the optical image sensors 746 and 748 signaling the start and end of the exposure time. The exposure time may be programmable between a few milliseconds ("ms") to a few seconds. Preferably the exposure time is approximately the inverse of the frame rate.

In some embodiments, the processor 1504 may apply a rolling shutter method to the optical image sensors 746 and 748 to read pixel data. Under this method, the exposure time for a given row of pixels of the pixel sets 1006 and 1008 begins just after the pixels in that row have been read out and then reset. A short time later, the next row (which is typically physically most proximate to the row just set) is read, and accordingly reset with its exposure time restarted. The sequential reading of each pixel row continues until the last or bottom row of the pixel sets 1006 and 1008 have been read and reset. The processor 1504 then returns to the top row of the pixel sets 1006 and 1008 to read pixel data for the next image.

In another embodiment, the processor 1504 applies a global shutter method. Under this method, the processor 1504 implements readout and reset in a manner similar to the rolling shutter method. However, in this method integration occurs simultaneously for all pixels in the pixel sets 1006 and 1008. The global shutter method has the advantage of reducing defects in an image compared to the rolling shutter method since all of the pixels are exposed at the same time. In comparison, in the rolling shutter method, there is a small time delay between exposing the lines of the pixel set. Small defects can develop during the times between line exposures, especially between top lines and bottom lines where small changes at the target site 700 between reads can occur.

2. Dynamic Range Example

The example processor 1504 may execute one or more programs 1510 to detect light that is outside of a dynamic range of the optical image sensors 746 and 748. Generally, extremely bright light completely fills a charge storage region of a pixel, thereby resulting in lost image information regarding the exact brightness level. Similarly, extremely low light or lack of light fails to impart a meaningful charge in a pixel, which also results in lost image information. Images created from this pixel data accordingly do not accurately reflect the light intensity at target site 700.

To detect light that is outside the dynamic range, the processor 1504 may execute one of several high dynamic range ("HDR") programs 1510 including, for example, a multiple-exposure program, a multi-slope pixel integration program, and a multi-sensor image fusion program. In an example, the multiple-exposure program may utilize HDR features integrated or embedded with the optical image sensors 746 and 748. Under this method, the pixel sets 1006 and 1008 are placed into the integration mode for a normal expose time. The lines of the pixel sets 1006 and 1008 are read and stored in a memory at the optical image sensors 746 and 748 and/or the memory 1506 of the image sensor controller 1502. After the read is performed by the processor 1504, each line in the pixel sets 1006 and 1008 is turned on again for a second exposure time that is less than the normal exposure time. The processor 1504 reads each of the lines of pixels after the second exposure time and combines this pixel data with the pixel data from the normal exposure time for the same lines. The processor 1504 may apply tone-mapping to choose between (or combine) the pixel data from the normal-length and short-length exposure times and map the resulting pixel data to a range that is compatible with downstream processing and display. Using the multiple-exposure program, the processor 1504 is able to expand the dynamic range of the optical image sensors 746 and 748 and compress the resulting range of pixel data for display.

The processor 1510 may operate a similar program for relatively dark light. However, instead of the second exposure time being less than the normal time, the second exposure time is greater than the normal time, thereby providing the pixels more time to accumulate a charge. The processor 1510 may use tone-mapping to adjust the read pixel data to compensate for the longer exposure time.

3. Frame Rate Example

The example processor 1510 may control or specify a frame rate for the optical image sensors 746 and 748. In some embodiments, the optical image sensors 746 and 748 include on-board timing circuitry and programmable control registers to specify the number of times per second each of the pixels within the pixel sets 1006 and 1008 are to be cycled through the imaging modes discussed above. A frame or image is formed each time the pixel set progresses through the three modes. A frame rate is the number of times per second the pixels in the pixel sets 1006 and 1008 are integrated, read, and reset.

The processor 1510 may be synchronized with the optical image sensors 746 and 748 such that reads are conducted at the appropriate time. In other examples, the processor 1510 is asynchronous with the optical image sensors 746 and 748. In these other examples, the optical image sensors 746 and 748 may store pixel data after a local read to a temporary memory or queue. The pixel data may then be read periodically by the processor 1510 for right and left image synchronization.

The processing of frames or images in a time-sequential manner (e.g., creation of an image stream) provides an illusion of motion conveyed as a video. The example processor 1510 is configured to program a frame rate that provides the appearance of a smooth video to an observer. A frame rate that is too low makes any motion appear choppy or uneven. Movie quality above a maximum threshold frame rate is not discernible to an observer. The example processor 1510 is configured to generate approximately 20 to 70 frames per second, preferably between 50 and 60 frames per second for typical surgical visualization.

4. Sensor Synchronization Example

The example processor 1504 of FIG. 15 is configured to control the synchronization of the optical image sensors 746 and 748. The processor 1504 may, for instance, provide power simultaneously to the optical image sensors 746 and 748. The processor 1504 may then provide a clock signal to both of the optical image sensors 746 and 748. The clock signal enables the optical image sensors 746 and 748 to operate independently in a free-run mode but in a synchronized and/or simultaneous manner. Accordingly, the optical image sensors 746 and 748 record pixel data at nearly the same time. The example processor 1504 receives the pixel data from the optical image sensors 746 and 748, constructs at least a fraction of the images and/or frames and synchronizes the images and/or frames (or fraction thereof) to account for any slight timing mismatches. Typically, the lag between the optical image sensors 746 and 748 is less than 200 microseconds. In other embodiments, the processor 1504 may use a synchronization pin to simultaneously activate the optical image sensors 746 and 748 after, for example, each reset mode.

B. Example Motor and Lighting Module

The example stereoscopic visualization camera 300 of FIG. 15 includes the motor and lighting module 1406 to control one or more motors or actuators for moving lenses of the optical elements 1402 and/or controlling lighting output from the light sources 708. The example motor and lighting module 1406 includes a motor and lighting controller 1520 that contains a processor 1522, a memory 1524, and a communications interface 1526 that are communicatively coupled together via communication bus 1528. The memory 1524 stores one or more programs 1530 that are executable on the processor 1522 to perform control, adjustment, and/or calibration of the lenses of the optical elements 1402 and/or the light sources 708. In some embodiments, the programs 1530 may be transmitted to the memory 1524 from the information processor module 1408 and/or the user input device 1410.

The communications interface 1526 is communicatively coupled to the communications interface 1508 of the image capture module 1404 and a communications interface 1532 of the information processor module 1408. The communications interface 1526 is configured to receive command messages, timing signals, status messages, etc. from the image capture module 1404 and the information processor module 1408. For example, the processor 1504 of the image capture module 1404 may send timing signals to the processor 1522 to synchronize timing between lighting control and exposure time of the optical image sensors 746 and 748. In another example, the information processing module 1408 may send command messages instructing certain light sources 708 to be activated and/or certain lenses of the optical elements 1402 to be moved. The commands may be in response to input received from an operator via, for example, the user input device 1410. Additionally or alternatively, the commands may be in response to a calibration routine and/or real-time adjustment to reduce or eliminate image misalignment and/or defects such as spurious parallax.

The example motor and lighting module 1406 includes drivers that provide power to control motors for adjusting an axial and/or radial position of the lenses of the optical elements 1402 and/or the light output from the light sources 708. Specifically, the motor and lighting module 1406 includes a NUV light driver 1534 to transmit a NUV signal to the NUV light source 708c, a NIR light driver 1536 to transmit a NIR signal to the NIR light source 708b, and a visible light driver 1538 to transmit a visible light signal to the visible light source 708a.

In addition, the motor and lighting module 1406 includes a filter motor driver 1540 to transmit a filter motor signal to a filter motor 1542, which controls the filter 740 of FIGS. 7 and 8. The motor and lighting module 1406 includes a rear zoom lens motor driver 1544 to transmit a rear zoom lens motor signal to a rear zoom lens motor 1546, a front zoom lens motor driver 1548 to transmit a front zoom lens motor signal to a front zoom lens motor 1550, and a rear working distance lens motor driver 1552 to transmit a working distance lens motor signal to a working distance lens motor 1554. The motor and lighting module 1406 may also include a motor and/or actuator to move and/or tilt the deflecting element 712.

The rear zoom lens motor 1546 is configured to rotate a drive screw that causes carrier 730 to move axially along a track or rail. The front zoom lens motor 1550 is configured to rotate a drive screw that causes carrier 724 to move axially along the track 1106 shown in FIGS. 11 and 12. The working distance lens motor 1554 is configured to rotate a drive screw that causes the rear working distance lens 702 to move axially along a track or rail.

The drivers 1536, 1538, and 1540 may include any type of lighting driver, transformer, and/or ballast. The drivers 1536, 1538, and 1540 are configured to output a pulse width modulation ("PWM") signal to control an intensity of light output by the light sources 708. In some embodiments, the processor 1522 may control the timing of the drivers 1536, 1538, and 1540 to correspond to a timing for applying a certain filter using the filter motor driver 1540.

The example drivers 1540, 1544, 1548, and 1552 may include, for example stepper motor drivers and/or DC motor drivers. Likewise, the motors 1542, 1546, 1550, and/or 1554 may include a stepper motor, a DC motor, or other electrical, magnetic, thermal, hydraulic, or pneumatic actuator. The motors 1542, 1546, 1550, and/or 1554 may include, for example, a rotary encoder, a slotted optical switch (e.g., a photointerrupter), and/or a linear encoder to report an angular position of a shaft and/or axle for feedback reporting and control. Alternative embodiments may include voice-coil motors, piezoelectric motors, linear motors, with suitable drivers, and equivalents thereof.

To control the drivers 1534, 1536, 1538, 1540, 1544, 1548, and 1552, the processor 1522 is configured to use a program 1530 for converting a command message into a digital and/or analog signal. The processor 1522 transmits the digital and/or analog signal to the appropriate driver, which outputs an analog power signal, such as a PWM signal corresponding to the received signal. The analog power signal provides power to an appropriate motor or actuator causing it to rotate (or otherwise move) by a desired amount.

The processor 1522 may receive feedback from the drivers 1534, 1536, 1538, 1540, 1544, 1548, and 1552, the motors 1542, 1546, 1550, and/or 1554, and/or the light sources 708. The feedback corresponds to, for example, a lighting level or lighting output. Regarding the motors, the feedback corresponds to a position of a motor (or other actuator) and/or an amount of movement. The processor 1522 uses a program 1530 to translate the received signal into digital feedback to determine, for example, a radial, tilt, and/or axial position of a lens based on an angular position of the corresponding motor or actuator shaft. The processor 1522 may then transmit a message with the position information to the information processor module 1408 for display to a user and/or to track a position of the lenses of the optical elements 1402 for calibration.

In some embodiments, the motor and lighting module 1406 may include additional drivers to change an axial, tilt, and/or radial position of individual lenses within the optical elements 1402. For example, the motor and lighting module 1406 may include drivers that control motors for actuating flexures 750 and 752 for the optical image sensors 746 and 748 for tilting and/or radial/axial adjustment. Further, the motor and lighting module 1406 may include drivers that control motors (or actuators) for individually tilting and/or adjusting front lenses 720 and 722, the front zoom lenses 726 and 728, the rear zoom lenses 732 and 734, the lens barrels 736 and 738, and/or final optical elements 745 and 747 radially along an x-axis or y-axis and/or axially. Independent adjustment of the lenses and/or sensors enables, for example, the motor and lighting controller 1520 to remove image defects and/or align the left and right images.

The following sections describe how the processor 1552 executes one or more programs 1530 to change a working distance, zoom, filter position, lens position, and/or light output.

1. Working Distance Example

The example processor 1522 of the motor and lighting module 1406 of FIG. 15 is configured to adjust a working distance of the stereoscopic visualization camera 300. The working distance is set by adjusting a distance between the rear working distance lens 704 and the front working distance lens 408. The processor 1522 adjusts the distance by causing the rear working distance lens 704 to move relative to the front working distance lens 408. Specifically, the processor 1522 sends a signal to the rear working distance lens motor driver 1552, which activates the working distance lens motor 1554 for a predetermined time proportional to an amount the rear working distance lens 704 is to be moved. The working distance lens motor 1554 drives a leadscrew through threads attached to a sliding track that holds the rear working distance lens 704. The working distance lens motor 1554 causes the lens 704 to move a desired distance, thereby adjusting the working distance. The working distance lens motor 1554 may provide a feedback signal to the processor 1522, which determines if the rear working distance lens 704 was moved the desired amount. If the movement is less or more than desired, the processor 1522 may send instructions further refining the position of the rear working distance lens 704. In some embodiments, the information processor module 1408 may determine feedback control for the rear working distance lens 704.

To determine a position of the rear working distance lens 704, the processor 1522 may operate one or more calibration programs 1530. For example, upon activation, the processor 1522 may instruct the working distance lens motor 1554 to drive a leadscrew to move the rear working distance lens 704 along a track or rail until triggering a limit switch at one end of the motion range. The processor 1522 may designate this stop position as a zero-point for the encoder of the motor 1554. Having knowledge of the current position of the rear working distance lens 704 and the corresponding encoder value, the processor 1522 becomes capable of determining a number of shaft rotations to cause the rear working distance lens 704 to move to a desired position. The number of shaft rotations is transmitted in an analog signal to the working distance lens motor 1554 (via the driver 1552) to accordingly move the lens 704 to a specified position.

2. Zoom Example

The example processor 1522 of FIG. 15 is configured to execute one or more programs 1530 to change a zoom level of the stereoscopic visualization camera 300. As discussed above, zoom (e.g., magnification change) is achieved by changing positions of the front zoom set 724 and the rear zoom set 730 relative to each other and relative to the front lens set 714 and the lens barrel set 718. Similar to the calibration procedure described above for the rear working distance lens 704, the processor 1522 may calibrate positions of the sets 724 and 730 along tracks or rails. Specially, the processor 1522 sends instructions causing the rear zoom lens motor 1546 and the front zoom lens motor 1550 to move the sets 724 and 730 (e.g., carriers) along a rail (or rails) to a stop position at a limit switch. The processor 1522 receives encoder feedback from the motors 1546 and 1550 to determine an encoder value associated with the stop position for the sets 724 and 730. The processor 1522 may then zero-out the encoder value or use the known encoder value at the stop position to determine how much the motors 1546 and 1550 are to be activated to achieve a desired position for the sets 724 and 730 along the rail.

In addition to calibration for stop position, the processor 1522 may execute programs 1530 that define locations for sets 724 and 730 to achieve a desired zoom level. For example, a known pattern of distance settings versus a set of desired zoom values may be stored as a program 1530 (or a look-up table) during a calibration procedure. The calibration procedure may include placing a template within the target site 700 and instructing the processor 522 to move the sets 724 and 730 until a certain designated marker or character is a certain size in right and left images or frames. For example, a calibration routine may determine positions of the set 724 and 730 on a rail corresponding to when character "E" on a template at the target site 700 is displayed in right and left images as having a height of 10 pixels.

In some embodiments, the information processor module 1408 may perform the visual analysis and send instructions to the processor 1522 regarding desired movement for the sets 724 and 730 to zoom in or zoom out. In addition, the information processor 1408 may send instructions for moving the focal plane such that the target site 700 at the desired zoom level is in focus. The instructions may include, for example, instructions to move the rear working distance lens 704 and/or moving the sets 724 and 730 together and/or individually. In some alternative embodiments, the processor 1522 may receive calibration parameters for the rail position of the front zoom set 724 and the rear zoom set 730 at certain zoom levels from the user input device 1410 or another computer.

The example processor 1522 and/or the information processor module 1408 may send instructions such that an image remains in focus while magnification changes. The processor 1522, for example, may use a program 1530 and/or a look-up-table to determine how certain lenses are to be moved along an optical axis to retain focus on the target site 700. The programs 1530 and/or look-up-table may specify magnification levels and/or set points on a rail and corresponding lens adjustments needed to keep the focal plane from moving.

Table 2 below shows an example program 1530 or look-up-table that may be used by the processor 1522 to retain focus while changing magnification. The position of the front zoom lens set 724 and the rear zoom lens set 730 is normalized based on a length of a rail to stop positions for the respective sets 724 and 730. To decrease magnification, the rear zoom lens set is moved toward the lens barrel set 718, thereby increasing a position along a rail. The front zoom lens set 724 is also moved. However, its movement does not necessarily equal the movement of the rear zoom lens set 730. Instead, the movement of the front zoom lens set 724 accounts for changing a distance between the sets 724 and 730 to retain the position of the focal plane to maintain focus while changing magnifications. For example, to decrease a magnification level from 10× to 9×, the processor 1522 instructs the rear zoom lens set 730 to move from position 10 to position 11 along a rail. In addition, the processor 1522 instructs the front zoom lens set 724 to move from position 5 to position 4 along a rail (or same rail as the set 730). Not only have the sets 724 and 730 moved to change magnification, the sets 724 and 730 have moved relative to each other to retain focus.

TABLE 2

| Magnification | Front Zoom Lens Set Position | Rear Zoom Lens Set Position |
|---|---|---|
| 10X | 5 | 10 |
| 9X | 4 | 11 |
| 8X | 3 | 12 |
| 7X | 4.5 | 14 |
| 6X | 6 | 17 |
| 5X | 8 | 20 |

It should be appreciated that Table 2 provides an example of how the sets 724 and 730 may be moved. In other examples, Table 2 may include additional rows to account for more precise magnifications and/or positions of the sets 724 and 730. Additionally or alternatively, Table 2 may include a column for the rear working distance lens 704. For example, the rear working distance lens 704 may be moved instead of or in conjunction with the front zoom lens set 724 to retain focus. Further, Table 2 may include rows specifying positions for the sets 724 and 730 and the rear working distance lens 704 to retain focus during changes in working distance.

The values in Table 2 may be determined through calibration and/or received from a remote computer or the user input device 1410. During calibration, the information processor module 1408 may operate a calibration program 1560 that progresses through different magnifications and/or working distances. A processor 1562 at the information processor module 1408 may perform image processing of the images themselves or received pixel data to determine when a desired magnification is achieved using, for example, a template with predetermined shapes and/or characters. The processor 1562 determines if the received images are in-focus. Responsive to determining images are out of focus, the processor 1562 sends instructions to the processor 1522 to adjust the front zoom lens set 724 and/or the rear working distance lens set 704. The adjustment may include iterative movements in forward and reverse directions along an optical path until the processor 1562 determines images are in focus. To determine an image is in focus, the processor 1562 may perform, for example, image analysis searching for images where light fuzziness is minimal and/or analyzing pixel data for differences in light values between adjacent pixel regions (where greater differences correspond to more in focus images). After determining an image is in focus at a desired working distance and magnification, the processor 1562 and/or the processor 1522 may then record positions of the sets 724 and 730 and/or the rear working distance lens 704 and corresponding magnification level.

3. Filter Position Example

The example processor 1522 of the motor and lighting module 1406 of FIG. 15 is configured to move the filter 740 into the right and left optical paths based on received instructions. In some examples, the filter 740 may include a mirror array. In these examples, the processor 1522 sends instructions to the filter motor driver 1540 to actuate one or more motors 1542 to change positions of the mirrors. In some instances, the driver 1540 may send an electrical charge along one or more paths to the filter 740, causing certain mirror elements to switch to an on or off position. In these examples, the filter type selection is generally binary based on which mirrors to actuate.

In other examples, the filter 740 may include a wheel with different types of filters such as an infrared cut filter, near-infrared bandpass filter, and near-ultraviolet cut filter. In these examples, the wheel is rotated by the filter motor 1542. The processor 1522 determines stop positions of the wheel corresponding to partitions between the different filters. The processor 1522 also determines rotary encoder value corresponding to each of the stop positions.

The processor 1522 may operate a calibration program 1530 and/or the processor 1562 may operate a calibration program 1560 to determine the stop positions. For example, the processor 1522 may rotate the filter wheel 740 slowly, with the processor 1562 determining when light received at the pixels changes (using either image analysis or reading pixel data from the image capture module 1404). A change in a light value at the pixels is indicative of a change in the filter type being applied to the optical paths). In some instances, the processor 1522 may change which light sources 708 are activated to create further distinction at the pixels when a different filter type is applied.

4. Light Control and Filter Example

As disclosed above, the processor 1522 may control the light sources 708 in conjunction with the filter 740 to cause light of a desired wavelength to reach the optical image sensors 746 and 748. In some examples, the processor 1522 may control or synchronize timing between activation of one or more of the light sources 708 and one or more of the filters 740. To synchronize timing, a program 1530 may specify a delay time for activating a certain filter. The processor 1522 uses this program 1530 to determine when, for example a signal to activate the filter 740 is to be transmitted relative to sending a signal to turn on a light source 708. The scheduled timing ensures the appropriate filter 740 is applied when the specified light source 708 is activated. Such a configuration enables features highlighted by one light source 708 (such as fluorescence) to be shown on top of or in conjunction with features displayed under a second light source 708, such as white or ambient light.

In some instances, the light sources 708 may be switched as fast as the light filters 740 may be changed, thereby enabling images recorded in different lights to be shown in conjunction on top of each other. For example, veins or other anatomical structures that emit fluorescence (due to an administered dye or contrast agent) may be shown on top of an image under ambient lighting. In this example, the veins would be highlighted relative to the background anatomical features shown in visible light. In this instance, the processor 1562 and/or a graphics processing unit 1564 (e.g., a video card or graphics card) of the information processor module 1408 combines or overlays one or more images recorded during application of one filter with images recorded during application of a subsequent filter.

In some embodiments, the processor 1522 may activate multiple light sources 708 at the same time. The light sources 708 can be activated simultaneously or sequentially to "interleave" light of different wavelengths to enable different information to be extracted using appropriate pixels at the optical image sensors 746 and 748. Activating the light sources simultaneously may help illuminate dark fields. For example, some applications use UV light to stimulate fluorescence at a target site 700. However, UV light is perceived by an operator as being very dark. Accordingly, the processor 1522 may activate the visible light source 1538 periodically to add some visible light to the viewing field so that the surgeon can observe the field-of-view without overwhelming pixels that are sensitive to UV light but can also detect some visible light. In another example, alternating between light sources 708 avoids, in some instances, washing out pixels of the optical image sensors 746 and 748 that have overlapping sensitivity at the edges of their ranges.

5. Light Intensity Control

The example processor 1522 of FIG. 15 is configured to execute one or more programs 1530 to change an intensity of or a level of illumination provided by the light sources 708. It should be appreciated that the depth of field is dependent on the level of illumination at the target site 700. Generally, higher illumination provides a greater depth of field. The processor 1522 is configured to ensure an appropriate amount of illumination is provided for a desired depth of field without washing out or overheating the field-of-view.

The visible light source 708a is driven by the visible light driver 1538 and outputs light in the human-visible part of the spectrum as well as some light outside that region. The NIR light source 708b is driven by the NIR light driver 1536 and outputs light primarily at a wavelength that referred to as near-infrared. The NUV light source 708c is driven by the NUV light driver 1534 and outputs light primarily at a wavelength that is deep in the blue part of the visible spectrum, which is referred to as near-ultraviolet. The respective light drivers 1534, 1536, and 1538 are controlled by commands provided by the processor 1522. Control of the respective output spectra of the light sources 708 is achieved by PWM signal, where a control voltage or current is switched between a minimum (e.g., off) and maximum (e.g., on) value. The brightness of the light that is output from the light sources 708 is controlled by varying the switching rate as well as the percentage of time the voltage or current is at the maximum level per cycle in the PWM signal.

In some examples, the processor 1522 controls an output of the light sources 708 based on a size of the field-of-view or zoom level. The processor 1522 may execute a program 1530 that specifies for certain light sensitive settings that light intensity becomes a function of zoom. The program 1530 may include, for example a look-up-table that correlates a zoom level to a light intensity value. The processor 1522 uses the program 1530 to select the PWM signal for the light source 708 based on the selected magnification level. In some examples, the processor 1522 may reduce light intensity as the magnification increases to maintain the amount of light provided to the field-of-view per unit of area.

C. Example Information Processor Module

The example information processor module 1408 within the stereoscopic visualization camera 300 of FIG. 15 is configured to analyze and process images/frames received from the image capture module 1404 for display. In addition, the information processor module 1408 is configured to interface with different devices and translate control instructions into messages for the image capture module 1404 and/or the motor and lighting module 1406. The information processor module 1408 may also provide an interface for manual calibration and/or manage automatic calibration of the optical elements 1402.

As shown in FIG. 15, the information processor module 1408 is communicatively and/or electrically coupled to the image capture module 1404 and the motor and lighting module 1406. For example, the communications channel 1514 in addition to communications channels 1566 and 1568 may include USB 2.0 or USB 3.0 connections. As such, the information processor module 1408 regulates and provides power to the modules 1404 and 1406. In some embodiments, the information processor module 1408 converts 110-volt alternating current ("AC") power from a wall outlet into a 5, 10, 12, and/or 24 volt direct current ("DC") supply for the modules 1404 and 1406. Additionally or alternatively, the information processor module 1408 receives electrical power from a battery internal to the housing 302 of the stereoscopic visualization camera 300 and/or a battery at the cart 510.

The example information processor module 1408 includes the communications interface 1532 to communicate bidirectionally with the image capture module 1404 and the motor and lighting module 1406. The information processor module 1408 also includes the processor 1562 configured to execute one or more programs 1560 to process images/frames received from the image capture module 1404. The programs 1560 may be stored in a memory 1570. In addition the processor 1562 may perform calibration of the optical elements 1402 and/or adjust the optical elements 1402 to align right and left images and/or remove visual defects.

Figure 16:
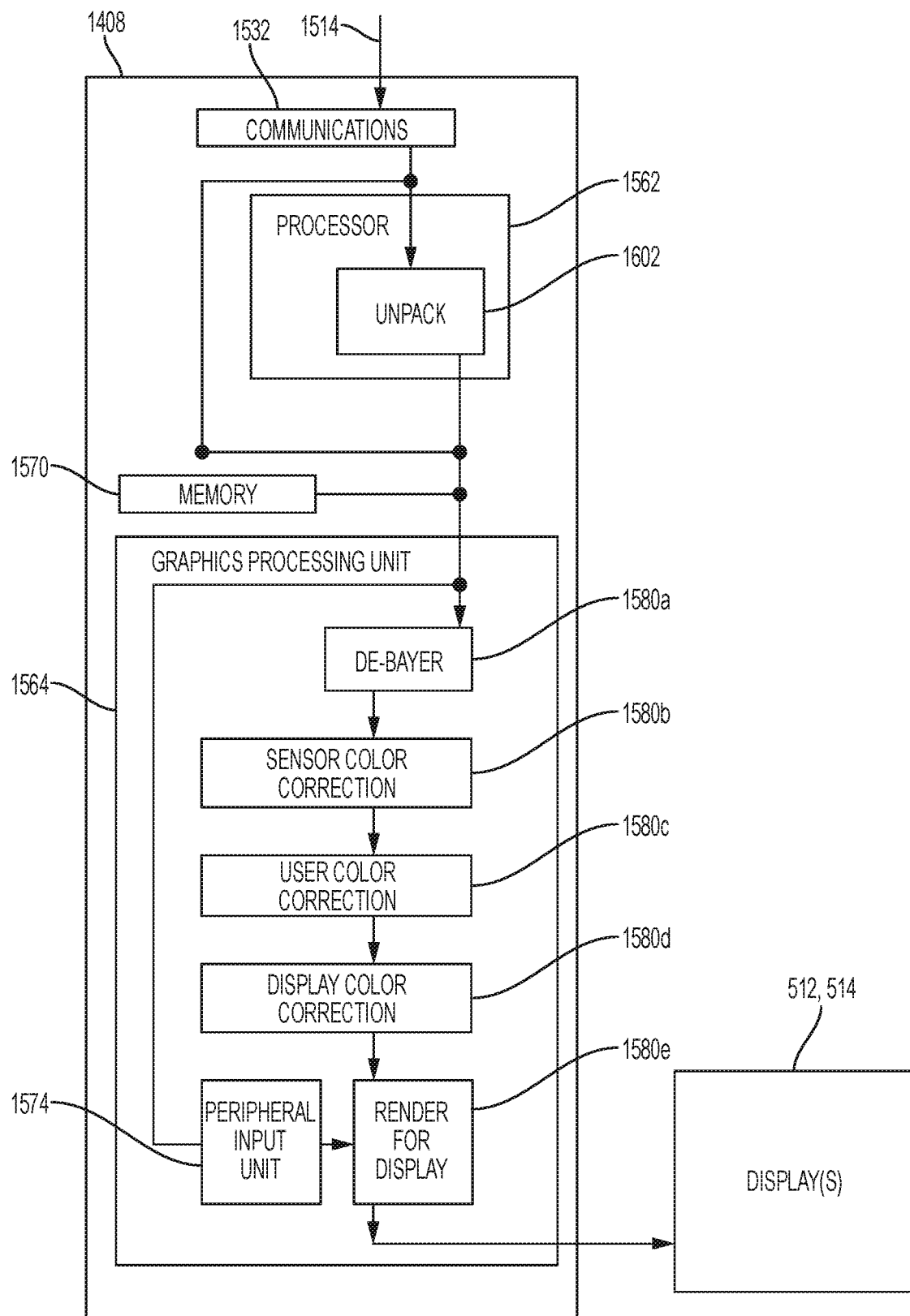
FIG. 16 shows a diagram of an information processor module of FIGS. 14 and 15, according to an example embodiment of the present disclosure.

To process images and/or frames into a rendered three-dimensional stereoscopic display, the example information processor module 1408 includes the graphics processing unit 1564. FIG. 16 shows a diagram of the graphics processing unit 1564, according to an example embodiment of the present disclosure. During operation, the processor 1562 receives images and/or frames from the image capture module 1404. An unpack routine 1602 converts or otherwise changes the images/frames from a format conducive for transmission across the communications channel 1514 into a format conducive for image processing. For instance, the images and/or frames may be transmitted across the communications channel 1514 in multiple messages. The example unpack routine 1602 combines the data from the multiple messages to reassemble the frames/images. In some embodiments, the unpack routine 1602 may queue frames and/or images until requested by the graphics processing unit 1564. In other examples, the processor 1562 may transmit each right and left image/frame pair after being completely received and unpacked.

The example graphics processing unit 1564 uses one or more programs 1580 (shown in FIG. 15) to prepare images for rendering. Examples of the programs 1580 are shown in FIGS. 15 and 16. The programs 1580 may be executed by a processor of the graphics processing unit 1564. Alternatively, each of the programs 1580 shown in FIG. 16 may be executed by a separate graphics processor, microcontroller, and/or application specific integrated circuit ("ASIC"). For example, a de-Bayer program 1580a is configured to smooth or average pixel values across neighboring pixels to compensate for a Bayer pattern applied to the pixel grids 1002 and 1004 of the right and left optical image sensors 746 and 748 of FIGS. 7 and 8. The graphics processing unit 1564 may also include programs 1580b, 1580c, and 1580d for color correction and/or white balance adjustment. The graphics processing unit 1564 also includes a renderer program 1580e for preparing color corrected images/frames for display on the display monitors 512 and 514. The graphics processing unit 1564 may further interact and/or include a peripheral input unit interface 1574, which is configured to combine, fuse, or otherwise include other images and/or graphics for presentation with the stereoscopic display of the target site 700. Further details of the programs 1580 and the information processor module 1408 more generally are discussed below.

The example information processor module 1408 may execute one or more programs 1562 to check for and improve latency of the stereoscopic visualization camera 300. Latency refers to the amount of time taken for an event to occur at the target site 700 and for that same event to be shown by the display monitors 512 and 514. Low latency provides a feeling that the stereoscopic visualization camera 300 is an extension of a surgeon's eyes while high latency tends to distract from the microsurgical procedure. The example processor 1562 may track how much time elapses between images being read from the optical image sensors 746 and 748 until the combined stereoscopic image based on the read images is transmitted for display. Detections of high latency may cause the processor 1562 to reduce queue times, increase the frame rate, and/or skip some color correction steps.

1. User Input Example

The example processor 1562 of the information processor module 1408 of FIG. 15 is configured to convert user input instructions into messages for the motor and lighting module 1406 and/or the image capture module 1402. User input instructions may include requests to change optical aspects of the stereoscopic visualization camera 300 including a magnification level, a working distance, a height of a focal plane (e.g., focus), a lighting source 708, and/or a filter type of the filter 740. The user input instructions may also include requests to perform calibration, including indications of an image being in focus and/or indications of image alignment, and/or indications of aligned ZRPs between left and right images. The user input instructions may further include adjustments to parameters of the stereoscopic visualization camera 300, such as frame rate, exposure time, color correction, image resolution, etc.

The user input instructions may be received from a user input device 1410, which may include the controls 305 of the control arm 304 of FIG. 3 and/or a remote control. The user input device 1410 may also include a computer, tablet computer, etc. In some embodiments, the instructions are received via a network interface 1572 and/or a peripheral input unit interface 1574. In other embodiments, the instructions may be received from a wired connection and/or a RF interface.

The example processor 1562 includes programs 1560 for determining an instruction type and determining how the user input is to be processed. In an example, a user may press a button of the control 305 to change a magnification level. The button may continue to be pressed until the operator has caused the stereoscopic visualization camera 300 to reach a desired magnification level. In these examples, the user input instructions include information indicative that a magnification level is to be, for example, increased. For each instruction received (or each time period in which a signal indicative of the instruction is received), the processor 1562 sends a control instruction to the motor and lighting processor 1406 indicative of the change in magnification. The processor 1522 determines from a program 1530 how much the zoom lens sets 724 and 730 are to be moved using, for example, Table 2. The processor 1522 accordingly transmits a signal or message to the rear zoom lens motor driver 1544 and/or the front zoom lens motor driver 1548 causing the rear zoom lens motor 1546 and/or the front zoom lens motor 1550 to move the rear zoom lens set 730 and/or the front zoom lens set 724 by an amount specified by the processor 1562 to achieve the desired magnification level.

It should be appreciated that in the above example, the stereoscopic visualization camera 300 provides a change based on user input but also makes automatic adjustments to maintain focus and/or a high image quality. For instance, instead of simply changing the magnification level, the processor 1522 determines how the zoom lens sets 724 and 730 are to be moved to also retain focus, thereby saving an operator from having to perform this task manually. In addition, the processor 1562 may, in real-time, adjust and/or align ZRPs within the right and left images as a magnification level changes. This may be done, for example, by selecting or changing locations of the pixel sets 1006 and 1008 with respect to pixel grids 1002 and 1004 of FIG. 10.

In another example, the processor 1562 may receive an instruction from the user input device 1410 to change a frame rate. The processor 1562 transmits a message to the processor 1504 of the image capture module 1404. In turn, the processor 1504 writes to registers of the right and left image sensors 746 and 748 indicative of the new frame rate. The processor 1504 may also update internal registers with the new frame rate to change a pace at which the pixels are read.

In yet another example, the processor 1562 may receive an instruction from the user input device 1410 to begin a calibration routine for ZRP. In response, the processor 1562 may execute a program 1560 that specifies how the calibration is to be operated. The program 1560 may include, for example, a progression or iteration of magnification levels and/or working distances in addition to a routine for verifying image quality. The routine may specify that for each magnification level, focus is to be verified in addition to ZRP. The routine may also specify how the zoom lens sets 724 and 730 and/or the rear working distance lens 704 are to be adjusted to achieve an in focus image. The routine may further specify how ZRP of the right and left images are to be centered for the magnification level. The program 1560 may store (to a look-up-table) locations of zoom lens sets 724 and/or the 730 and/or the rear working distance lens 704 in addition to locations of pixel sets 1006 and 1008 and the corresponding magnification level once image quality has been verified. Thus, when the same magnification level is requested at a subsequent time, the processor 1562 uses the look-up-table to specify positions for the zoom lens sets 724 and/or the 730 and/or the rear working distance lens 704 to the motor and lighting module 1406 and positions for the pixel sets 1006 and 1008 to the image capture module 1404. It should be appreciated that in some calibration routines, at least some of the lenses of the optical elements 1402 may be adjusted radially/rotationally and/or tilted to center ZRPs and/or align right and left images.

2. Interface Example

To facilitate communications between the stereoscopic visualization camera 300 and external devices, the example information processor module 1408 includes the network interface 1572 and the peripheral input unit interface 1574. The example network interface 1572 is configured to enable remote devices to communicatively couple to the information processor module 1408 to, for example, store recorded video, control a working distance, zoom level, focus, calibration, or other features of the stereoscopic visualization camera 300. In some embodiments, the remote devices may provide values or parameters for calibration look-up-tables or more generally, programs 1530 with calibrated parameters. The network interface 1572 may include an Ethernet interface, a local area network interface, and/or a Wi-Fi interface.

The example peripheral input unit interface 1574 is configured to communicatively couple to one or more peripheral devices 1576 and facilitate the integration of stereoscopic image data with peripheral data, such as patient physiological data. The peripheral input unit interface 1574 may include a Bluetooth® interface, a USB interface, an HDMI interface, SDI, etc. In some embodiments, the peripheral input unit interface 1574 may be combined with the network interface 1572.

The peripheral devices 1576 may include, for example, data or video storage units, patient physiological sensors, medical imaging devices, infusion pumps, dialysis machines, and/or tablet computers, etc. The peripheral data may include image data from a dedicated two-dimensional infrared-specialized camera, diagnostic images from a user's laptop computer, and/or images or patient diagnostic text from an ophthalmic device such as the Alcon Constellation® system and the WaveTec Optiwave Refractive Analysis (ORA™) system.

The example peripheral input unit interface 1574 is configured to convert and/or format data from the peripheral devices 1576 into an appropriate digital form for use with stereoscopic images. Once in digital form, the graphics processing unit 1564 integrates the peripheral data with other system data and/or the stereoscopic images/frames. The data is rendered with the stereoscopic images for display on the display monitors 512 and/or 514.

To configure the inclusion of peripheral data with the stereoscopic images, the processor 1562 may control an integration setup. In an example, the processor 1562 may cause the graphics processing unit 1564 to display a configuration panel on the display monitors 512 and/or 514. The configuration panel may enable an operator to connect a peripheral device 1576 to the interface 1574 and the processor 1562 to subsequently establish communications with the device 1576. The processor 1564 may then read which data is available or enable the operator to use the configuration panel to select a data directory location. Peripheral data in the directory location is displayed in the configuration panel. The configuration panel may also provide the operator an option to overlay the peripheral data with stereoscopic image data or display as a separate picture.

Selection of peripheral data (and overlay format) causes the processor 1562 to read and transmit the data to the graphics processing unit 1564. The graphics processing unit 1564 applies the peripheral data to the stereoscopic image data for presentation as an overlay graphic (such as fusing a preoperative image or graphic with a real-time stereoscopic image), a "picture-in-picture," and/or a sub-window to the side or on top of the main stereoscopic image window.

3. De-Bayer Program Example

The example de-Bayer program 1580*a* of FIG. 16 is configured to produce images and/or frames with values for red, green, and blue color at every pixel value. As discussed above, the pixels of the right and left optical image sensors 746 and 748 have a filter that passes light in the red wavelength range, the blue wavelength range, or the green wavelength range. Thus, each pixel only contains a portion of the light data. Accordingly, each image and/or frame received in the information processor module 1408 from the image capture module 1404 has pixels that contain either red, blue, or green pixel data.

The example de-Bayer program 1580*a* is configured to average the red, blue, and green pixel data of adjacent and/or neighboring pixels to determine more complete color data for each pixel. In an example, a pixel with red data and a pixel with blue data are located between two pixels with green data. The green pixel data for the two pixels is averaged and assigned to the pixel with red data and the pixel with blue data. In some instances, the averaged green data may be weighted based on a distance of the pixel with red data and the pixel with blue data from the respective green pixels. After the calculation, the pixels with originally only red or blue data now include green data. Thus, after the de-Bayer program 1580*a* is executed by the graphics processing unit 1564, each pixel contains pixel data for an amount of red, blue, and green light. The pixel data for the different colors is blended to determine a resulting color on the color spectrum, which may be used by the renderer program 1580*e* for display and/or the display monitors 512 and 514. In some examples, the de-Bayer program 1580*a* may determine the resulting color and store data or an identifier indicative of the color.

4. Color Correction Example

The example color correction programs 1580*b*, 1580*c*, and 1580*d* are configured to adjust pixel color data. The sensor color correction program 1580*b* is configured to account or adjust for variability in color sensing of the optical image sensors 746 and 748. The user color correction program 1580*c* is configured to adjust pixel color data based on perceptions and feedback of an operator. Further, the display color correction program 1580*d* is configured to adjust pixel color data based on a display monitor type.

To correct color for sensor variability, the example color correction program 1580*b* specifies a calibration routine that is executable by the graphics processing unit 1564 and/or the processor 1562. The sensor calibration includes placing a calibrated color chart, such as the ColorChecker® Digital SG by X-Rite, Inc. at the target site 700. The processor 1562 and/or the graphics processing unit 1564 executes the program 1580*b*, which includes sending instructions to the image capture module 1404 to record right and left images of the color chart. Pixel data from the right and left images (after being processed by the de-Bayer program 1580*a*) may be compared to pixel data associated with the color chart, which may be stored to the memory 1570 from a peripheral unit 1576 and/or a remote computer via the network interface 1572. The processor 1562 and/or the graphics processing unit 1564 determines differences between the pixel data. The differences are stored to the memory 1570 as calibration data or parameters. The sensor color correction program 1580*b* applies the calibration parameters to subsequent right and left images.

In some examples, the differences may be averaged over regions of pixels such that the program 1580*b* finds a best-fit of color correction data that can be applied globally to all of the pixels of the optical images sensors 746 and 748 to produce colors as close to the color chart as possible. Additionally or alternatively, the program 1580*b* may process user input instructions received from the user unit device 1410 to correct colors. The instructions may include regional and/or global changes to red, blue, and green pixel data based on operator preferences.

The example sensor color correction program 1580*b* is also configured to correct for white balance. Generally, white light should result in red, green, and blue pixels having equal values. However, differences between pixels can result from color temperature of light used during imaging, inherent aspects of the filter and sensing element of each of the pixels, and spectral filtering parameters of, for example, the deflecting element 712 of FIGS. 7 and 8. The example sensor color correction program 1580*b* is configured to specify a calibration routine to correct for the light imbalances.

To perform white balance, the processor 1562 (per instructions from the program 1580*b*) may display an instruction on the display monitor 512 and/or 514 for an operator to place a neutral card at the target site 700. The processor 1562 may then instruct the image capture module 1404 to record one or more images of the neutral card. After processing by the unpack routine 1602 and the de-Bayer program 1580*a*, the program 1580*b* determines regional and/or global white balance calibration weight values for each of the red, blue, and green data such that each of the pixels have substantially equal values of red, blue, and green data. The white balance calibration weight values are stored to the memory 1570. During operation, the graphics processing unit 1564 uses the program 1580*b* to apply the white balance calibration parameters to provide white balance.

In some examples, the program 1580*b* determines white balance calibration parameters individually for the right and left optical image sensors 746 and 748. Of these examples, the program 1580*b* may store separate calibration parameters for the left and right images. In other instances, the sensor color correction program 1580*b* determines a weighting between the right and left views such that color pixel data is nearly identical for the right and left optical image sensors 746 and 748. The determined weight may be applied to the white balance calibration parameters for subsequent use during operation of the stereoscopic visualization camera 300.

In some embodiments, the sensor color correction program 1580*b* of FIG. 16 specifies that the white balance calibration parameters are to be applied as a digital gain on the pixels of the right and left optical image sensors 746 and 748. For example, the processor 1504 of the image capture module 1404 applies the digital gain to pixel data read from each of the pixels. In other embodiments, the white balance calibration parameters are to be applied as an analog gain for each pixel's color sensing element.

The example sensor color correction program 1580b may perform white balancing and/or color correction when the different light sources 708 and/or filter types of the filter 740 are activated. As a result, the memory 1570 may store different calibration parameters based on which light source 708 is selected. Further, the sensor color correction program 1580b may perform white balancing and/or color correction for different types of external light. An operator may use the user input device 1410 to specify characteristics and/or a type of the external light source. This calibration enables the stereoscopic visualization camera 300 to provide color correction and/or white balance for different lighting environments.

The example program 1580b is configured to perform calibration on each of the optical image sensors 746 and 748 separately. Accordingly, the program 1580b applies different calibration parameters to the right and left images during operation. However, in some examples, calibration may only be performed on one sensor 746 or 748 with the calibration parameters being used for the other sensor.

The example user color correction program 1580c is configured to request operator-provided feedback regarding image quality parameters such as brightness, contrast, gamma, hue, and/or saturation. The feedback may be received as instructions from the user input device 1410. Adjustments made by the user are stored as user calibration parameters in the memory 1570. These parameters are subsequently applied by the user color correction program 1580c to right and left optical images after color correction for the optical image sensors 746 and 748.

The example display color correction program 1580d of FIG. 16 is configured to correct image color for a display monitor using, for example, the Datacolor™ Spyder color checker. The program 1580d, similar to the program 1580b, instructs the image capture module 1404 to record an image of a display color template at the target scene 700. The display color correction program 1580d operates a routine to adjust pixel data to match an expected display output stored in a look-up-table in the memory 1570. The adjusted pixel data may be stored as display calibration parameters to the memory 1570. In some examples, a camera or other imaging sensor may be connected to the peripheral input unit interface 1574, which provides images or other feedback regarding color recorded from the display monitors 512 and 514, which is used to adjust the pixel data.

5. Stereoscopic Image Display Example

The example renderer program 1580e of the graphics processing unit 1564 of FIG. 16 is configured to prepare right and left images and/or frames for three-dimensional stereoscopic display. After the pixel data of the right and left images is color corrected by the programs 1580b, 1580c, and 1580d, the renderer program 1580e is configured to draw left-eye and right-eye data into a format suitable for stereoscopic display and place the final rendered version into an output buffer for transmission to one of the display monitors 512 or 514.

Generally, the renderer program 1580e receives a right image and/or frame and a left image and/or frame. The renderer program 1580e combines the right and left images and/or frames into a single frame. In some embodiments, the program 1580e operates a top-bottom mode and condenses the left image data in height by half. The program 1580e then places the condensed left image data in a top half of the combined frame. Similarly, the program 1580e condenses the right image data in height by half and places the condensed right image data in a bottom half of the combined frame.

In other embodiments, the renderer program 1580e operates a side-by-side mode where each of the left and right images are condensed in width by half and combined in a single image such that the left image data is provided on a left half of the image while right image data is provided on a right half of the image. In yet an alternative embodiment, the renderer program 1580e operates a row-interleaved mode where every other line in the left and right frames is discarded. The left and right frames are combined together to form a complete stereoscopic image.

The example renderer program 1580e is configured to render combined left and right images separately for each connected display monitor. For instance, if both the display monitors 512 and 514 are connected, the renderer program 1580e renders a first combined stereoscopic image for the display monitor 512 and a second combined stereoscopic image for the display monitor 514. The renderer program 1580e formats the first and second combined stereoscopic images such that they are compatible with the type and/or screen size of the display monitors and/or screen.

In some embodiments, the renderer program 1580e selects the image processing mode based on how the display monitor is to display stereoscopic data. Proper interpretation of stereoscopic image data by the brain of an operator requires that the left eye data of the stereoscopic image be conveyed to the operator's left eye and the right eye data of the stereoscopic image be conveyed to the operator's right eye. Generally, display monitors provide a first polarization for left eye data and a second opposing polarization for the right eye data. Thus, the combined stereoscopic image must match the polarization of the display monitor.

Figure 17:
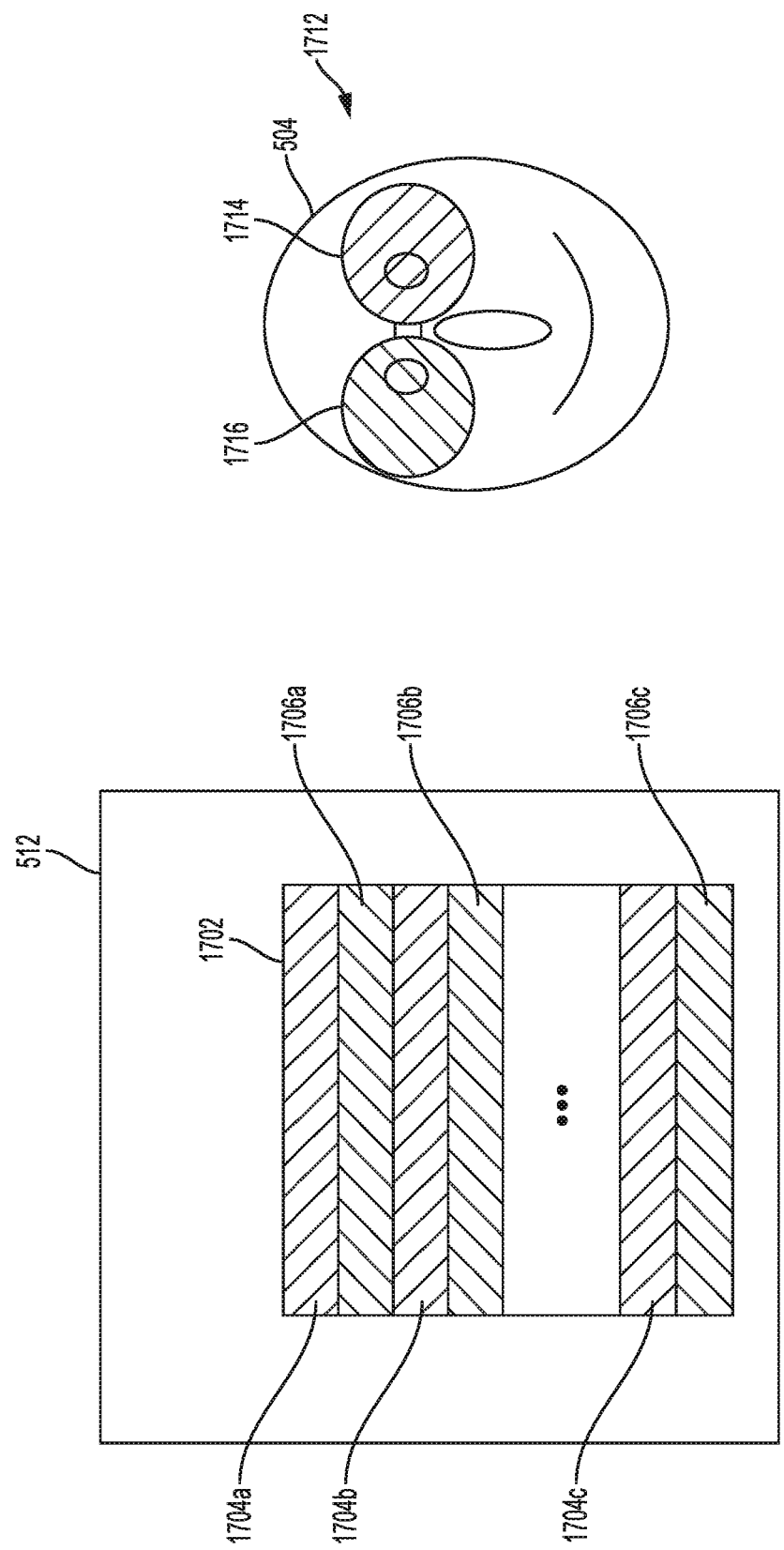
FIG. 17 shows an example of a display monitor, according to an example embodiment of the present disclosure.

FIG. 17 shows an example of the display monitor 512, according to an example embodiment of the present disclosure. The display monitor 512 may be, for example, the LG® 55LW5600 three-dimensional television with a screen 1702. The example display monitor 512 uses a polarization film on the screen 1702 such that all odd rows 1704 have a first polarization and all even rows 1706 have an opposing polarization. For compatibility with the display monitor 512 shown in FIG. 17, the renderer program 1580e would have to select the row-interleaved mode such that the left and right image data are on alternating lines. In some instances, the renderer program 1580e may request (or otherwise receive) display characteristics of the display monitor 512 prior to preparing the stereoscopic image.

To view the stereoscopic image displayed on the screen 1702, the surgeon 504 (remember him from FIG. 5) wears glasses 1712 that include a left lens 1714 that comprises a first polarization that matches the first polarization of the rows 1704. In addition, the glasses 1712 include a right lens 1716 that comprises a second polarization that matches the second polarization of the rows 1706. Thus, the left lens 1714 only permits a majority of the light from the left image data from the left rows 1704 to pass through while blocking a majority of the light from the right image data. In addition, the right lens 1716 permits a majority of the light from the right image data from the right rows 1706 to pass through while blocking a majority of the light from the left image data. The amount of light from the "wrong" view that reaches each respective eye is known as "crosstalk" and is generally held to a value low enough to permit comfortable viewing. Accordingly, the surgeon 504 views left image data recorded by the left optical image sensor 748 in a left eye while viewing right image data recorded by the right optical image sensor 746 in a right eye. The surgeon's brain fuses the two views together to create a perception of three-dimensional distance and/or depth. Further, the use of such a display monitor is advantageous for observing the accuracy of the stereoscopic visualization camera 300. If the surgeon or operator does not wear glasses, then both left and right views are observable with both eyes. If a planar target is placed at the focal plane, the two images will be theoretically aligned. If misalignment is detected, a re-calibration procedure can be initiated by the processor 1562.

The example renderer program 1580e is configured to render the left and right views for circular polarization. However, in other embodiments, the renderer program 1580e may provide a stereoscopic image compatible with linear polarization. Regardless of which type of polarization is used, the example processor 1562 may execute a program 1560 to verify or check a polarity of the stereoscopic images being output by the renderer program 1580e. To check polarity, the processor 1562 and/or the peripheral input unit interface 1574 inserts diagnostic data into the left and/or right images. For example, the processor 1562 and/or the peripheral input unit interface 1574 may overlay "left" text onto the left image and "right" text onto the right image. The processor 1562 and/or the peripheral input unit interface 1574 may display a prompt instructing an operator to close one eye at a time while wearing the glasses 1712 to confirm the left view is being received at the left eye and the right view is being received at the right eye. The operator may provide confirmation via the user input device 1410 indicating whether the polarization is correct. If the polarization is not correct, the example renderer program 1580e is configured to reverse locations where the left and right images are inserted into the combined stereoscopic image.

In yet other embodiments, the example renderer program 1580e is configured to provide for frame sequential projection instead of creating a combined stereoscopic image. Here, the renderer program 1580e renders the left images and or frames time-sequentially interleaved with the right images and/or frames. Accordingly the left and right images are alternately presented to the surgeon 504. In these other embodiments, the screen 1702 is not polarized. Instead, the left and right lenses of the glasses 1712 may be electronically or optically synchronized to their respective portion of a frame sequence, which provides corresponding left and right views to a user to discern depth.

In some examples, the renderer program 1580e may provide certain of the right and left images for display on separate display monitors or separate windows on one display monitor. Such a configuration may be especially beneficial when lenses of right and left optical paths of the optical elements 1402 are independently adjustable. In an example, a right optical path may be set a first magnification level while a left optical path is set at a second magnification level. The example renderer program 1580e may accordingly display a stream of images from the left view on the display monitor 512 and a stream of images from the right view on the display monitor 514. In some instances, the left view may be displayed in a first window on the display monitor 512 while the right view is displayed in a second window (e.g., a picture-in-picture) of the same display monitor 512. Thus, while not stereoscopic, the concurrent display of the left and right images provides useful information to a surgeon.

In another example, the light sources 708 and the filter 740 may be switched quickly to generate alternating images with visible light and fluorescent light. The example renderer program 1580e may combine the left and right views to provide a stereoscopic display under different lighting sources to highlight, for example, a vein with a dye agent while showing the background in visible light.

In yet another example, a digital zoom may be applied to the right and/or left optical image sensor 746 or 748. Digital zoom generally affects the perceived resolution of the image and is dependent on factors such as the display resolution and the preference of the viewer. For example, the processor 1504 of the image capture module 1404 may apply digital zooming by creating interpolated pixels synthesized and interspersed between the digitally-zoomed pixels. The processor 1504 may operate a program 1510 that coordinates the selection and interpolation pixels for the optical image sensors 746 and 748. The processor 1504 transmits the right and left images with digital zoom applied to the information processor module 1408 for subsequent rendering and display.

In some embodiments, the processor 1504 receives instructions from the processor 1562 that a digital zoom image is to be recorded between images without digital zoom to provide a picture-in-picture (or separate window) display of a digital zoom of a region of interest of the target site 700. The processor 1504 accordingly applies digital zooming to every other read from the pixel grids 1002 and 1004. This enables the renderer program 1580e to display simultaneously a stereoscopic full resolution image in addition to a digitally-zoomed stereoscopic image. Alternatively, the image to be zoomed digitally is copied from the current image, scaled, and placed during the render phase in the proper position overlaid atop the current image. This alternatively configuration avoids the "alternating" recording requirement.

6. Calibration Example

The example information processor module 1408 of FIGS. 14 to 16 may be configured to execute one or more calibration programs 1560 to calibrate, for example, a working distance and/or magnification. For example, the processor 1562 may send instructions to the motor and lighting module 1406 to perform a calibration step for mapping a working distance (measured in millimeters) from the main objective assembly 702 to the target site 700 to a known motor position of the working distance lens motor 1554. The processor 1562 performs the calibration by sequentially moving an object plane in discrete steps along the optical axis and re-focusing the left and right images, while recording encoder counts and the working distance. In some examples, the working distance may be measured by an external device, which transmits the measured working distance values to the processor 1562 via the peripheral input unit interface 1574 and/or an interface to the user input device 1410. The processor 1562 may store the position of the rear working distance lens 704 (based on position of the working distance lens motor 1554) and the corresponding working distance.

The example processor 1562 may also execute a program 1560 to perform magnification calibration. The processor 1562 may set the optical elements 1402, using the motor and lighting module 1406 to select magnification levels. The processor 1562 may record positions of the optical elements 1402, or corresponding motor positions with respect to each magnification level. The magnification level may be determined by measuring a height in an image of an object of a known size. For example, the processor 1562 may measure an object as having a height of 10 pixels and use a lookup-table to determine that a 10 pixel height corresponds to a 5× magnification.

To match the stereoscopic perspectives of two different imaging modalities it is often desirable to model them both as if they are simple pinhole cameras. The perspective of a 3D computer model, such as a Mill brain tumor, can be viewed from user-adjustable directions and distances (e.g. as if the images are recorded by a synthesized stereoscopic camera). The adjustability can be used to match the perspective of the live surgical image, which must therefore be known. The example processor 1562 may calibrate one or more of these pinhole camera model parameters such as, for example, a center of projection ("COP") of the right and left optical image sensors 746 and 748. To determine center of projection, the processor 1562 determines a focus distance from the center of projection to an object plane. First, the processor 1562 sets the optical elements 1402 at a magnification level. The processor 1562 then records measurements of a height of an image at three different distances along the optical axis including at the object plane, a distance d less than the object plane distance, and a distance d greater than the object plane distance. The processor 1562 uses an algebraic formula for similar triangles at the two most extreme positions to determine the focus distance to the center of projection. The processor 1562 may determine focus distances at other magnifications using the same method or by determining a ratio between the magnifications used for calibration. The processor may use a center of projection to match the perspective of an image of a desired fusion object, such as an Mill tumor model, to a live stereoscopic surgical image. Additionally or alternatively, existing camera calibration procedures such as OpenCV calibrateCamera may be used to find the above-described parameters as well as additional camera information such as a distortion model for the optical elements 1402.

The example processor 1562 may further calibrate the left and right optical axes. The processor 1562 determines an interpupillary distance between the left and right optical axes for calibration. To determine the interpupillary distance, the example processor 1562 records left and right images where pixel sets 1006 and 1008 are centered at the pixel grids 1002 and 1004. The processor 1562 determines locations of ZRPs (and/or distances to a displaced object) for the left and right images, which are indicative of image misalignment and degree of parallax. In addition, the processor 1562 scales the parallax and/or the distance based on the magnification level. The processor 1562 then determines the interpupillary distance using a triangulation calculation taking into account the degree of parallax and/or the scaled distance to the object in the display. The processor 1562 next associates the interpupillary distance with the optical axis at the specified magnification level as a calibration point.

VI. Image Alignment and Spurious Parallax Adjustment Embodiment

Similar to human vision, stereoscopic images comprise right views and left views that converge at a point of interest. The right and left views are recorded at slightly different angles from the point of interest, which results in parallax between the two views. Items in the scene in front of or behind the point of interest exhibit parallax such that distance or depth of the items from the viewer can be deduced. The accuracy of the perceived distance is dependent on, for example, the clarity of the viewer's eyesight. Most humans exhibit some level of imperfection in their eyesight, resulting in some inaccuracies between the right and left views. However, they are still able to achieve stereopsis, with the brain fusing the views with some level of accuracy.

When left and right images are recorded by a camera instead of being viewed by a human, the parallax between the combined images on a display screen produces stereopsis, which provides an appearance of a three-dimensional stereoscopic image on a two-dimensional display. Errors in the parallax can affect the quality of the three-dimensional stereoscopic image. The inaccuracy of the observed parallax in comparison to a theoretically perfect parallax is known as spurious parallax. Unlike humans, cameras do not have brains that automatically compensate for the inaccuracies.

If spurious parallax becomes significant, the three-dimensional stereoscopic image may be unviewable to the point of inducing vertigo, headaches, and nausea. There are many factors that can affect the parallax in a microscope and/or camera. For instance, optical channels of the right and left views may not be exactly equal. The optical channels may have unmatched focus, magnification, and/or misalignment of points of interest. These issues may have varying severity at different magnifications and/or working distances, thereby reducing efforts to correct through calibration.

Figure 2:
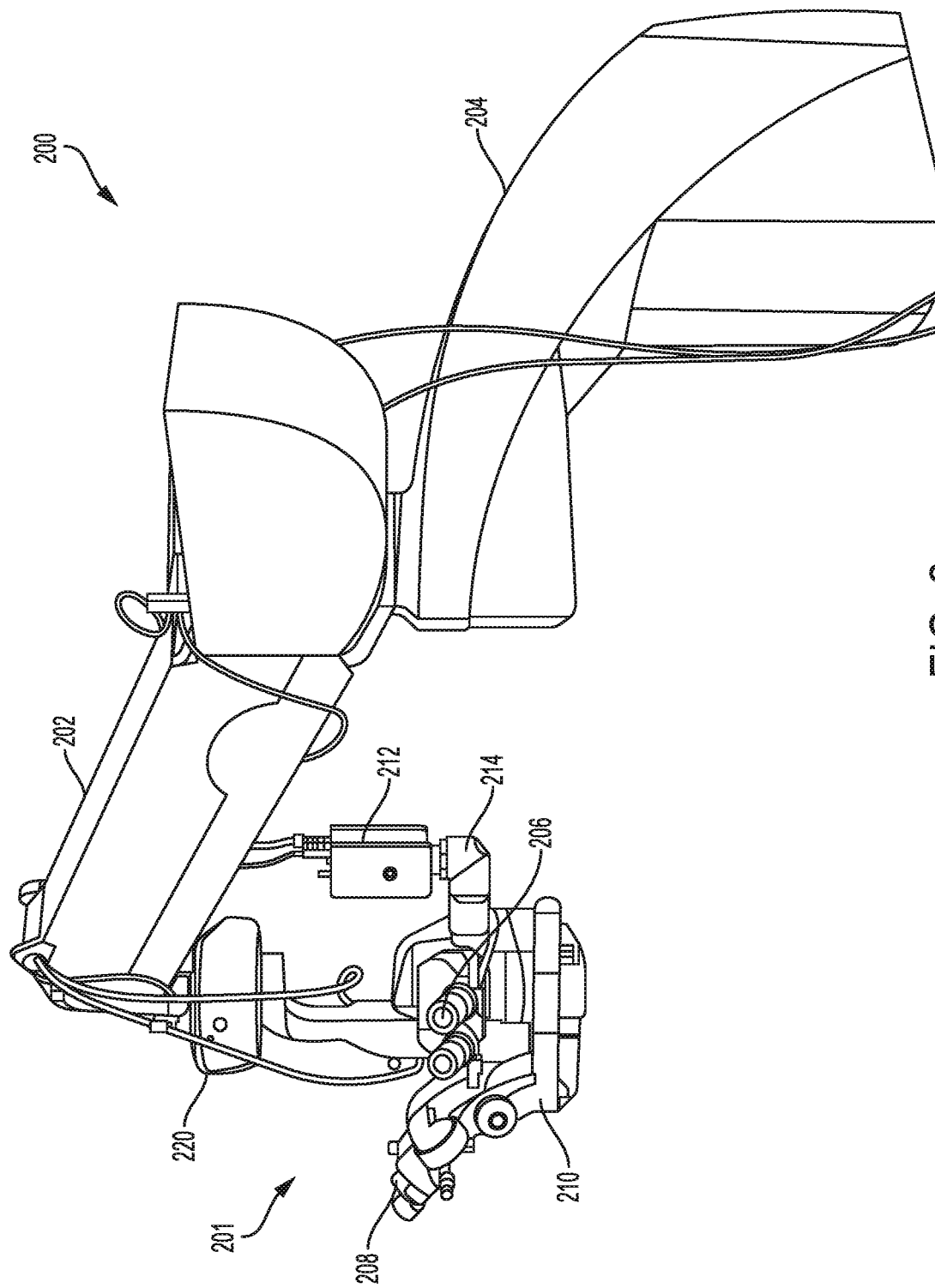
FIG. 2 shows a diagram of a prior art surgical microscope.

Known surgical microscopes, such as the surgical microscope 200 of FIG. 2 are configured to provide an adequate view through the oculars 206. Often, the image quality of optical elements of known surgical microscopes is not sufficient for stereoscopic cameras. The reason for this is because manufacturers of surgical microscopes assume the primary viewing is through oculars. Any camera attachment (such as the camera 212) is either monoscopic and not subject to spurious parallax or stereoscopic with low image resolution where spurious parallax is not as apparent.

International standards, such as ISO 10936-1:2000, *Optics and optical instruments—Operation microscopes—Part 1: Requirements and test methods*, have been developed to provide specification limits for image quality of surgical microscopes. The specification limits are generally set for viewing through the oculars of a surgical microscope and do not consider three-dimensional stereoscopic display. For example, regarding spurious parallax, ISO 10936-1:2000 specifies that the difference in vertical axes between the left and right views should be less than 15 arc-minutes. Small angular deviations of axes are often quantified in arc-minutes, which corresponds to $\frac{1}{60}^{th}$ of a degree, or arc-seconds, which corresponds to $\frac{1}{60}^{th}$ of an arc-minute. The 15 arc-minute specification limit corresponds to a 3% difference between left and right views for a typical surgical microscope with a working distance of 250 mm and a field-of-view of 35 mm (which has an angular field-of-view of 8°).

The 3% difference is acceptable for ocular viewing where a surgeon's brain is able to overcome the small degree of error. However, this 3% difference produces noticeable differences between left and right views when viewed stereoscopically on a display monitor. For example, when the left and right views are shown together, a 3% difference results in an image that appears disjointed and difficult to view for extended periods of time.

Another issue is that known surgical microscopes may satisfy the 15 arc-minute specification limit at only one or a few magnification levels and/or only individual optical elements may satisfy a certain specification limit. For example, individual lenses are manufactured to meet certain criteria. However, when the individual optical elements are combined in an optical path, small deviations from the standard may be amplified rather than canceled. This can be especially pronounced when five or more optical elements are used in an optical path including a common main objective lens. In addition, it is very difficult to perfectly match optical elements on parallel channels. At most, during manufacture, the optical elements of a surgical microscope are calibrated only at one or a few certain magnification levels to meet the 15 arc-minute specification limit. Accordingly, the error may be greater between the calibration points despite the surgical microscope allegedly meeting the ISO 10936-1:2000 specifications.

In addition, the ISO 10936-1:2000 specification permits larger tolerances when additional components are added. For example, adding second oculars (e.g., the oculars 208) increases the spurious parallax by 2 arc-minutes. Again, while this error may be acceptable for viewing through oculars 206 and 208, image misalignment becomes more pronounced when viewed stereoscopically through the camera.

In comparison to known surgical microscopes, the example stereoscopic visualization camera 300 disclosed herein is configured to automatically adjust at least some of the optical elements 1402 to reduce or eliminate spurious parallax. Embedding the optical elements within the stereoscopic visualization camera 300 enables fine adjustments to be made automatically (sometimes in real-time) for three-dimensional stereoscopic display. In some embodiments, the example stereoscopic visualization camera 300 may provide an accuracy of 20 to 40 arc-seconds, which is close to a 97% reduction in optical error compared to the 15 arc-minute accuracy of known surgical microscopes.

The improvement in accuracy enables the example stereoscopic visualization camera 300 to provide features that are not capable of being performed with known stereoscopic microscopes. For example, many new microsurgical procedures rely on accurate measurements in a live surgical site for optimal sizing, positioning, matching, directing, and diagnosing. This includes determining a size of a vessel, an angle of placement of a toric Intra Ocular Lens ("IOL"), a matching of vasculature from a pre-operative image to a live view, a depth of a tumor below an artery, etc. The example stereoscopic visualization camera 300 accordingly enables precise measurements to be made using, for example, graphical overlays or image analysis to determine sizes of anatomical structures.

Known surgical microscopes require that a surgeon place an object of a known size (such as a micro-ruler) into the field-of-view. The surgeon compares the size of the object to surrounding anatomical structure to determine an approximate size. However, this procedure is relatively slow since the surgeon has to place the object in the proper location, and then remove it after the measurement is performed. In addition, the measurement only provides an approximation since the size is based on the surgeon's subjective comparison and measurement. Some known stereoscopic cameras provide graphical overlays to determine size. However, the accuracy of these overlays is reduced if spurious parallax exists between the left and right views.

A. ZRP as a Source of Spurious Parallax

Figure 18:
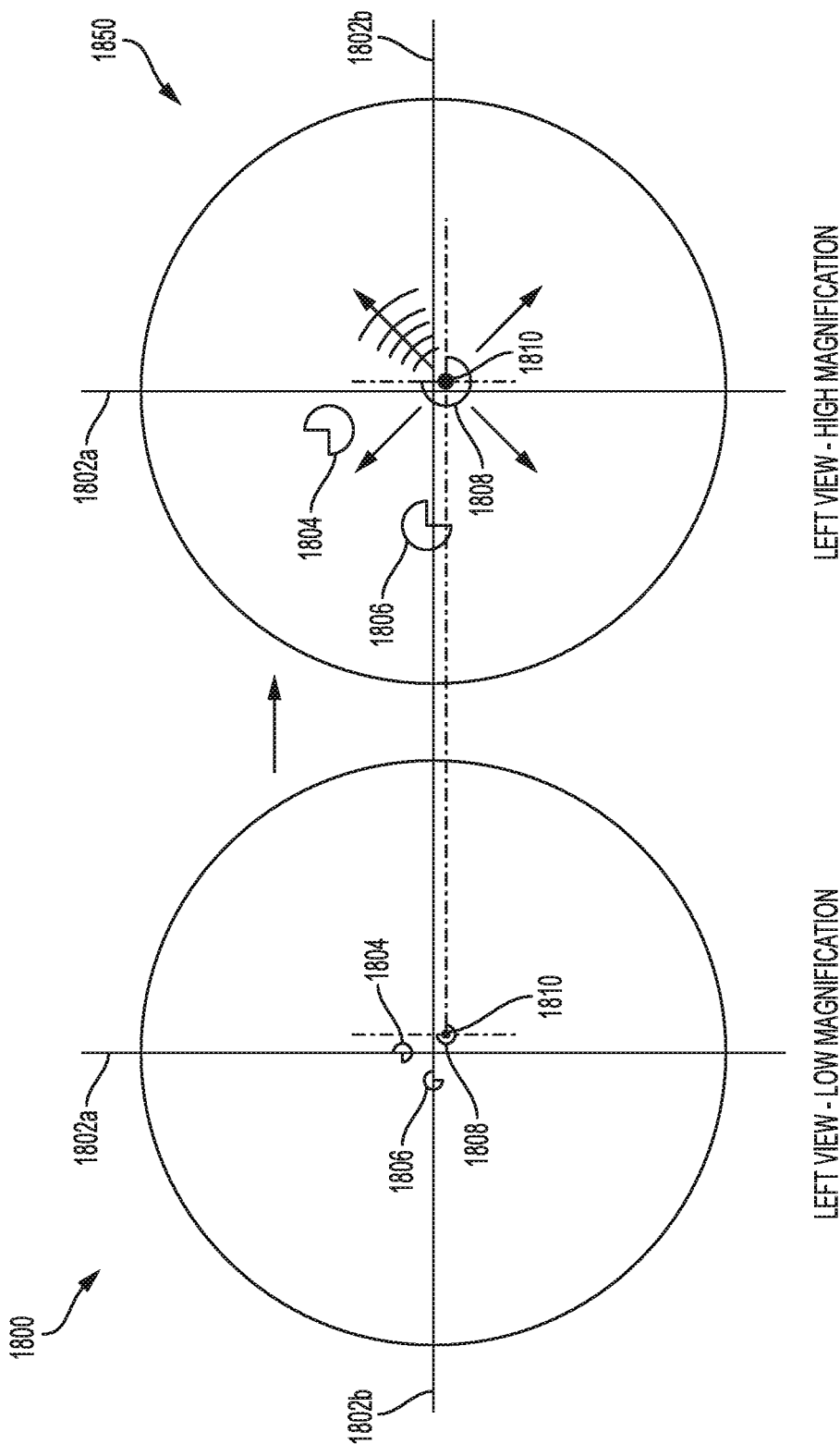
FIGS. 18 to 21 show diagrams illustrative of spurious parallax between right and left optical paths.
Figure 19:
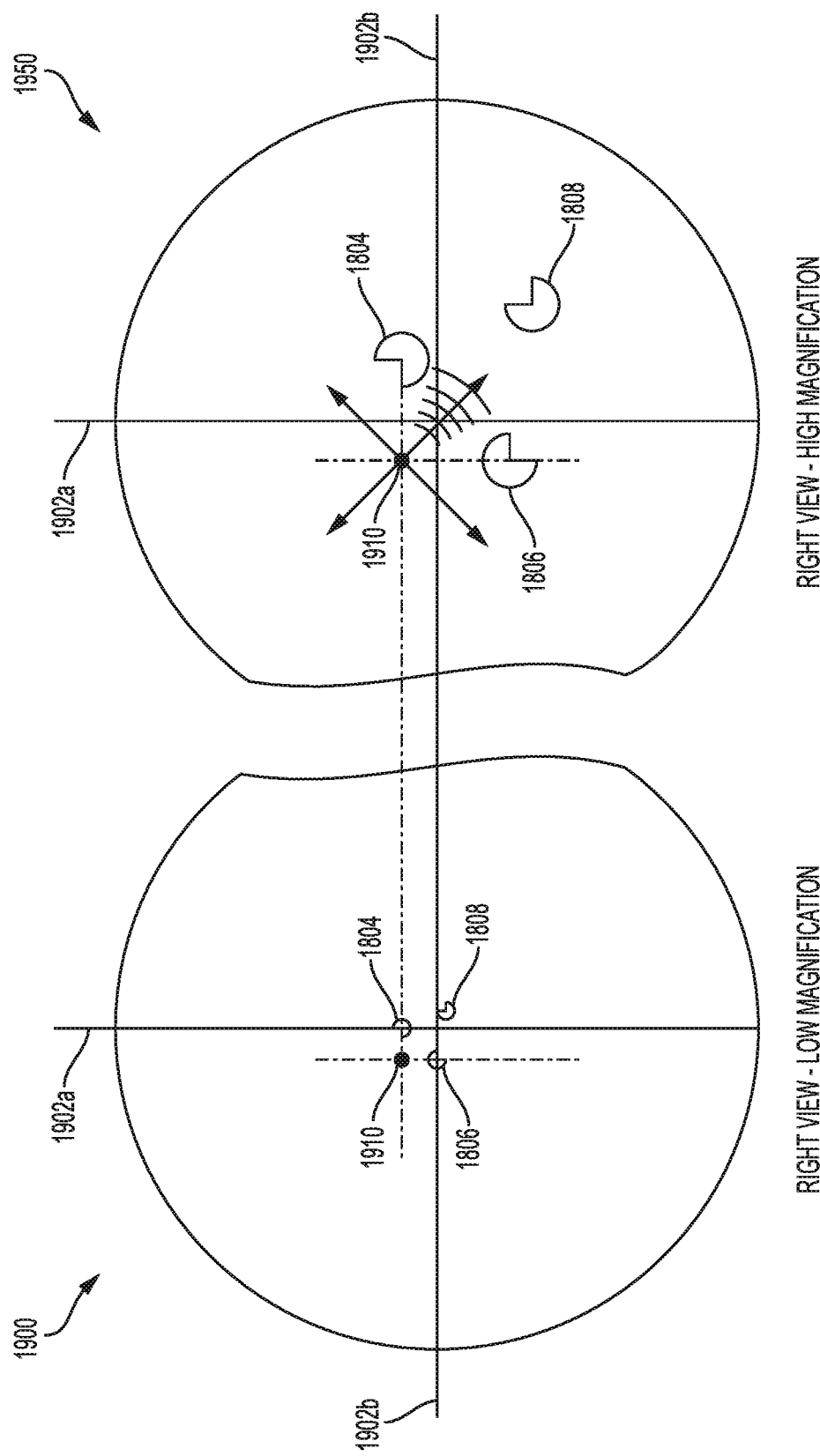

ZRP inaccuracy provides a significant source of error between left and right images resulting in spurious parallax. ZRP, or zoom repeat point, refers to a point in a field-of-view that remains in a same location as a magnification level is changed. FIGS. 18 and 19 show examples of ZRP in a left and right field-of-view for different magnification levels. Specifically, FIG. 18 shows a left field-of-view 1800 for a low magnification level and a left field-of-view 1850 for a high magnification level In addition, FIG. 19 shows a right field-of-view 1900 for a low magnification level and a right field-of-view 1950 for a high magnification level.

It should be noted that FIGS. 18 and 19 show crosshairs 1802 and 1902 to provide an exemplary point of reference for this disclosure. The crosshairs 1802 include a first crosshair 1802*a* positioned along a y-direction or y-axis and a second crosshair 1802*b* positioned along an x-direction or x-axis. Additionally, crosshairs 1902 include a first crosshair 1902*a* positioned along a y-direction or y-axis and a second crosshair 1902*b* positioned along an x-direction or x-axis In actual implementation, the example stereoscopic visualization camera 300 by default typically does not include or add crosshairs to the optical path unless requested by an operator.

Ideally, the ZRP should be positioned at a central location or origin point. For example, the ZRP should be centered in the crosshairs 1802 and 1902. However, inaccuracies in the optical elements 1402 and/or slight misalignments between the optical elements 1402 cause the ZRP to be located away from the center of the crosshairs 1802 and 1902. The degree of spurious parallax corresponds to how far each of the ZRPs of the left and right views is located away from the respective centers in addition to ZRPs being misaligned between the left and right views. Moreover, inaccuracies in the optical elements 1402 may cause the ZRP to drift slightly as magnification changes, thereby further causing a greater degree of spurious parallax.

FIG. 18 shows three crescent-shaped objects 1804, 1806, and 1808 in the field-of-views 1800 and 1850 of the target site 700 of FIG. 7. It should be appreciated that the field-of-views 1800 and 1850 are linear field-of-views with respect to the optical image sensors 746 and 748. The objects 1804, 1806, and 1808 were placed in the field-of-view 1800 to illustrate how spurious parallax is generated from left and right image misalignment. The object 1804 is positioned above crosshair 1802*b* along crosshair 1802*a*. The object 1806 is positioned along crosshair 1802*b* and to the left of the crosshair 1802*a*. The object 1808 is positioned slightly below the crosshair 1802*b* and to the right of the crosshair 1802*a*. A ZRP 1810 for the left field-of-view 1800 is positioned in a notch of the object 1808.

The left field-of-view 1800 is changed to the left field-of-view 1850 by increasing the magnification level (e.g., zooming) using the zoom lens assembly 716 of the example stereoscopic visualization camera 300. Increasing the magnification causes the objects 1804, 1806, and 1808 to appear to expand or grow, as shown in the field-of-view 1850. In the illustrated example, the field-of-view 1850 is approximately 3× the magnification level of the field-of-view 1800.

Compared to the low magnification field-of-view 1800, the objects 1804, 1806, and 1808 in high magnification field-of-view 1850 have increased in size by about 3× while also moving apart from each other by 3× with respect to the ZRP 1810. In addition, the positions of the objects 1804, 1806, and 1808 have moved relative to the crosshairs 1802. The object 1804 is now shifted to the left of the crosshair 1802*a* and shifted slightly further from the crosshair 1802*b*. In addition, the object 1806 is now shifted further to the left of crosshair 1802*a* and slightly above the crosshair 1802*b*. Generally, the object 1808 is located in the same (or nearly the same) position with respect to the crosshairs 1802, with the ZRP 1810 being located in the exact same (or nearly the same) position with respect to the crosshairs 1802 and the object 1806. In other words, as magnification increases, the objects 1804, 1806, and 1808 (and anything else in the field-of-view 1850) appear to move away and outward from the ZRP 1810.

The same objects 1804, 1806, and 1808 are shown in the right field-of-views 1900 and 1950 illustrated in FIG. 19. However, the location of the ZRP is different. Specifically, ZRP 1910 is located above crosshair 1902b and to the left of crosshair 1902a in the right field-of-views 1900 and 1950. Thus, the ZRP 1910 is located at a different location than the ZRP 1810 in the left field-of-views 1800 and 1850. In the illustrated example, it is assumed that the left and right optical paths are perfectly aligned at the first magnification level. Accordingly, the objects 1804, 1806, and 1808 shown in the right field-of-view 1900 in the same location as the same objects 1804, 1806, and 1808 in the left field-of-view 1800. Since the left and right views are aligned, no spurious parallax exists.

However, in the high magnification field-of-view 1950, the objects 1804, 1806, and 1808 expand and move away from the ZRP 1910. Given the location of the ZRP 1910, the object 1804 moves or shifts to the right and the object 1806 moves or shifts downward. In addition, the object 1808 moves downward and to the right compared to its location in the field-of-view 1900.

Figure 20:
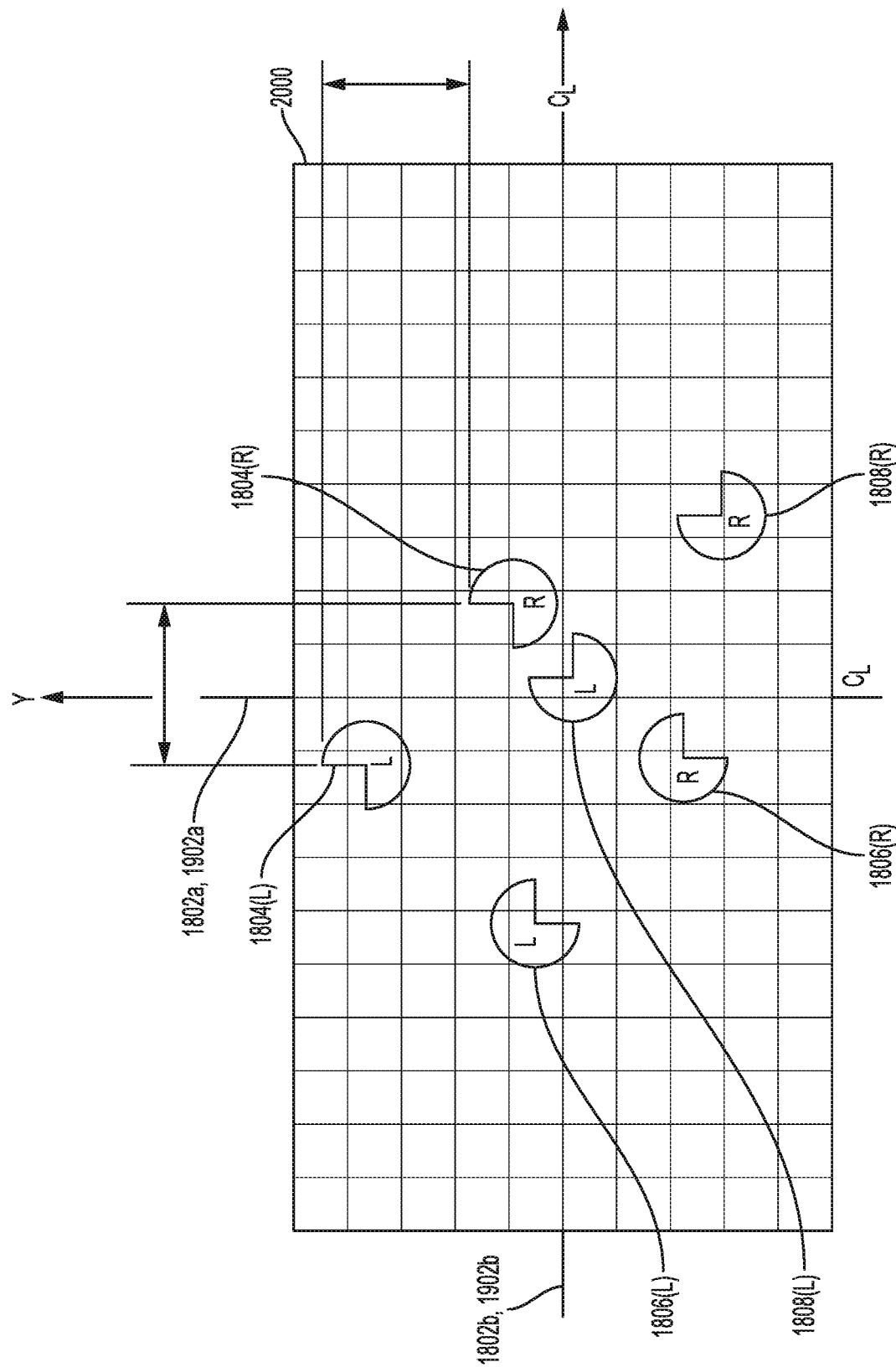

FIG. 20 shows a pixel diagram comparing the high magnification left field-of-view 1850 to the high magnification right field-of-view. A grid 2000 may represent locations of the objects 1804(L), 1806(L), and 1808(L) on the pixel grid 1004 of the left optical image sensor 748 overlaid with locations of the objects 1804(R), 1806(R), and 1808(R) on the pixel grid 1002 of the left optical image sensor 746. FIG. 20 clearly shows that the objects 1804, 1806, and 1808 are in different positions for the left and right field-of-views 1850 and 1950. For example, the object 1804(R) is located to the right of crosshair 1902a and above crosshair 1902b while the same object 1804(L) is located to the left of cross hair 1802a and further above cross hair 1802b.

The difference in positions of the objects 1804, 1806, and 1808 corresponds to spurious parallax, which is created by deficiencies in the optical alignment of the optical elements 1402 that produce ZRPs 1810 and 1910 in different locations. Assuming no distortion or other imaging errors, the spurious parallax shown in FIG. 20 is generally the same for all points within the image. When viewed through oculars of a surgical microscope (such as microscope 200 of FIG. 2), the difference in location of the objects 1804, 1806, and 1808 may not be noticeable. However, when viewed on the display monitors 512 and 514 in a stereoscopic image, the differences become readily apparent and can result in headaches, nausea, and/or vertigo.

Figure 21:
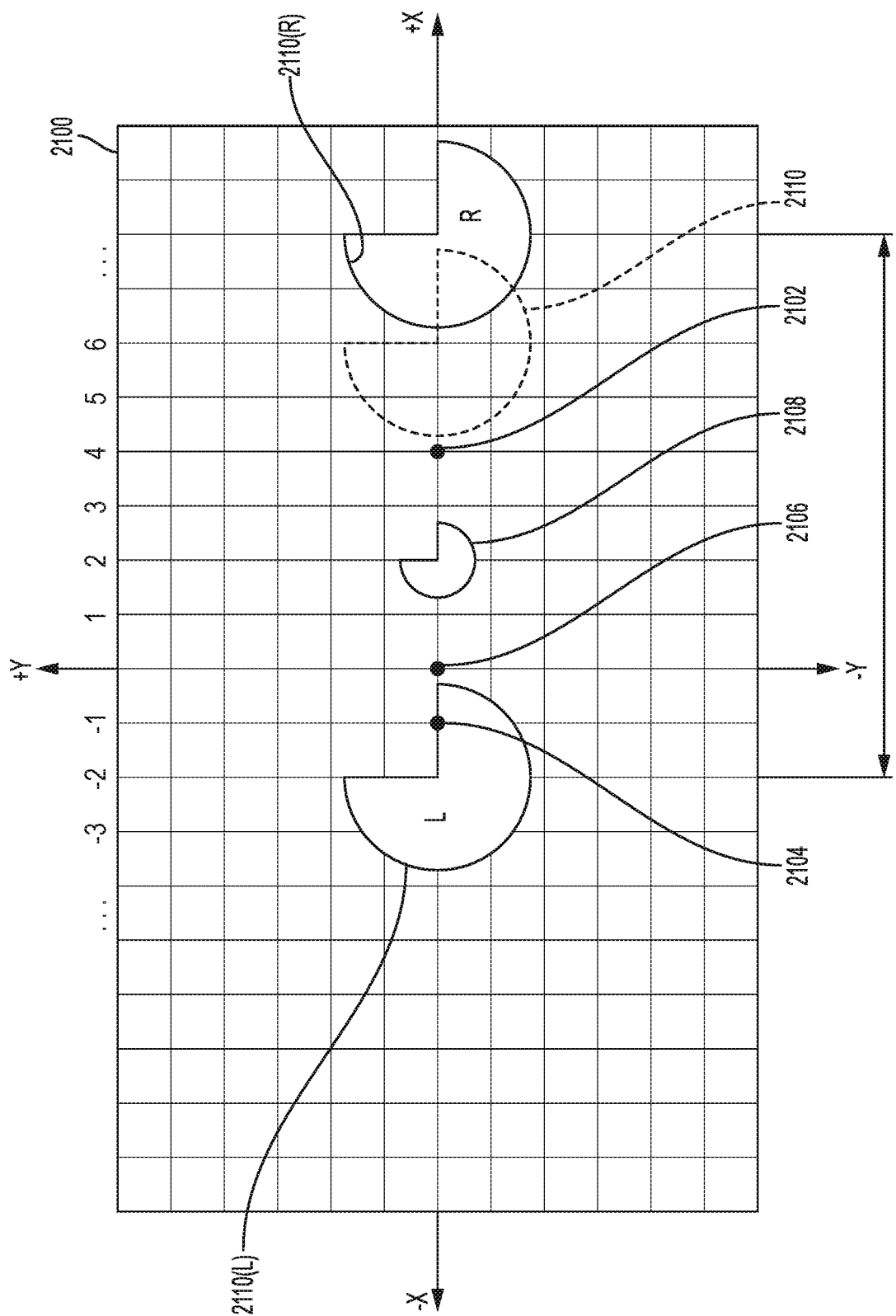

FIG. 21 shows a diagram illustrative of spurious parallax with respect to left and right ZRPs. The diagram includes a pixel grid 2100 that includes overlays of the right and left pixel grids 1002 and 1004 of FIG. 10. In this illustrated example, a left ZRP 2102 for the left optical path is located at +4 along the x-axis and 0 along the y-axis. In addition, a right ZRP 2104 for the right optical path is located at −1 along the x-axis and 0 along the y-axis. An origin 2106 is shown at the intersection of the x-axis and the y-axis.

In this example, object 2108 is aligned with respect to the left and right images at a first low magnification. As magnification is increased by 3×, the object 2108 increased in size and moved away from the ZRPs 2102 and 2104. Outlines object 2110 shows a theoretical location of the object 2108 at the second higher magnification based on the ZRPs 2102 and 2104 being aligned with the origin 2106. Specifically, a notch of the object 2108 at the first magnification level is at location+2 along the x-axis. With 3× magnification, the notch moves 3× along the x-axis such that the notch is located at +6 along the x-axis at the higher magnification level. In addition, since the ZRPs 2102 and 2104 would be theoretically aligned at the origin 2106, the object 2110 would be aligned between the left and right views (shown in FIG. 21 as a single object given the overlay).

However, in this example, misalignment of the left and right ZRPs 2102 and 2104 causes the object 2110 to be misaligned between the left and right views at higher magnification. Regarding the right optical path, the right ZRP 2104 is located at −1 along the x-axis such that it is 3 pixels away from the notch of the object 2108 at low magnification. When magnified 3×, this difference becomes 9 pixels, which is shown as object 2110(R). Similarly, the left ZRP 2102 is located at +4 pixels along the x-axis. At 3× magnification, the object 2108 moves from being 2 pixels away to 6 pixels away, which is shown as object 2110(L) at −2 along the x-axis.

The difference in positions of the object 2110(L) and the object 2110(R) corresponds to the spurious parallax between the left and right views at the higher magnification. If the right and left views were combined into a stereoscopic image for display, the location of the object 2110 would be misaligned at each row if the renderer program 1850e uses a row-interleaved mode. The misalignment would be detrimental to generating stereopsis and may produce an image that appears blurred or confusing to an operator.

B. Other Sources of Spurious Parallax

While ZRP misalignment between left and right optical paths is a significant source of spurious parallax, other sources of error also exist. For example, spurious parallax may result from non-equal magnification changes between the right and left optical paths. Differences in magnification between parallel optical paths may result from slight variances in the optical properties or characteristics of the lenses of the optical elements 1402. Further, slight differences may result from positioning if each of the left and right front zoom lenses 726 and 728 and each of the left and right rear zoom lenses 736 and 738 of FIGS. 7 and 8 are independently controlled.

Referring back to FIGS. 18 and 19, differences in magnification change produce differently sized objects and different spacing between the objects for the left and right optical paths. If, for example, the left optical path has a higher magnification change, then the objects 1804, 1806, and 1808 will appear larger and move a greater distance from the ZRP 1810 compared to the objects 1804, 1806, and 1808 in the right field-of-view 1950 in FIG. 19. The difference in the location of the objects 1804, 1806, and 1808, even if the ZRPs 1810 and 1910 are aligned, results in spurious parallax.

Another source of spurious parallax results from unequal focusing of the left and right optical paths. Generally, any difference in focus between left and right views may cause a perceived diminishment in image quality and potential confusion over whether the left or right view should predominate. If the focus difference is noticeable, it can result in an Out-Of-Focus ("OOF") condition. OOF conditions are especially noticeable in stereoscopic images where left and right views are shown in the same image. In addition, OOF conditions are not easily correctable since re-focusing an out-of-focus optical path usually results in the other optical path becoming unfocused. Generally, a point needs to be determined where both optical paths are in focus, which may include changing positions of left and right lenses along an optical path and/or adjusting a working distance from the target site 700.

Figure 22:
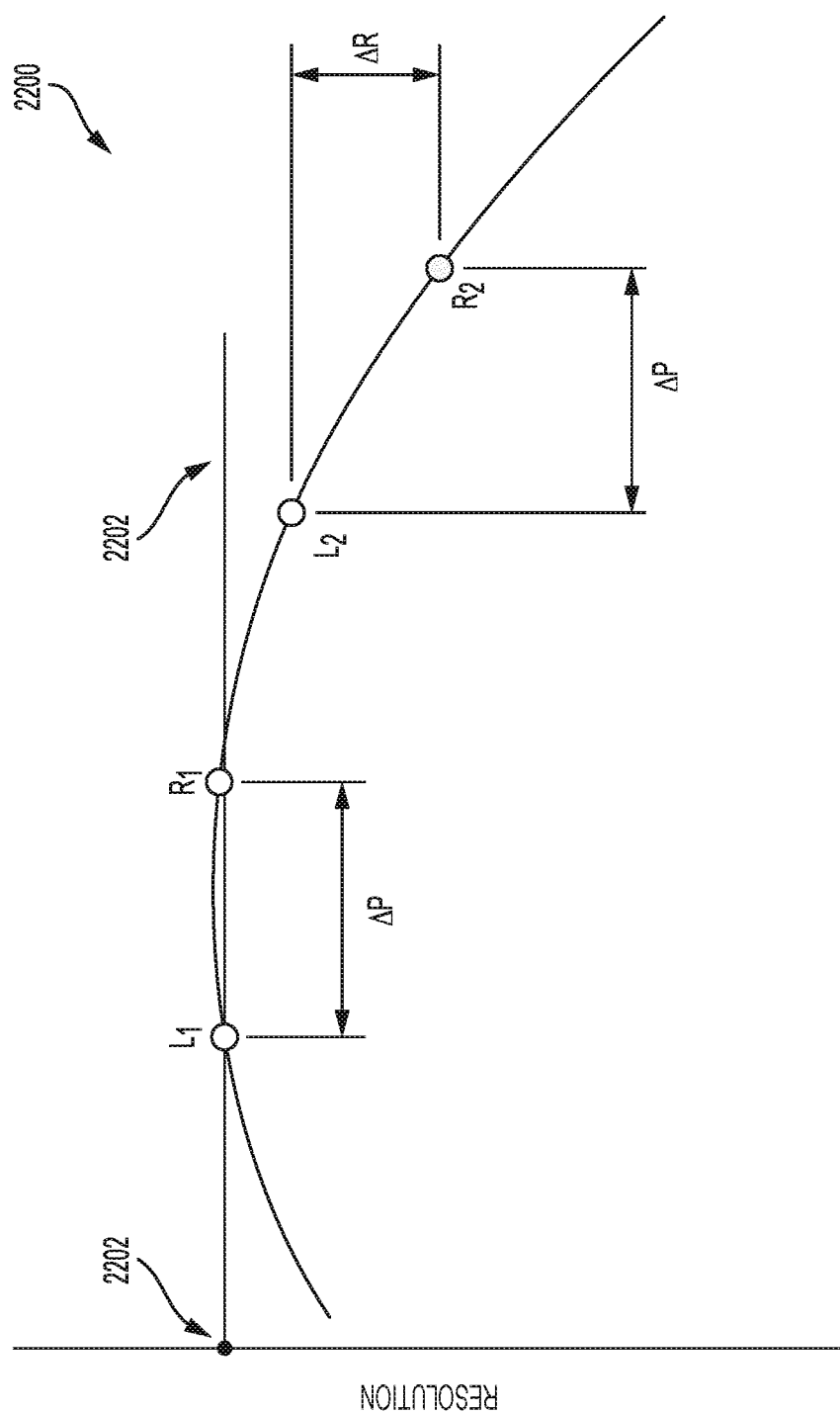
FIG. 22 shows a diagram illustrative of an out-of-focus condition in relation to a position of two parallel lenses for respective right and left optical paths.

FIG. 22 shows a diagram illustrative of how an OOF condition develops. The diagram relates perceived resolution (e.g., focus) to a lens position relative to an optimal resolution section 2202. In this example the left rear zoom lens 734 is at position L1 while the right rear zoom lens 732 is at position R1. At position L1 and R1, the rear zoom lenses 732 and 734 are in a range of optimal resolution 2202 such that the left and right optical paths have matched focus levels. However, there is a difference in the positions of L1 and R1, corresponding to distance ΔP. At a later time, the working distance 706 is changed such that a point is out-of-focus. In this example, both rear zoom lenses 732 and 734 move the same distance to locations L2 and R2 such that distance ΔP does not change. However, the position change results in a significant change in resolution ΔR such that the left rear zoom lens 734 has a higher resolution (e.g., better focus) that the right rear zoom lens 732. The resolution ΔR corresponds to the OOF condition, which results in spurious parallax from misalignment of focus between the right and left optical paths.

Yet another source of spurious parallax can result from imaging objects that are moving at the target site 700. The spurious parallax results from small synchronization errors between exposures of the right and left optical image sensors 746 and 748. If the left and right views are not recorded simultaneously, then the object appears to be displaced or misaligned between the two views. The combined stereoscopic image shows the same object at two different locations for the left and right views.

Moreover, another source of spurious parallax involves a moving ZRP point during magnification. The examples discussed above in Section IV(A) assume that the ZRPs of the left and right views do not move in the x-direction or the y-direction. However, the ZRPs may shift during magnification if the zoom lenses 726, 728, 732, and/or 734 do not move exactly parallel with the optical path or axis (e.g., in the z-direction). As discussed above in reference to FIG. 11, the carrier 724 may shift or rotate slightly when a force is applied to the actuation section 1108. This rotation may cause the left and right ZRPs to move slightly when a magnification level is changed.

In an example, during a magnification change, the carrier 730 moves in a single direction while the carrier 724 moves in the same direction for a portion of the magnification change and in an opposite direction for a remaining portion of the magnification change for focus adjustment. If the axis of motion of the carrier 724 is tilted or rotated slightly with respect to the optical axis, the ZRP of the left and/or right optical paths will shift in one direction for the first portion followed by a shift in a reverse direction for the second portion of the magnification change. In addition, since the force is applied unequally, the right and left front zoom lenses 726 and 728 may experience varying degrees of ZRP shift between the left and right optical paths. Altogether, the change in position of the ZRP results in misaligned optical paths, thereby producing spurious parallax.

C. Reduction in Spurious Parallax Facilitates Incorporating Digital Graphics and Images with a Stereoscopic View As surgical microscopes become more digitalized, designers are adding features that overlay graphics, images, and/or other digital effects to the live-view image. For example, guidance overlays, fusion of stereoscopic Magnetic Resonance Imaging ("MRI") images, and/or external data may be combined with images recorded by a camera, or even displayed within oculars themselves. Spurious parallax reduces the accuracy of the overlay with the underlying stereoscopic image. Surgeons generally require, for example, that a tumor visualized via MRI be placed as accurately as possible, often in three dimensions, within a fused live surgical stereoscopic view. Otherwise, the preoperative tumor image provides little information to the surgeon, thereby detracting from the performance.

For example, a surgical guide may be aligned with a right view image while misaligned with the left view. The misaligned surgical guide between the two views is readily apparent to the operator. In another example, a surgical guide may be aligned separately with left and right views in the information processor module 1408 prior to the graphics processing unit 1564 creating the combined stereoscopic image. However, misalignment between the left and right views creates misalignment between the guides, thereby reducing the effectiveness of the guides and creating confusion and delay during the microsurgical procedure.

Figure 23:
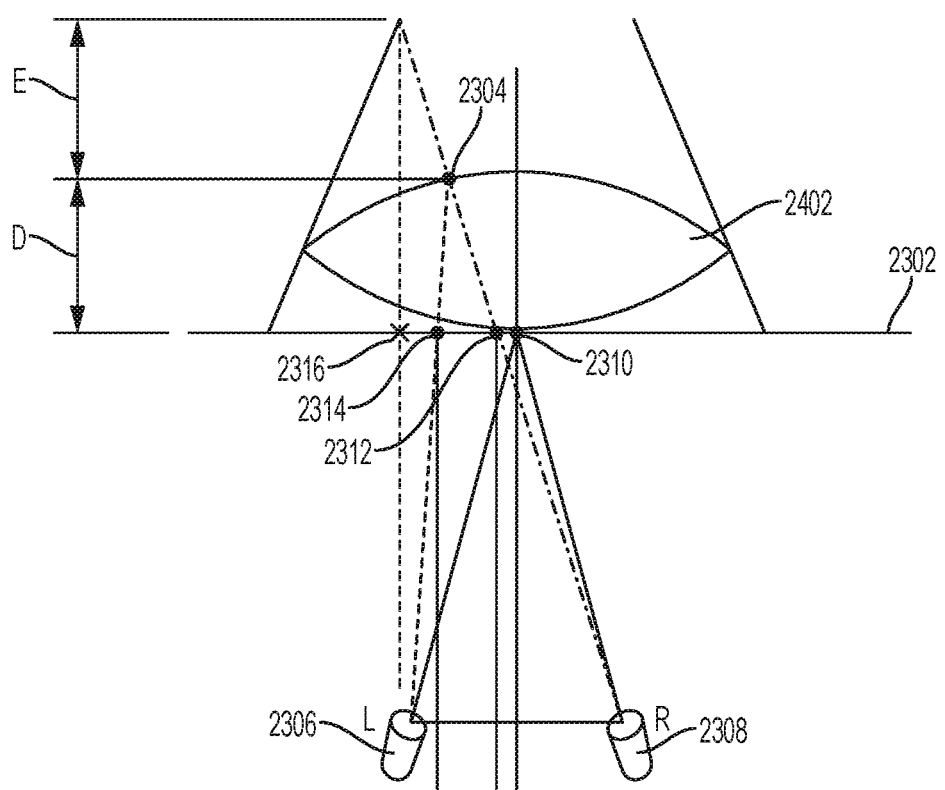
FIGS. 23 and 24 show diagrams illustrative of how spurious parallax causes digital graphics and/or images to lose accuracy when fused to a stereoscopic image.
Figure 24:
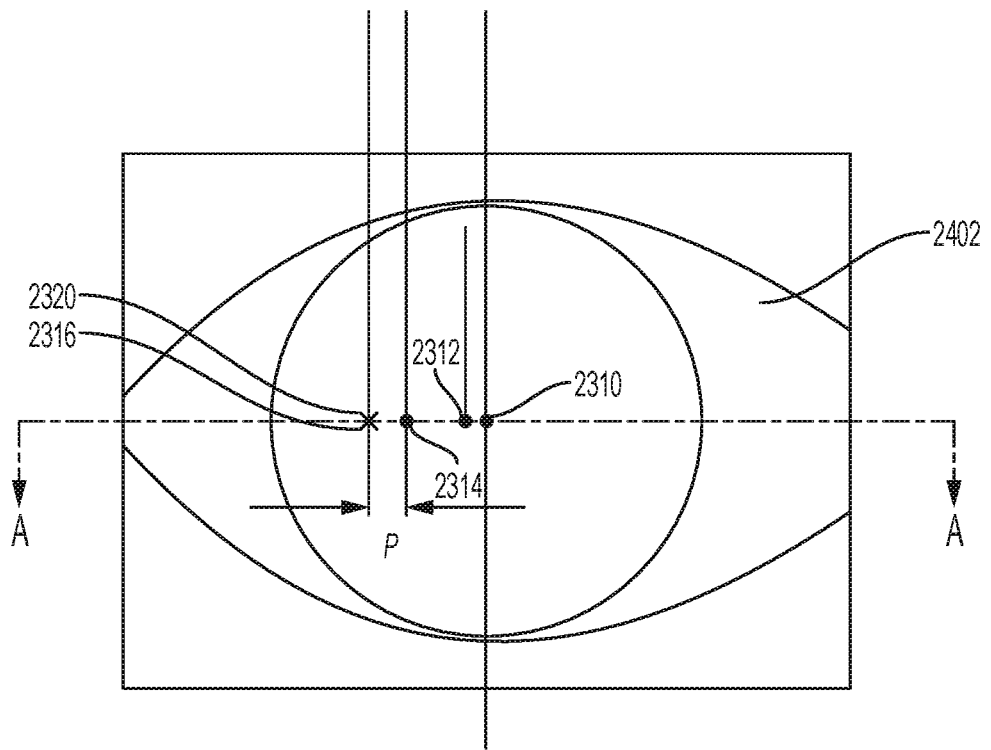

U.S. Pat. No. 9,552,660, titled "IMAGING SYSTEM AND METHODS DISPLAYING A FUSED MULTIDIMENSIONAL RECONSTRUCTED IMAGE," (incorporated herein by reference) discloses how preoperative images and/or graphics are visually fused with a stereoscopic image. FIGS. 23 and 24 show diagrams that illustrate how spurious parallax causes digital graphics and/or images to lose accuracy when fused to a stereoscopic image. FIG. 24 shows a front view of a patient's eye 2402 and FIG. 23 shows a cross-sectional view of the eye along plane A-A of FIG. 24. In FIG. 23, the information processor module 1408 is instructed to determine a caudal distance d from a focus plane 2302 to, for example, an object of interest 2304 on a posterior capsule of the eye 2402. The information processor module 1408 operates a program 1560 that specifies, for example, that the distance d is determined by a triangulation calculation of image data from the left and right views of the eye 2402. A view 2306 is shown from a perspective of the left optical image sensor 748 and a view 2308 is shown from a perspective of the right optical image sensor 746. The left and right views 2306 and 2308 are assumed to be coincident with an anterior center 2310 of the eye 2402. In addition, the left and right views 2306 and 2308 are two-dimensional views of the object 2304 projected onto a focal plane 2302 as theoretical right projection 2312 and theoretical left projection 2314. In this example, processor 1562 determines the distance d to the object of interest 2304 by calculating an intersection of an extrapolation of the theoretical right projection 2312 and an extrapolation of the theoretical left projection 2314 using a triangulation routine.

However, in this example spurious parallax exists, which causes an actual left projection 2316 to be located to the left of the theoretical left projection 2314 by a distance P, as shown in FIGS. 23 and 24. The processor 1562 uses the actual left projection 2316 and the right projection 2312 to determine a distance to an intersection 2320 of an extrapolation of the right projection 2312 and an extrapolation of the actual left projection 2316 using the triangulation routine. The distance of the intersection point 2320 is equal to the distance d plus an error distance e. The spurious parallax accordingly results in an erroneous distance calculation using data taken from a stereoscopic image. As shown in FIGS. 23 and 24, even a small degree of spurious parallax may create a significant error. In the context of a fused image, the erroneous distance may result in an inaccurate placement of a tumor three-dimensional visualization for fusion with a stereoscopic image. The inaccurate placement may delay the surgery, hinder the performance of the surgeon, or cause the entire visualization system to be disregarded. Worse yet, a surgeon may rely on the inaccurate placement of the tumor image and make a mistake during the microsurgery procedure.

D. The Example Stereoscopic Visualization Camera Reduces or Eliminates Spurious Parallax The example stereoscopic visualization camera 300 of FIGS. 3 to 16 is configured to reduce or eliminate visual defects, spurious parallax, and/or misaligned optical paths that typically result in spurious parallax. In some examples, the stereoscopic visualization camera 300 reduces or eliminates spurious parallax by aligning ZRPs of the left and right optical paths to the respective centers of pixel sets 1006 and 1008 of the right and left optical image sensors 746 and 748. Additionally or alternatively, the stereoscopic visualization camera 300 may align the optical paths of the left and right images. It should be appreciated that the stereoscopic visualization camera 300 may perform actions to reduce spurious parallax during calibration. Additionally, the stereoscopic visualization camera 300 may reduce detected spurious parallax in real-time during use.

Figure 25:
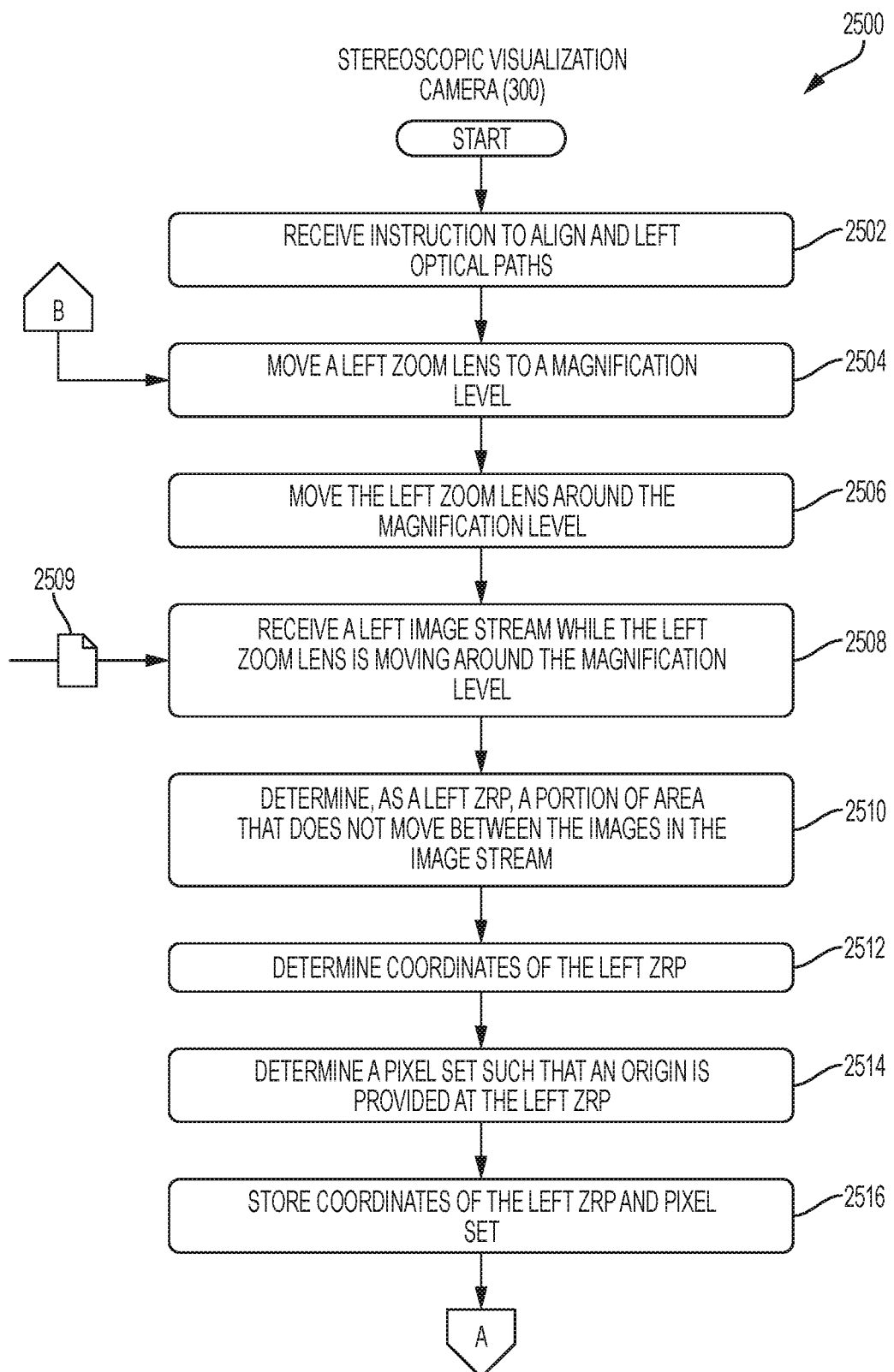
FIGS. 25 and 26 illustrate a flow diagram showing an example procedure to reduce or eliminate spurious parallax, according to an example embodiment of the present disclosure.
Figure 26:
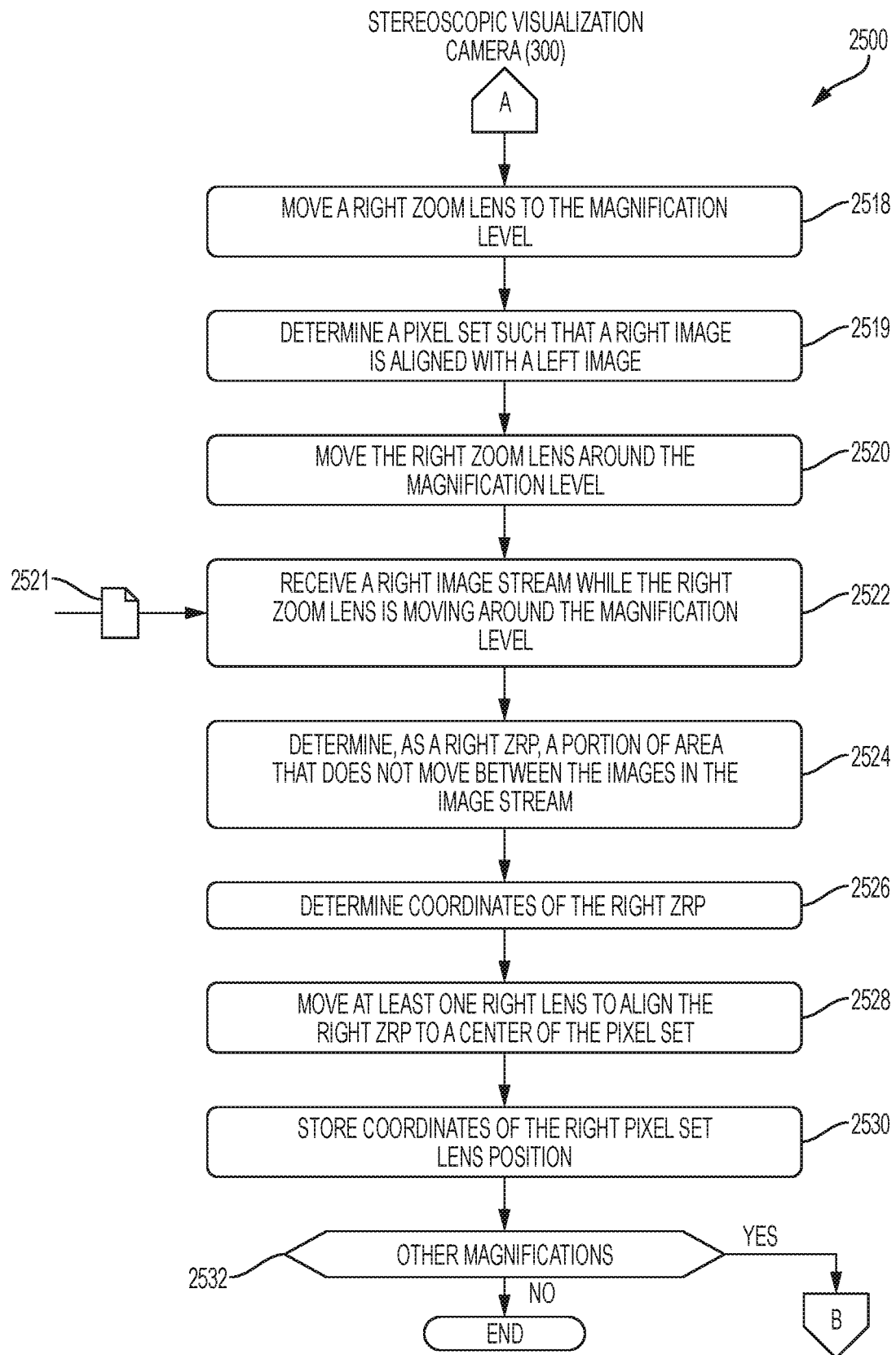

FIGS. 25 and 26 illustrate a flow diagram showing an example procedure 2500 to reduce or eliminate spurious parallax, according to an example embodiment of the present disclosure. Although the procedure 2500 is described with reference to the flow diagram illustrated in FIGS. 25 and 26, it should be appreciated that many other methods of performing the steps associated with the procedure 2500 may be used. For example, the order of many of the blocks may be changed, certain blocks may be combined with other blocks, and many of the blocks described are optional. Further, the actions described in procedure 2500 may be performed among multiple devices including, for example the optical elements 1402, the image capture module 1404, the motor and lighting module 1406, and/or the information processor module 1408 of the example stereoscopic visualization camera 300. For example, the procedure 2500 may be performed by one of the programs 1560 of the information processor module 1408.

The example procedure 2500 begins when the stereoscopic visualization camera 300 receives an instruction to align right and left optical paths (block 2502). The instructions may be received from the user input device 1410 in response to an operator requesting that the stereoscopic visualization camera 300 perform a calibration routine. In other examples, the instructions may be received from the information processor module 1408 after determining right and left images are misaligned. The information processor module 1408 may determine images are not aligned by executing a program 1560 that overlays right and left images and determines differences in pixel values, where greater differences over large areas of pixels are indicative of misaligned images. In some examples, the program 1560 may compare the pixel data of the left and right images without performing an overlay function, where, for example, left pixel data is subtracted from right pixel data to determine a severity of misalignment.

After receiving instructions to reduce spurious parallax, the example stereoscopic visualization camera 300 locates a ZRP of one of the left or right optical path. For illustrative purposes, procedure 2500 includes the ZRP of the left optical path being determined first. However, in other embodiments, the procedure 2500 may determine the ZRP of the right optical path first. To determine the left ZRP, the stereoscopic visualization camera 300 moves at least one zoom lens (e.g., the left front zoom lens 728 and/or the left rear zoom lens 734) to a first magnification level along a z-direction of the left optical path (block 2504). In instances where the front zoom lenses 726 and 728 are connected to the same carrier 724 and the rear zoom lenses 732 and 734 are connected to the same carrier 730, the movement of the left lenses causes the right lenses to also move. However, only movement of the left lenses is considered during this section of the procedure 2500.

At the first magnification level, the stereoscopic visualization camera 300 causes the left zoom lens to move along the z-direction (block 2506). The movement may include, for example, back-and-forth movement around the first magnification level. For example, if the first magnification level is 5×, the movement may be between 4× and 6×. The movement may also include movement in one direction, such as from 5× to 4×. During this movement, the stereoscopic visualization camera 300 may adjust one or more other lenses to maintain focus of the target site 700. At block 2508, during the movement of the left zoom lens, the stereoscopic visualization camera 300 records a stream or a sequence of images and/or frames 2509 of the target site 700 using, for example, the left optical image sensor 748. The images 2509 are recorded using an oversized pixel set 1008 configured to encompass an origin of the pixel grid 1004 and potential locations of the left ZRP.

The example processor 1562 of the information processor module 1408 analyzes the image stream to locate a portion of area that does not move in an x-direction or a y-direction between the images (block 2510). The portion of the area may include one or a few pixels and corresponds to the left ZRP. As discussed above, during a magnification change, objects move away from the ZRP or move towards the ZRP. Only objects at the ZRP remain constant in position with respect to the field-of-view as magnification changes. The processor 1562 may calculate deltas between the stream of images for each pixel using pixel data. An area with the smallest delta across the image stream corresponds to the left ZRP.

The example processor 1562 of the information processor module 1408 next determines coordinates of a portion of the area that does not move between the image stream (e.g., determines a location of the left ZRP) with respect to the pixel grid 1004 (block 2512). In other examples, the processor 1562 of the information processor module 1408 determines a distance between the origin and the portion of the area corresponding to the left ZRP. The distance is used to determine a position of the left ZRP on the pixel grid 1004. Once the location of the left ZRP is determined, the processor 1562 of the information processor module 1408 determines a pixel set (e.g., the pixel set 1008) for the left optical image sensor 748 such that the left ZRP is located at a center (within one pixel) of the pixel set (block 2514). At this point, the left ZRP is centered within the left optical path.

In some examples, blocks 2504 to 2514 may be performed iteratively by re-selecting the pixel set until the left ZRP is within a pixel of the origin and spurious parallax is minimized. After the pixel grid is determined, the processor 1562 of the information processor module 1408 stores at least one of coordinates of the pixel set and/or coordinates of the left ZRP to the memory 1570 as a calibration point (block 2516). The processor 1562 of the information processor module 1408 may associate the first magnification level with the calibration point such that the same pixel set is selected when the stereoscopic visualization camera 300 returns to the first magnification level.

Figure 27:
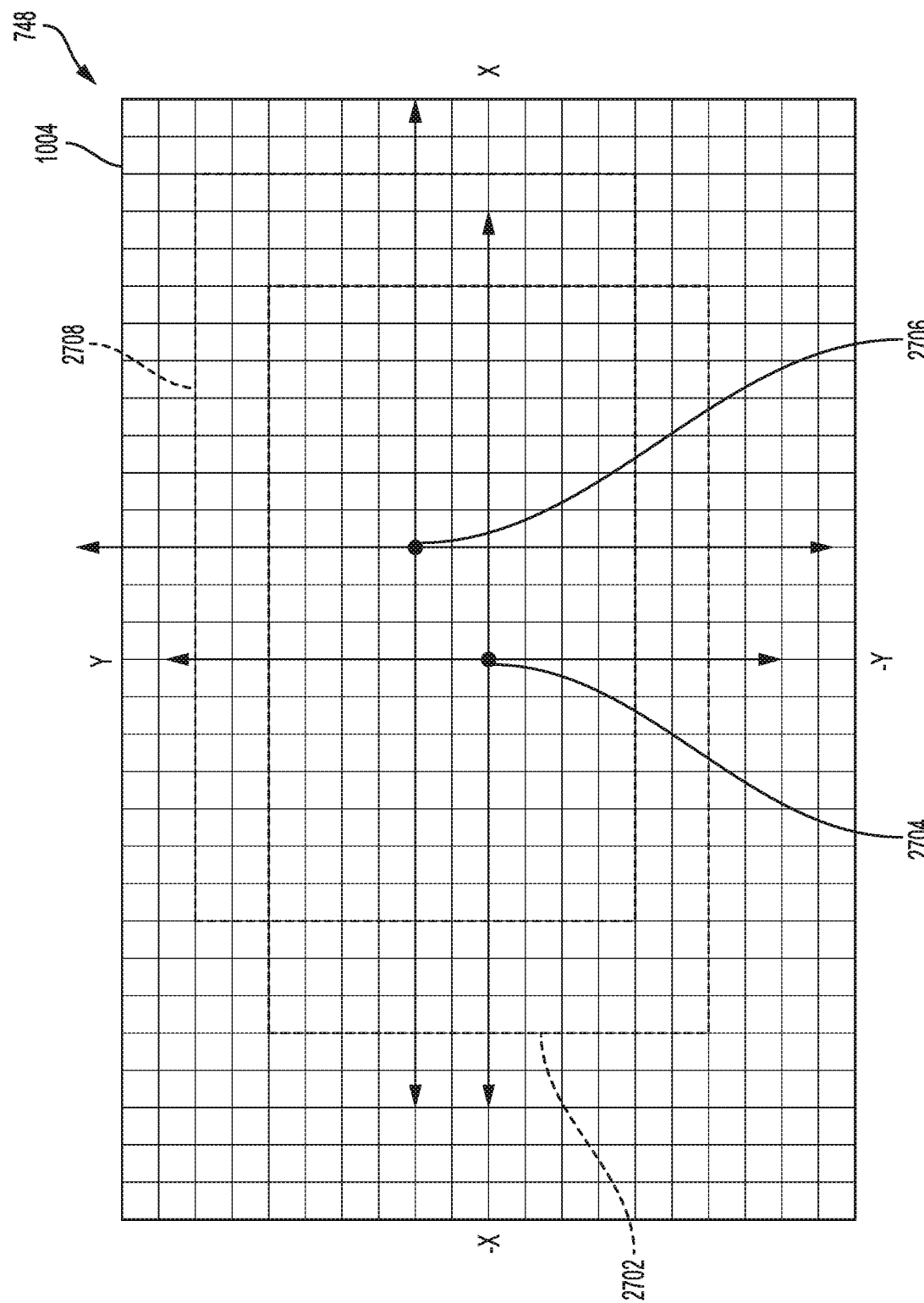
FIG. 27 shows a diagram illustrative of how a zoom repeat point is adjusted with respect to a pixel grid of an optical image sensor, according to an example embodiment of the present disclosure.

FIG. 27 shows a diagram illustrative of how the left ZRP is adjusted with respect to the pixel grid of the left optical image sensor 748. Initially, an initial (e.g., oversized) pixel set 2702 is selected, which is centered on origin 2704. The pixel set 2702 is large enough to record potential ZRPs in the image stream. In this illustrated example, a left ZRP 2706 is located above and to the right of the origin 2704. The processor 1562 of the information processor module 1408 determines pixel set 2708 based on a location of the left ZRP 2706 such that the left ZRP 2706 is located or positioned at a center of the pixel set 2708.

After the left ZRP is determined and aligned with an origin of a pixel set in FIG. 25, the example procedure 2500 aligns the left and right images in FIG. 26. To align the images, the example processor 1562 compares pixel data from left and right images recorded after the left ZRP is aligned with the origin. In some embodiments, the processor 1562 overlays the left and right images to determine differences using, for example, a subtraction and/or template method. The processor 1562 selects or determines a pixel set for the right optical path such that the resulting right images align or coincide with the left images (block 2519).

The example processor 1562, in the illustrated embodiment, determines the right ZRP. The steps are similar to steps discussed in blocks 2504 to 2512 for the left ZRP. For example, at block 2518 the stereoscopic visualization camera 300 moves a right zoom lens to the first magnification level. In some embodiments, the magnification level for the right lens is different than the magnification level used for determining the left ZRP. The example processor 1562 of the information processor module 1408 then moves the right zoom lens around the magnification level and receives a stream of images 2521 from the right optical image sensor 746 during the movement (blocks 2520 and 2522). The example processor 1562 of the information processor module 1408 determines the right ZRP from the right stream of images by locating a portion of an area that does not move between the images (block 2524). The processor 1562 next determines coordinates of the right ZRP and/or a distance between a center of an aligned pixel set 1006 to the right ZRP (block 2526).

The processor 1562 then instructs the motor and lighting module 1406 to move at least one lens in the right optical path in at least one of an x-direction, a y-direction, and/or a tilt-direction to align the right ZRP with the center of the aligned pixel set 1006 using, for example, the distance or coordinates of the right ZRP (block 2528). In other words, the right ZRP is moved to coincide with the center of the aligned pixel set 1006. In some examples, the right front lens 720, the right lens barrel 736, the right final optical element 745, and/or the right image sensor 746 is moved (using for example a flexure) in the x-direction, the y-direction and/or a tilt-direction with respect to the z-direction of the right optical path. The degree of movement is proportional to the distance of the right ZRP from the center of the pixel set 1006. In some embodiments, the processor 1562 digitally changes properties of the right front lens 720, the right lens barrel 736, and/or the right final optical element 745 to have the same effect as moving the lenses. The processor 1562 may repeat steps 2520 to 2528 and/or use subsequent right images to confirm the right ZRP is aligned with the center of the pixel set 1006 and/or to iteratively determine further lens movements needed to align the right ZRP with the center of the pixel set.

The example processor 1562 stores coordinates of the right pixel set and/or the right ZRP to the memory 1570 as a calibration point (block 2530). The processor 1562 may also store to the calibration point a position of the right lens that was moved to align the right ZRP. In some examples, the calibration point for the right optical path is stored with the calibration point for the left optical path in conjunction with the first magnification level. Thus, the processor 1562 applies the data within the calibration point to the optical image sensors 746 and 748 and/or radial positioning of one or more optical elements 1402 when the stereoscopic visualization camera 300 is subsequently set to the first magnification level.

In some examples, the procedure 2500 may be repeated for different magnification levels and/or working distances. Accordingly, the processor 1562 determines if ZRP calibration is needed for another magnification level or working distance (block 2532). If another magnification level is to be selected, the procedure 2500 returns to block 2504 in FIG. 25. However, if another magnification level is not needed, the example procedure ends.

Each of the calibration points may be stored in a look-up-table. Each row in the table may correspond to a different magnification level and/or working distance. Columns in the look-up-table may provide coordinates for the left ZRP, the right ZRP, the left pixel set, and/or the right pixel set. In addition, one or more columns may specify relevant positions (e.g., radial, rotational, tilt, and/or axial positions) of the lenses of the optical elements 1402 to achieve focus at the magnification level in addition to aligned right and left images.

The procedure 2500 accordingly results in the right ZRP and the left ZRP in addition to views of the target site to be aligned to pixel grids of the respective optical image sensors 746 and 748 as well as to each other in a three-dimensional stereoscopic image. In some instances, the left and right images and the corresponding ZRPs have an accuracy and alignment to within one pixel. Such accuracy may be observable on the display 514 or 514 by overlaying left and right views (e.g., images from the left and right optical paths) and observing both views with both eyes, rather than stereoscopically.

It should be appreciated that in some examples, a right pixel set is first selected such that the right ZRP is aligned with or coincident with an origin of the pixel set. Then, the right and left optical images may be aligned by moving one or more right and/or left lenses of the optical elements 1402. This alternative procedure still provides right and left ZRPs that are centered and aligned between each other and with respect to the optical image sensors 746 and 748.

The procedure 2500 ultimately reduces or eliminates spurious parallax in the stereoscopic visualization camera 300 throughout a full optical magnification range by ensuring left and right ZRPs remain aligned and the right and left images remain aligned. In other words, the dual optics of the right and left optical images sensors 746 and 748 are aligned such that parallax at a center of an image between the left and right optical paths is approximately zero at the focal plane. Additionally, the example stereoscopic visualization camera 300 is par focal across the magnification range, and par central across magnification and working distance ranges since the ZRP of each optical path has been aligned to a center of the respective pixel set. Accordingly, changing only the magnification will maintain a focus of the target site 700 in both optical image sensors 746 and 748 while being trained on the same center point.

The above procedure 2500 may be performed at calibration before a surgical procedure is performed and/or upon request by an operator. The example procedure 2500 may also be performed prior to image registration with a pre-operative microsurgical image and/or surgical guidance graphics. Further, the example procedure 2500 may be performed in real-time automatically during operation of the stereoscopic visualization camera 300.

1. Template Matching Example

Figure 28:
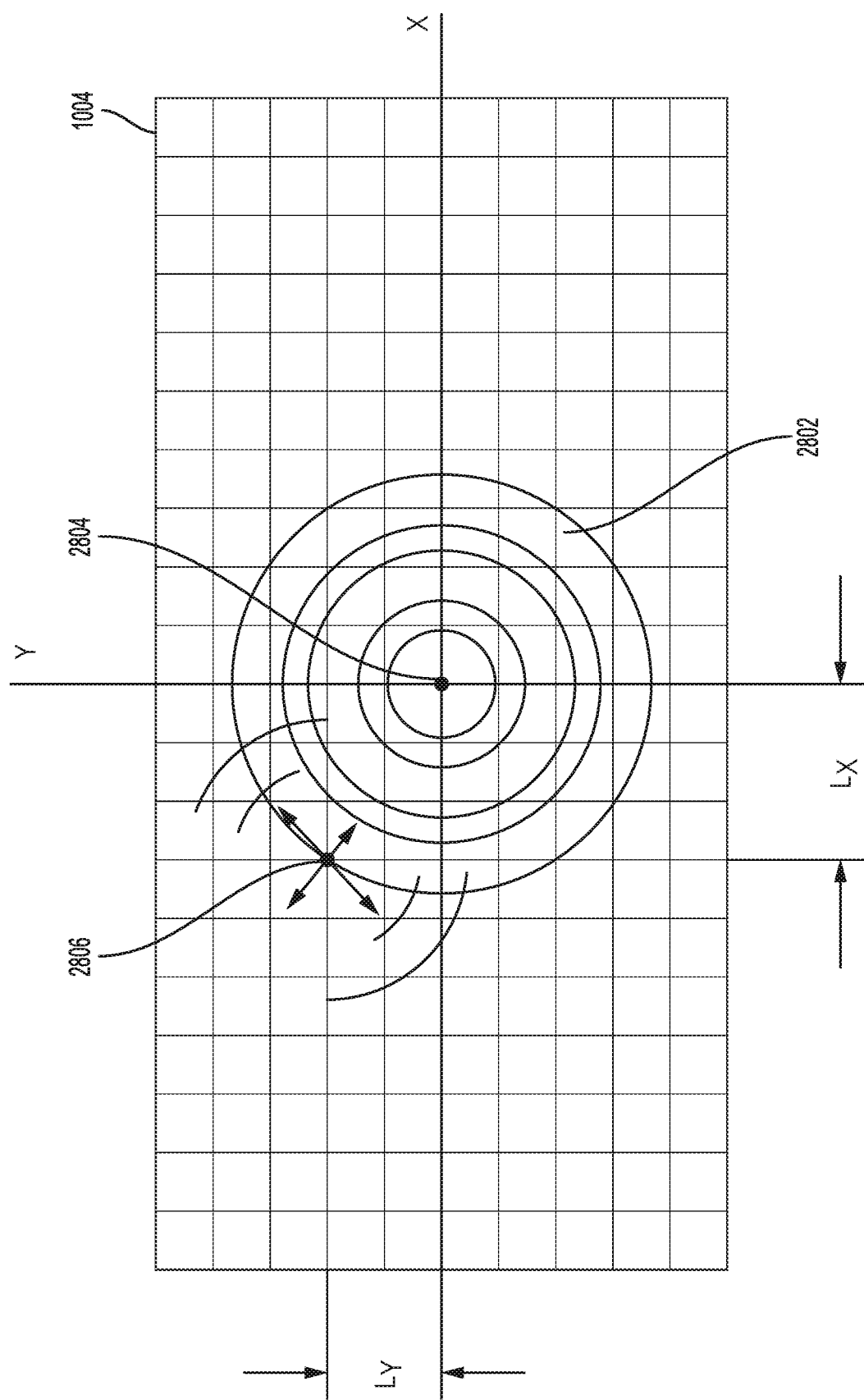
FIGS. 28 to 32 show diagrams illustrative of a template matching program to locate a zoom repeat point, according to an example embodiment of the present disclosure.

In some embodiments, the example processor 1562 of the information processor module 1408 is configured to use a program 1560 in conjunction with one or more templates to determine a position of the right ZRP and/or the left ZRP. FIG. 28 shows a diagram illustrative of how the processor 1562 uses a target template 2802 to determine a location of a left ZRP. In this example, FIG. 28 shows a first left image including the template 2802 aligned with an origin 2804 or center of the left pixel grid 1004 of the left optical image sensor 748. The template 2802 may be aligned by moving the stereoscopic visualization camera 300 to the appropriate location. Alternatively, the template 2802 may be moved at the target site 700 until aligned. In other examples, the template 2802 may include another pattern that does not need alignment with a center of the pixel grid 1004. For example, the template may include a graphical wave pattern, a graphical spirograph pattern, a view of a surgical site of a patient and/or a grid having visually distinguishable features with some degree of non-periodicity in both the x and y-directions. The template is configured to prevent a subset of a periodic image from being perfectly aligned onto the larger image in a plurality of locations, which makes such templates unsuitable for matching. A template image that is suitable for template matching is known as a "template match-able" template image.

The template 2802 shown in FIG. 28 is imaged at a first magnification level. A left ZRP 2806 is shown with respect to the template 2802. The ZRP 2806 has coordinates of $L_x$, $L_y$ with respect to the origin 2804. However, at this point in time, the processor 1562 has not yet identified the left ZRP 2806.

Figure 29:
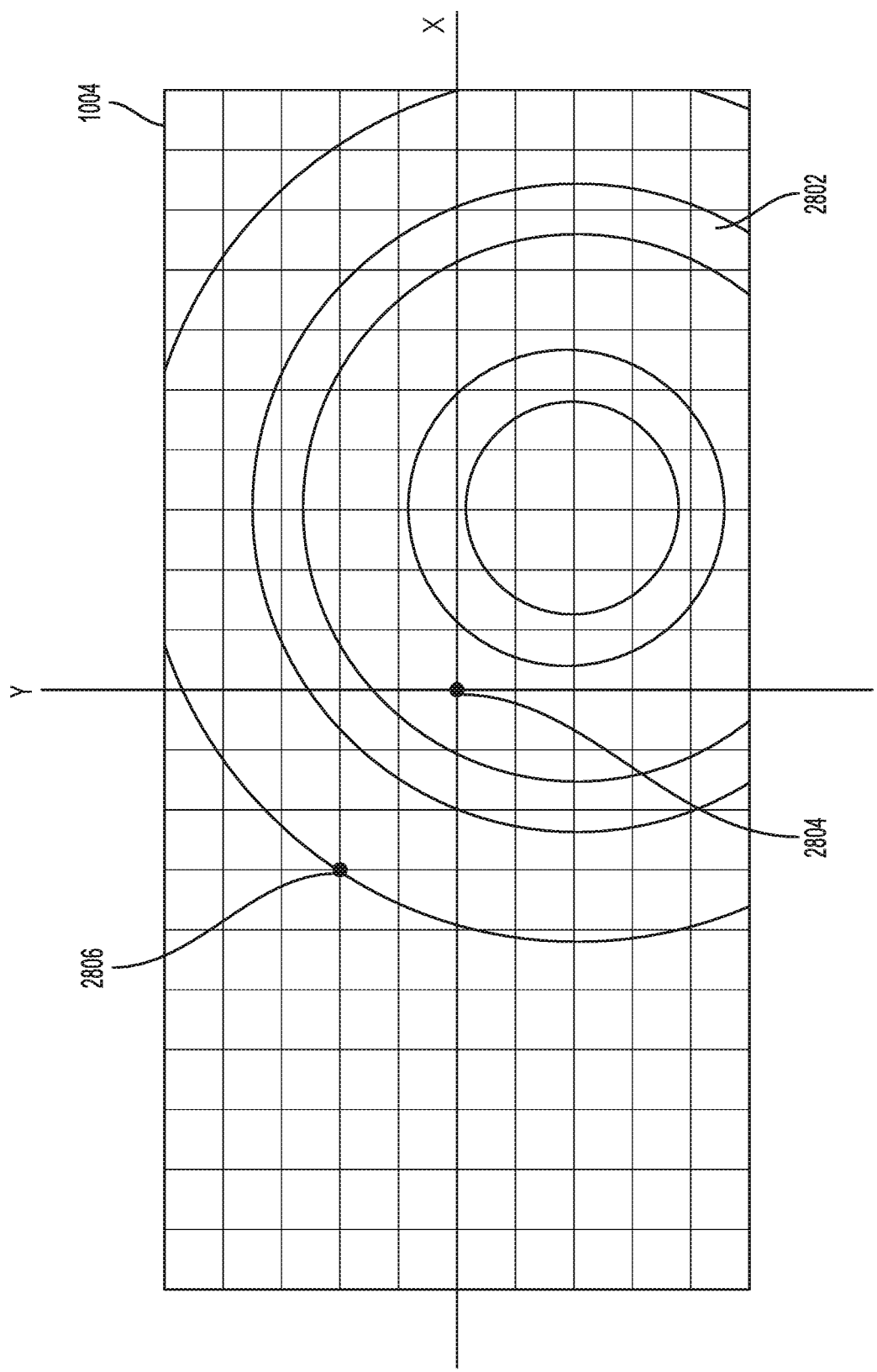

To locate the ZRP 2806, the processor 1562 causes a left zoom lens (e.g., the left front zoom lens 728 and/or the left rear zoom lens 734) to change magnification from the first magnification level to a second magnification level, specifically in this example, from 1× to 2×. FIG. 29 shows a diagram of a second left image including the target 2802 on the pixel grid 1004 with the magnification level doubled. From the first magnification level to the second magnification level, portions of the target 2802 increase in size and expand uniformly away from the left ZRP 2806, which remains stationary with respect to the first and second images. In addition, a distance between the origin 2804 of the pixel grid 1004 and the left ZRP 2806 remains the same.

Figure 30:
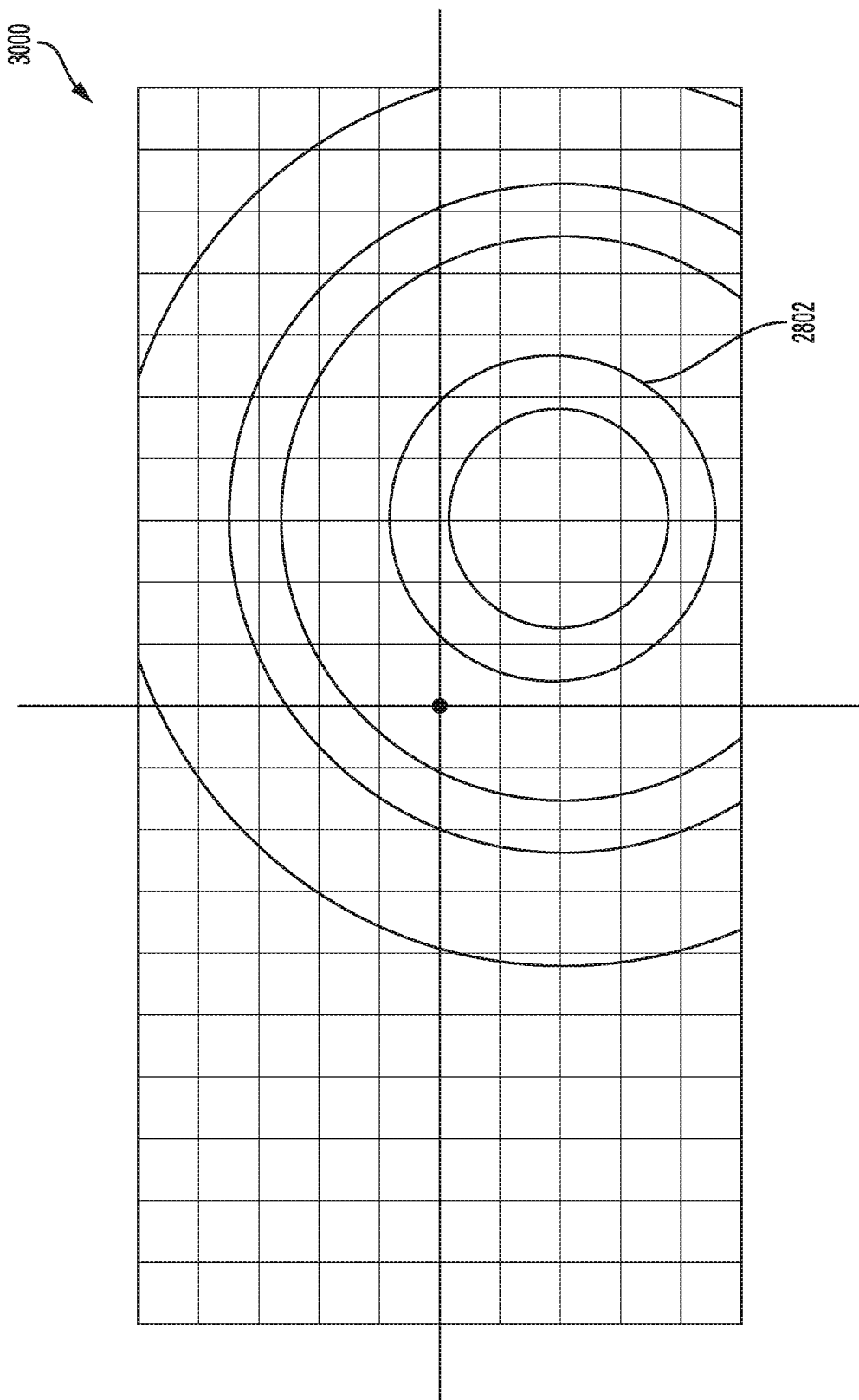

The example processor 1562 synthesizes a digital template image 3000 from the second image shown in FIG. 29. To create the digital template image, the processor 1562 copies the second image shown in FIG. 29 and scales the copied image by the reciprocal of the magnification change from the first to the second magnification. For example, if the magnification change from the first image to the second image was by a factor of 2, then the second image is scaled by ½. FIG. 30 shows a diagram of the digital template image 3000, which includes the template 2802. The template 2802 in the digital template image 3000 of FIG. 30 is scaled to be the same size as the template 2802 in the first left image shown in FIG. 28.

Figure 31:
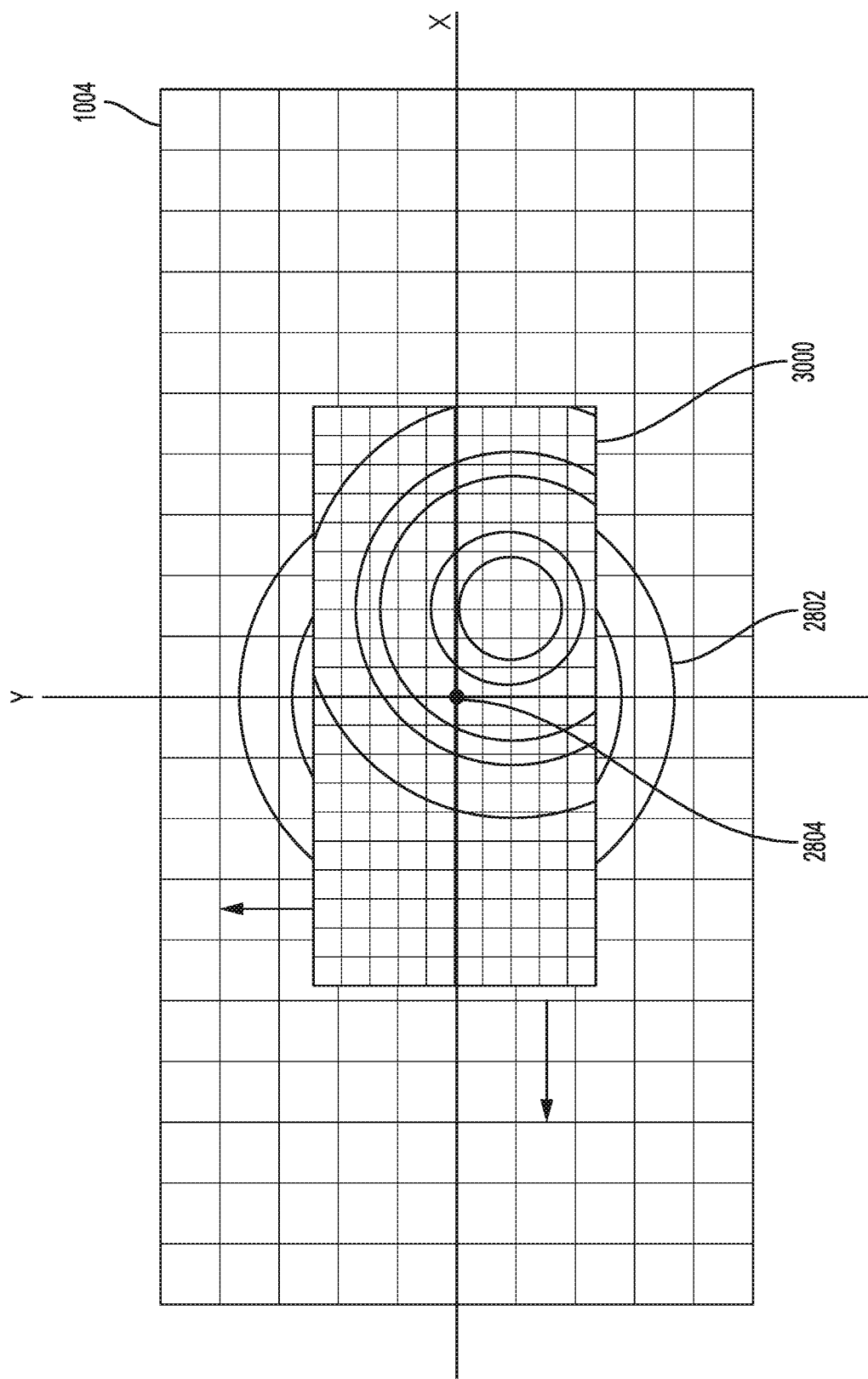

The example processor 1562 uses the digital template image 3000 to locate the left ZRP 2806. FIG. 31 shows a diagram that shows the digital template image 3000 superimposed on top of the first left image (or a subsequent left image recorded at the first magnification level) recorded in the pixel grid 1004. The combination of the digital template image 3000 with the first left image produces a resultant view, as illustrated in FIG. 31. Initially the digital template image 3000 is centered at the origin 2804 of the pixel grid 1004.

The example processor 1562 compares the digital template image 3000 to the underlying template 2802 to determine if they are aligned or matched. The example processor 1562 then moves the digital template image 3000 one or more pixels either horizontally or vertically and performs another comparison. The processor 1562 iteratively moves the digital template image 3000 compiling a matrix of metrics for each location regarding how close the digital template image 3000 matches the underlying template 2802. The processor 1562 selects the location in the matrix corresponding to the best matching metric. In some examples, the processor 1562 uses the OpenCV™ Template Match function.

Figure 32:
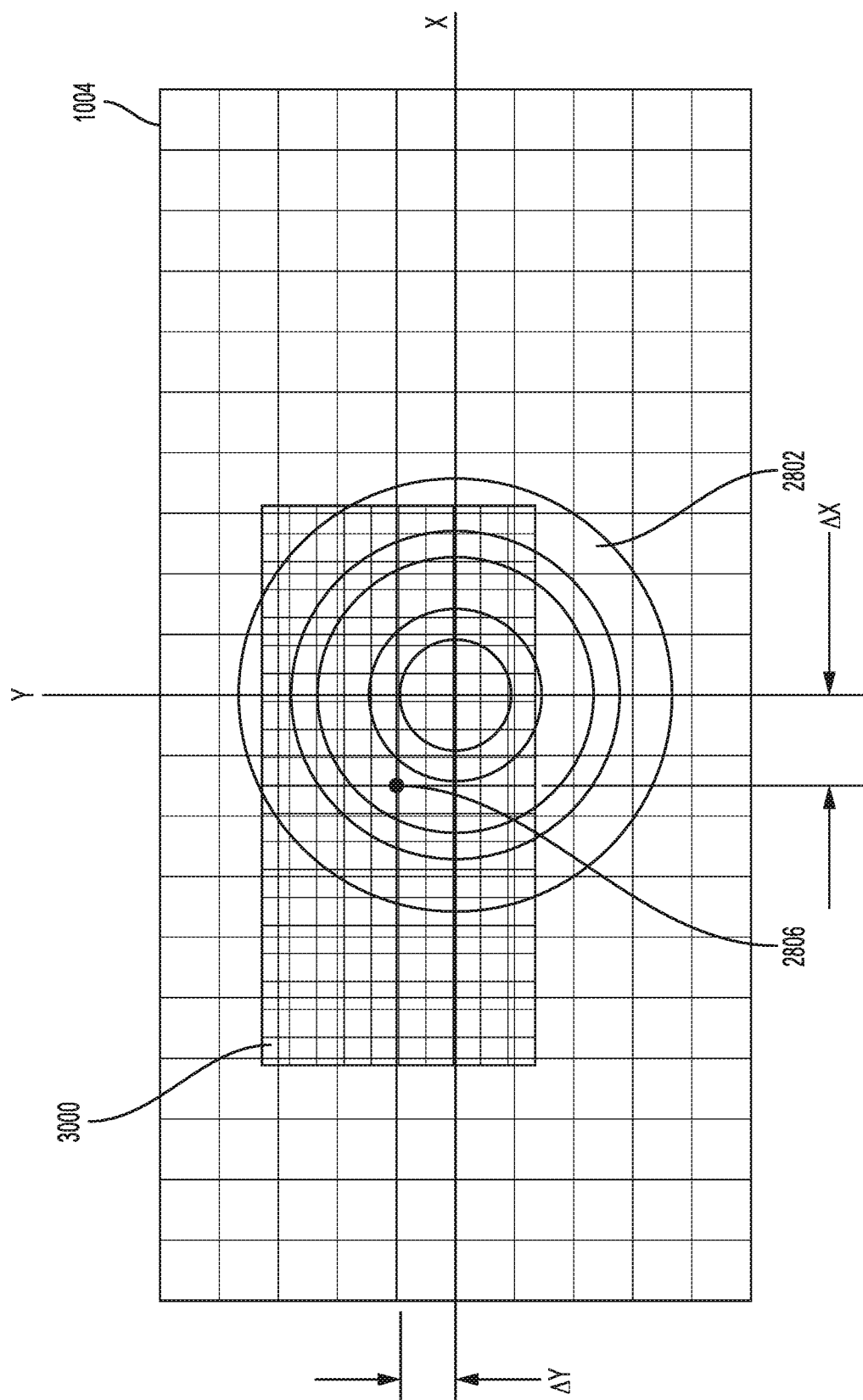

FIG. 32 shows a diagram with the digital template image 3000 aligned with the template 2802. The distance that the digital template image 3000 was moved to achieve optimal matching is shown as Δx and Δy. Knowing the digital template image 3000 was synthesized at a scale of M1/M2 (the first magnification level divided by the second magnification level), the processor 1562 determines the coordinates ($L_x$, $L_y$) of the left ZRP 2806 using Equations (1) and (2) below.

$$Lx = \Delta x/(M1/M2) \qquad \text{Equation (1)}$$

$$Ly = \Delta y/(M1/M2) \qquad \text{Equation (2)}$$

After the coordinates (Lx, Ly) of the left ZRP 2806 are determined, the example processor 1562 selects or determines a pixel subset with an origin that is aligned or coincides with the left ZRP 2806, as discussed above in conjunction with procedure 2500 of FIGS. 25 and 26. In some embodiments, the processor 1562 may use template matching iteratively to converge on a highly accurate ZRP position and/or pixel subset. Further, while the above example discussed locating the left ZRP, the same template matching procedure can be used to locate the right ZRP.

In some embodiments, the above-described template matching program 1560 may be used to align the left and right images. In these embodiments, left and right images are recorded at a magnification level. Both the images may include, for example, the target template 2802 of FIG. 28. A portion of the right image is selected and overlaid with the left image. The portion of the right image is then shifted around the left image by one or more pixels horizontally and/or vertically. The example processor 1562 performs a comparison at each location of the portion of the right image to determine how close a match exists with the left image. Once an optimal location is determined, a pixel set 1006 of the right pixel grid 1002 is determined such that the right image is generally coincident with the left image. The location of the pixel set 1006 may be determined based on how much the portion of the right image was moved to coincide with the left image. Specifically, the processor 1562 uses an amount of movement in the x-direction, the y-direction, and/or the tilt-direction to determine corresponding coordinates for the right pixel set 1006.

2. Right and Left Image Alignment Example

In some embodiments, the example processor 1562 of the information processor module 1408 of FIGS. 14 to 16 displays an overlay of right and left images on the display monitor 512 and/or 514. The processor 1562 is configured to receive user feedback for aligning the right and left images. In this example each pixel data for the right and left images is precisely mapped to a respective pixel of the display monitor 512 using, for example, the graphics processing unit 1564. The display of overlaid left and right images makes any spurious parallax readily apparent to an operator. Generally, with no spurious parallax, the left and right images should almost exactly align.

If an operator detects spurious parallax, the operator may actuate controls 305 or the user input device 1410 to move either the right or left image for alignment with the other of the right and left image. Instructions from the controls 305 may cause the processor 1562 to accordingly adjust the location of the left or right pixel set in real-time, such that subsequent images are displayed on the display monitor 512 reflective of the operator input. In other examples, the instructions may cause the processor 1562 to change a position of one or more of the optical elements 1402 via radial adjustment, rotational adjustment, axial adjustment, or tilting. The operator continues to provide input via controls 305 and/or the user input device 1410 until the left and right images are aligned. Upon receiving a confirmation instruction, the processor 1562 stores a calibration point to a look-up-table reflective of the image alignment at the set magnification level.

Additionally or alternatively, the template match method described above may be used to perform image alignment while focused on a planar target that is approximately orthogonal to a stereo optical axis of the stereoscopic visualization camera 300. Moreover, the template match method may be used to align the left and right views in real-time whenever a "template match-able" scene is in view of both the left and right optical paths. In an example, a template image is copied from a subset of, for instance, the left view, centered upon or near the center of the view. Sampling from the center for an in-focus image ensures that a similar view of the target site 700 will be present in the other view (in this example the right view). For out-of-focus images, this is not the case such that in the current embodiment this alignment method is performed only after a successful auto-focus operation. The selected template is then matched in the current view (or a copy thereof) of the other view (in this example the right view) and only a y-value is taken from the result. When the views are aligned vertically, the y-value of the template match is at or near zero pixels. A non-zero y-value indicates vertical misalignment between the two views and a correction using the same value of y is applied either to select the pixel readout set of the first view or a correction using the negated value of y is applied to the pixel readout set of the other view. Alternatively, the correction can be applied in other portions of the visualization pipeline, or split between pixel readout set(s) and said pipeline.

In some examples, the operator may also manually align a right ZRP with an origin of the pixel grid 1002. For instance, after determining a location of the right ZRP, the processor 1562 (and/or the peripheral input unit interface 1574 or graphics processing unit 1564) causes the right ZRP to be highlighted graphically on a right image displayed by the display monitor 512. The processor 1562 may also display a graphic indicative of the origin of the pixel grid 1002. The operator uses controls 305 and/or the user input device 1410 to steer the right ZRP to the origin. The processor 1562 uses instructions from the controls 305 and/or the user input device 1410 to accordingly move one or more of the optical elements 1402. The processor 1562 may provide a stream of right images in real-time in addition to graphically displaying the current location of the right ZRP and origin to provide the operator updated feedback regarding positioning. The operator continues to provide input via controls 305 and/or the user input device 1410 until the right ZRP is aligned. Upon receiving a confirmation instruction, the processor 1562 stores a calibration point to a look-up-table reflective of positions of the optical elements 1402 at the set magnification level.

3. Comparison of Alignment Error

The example stereoscopic visualization camera 300 produces less alignment error between right and left images compared to known digital surgical microscopes with stereoscopic cameras. The analysis discussed below compares spurious parallax generated by ZRP misalignment for a known digital surgical microscope with camera and the example stereoscopic visualization camera 300. Initially, both cameras are set at a first magnification level with a focal plane positioned on a first position of a patient's eye. Equation (3) below is used to determine working distance ("WD") from each camera to the eye.

$$WD = (IPD/2)/\tan(\alpha) \qquad \text{Equation (3)}$$

In this equation, IPD corresponds to the interpupillary distance, which is approximately 23 mm. In addition, α is one-half of an angle between, for example, the right optical image sensor 746 and the left optical image sensor 748, which is 2.50° in this example. The convergence angle is two times this angle, which is 5°, in this example. The resulting working distance is 263.39 mm.

The cameras are zoomed in to a second magnification level and triangulated on a second position of the patient's eye. In this example the second position is at the same physical distance from the camera as the first position, but presented at the second magnification level. The change in magnification generates spurious horizontal parallax due to misalignment of one or both of the ZRPs with respect to a center of a sensor pixel grid. For the known camera system, the spurious parallax is determined to be, for example, 3 arc-minutes, which corresponds to 0.05°. In Equation (3) above, the 0.05° value is added to α, which produces a working distance of 258.22 mm. The difference in working distance is 5.17 mm (263.39 mm–258.22 mm), which corresponds to the error of the known digital surgical microscope with camera attachment.

In contrast, the example stereoscopic visualization camera 300 is capable of automatically aligning ZRPs to be within one pixel of a center of a pixel set or grid. If the angular field-of-view is 5° and recorded with a 4k image sensor used in conjunction with a 4k display monitor, the one pixel accuracy corresponds to 0.00125° (5°/4000) or 4.5 arc-seconds. Using Equation (3) above, the 0.00125° value is added to α, which produces a working distance of 263.25 mm. The difference in working distance for the stereoscopic visualization camera 300 is 0.14 mm (263.39 mm–263.25 mm). When compared to the 5.17 mm error of the known digital surgical microscope, the example stereoscopic visualization camera 300 reduces alignment error by 97.5%.

In some embodiments, the stereoscopic visualization camera 300 may be more accurate at higher resolutions. In the example above, the resolution is about 4.5 arc-seconds for a 5° field-of-view. For an 8K ultra-high definition system (with 8000 pixels in each of 4000 rows) with a field-of-view of 2°, the resolution of the stereoscopic visualization camera 300 is approximately 1 arc-second. This means that ZRP of the left and right views may be aligned to one pixel or 1 arc-second. This is significantly more precise than known digital microscope systems that have spurious parallax on the order of arc-minutes.

4. Reduction of Other Sources of Spurious Parallax

The above-examples discuss how the example stereoscopic visualization camera 300 reduces spurious parallax as a result of misaligned ZRPs and/or left and right images themselves. The stereoscopic visualization camera 300 may also be configured to reduce other sources of spurious parallax. For example, the stereoscopic visualization camera 300 may reduce spurious parallax due to motion by simultaneously clocking the right and left optical image sensors 746 and 748 to record images at substantially the same instant.

The example stereoscopic visualization camera 300 may also reduce spurious parallax due to dissimilar magnification between the left and right optical paths. For example, the stereoscopic visualization camera 300 may set the magnification level based on the left optical path. The stereoscopic visualization camera 300 may then make automatic adjustments so that the magnification of the right image matches the left. The processor 1562, for example, may use image data to calculate control parameters, for example by measuring a number of pixels between certain features common in the left and right images. The processor 1562 may then equalize the magnification levels of the left and right images by digital scaling, inserting interpolative pixels, and/or deleting extraneous pixels. The example processor 1562 and/or the graphics processing unit 1564 may re-render the right image such that the magnification is matched to the left image. Additionally or alternatively, the stereoscopic visualization camera 300 may include independent adjustment of the left and right optical elements 1402. The processor 1562 may separately control the left and right optical elements 1402 to achieve the same magnification. In some examples, the processor 1562 may first set, for example, the left magnification level then separately adjust the right optical elements 1402 to achieve the same magnification level.

The example stereoscopic visualization camera 300 may further reduce spurious parallax due to dissimilar focus. In an example, the processor 1562 may execute a program 1560 that determines a best focus for each optical path for a given magnification and/or working distance. The processor 1562 first performs a focusing of the optical elements 1402 at a point of best resolution. The processor 1562 may then check the OOF condition at a suitable non-object-plane location and match the focus for the left and right images. The processor 1562 next re-checks the focus at best resolution and adjusts the focus iteratively until both left and right optical elements 1402 focus equally well both on and away from an object plane.

The example processor 1562 may measure and verify optimal focus by monitoring a signal relating to the focus of one or both of the right and left images. For example, a "sharpness" signal is generated by the graphics processing unit 1564 for the left and right images simultaneously and/or in synchronization. The signal changes as focus changes and may be determined from an image-analysis program, an edge detection analysis program, a bandwidth of Fourier transforms of pattern intensity program, and/or a modulation transfer function ("MTF") measurement program. The processor 1562 adjusts a focus of the optical elements 1402 while monitoring for a maximum signal indicative of a sharp image.

To optimize the OOF condition, the processor 1562 may monitor sharpness signals for both the left and right images. If the focus is moved off of the object plane and the signal related to, for example, the left image increases but the signal related to the right image decreases, the processor 1562 is configured to determine the optical elements 1402 are moving out of focus. However, if the signals related to both the right and left images are relatively high and approximately equal, the processor 1562 is configured to determine the optical elements 1402 are properly positioned for focusing.

5. Benefits of Low Spurious Parallax

The example stereoscopic visualization camera 300 has a number of advantages over known digital surgical microscopes as a result of the low spurious parallax between right and left images. For example, almost perfectly aligned left and right images produce an almost perfect stereoscopic display for a surgeon, thereby reducing eye fatigue. This allows the stereoscopic visualization camera 300 to be used as an extension of a surgeon's eyes rather than a cumbersome tool.

In another example, precisely aligned left and right images allow accurate measurements of the surgical site to be digitally taken. For instance, a size of a patient's ocular lens capsule may be measured such that a properly-sized IOL can be determined and accurately implanted. In another instance, a motion of a moving blood vessel may be measured such that an infrared fluorescein overlay can be accurately placed in a fused image. Here, the actual motion velocity is generally not of interest to the surgeon but critical for the placement and real-time adjustment of the overlaid image. Properly matched scale, registration, and perspective of the overlaid images are all important to provide an accurately-fused combined live stereoscopic image and an alternate-mode image.

In some examples, the processor 1562 may enable an operator to draw measurement parameters on the display monitor 512. The processor 1562 receives the drawn coordinates on a screen and accordingly translates the coordinates to the stereoscopic image. The processor 1562 may determine measurement values by scaling the drawn ruler on the display monitor 512 to a magnification level shown in the stereoscopic images. The measurements made by the processor 1562 include point-to-point measurements of two or three locations displayed in the stereoscopic display, point-to-surface measurements, surface characterization measurements, volume determination measurements, velocity verification measurements, coordinate transformations, instrument and/or tissue tracking, etc.

VII. Example Robotics System for the Stereoscopic Visualization Camera

As discussed in connection with FIGS. 5 and 6, an example stereoscopic visualization camera 300 may be connected to a mechanical or robotic arm 506 as part of a stereoscopic visualization platform or stereoscopic robotic platform 516. The example robotic arm 506 is configured to enable an operator to position and/or orient the stereoscopic visualization camera 300 above and/or next to a patient during one or more procedures. Accordingly, the robotic arm 506 enables an operator to move the stereoscopic visualization camera 300 to a desired field-of-view ("FOV") of a target surgical site. Surgeons generally prefer cameras to be positioned and/or orientated in a FOV that is similar to their own FOV to enable easier visual orientation and correspondence between images displayed on a screen and the surgeon's FOV. The example robotic arm 506 disclosed herein provides structural flexibility and assisted control to enable positioning to coincide or to be consistent with a surgeon's FOV without blocking the surgeon's own FOV.

In contrast to the stereoscopic robotic platform 516 disclosed herein, known stereomicroscope holding devices include a simple mechanical arm that is manually moved by an operator. These devices include multiple rotational joints equipped with electromechanical brakes that allow manual repositioning. Further, to allow an operator to change a view easily and without interrupting a procedure, some known holding devices have motorized joints. The motorized joints have various levels of complexity ranging from, for example, simple X-Y positioning up to devices comprising multiple independent rotational joints that manipulate connected rigid arms. During most procedures, it is desirable to obtain views from various directions quickly and easily. However, known stereomicroscope holding devices suffer from one or more problems.

Known stereomicroscope holding devices have limited position, direction, and/or orientation accuracy that is generally limited by the manual ability of the surgeon to manipulate the microscope to view desirable aspects of the image. Holding devices with multiple joints can be especially cumbersome to operate since device manipulation usually results in all the joints moving at the same time. Oftentimes, an operator is watching how an arm moves. After the arm is positioned in a desired location, the operator checks whether the imaging device's FOV is aligned in the desired location. Many times, even if the device is aligned properly, a focus of the device has to be adjusted. Further known stereomicroscope holding devices cannot provide consistent FOV or focal planes with respect to other objects in a targeted surgical site because the devices do not have arm position memories, or the memories are inaccurate as a patient is moved or shifted during a procedure.

Known stereomicroscope holding devices generally have positioning systems in which control is independent of microscope parameters such as object plane focus distance, magnification and illumination. For these devices, coordination of positioning and, for example, zooming must be performed manually. In an example, an operator may reach a lens limit for focusing or changing a working distance. The operator has to manually change a position of the holding device, and then refocus the stereomicroscope.

Known stereomicroscope holding devices are intended solely for observation of a surgical site. The known devices do not determine locations or distances from tissue within a FOV to another object outside the FOV. The known devices also do not provide comparisons of tissue with other objects within a live surgical site to form an alternative viewing modality, such as combining an MM image with a live view. Instead, views from known devices are displayed separately and unaligned from other medical images or templates.

Additionally, known stereomicroscope holding devices have parameters that may not be accurate since there is less emphasis on precision, other than for observation. The requirements in ISO Standard 10936-1:2000(E) "*Optics and optical instruments—Operation microscopes—Part 1: Requirements and test methods*", have largely been derived to achieve reasonable stereoscopic optical image quality using oculars by a normal human operator. The operator's brain combines the views into the mind's image to achieve stereopsis. The views are generally not combined or compared together otherwise. As long as the operator sees an acceptable image and does not suffer from deleterious effects like headaches their needs have been met. The same is true for stereomicroscope holding devices, where some instability, arm sag, and imprecise movement control are permitted. However, when high-resolution digital cameras are used with known holding devices, the structural inaccuracies are readily observable and may detract from their use, especially for microsurgical procedures.

As mentioned above, known stereomicroscope holding devices may sag due to the weight of a camera. Generally, known robotic positioning systems are calibrated to determine compliance or inaccuracy only for the system itself. The stereomicroscope holding devices do not take into account the camera or any inaccuracy between a camera mount and the holding device. Sag is generally compensated by an operator manually positioning the camera while observing an image on a display. In systems that provide motorized motion, changes in sag occur, for example, when a center-of-gravity ("CG") of the camera is re-positioned on an opposite side of a rotational axis of an arm joint, where restoring torque moment about the axis reverses direction. Subsequently any compliance or sag in the mechanism, which is compensated by an operator by adjusting the position, direction, and/or orientation of the camera, now adds to the position, direction, and/or orientation error. In some cases, for example when the camera is moved through a robotic singularity point, the moment reversal occurs quickly and the resulting camera image shifts in error quickly and excessively. Such error limits the ability of known stereomicroscope holding devices to, for example, accurately follow or track tissue or instruments in the site.

Known stereomicroscope holding devices include features for spatially locating and tracking surgical instruments and providing their subsequent representative display on a monitor. However, these known systems require an additional stereoscopic locating camera or triangulation device, prominently located, as well as conspicuous fiducial devices on the instruments. The added devices add to complexity, cost and operational obtrusiveness.

The example stereoscopic robotic platform 516 disclosed herein includes an example stereoscopic visualization camera 300 connected to a mechanical or robotic arm 506. FIGS. 5 and 6 illustrate an example of the stereoscopic robotic platform 516. Stereoscopic images recorded by the camera 300 are displayed via one or more display monitors 512, 514. The robotic arm 506 is mechanically connected to a cart 510, which may also support one or more of the display monitors 512, 514. The robotic arm may include, for example, an articulated robotic arm generally anthropomorphic in size, nature, function, and operation.

Figure 33:
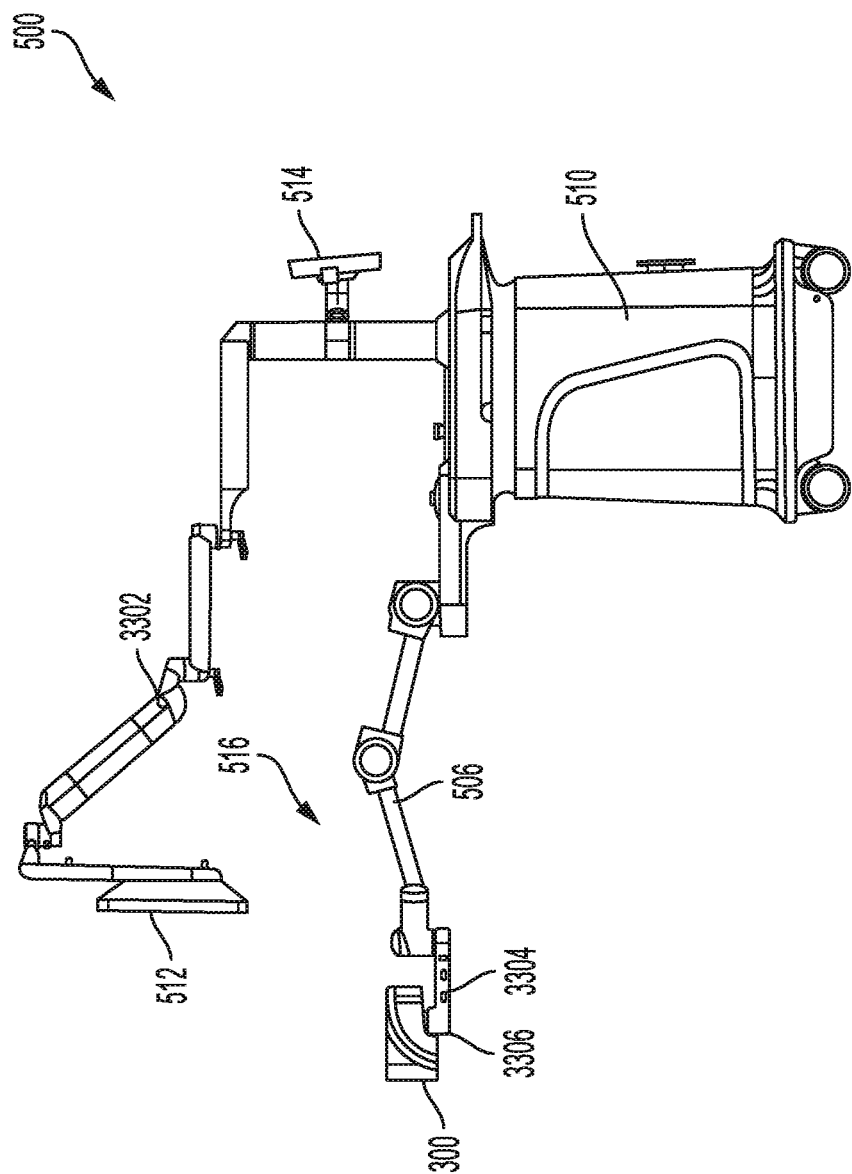
FIG. 33 shows a side-view of the microsurgical environment of FIG. 5, according to an example embodiment of the present disclosure.

FIG. 33 shows a side-view of the microsurgical environment 500 of FIG. 5, according to an example embodiment of the present disclosure. In the illustrated example, the display monitor 512 may be connected to the cart 510 via a mechanical arm 3302 with one or more joints to enable flexible positioning. In some embodiments, the mechanical arm 3302 may be long enough to extend over a patient during surgery to provide relatively close viewing of a surgeon.

FIG. 33 also illustrates a side-view of the stereoscopic robotic platform 516, including the stereoscopic visualization camera 300 and the robotic arm 506. The camera 300 is mechanically coupled to the robotic arm 506 via a coupling plate 3304. In some embodiments, the coupling plate 3304 may include one or more joints that provide for further degrees of positioning and or orientation of the camera 300. In some embodiments, the coupling plate 3304 has to be manually moved or rotated by an operator. For example, the coupling plate 3304 may have a joint that enables the camera 300 to be positioned quickly between having an optical axis along a z-axis (i.e., pointing downward toward a patient) and an optical axis along an x-axis or y-axis (i.e., pointing sideward toward a patient).

The example coupling plate 3304 may include a sensor 3306 configured to detect forces and/or torques imparted by an operator for moving the camera 300. In some embodiments, an operator may position the camera 300 by gripping the control arms 304a and 304b (shown in FIG. 3). After the operator has clutched the control arms 304a and 304b with their hands, the user may position and/or orient the camera 300 with assistance from the robotic arm 306. The sensor 3306 detects a force vector or torque angle provided by the operator. The example platform 516 disclosed herein uses the sensed force/torque to determine which joints of the robotic arm 506 should be rotated (and how quickly the joints should be rotated) to provide assisted movement of the camera 300 that corresponds to the forces/torques provided by the operator. The sensor 3306 may be located at an interface between the coupling plate 3304 and the camera 300 for detecting the forces and/or torques imparted by an operator via the control arms 304.

In some embodiments, the sensor 3306 may include, for example, a six-degrees-of-freedom haptic force-sensing module. In these embodiments, the sensor 3306 may detect translational force or motion in the x-axis, y-axis, and z-axis. The sensor 3306 may also separately detect rotational force or motion around a yaw-axis, a pitch-axis, and a roll-axis. The decoupling of the translational force and the rotational force may enable the stereoscopic robotic platform 516 to more easily calculate direct and/or reverse kinematics for control of the robot arm 506.

The example sensor 3306 may be configured to detect force since the robotic arm 506 may not be movable by a user alone. Instead, the sensor 3306 detects translational and rotational force applied by a user, which is used by the stereoscopic robotic platform 516 to determine which joints to rotate to provide assisted movement control of the robotic arm 506. In other examples, the robotic arm 506 may permit operator movement without assistance, or at least initial assistance. In these other examples, the sensor 3306 detects motion imparted by the user, which is used by the stereoscopic robotic platform 516 to subsequently cause one or more joints to rotate, thereby providing assisted movement. The time between initial detection of motion or the force resulting in the motion, until the stereoscopic robotic platform 516 causes the joints to rotate may be less than 200 milliseconds ("ms"), 100 ms, 50 ms, or as few as 10 ms, where the user does not notice the initial time of unassisted movement of the robotic arm 506.

The example sensor 3306 may output digital data that is indicative of the rotational force/motion and digital data that is indicative of the translational force/motion. In this example, the digital data may have 8, 16, 32, or 64 bit resolution for the detected force/motion in each axis. Alternatively, the sensor 3306 may transmit an analog signal that is proportional to the sensed force and/or motion. The example sensor 3306 may transmit the data at a periodic sampling rate of, for example, 1 ms, 5 ms, 10 ms, 20 ms, 50 ms, 100, ms, etc. Alternatively, the sensor 3306 may provide a near-continuous stream of force/motion data.

In some embodiments, the example sensor 3306 may instead be located in one or more of the control arms 304a and 304b or between the control arms 304a and 304b and the housing 302. In examples, where each of the control arms 304a and 304b include sensor 3306, the example stereoscopic robotic platform 516 may receive two sets of translational and rotational force or motion. In these examples, the stereoscopic robotic platform 516 may average the values from the sensors 3306.

In the illustrated embodiments, a first end of the robotic arm 506 is mounted to the cart 510 while a second, opposite end of the robotic arm is mechanically connected to stereoscopic visualization camera 300 (e.g., a robot end effector). FIG. 33 shows the robotic arm 506 holding the stereoscopic visualization camera 300 in an extended position, such as positioning the stereoscopic visualization camera 300 above a surgical site while keeping the rest of the platform 516 out of the way of a surgeon. The cart 510 is configured to securely hold the stereoscopic robotic platform 516 and is weighted and balanced to prevent tipping under prescribed operating positions.

The example stereoscopic robotic platform 516 is configured to provide the following benefits.

1. Enhanced visualization. Communication between the robotic arm 506 and the stereoscopic visualization camera 300 enables the platform 516 to point and steer the camera 300 to quickly and more accurately visualize surgical sites. For example, the robotic arm 506 can move the camera 300 along its optical axis to extend the range of focusing and zooming beyond that contained in just the camera. The relatively small size of the platform 516 provides for Heads-Up Surgery® in a wider variety of surgical procedures and orientations, thereby improving surgical efficiency and surgeon ergonomics.
2. Enhanced dimensional performance. The example stereoscopic visualization camera 300, with its accurate measurement capability of all points within the stereoscopic image, is configured to communicate the measurement information to the robotic arm 506. The robotic arm 506, in turn, comprises accurate position, direction, and/or orientation determination capability and is registered to the camera 300 such that the dimensions within and between images can be accurately transformed respective to a coordinate system common to the stereoscopic robotic platform 516 and an anatomy of a patient.
3. The quality and accuracy of stereoscopic image data from the stereoscopic visualization camera 300 enables it to be combined with image or diagnostic data from external sources of various modalities to construct fused images. Such fused images can be used by surgeons to perform procedures more accurately and efficiently and to achieve better patient outcomes.
4. The stereoscopic visualization camera 300, the robotic arm 506, and/or image and motion processors (e.g., processor 1408 of FIG. 14) can be programmed for beneficial procedural applications. For example, a specific visualization site position, direction, and/or orientation can be saved, and then returned to later in the procedure. Precise motion paths can be programmed to, for example, follow a specific length or line of tissue. In other examples, pre-programmed waypoints can be set, thereby permitting an operator to change a position and/or orientation of the robotic arm 506 based upon which step is being performed during a medical procedure.

5. The stereoscopic robotic platform 516 provides for intrinsically guided surgery by use and analysis of accurate image position information. Such guidance can be communicated to other devices, such as another robotic system that performs at least portions of a surgical procedure. Components of the stereoscopic robotic platform 516 that share functionality with components of such other devices may be integrated together into a package to achieve efficiencies of performance, accuracy, and cost.

A. Robotic Arm Embodiment

Figure 34:
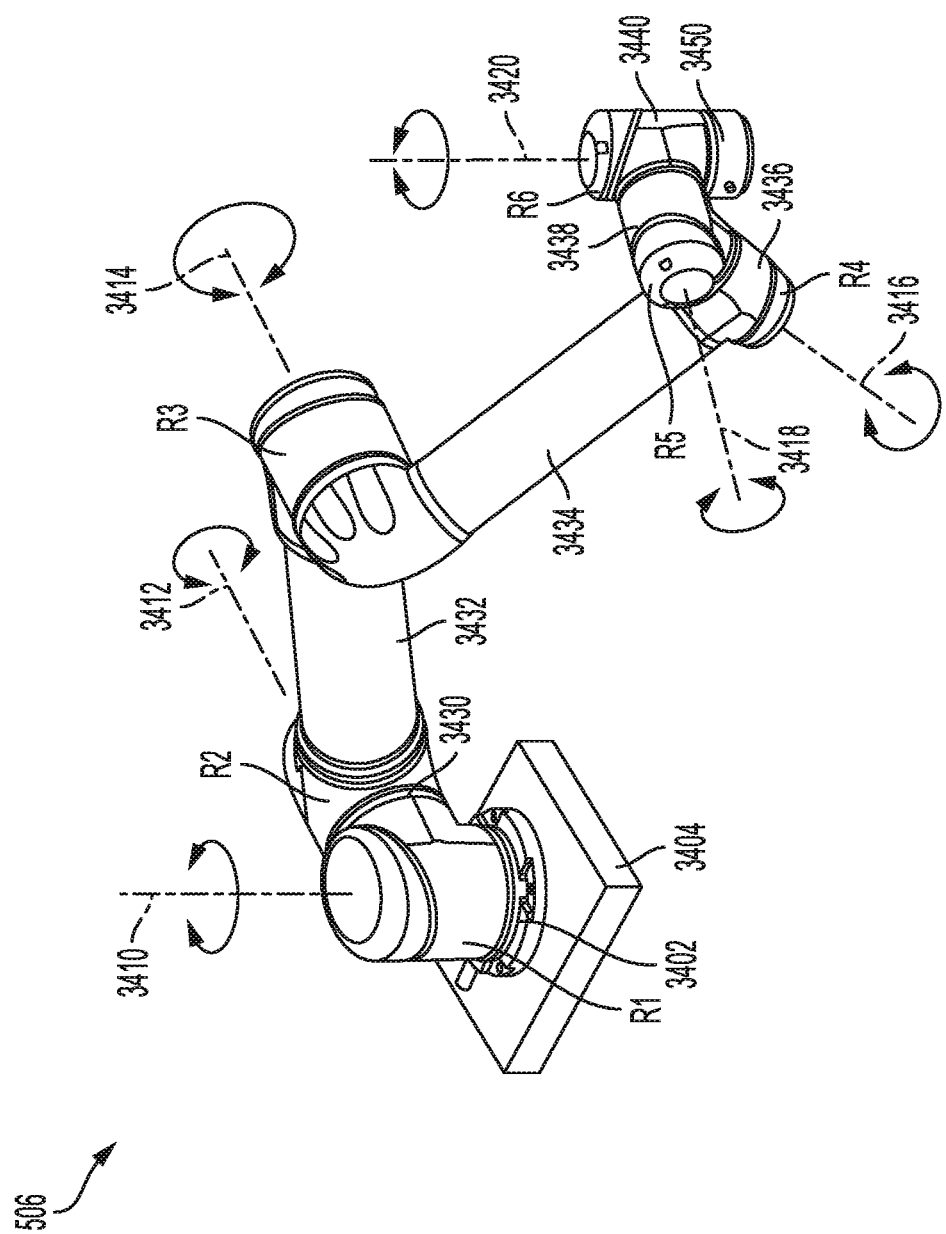
FIG. 34 shows an embodiment of the example robotic arm of FIG. 5, according to an example embodiment of the present disclosure.

FIG. 34 illustrates an embodiment of the example robotic arm 506, according to an example embodiment of the present disclosure. In some embodiments, the robotic arm 506 is similar to or comprises model UR5 from Universal Robots S/A. The exterior surfaces of the robotic arm 506 comprise aluminum and plastic materials, which are compatible for use in an operating room and easily cleaned.

While the robotic arm 506 is described herein as being electromechanical, in other examples, the robotic arm 506 may be mechanical, hydraulic, or pneumatic. In some embodiments, the robotic arm 506 may have mixed actuation mechanisms, for example, using a vacuum chuck with a control valve to hold and manipulate the camera 300. Further, while the robotic arm 506 is described below as including a certain number of joints and links, it should be appreciated that the robotic arm 506 may include any number of joints, any lengths of links, and/or comprise any types of joints, or sensors.

As described herein, the robotic arm 506 is situated and the joints are oriented to provide an unrestricted view of an operating field while providing a 3D stereoscopic display for an operator for any surgical procedure for a patient. Movement of the robotic arm 506 in noncritical motions is provided to be fast enough for an operator to be convenient yet safe. Movement of the robotic arm 506 is controlled during surgery to be meticulous and accurate. In addition, movement of the robotic arm is controlled to be smooth and predictable through the entire range of motion required for a surgical procedure. As described herein, movement of the robotic arm 506 is controllable by remote control or via manual manipulation of the arm itself. In some embodiments, the robotic arm 506 is configured to be positionable with minimal force (e.g., via an assisted guidance feature) with just the use of, for example, a single auricular finger.

In some embodiments, the robotic arm 506 may include mechanically or electronically locking brakes on the joints. The brakes may be engaged once the aim or "pose", which is generally the location and direction, of the camera 300 after it is set by an operator. The robotic arm 506 may include a locking or unlocking switch or other input device to prevent undesired manual or accidental motion. When locked, the example robotic arm provides sufficient stability that enables the stereoscopic visualization camera 300 to provide a stable, clear image. The robotic arm 506 may additionally or alternatively include one or more dampening devices to absorb or attenuate vibrations following movement of the stereoscopic visualization camera 300 to a new pose. The dampening devices may include, for example, fluid-filled linear or rotational dampeners, rubber-based vibration isolation mounting dampeners, and/or tuned mass-spring dampeners. Alternatively, or in addition, the arm 506 may include electromechanical dampening, for example, through the use of a proportional integral derivative ("PID") servo system.

The example robotic arm 506 may be configured with a stowage position to which one or more links are returned for transportation and storage. A stowage position enables the robotic arm to be transported and stored in a concise footprint yet deployed with a long reach required in some surgical procedures. Cables, such as those routed for the stereoscopic visualization camera 300, are provided along the robotic arm 506 so as to avoid interference with a surgical procedure.

In the illustrated embodiment of FIG. 34, the robotic arm 506 includes six joints, labeled R1, R2, R3, R4, R5, and R6. In other embodiments, the robotic arm 506 may include fewer or additional joints. Additionally, in some embodiments, at least some of the joints R1 to R6 have rotational motion capabilities of +/−360°. The rotational motion may be provided by an electromechanical subsystem that includes, for each joint, an electric motor configured to drive a mechanical rotational joint through one or more anti-backlash joint gearboxes. Each of the joints R1 to R6 may include one or more rotational sensors to detect joint position. Further, each joint may include a slip clutch and/or an electromechanical brake.

Each of the joints R1 to R6 may have an overall repeatability of motion (with the camera 300 attached) of approximately +/−1/10 of a millimeter ("mm"). The joints may be have variable rotational speeds that can be controlled between 0.5° to 180° per second. Together, this translates to camera movement between 1 mm per second to 1 meter per second. In some embodiments, the stereoscopic robotic platform 516 may have speed governors for one or more of the joints R1 to R6 that are in place during surgical procedures. Each of the joints R1 to R6 may be electrically connected to a power source and/or command line in a controller of the robotic arm 506. Wires for power and command signals may be routed internally within the joints and links. Further, one or more of the joints may include dampeners, such as o-rings for connection to links. The dampeners may, for example, reduce or absorb vibrations in the robotic arm 506, vibrations from the cart 510, and/or vibrations imparted via the stereoscopic visualization camera 300.

Joint R1 includes a base joint that is mechanically coupled to a flange 3402, which is secured to a stationary structure 3404. The flange 3402 may include any type of mechanical connector. The stationary structure 3404 may include, for example, the cart 510 of FIG. 5, a wall, a ceiling, a table, etc. The joint R1 is configured to rotate around a first axis 3410, which may include the z-axis.

Joint R1 is connected to joint R2 via a link 3430. The example link 3430 includes a cylinder or other tubular structure configured to provide structural support for the downstream sections of the robotic arm 506. The link 3430 is configured to provide a rotational secure connection with joint R2 to enable joint R2 to rotate while the link 3430 is held in place by its connection to the joint R1. Joint R2 may include, for example, a shoulder joint configured to rotate around an axis 3412. The example axis 3412 is configured to be perpendicular (or substantially perpendicular) to axis 3410. The axis 3412 is configured to be within an x-y plane given the rotation of the joint R1 around the z-axis.

Joint R2 is mechanically coupled to joint R3 via link 3432. The link 3432 is configured to have a greater length than the link 3430 and is configured to provide structural support for downstream portions of the robotic arm 506. Joint R3 may include, for example, an elbow joint. Together with joint R2, joint R3 provides extensible positioning and/or orientating of the robotic arm 506. The joint R3 is configured to rotate around an axis 3414, which is perpendicular or orthogonal to the axis 3410 and parallel to the axis 3412.

Joint R3 is connected to joint R4 via link 3434, which provides structural support for downstream portions of the robotic arm 506. The example joint R4 may be, for example, a first wrist joint configured to provide rotation around axis 3416, which may be orthogonal to the axes 3412 and 3414. Joint R4 is mechanically connected to joint R5 via link 3436. Joint R5 may be a second wrist joint configured to provide rotation around an axis 3418, which is orthogonal to axis 3416. Joint R5 is mechanically connected to joint R6 via link 3438. Joint R6 may be a third wrist joint configured to rotate around axis 3420, which is orthogonal to the axis 3418. Together, the wrist joints R4 to R6 provide precise flexibility in positioning the stereoscopic visualization camera 300 described herein.

The example robotic arm 506 includes a connector 3450. The example connector 3450 is connected to joint R6 via link 3440. In some embodiments, the example link 3440 may include a sleeve that enables joint R6 to rotate the connector 3450. As discussed herein, the connector 3450 may be configured to mechanically couple to the coupling plate 3304 or the stereoscopic visualization camera 300 directly when a coupling plate is not used. The connector 3450 may include one or more screws to secure the robotic arm 506 to the coupling plate 3304 and/or the stereoscopic visualization camera 300.

In some embodiments, the robotic arm 506 of the illustrated example may have a maximum reach of 85 mm, in an orientation roughly similar to a human arm. The arm 506 may have a payload capacity of 5 kilograms. Further, the arm 506 may be configured as a "collaborative" device to enable safe operation in the proximity of humans. For example, the maximum force that the robotic arm 506 can apply to external surfaces is controlled. Should a portion of the robot arm unexpectedly contact another object, the collision is detected, and motion is instantly ceased. During an emergency stop situation where for example, power is lost the joints R1 to R6 can be back-driven or manually rotated such that an operator can grab part of the robotic system and swing it out of the way. For example, slip clutches within the joints limit the maximum torque the joint motor can apply rotationally to the arm 506 during operation. When powered off, the slip clutches of the joints slip when manually manipulated to allow an operator to quickly move the robotic arm 506 out of the way.

Figure 35:
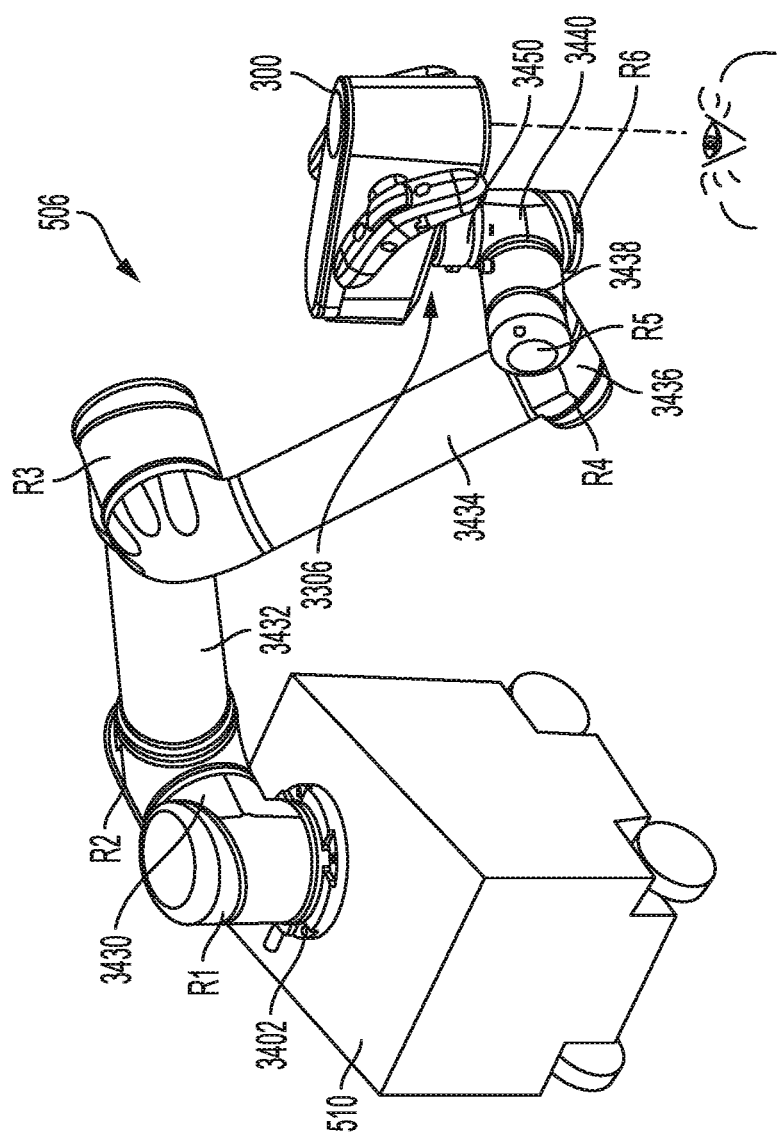
FIG. 35 shows a diagram of the robotic arm of FIGS. 33 and 34 connected to a cart, according to an example embodiment of the present disclosure.

FIGS. 35 to 40 illustrate example configurations of the robotic arm 506 and the stereoscopic visualization camera 300, according to example embodiments of the present disclosure. FIG. 35 shows a diagram of the robotic arm 506 connected to the cart 510 via the flange 3402. In this example, the stereoscopic visualization camera 300 is connected directly to the connector 3540. In this embodiment, the connector 3540 and/or the stereoscopic visualization camera 300 may include the sensor 3306 of FIG. 33 for sensing translational and/or rotational force/motion imparted by an operator on the stereoscopic visualization camera 300. If the connector 3540 includes the sensor 3306, the output force/motion data may be transmitted through the robotic arm 506 to a controller. If, for example, the sensor 3306 is located on the stereoscopic visualization camera 300, the output data may be transmitted with control data to a separate controller. In some embodiments, a controller may be provided in the cart 510 or separately at a server.

Figure 36:
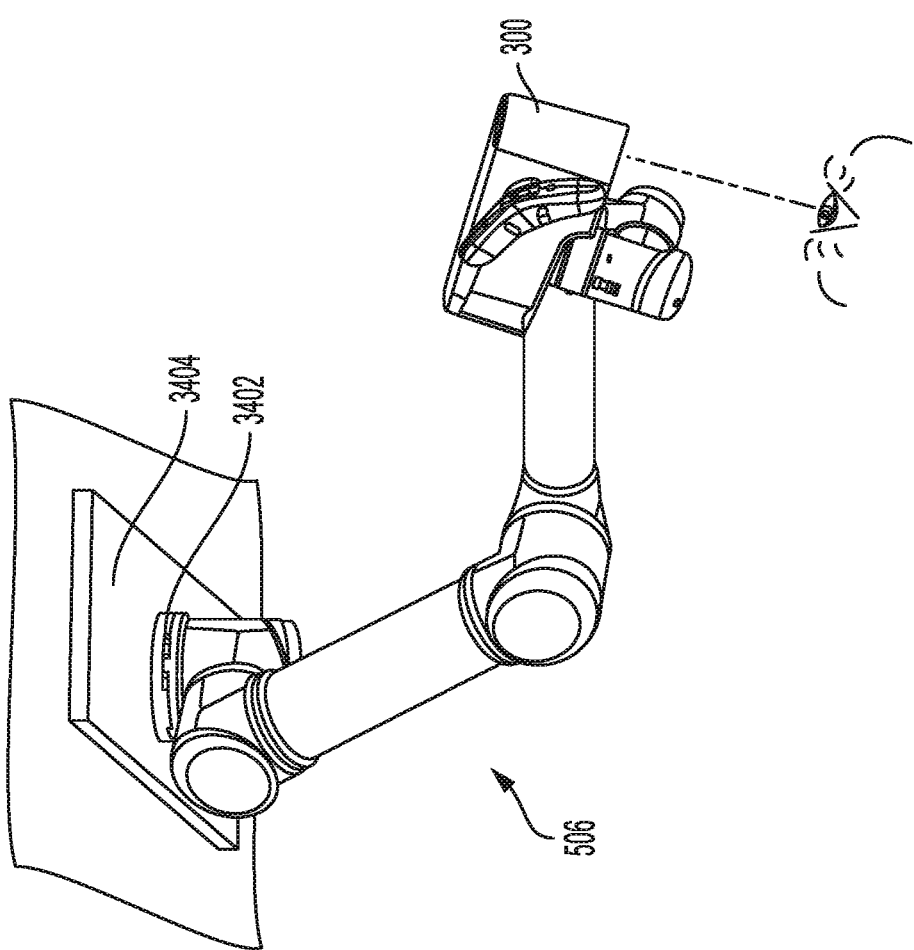
FIG. 36 shows a diagram where the robotic arm of FIGS. 33 and 34 is mounted to a ceiling plate, according to an example embodiment of the present disclosure.

FIG. 36 shows an embodiment where the robotic arm 506 is mounted to a ceiling plate 3404 via the flange 3402. The robotic arm may be suspended from the ceiling of an operating room to reduce floor space clutter. The robotic arm 506, including the joints, can be positioned above and traversed from the area where surgical activity is being performed, out of the way of the surgeon and operating room staff, yet still providing functional positioning and/or orientating of the camera 300 while providing a clear view of the display monitors 512 and 514.

Figure 37:
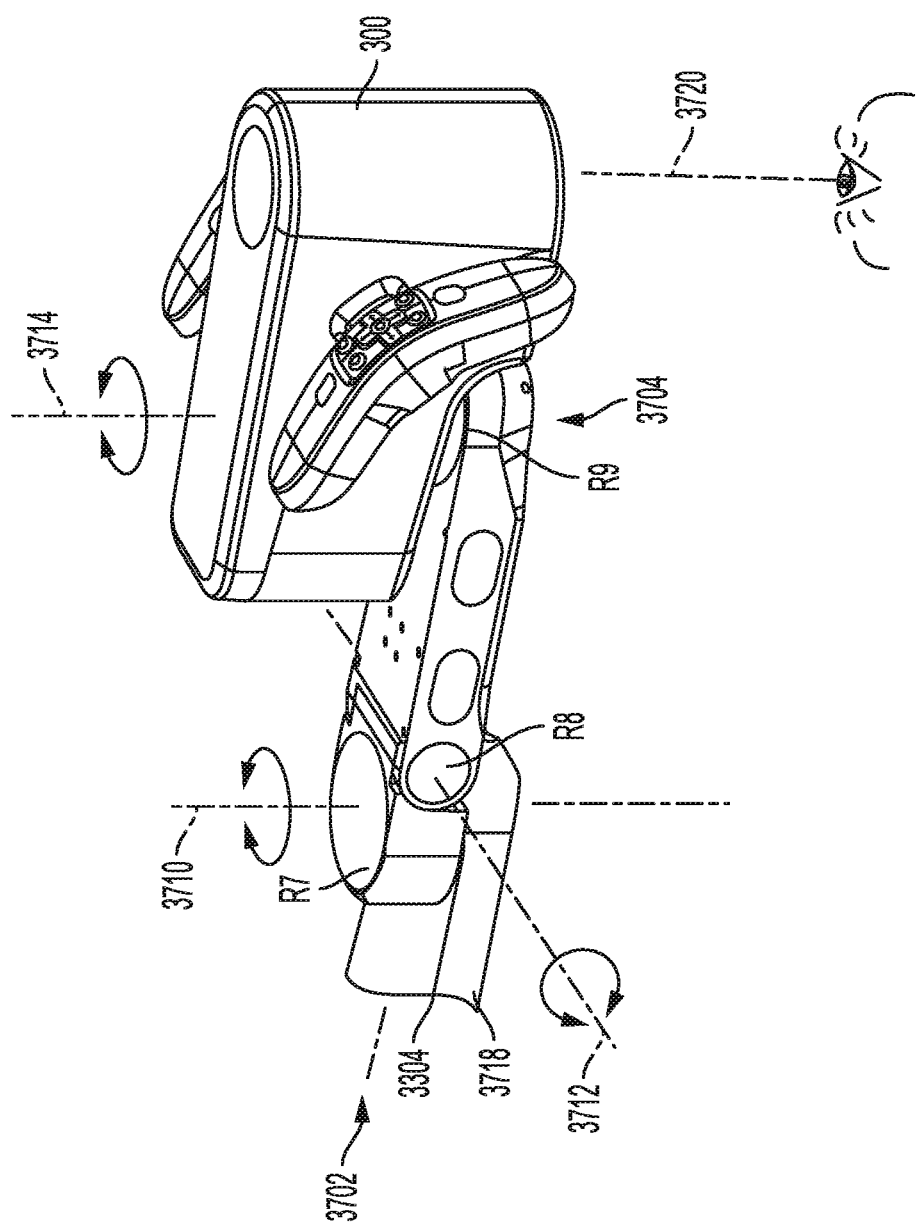
FIG. 37 shows an embodiment of a coupling plate for the robotic arm, according to an example embodiment of the present disclosure.

FIG. 37 shows an embodiment of the coupling plate 3304. In the illustrated example, a first end 3702 of the coupling plate 3304 is connected to the connector 3450 of the robotic arm 506. A second end 3704 of the coupling plate 3304 is connected to the stereoscopic visualization camera 300. The example coupling plate 3304 is configured to provide additional degrees of freedom for moving the stereoscopic visualization camera 300. The coupling plate 3304 also extends the maximum reach of the robotic arm 506. The coupling plate 3304 may have a length between 10 cm to 100 cm.

The coupling plate 3304 may include one or more joints. In the illustrated example, the coupling plate 3304 includes joints R7, R8, and R9. The example joints are mechanical joints that provide rotation around respective axes. The joints R7 to R9 may comprise rotatable latching mechanisms that are movable after an operator actuates a release button or lever. Each joint R7 to R9 may have its own release button, or a single button may release each of the joints R7 to R9.

The joints R7 to R9 may be connected together via respective links. In addition, a link 3718 is provided for connection to the connector 3450 of the robotic arm 506. Joint R7 is configured to rotate around axis 3710, while joint R8 is configured to rotate around axis 3712, and joint R9 is configured to rotate around axis 3714. The axes 3710 and 3714 are parallel with each other and orthogonal to the axis 3712. Joints R7 and R9 may be configured to provide +/−360° rotation. In other examples, joints R7 and R9 may provide +/−90°, +/−180° rotation or +/−270° rotation around the respective axes 3710 and 3714. Joint R8 may provide +/−90° rotation around the axis 3712. In some examples, joint R8 may only be set at +90°, 0°, and −90°.

In some embodiments, joints R7 to R9 may include motors that provide continuous movement. Joints R7 to R9 may also include control devices, such as switches or position sensors that communicate or provide data indicative or a rotational position. In this manner, the joints R7 to R9 may be similar to the joints R1 to R6 of the robotic arm 506 and provide for assisted movement and positioning sensing for feedback control. Power and control for joints R7 to R9 may be provided via wires routed through the robotic arm 506, power/wire connectors within the connector 3450, and/or wires external to the robotic arm 506.

Figure 38:
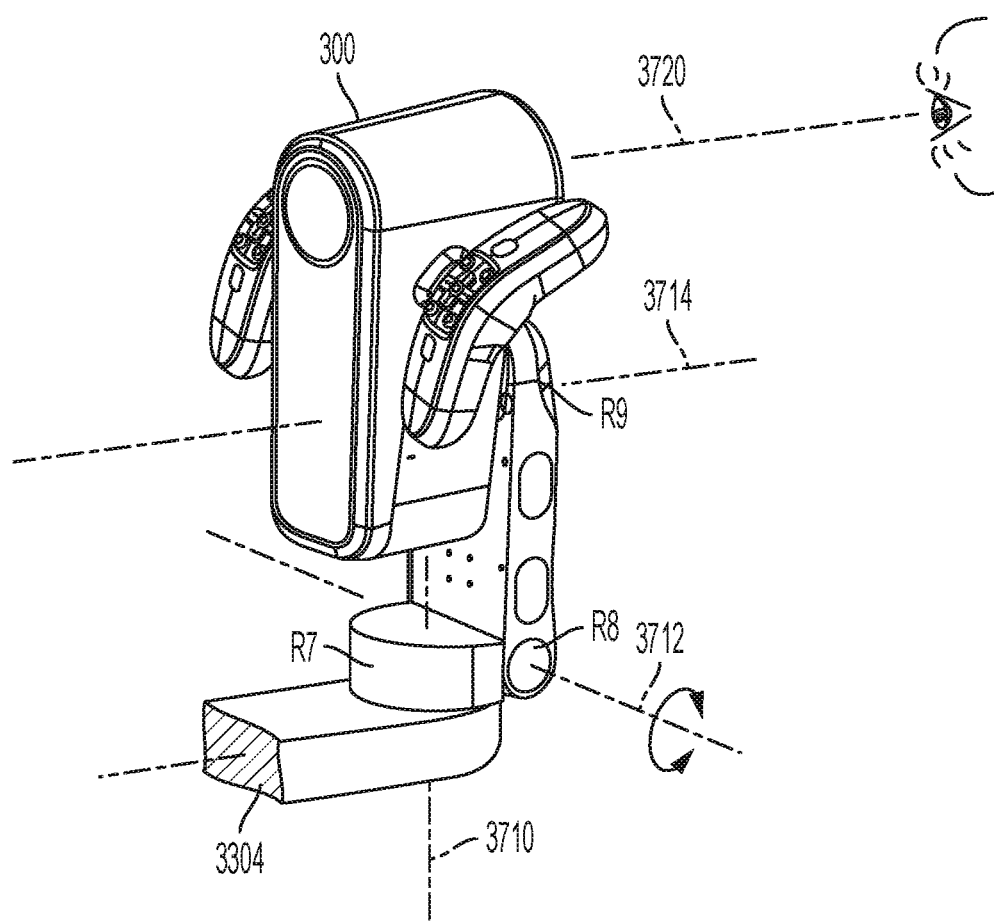
FIGS. 38 to 40 show diagrams of the coupling plate in different rotational positions, according to example embodiments of the present disclosure.

FIG. 37 shows an example where the stereoscopic visualization camera 300 is positioned in a horizontal orientation such that an optical axis 3720 is provided along a z-axis. The horizontal orientation may be used for imaging patients that are lying down. In contrast, FIG. 38 shows an embodiment where joint R8 is rotated by 90° to position the camera 300 in a vertical orientation such that the optical axis 3720 is provided along an x-axis or y-axis that is orthogonal to the x-axis. The vertical orientation may be used for imaging patients that are sitting. It should be appreciated that joint R8 enables the stereoscopic visualization camera 300 to quickly be re-orientated between horizontal and vertical positions based on the procedure.

In the illustrated examples of FIGS. 36 and 37, the example sensor 3306 may be located at, for example, the connector 3450 of the robotic arm (with the connection of the coupling plate 3304) and/or at the first end 3702 of the coupling plate (at the connection with the connector 3450). Alternatively or additionally, the example sensor 3306 may be located at, for example, the second end 3704 of the coupling plate (at the connection with the camera 300) and/or at the camera 300 at the connection with the second end 3704 of the coupling plate 3304.

Figure 39:
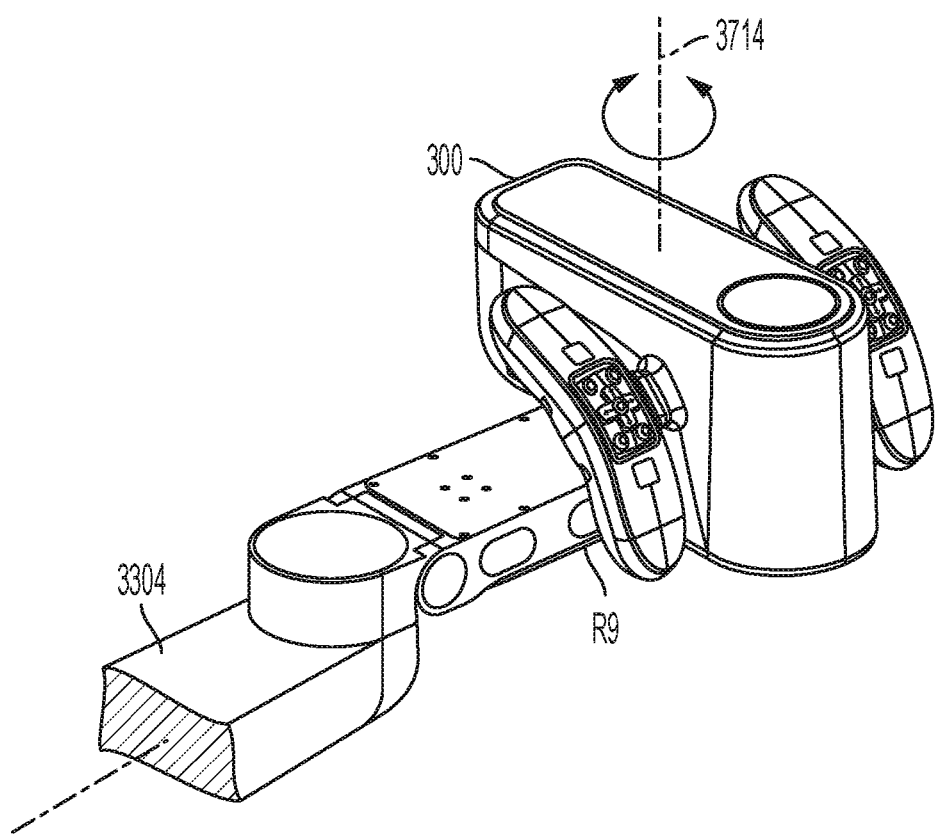
Figure 40:
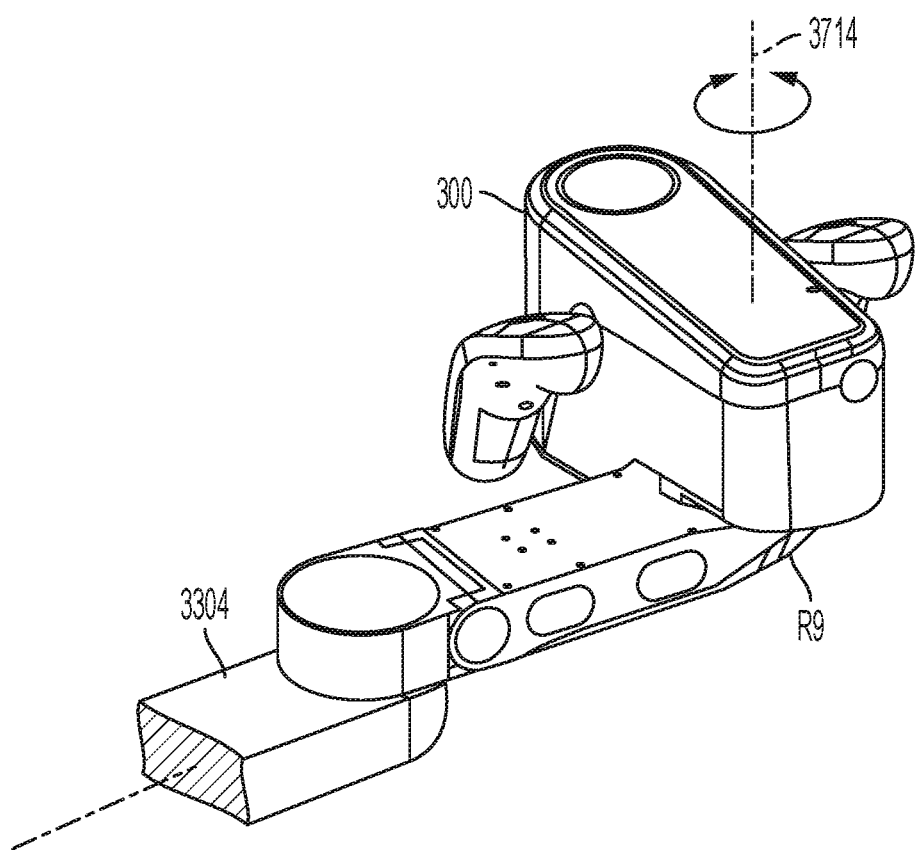

FIGS. 39 and 40 show the stereoscopic visualization camera 300 in the horizontal orientation and rotated +90° around the axis 3714 of joint R9. FIG. 40 shows an example of the stereoscopic visualization camera 300 in the horizontal orientation and rotated −90° around the axis 3714 of joint R9.

As illustrated in FIGS. 34 to 40, the example robotic arm 506 is configured to provide support for the stereoscopic visualization camera 300 and allow for precise positioning and/or orientating and aiming of the camera's optical axis. Since the stereoscopic visualization camera 300 does not have oculars and does not need to be oriented for a surgeon's eyes, there are many desirable positions and/or orientations for imaging that may be achieved that were not previously practical. A surgeon can perform with the view most optimal for a procedure rather than that most optimal for his orientation to the oculars.

The example robotic arm 506, when used with the stereoscopic visualization camera 300, enables a surgeon to see around corners and other locations that are not readily visible. The robotic arm 506 also enables patients to be placed into different positions including supine, prone, sitting, semi-sitting, etc. Accordingly, the robotic arm 506 enables the patient to be placed in the best position for a specific procedure. The example robotic arm 506, when used with the stereoscopic visualization camera 300 can be installed for the least obtrusive position. The arm 506 and camera 300 accordingly provide a surgeon numerous possibilities for visual locations and orientations while being conveniently located and oriented out of the way.

The arrangement of the links and joints of the robotic arm 506 and/or the coupling plate 3304, along with the motorized six (or nine) degrees of freedom generally allow the camera 300 to be positioned as desired with the link and joint configuration not unique to the pose of the camera. As discussed in more detail below, the joints and links of the arm 506 and/or the plate 3304 may be manually repositioned and/or reoriented without changing the pose or FOV of the camera 300. This configuration allows, for example, an elbow joint to be moved out of an occluding line of sight without changing the view of the surgical site through the camera 300. Further, a control system can determine the location and pose of the camera 300 and calculate and display alternative positions and/or orientations of the robotic arm 506 to, for example, avoid personnel or display occlusion. Use of the various positions and/or orientations of the coupling plate 3304 along with an ability of an image processor to flip, invert, or otherwise reorient the displayed image permit even more robot arm 506 positions and/or orientations.

The robotic arm 506 and/or coupling plate 3304 is/are generally situated, and the joints are positioned such that joint singularities are avoided in any general movement. The avoidance of joint singularities provides better robotic control of hysteresis and backlash. Further, the lengths and configurations of the links and joints of the robotic arm 506 and/or the coupling plate 3304 provide for smooth movement along most any desirable motion paths. For example, repositioning and/or reorienting of the robotic arm 506 enables it to change the direction of the camera 300 view of a target point within a surgical site without changing a focal point, thereby permitting a surgeon to view the same target point from different directions/orientations. In another example, the robotic arm 506 is capable of changing a working distance to a target point without changing a focal point by translating the camera 300 along the line of sight towards or away from the target point. Numerous similar motion paths are attainable as desired using the robotic arm 506 and/or the coupling plate 3304 with the stereoscopic visualization camera 300 of the stereoscopic robotic platform 516.

B. Robotic Control Embodiment

Figure 41:
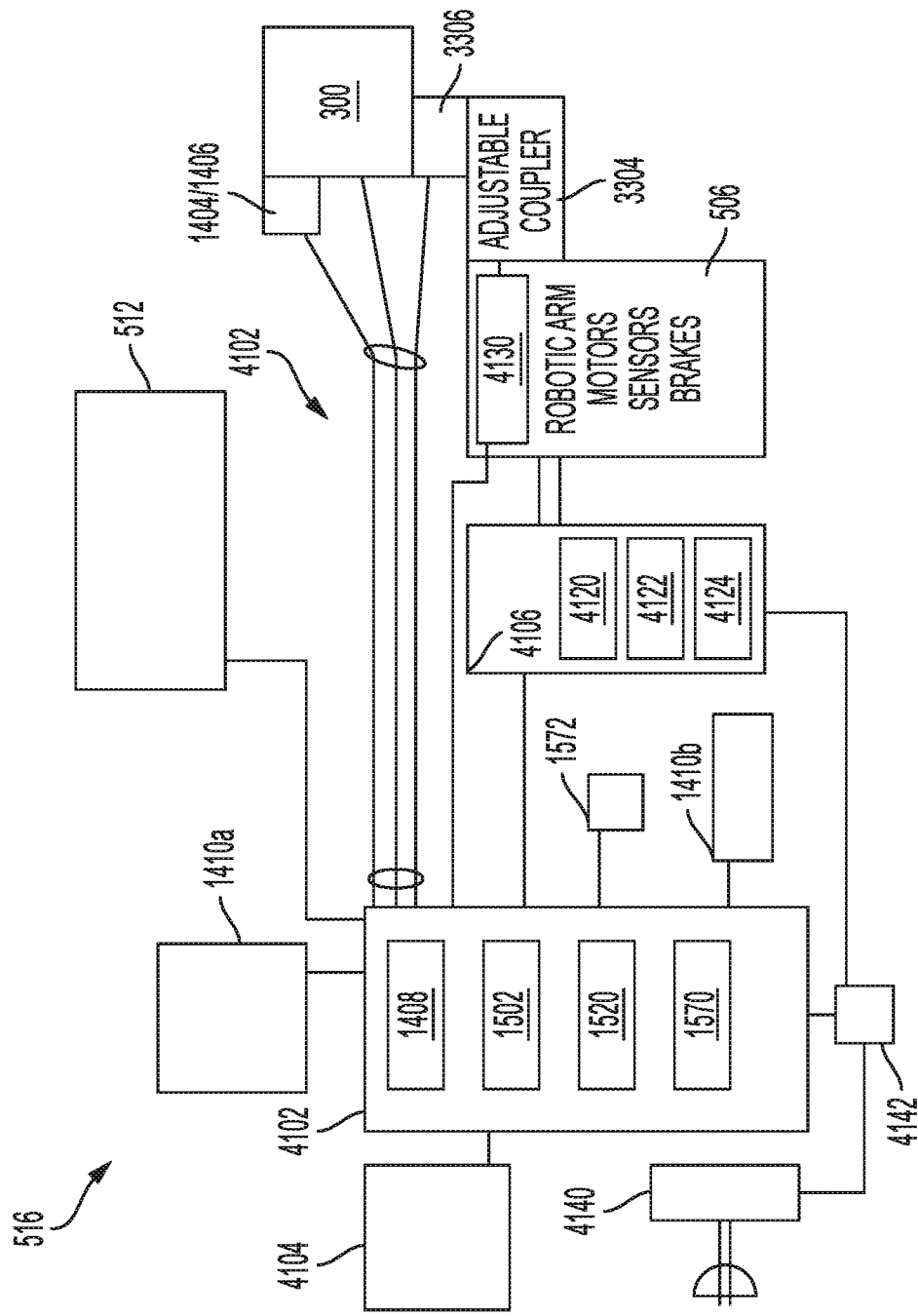
FIG. 41 illustrates an embodiment of the stereoscopic robotic platform of FIGS. 3 to 40, according to an example embodiment of the present disclosure.

The example robotic arm 506 and/or the coupling plate 3304 of FIGS. 34 to 40 may be controlled by one or more controllers. FIG. 41 illustrates an embodiment of the stereoscopic robotic platform 516 of FIGS. 3 to 40, according to an example embodiment of the present disclosure. The example stereoscopic robotic platform 516 includes the stereoscopic visualization camera 300 and corresponding image capture module 1404 and motor and lighting module 1406 described in connection with FIGS. 14 and 15.

In the illustrated embodiment, the stereoscopic robotic platform 516 includes a server or processor 4102 that is located remote from the stereoscopic visualization camera 300. The processor 4102 may include, for example, a laptop computer, a workstation, a desktop computer, a tablet computer, a smartphone, etc. configured with one or more software programs defined by instructions stored in the memory 1570 that, when executed by the processor 4102, cause the processor 4102 to perform the operations described here. The example processor 4102 in this example is configured to include (or perform the operations described in connection with) the information processor module 1408, the image sensor controller 1502, and/or the motor and lighting controller 1520 of FIGS. 14 to 16.

In some examples, at least some of the operations of the image sensor controller 1502, and/or the motor and lighting controller 1520 may be shared with the image capture module 1404 and motor and lighting module 1406, respectively. For example, the processor 4102 may generate commands for changing focus, magnification, and/or working distance, and via a first portion of the motor and lighting controller 1520, and a second portion of the motor and lighting controller 1520 within the motor and lighting module 1406 controls the drivers 1534 to 1552. Additionally or alternatively, a first portion of the information processor module 1408 located operationally in the processor 4102 is configured to receive individual left/right images and/or stereoscopic images from a second portion of the information processor module 1408 in the image capture module 1404. The first portion of the information processor module 1408 may be configured for processing the images for display on one or more display monitors 512 and/or 514 including, visually fusing images with graphical guidelines/text, image overlays from a MM machine, X-ray, or other imaging device, and/or fluorescence images.

The processor 4102 is electrically and/or communicatively coupled to the image capture module 1404 and motor and lighting module 1406 of the stereoscopic visualization camera 300 via a wire harness 4102. In some embodiments, the harness 4102 may be external to the robotic arm 506. In other embodiments, the wire harness 4102 may be internal or routed through the robotic arm. In yet other embodiments, the image capture module 1404 and motor and lighting module 1406 may communicate wirelessly with the processor 4102 via Bluetooth®, for example.

The example processor 4102 is also electrically and/or communicatively coupled to the sensor 3306 via the wire harness 4102. The processor 4102 is configured to receive, for example, rotational and/or translational output data from the sensor 3306. The data may include digital data and/or analog signals. In some embodiments, the processor 4102 receives a near-continuous stream of output data from the sensor 3306 indicative of detected force and/or motion. In other examples, the processor 4102 receives output data at periodic sampled intervals. In yet other examples, the processor 4102 periodically transmits a request message requesting the output data.

In the illustrated example, the processor 4102 is further communicatively coupled to at least one of a display monitor 512, input devices 1410*a*, 1410*b*, and other devices/systems 4104 (e.g., medical imaging devices such as an X-ray machine, a computed tomography ("CT") machine, a magnetic resonance imaging ("MRI") machine, a camera a workstation for storing images or surgical guidelines, etc.). The input device 1410*a* may include a touch screen device and the input device 1410*b* may include a foot switch. The touch screen input device 1410*a* may be integrated with the display monitor 512 and/or provided as a separate device on, for example, the cart 510 of FIG. 5. The example display monitor 512 is configured to display one or more user interfaces that include a stereoscopic video (or separate two-dimensional left and right videos) of a target surgical site recorded by the stereoscopic visualization camera 300.

The touch screen input device 1410*a* is configured to provide one or more user interfaces for receiving user inputs related to the control of the stereoscopic visualization camera 300, the coupling plate 3304, and/or the robotic arm 506. The input device 1410*a* may include one or more graphical control buttons, sliders, etc. that are configured to enable an operator to specify, set, or otherwise provide instructions for controlling a working distance, focus, magnification, source and level of illumination, filters, and/or digital zoom of the stereoscopic visualization camera 300. The input device 1410*a* may also include one or more control buttons to enable an operator to select surgical guidance graphics/text, a video and/or an image for fusing and/or otherwise superimposing on the displayed stereoscopic video displayed on the display monitor 512. The input device 1410*a* may also include a user interface that is configured to enable an operator input or create a surgical procedure visualization template. The input device 1410*a* may further include one or more control buttons for controlling the robotic arm 506 and/or the coupling plate 3304, including options for controlling operational parameters such as speed, motion, deployment/stowing, calibration, target-lock, storing a view position, and/or changing or inputting a new orientation of the camera 300. The user interface controls for the robotic arm 506 and/or the coupling plate 3304 may include controls for moving the camera 300, which are translated into commands for the individual joints R1 to R9. Additionally or alternatively, the user interface controls for the robotic arm 506 and/or the coupling plate 3304 may include controls for moving each of joints R1 to R9 individually. Inputs received via the input device 1410*a* are transmitted to the processor 4102 for processing.

The example foot switch input device 1410 may include, for example, a food pedal configured to receive inputs for controlling a position of the stereoscopic visualization camera 300, the coupling plate 3304, and/or the robotic arm 506. For example, the foot plate input device 1410*b* may include controls for moving the camera 300 along the x-axis, the y-axis, and/or the z-axis. The foot plate input device 1410*b* may also include controls for storing a position of the camera 300 and/or returning to a previously stored position. The foot plate input device 1410*b* may further include controls for changing a focus, zoom, magnification, etc. of the camera 300.

In other embodiments, the stereoscopic robotic platform 516 may include additional and/or alternative input devices 1410, such as a joystick, mouse, or other similar 2D or 3D manual input device. The input devices 1410 are configured to provide inputs similar to an X-Y panning device, with additional degrees of freedom resulting in flexibility of system motion. Input devices with 3D capabilities, such as a 3D mouse or six-degree of freedom controller are well suited for flexible and convenient input commands. A major benefit of these user control devices is that the surgical image can be easily viewed while the motion is occurring. Further, a surgeon can view what is happening around the entire surgical and nearby sites to avoid, for example, bumping the camera 300 into surgical staff and/or nearby equipment.

Optionally, the input device 1410 may include a head, eye, or glasses-mounted tracking device, a voice recognition device, and/or a gesture input device. These types of input devices 1410 facilitate "hands-free" operability such that an operator does not need to touch anything with their sterile gloves. A gesture-recognizing control may be used, where certain operation hand motions are recognized and translated into control signals for the camera 300, the coupling plate 3304, and/or the robotic arm 506. A similar function is provided by a voice-recognition device, where a microphone senses a command from an operator, such as "move the camera left", recognizes the speech as a command, and converts it into appropriate camera and/or robot control signals. Alternate embodiments include an eye tracking device that is configured to determine a position of an operator's eyes with respect to a 3D display, and can adjust the view depending on where in the displayed scene the operator is looking.

Other embodiments include a device configured to track a position of an operator's head (via for example a trackable target or set of targets that are mounted on an operator's 3D glasses) in a frame of reference and a footswitch to activate "head tracking". The example tracking input device is configured to store a starting position of an operator's head at activation time and then detects head position continually at some short time interval. The tracking input device in conjunction with the processor 4102 may calculate a movement delta vector between a current position and the starting position and convert the vector into corresponding robotic arm or camera lens movements. For example, a tracking input device 1410 and the processor 4102 may convert left/right head movements into robotic arm movements such that an image onscreen moves left/right. The tracking input device 1410 and the processor 4102 may also convert up/down head movements into robotic arm or camera lens movements such that an image onscreen moves up/down, and may convert forward/back head movements into robotic arm or camera lens movements such that an image onscreen zooms in/out. Other movement conversions are possible, for example, by converting head rotation into a "lock-to-target" motion of the robotic arm 506. As described here, lock-to-target is configured to maintain a focal point of the robotic platform 516 on the same point in a scene or FOV to within some tolerance and pivot the robotic arm 506 (and hence the view) in a direction which mimics the head movement of an operator.

Prior to certain surgical procedures, a surgical plan is created that establishes desired paths for instruments and visualization. In some embodiments, the input device 1410 is configured to follow such a predetermined path with little further input from an operator. As such, the operator can continue operating while the view of the surgical site is automatically changing as pre-planned. In some embodiments, the surgical plan may include a set of pre-planned waypoints, corresponding to camera positions, magnification, focus, etc. An operator may actuate the input device 1410 to progress through the waypoints (causing the processor 4102 to move the robotic arm 506, the coupling plate 3304, and/or the camera 300 as planned) as the surgical procedure progresses.

In the illustrated embodiment, the example sensor 3306 is an input device. The sensor 3306 is configured to detect an operator's movement or force on the stereoscopic visualization camera 300 and convert the detected force/movement into rotational and/or translational data. The sensor 3306 may include a motion-anticipation input device, such as a six-degrees-of-freedom haptic force-sensing module or an opto-sensor (e.g., force/torque sensor), that enables the robotic arm 506 to respond electromechanically to an operator's gentle push on the camera 300. The opto-sensor may include an electro-optical device configured to transform applied forces and/or torques into electrical signals, thereby enabling a desired force/torque input by an operator to be sensed and transformed into a motion request that is provided in the sensed linear and/or rotational direction(s). In other embodiments, other sensors types may be used for the sensor 3306. For example, the sensor 3306 may include a strain gauge or piezoelectric device that is configured to sense a haptic request from an operator.

In an embodiment, a surgeon holds one or more of the control arms 304 and actuates or pushes a release button (which may be located on one or both of the control arms 304). Actuation of the release button causes the camera 300 to transmit a message to the processor 4102 indicative that an operator desires to begin an "assisted-movement" mode. The processor 4102 configures the robotic arm 506 and/or the coupling plate 3304 to enable the surgeon to gently steer the camera 300 in a desired direction. During this movement, the processor 4102 causes the robotic arm 506 and/or the coupling plate to move the camera 300 in a "power steering" manner, safely supporting its weight and automatically determining which joints should be activated and which should be braked in a coordinated manner to achieve the surgeon's desired movement.

In the illustrated example, the stereoscopic robotic platform 516 of FIG. 41 includes a robotic arm controller 4106 that is configured to control the robotic arm 506 and/or the coupling plate 3304. The robotic arm controller 4106 may include a processor, a server, a microcontroller, a workstation, etc. configured to convert one or more messages or instructions from the processor 4102 into one or more messages and/or signals that cause any one of joints R1 to R9 to rotate. The robotic arm controller 4106 is also configured to receive and convert sensor information, such as joint position and/or speed from the robotic arm 506 and/or the coupling plate 3304 into one or more messages for the processor 4102.

In some embodiments, the robotic arm controller 4106 is configured as a stand-alone-module located between the processor 4102 and the robotic arm 506. In other embodiments, the robotic arm controller 4106 may be included within the robotic arm 506. In yet other embodiments, the robotic arm controller 4106 may be included with the processor 4102.

The example robotic arm controller 4106 includes one or more instructions stored in a memory 4120 that are executable by a robotic processor 4122. The instructions may be configured into one or more software programs, algorithms, and/or routines. The memory 4120 may include any type of volatile or non-volatile memory. The example robotic processor 4122 is communicatively coupled to the processor 4102 and is configured to receive one or more messages related to operation of the robotic arm 506 and/or the coupling plate 3304. The example robotic processor 4120 is also configured to transmit to the processor 4102 one or more messages that are indicative of positions and/or speeds of joints R1 to R9. The one or more messages may also be indicative that a joint has reached a travel-stop or is being prevented from moving.

The example processor 4120 is configured to determine which joints R1 to R9 are powered in a coordinated manner such that a totality of all motions of all the joints results in the desired image motion at the camera 300. In a "move the camera left" example there may be complex motions of several joints which cause the camera's surgical image to appear to simply and smoothly translate to the left, from a relative viewpoint of a surgeon. It should be noted that in the "move the camera left" example, depending on how the camera 300 is connected to the robotic arm 506 through the coupling plate 3304, the control signals to specific joints may be drastically different depending on the position/orientation.

The memory 4120 may include one or more instructions that specify how joints R1 to R9 are moved based on a known position of the joints. The robotic arm controller 4106 is configured to execute the one or more instructions to determine how instructed camera movement is translated into joint movement. In an example, the robotic arm controller 4106 may receive messages from the processor 4102 indicative that the stereoscopic visualization camera 300 is to move downward along a z-axis and move sideward in an x-y plane. In other words, the processor 4102 transmits indicative of inputs received via the input devices 1410 regarding desired movement of the camera 300. The example robotic arm controller 4106 is configured to translate the vectors of movement in 3-dimensional coordinates into joint position movement information that achieves the desired position/orientation. The robotic arm controller 4106 may determine or take into account the current location of the links and joints of the robotic arm 506 and/or the coupling plate 3304 (and/or a position/orientation of the camera 300) in conjunction with the desired movement to determine a movement delta vector. In addition, the robotic arm controller 4106 may perform one or more checks to ensure the desired movement does not cause the camera 300 to enter into or progress close to a restricted area, as specified by one or more three-dimensional boundaries that are defined in the same coordinate system as the arm 506 and coupling plate 3304. Areas close to a boundary may specify a reduced scale factor that is applied by the robotic arm controller 4106 when movement signals are sent to the joints, which causes the joints to move slower as the robotic arm 506 approaches a boundary, and not move any further past a boundary.

After the boundary checks are performed, the robotic arm controller 4106 uses the movement delta and the current position/orientation of each of joints R1 to R9 to determine an optimal or near optimal movement sequence for rotating one or more of the joints to cause the robotic arm 506 to move the camera 300 into the specified location. The robotic arm controller 4106 may use, for example, an optimization routine that determines a minimal amount of joint movement needed to satisfy the movement delta vector. After the amount of joint movement is determined, the example robotic arm controller 4106 is configured to send one or more messages (indicative of an amount of rotation and speed of rotation, taking into account any scale factors) to a motor controller 4124. The robotic arm controller 4106 may transmit a sequence of messages to cause the robotic arm 506 and/or coupling plate 3304 to move in a defined or coordinated sequence. The sequence of messages may also cause a change in joint speed as, for example, the robotic arm 506 approaches a virtual or physical boundary.

The example motor controller 4124 is configured to translate or covert the received messages into analog signals, such as pulse-width modulated ("PWM") signals that cause one or more of joints R1 to R9 to rotate. The motor controller 4124 may, for example, select the input line to the appropriate joint motor, where a pulse duration is used for controlling a duration of time that the motor rotates and a frequency, duty cycle, and/or amplitude of the pulse is used to control rotation speed. The motor controller 4124 may also provide power for the joint motors and corresponding joint sensors.

In some embodiments, the robotic arm controller 4106 in combination with the motor controller 4124 is configured to receive or read joint sensor position information and determine, through kinematics, the location and orientation of the robotic joints and camera 300. Each joint R1 to R9 may include at least one sensor that detects and transmits data indicative of joint position, joint rotational speed, and/or joint rotational direction. In some embodiments, the sensors transmit only position information, and speed/direction are determined by the robotic arm controller 4106 based on differences in the position information over time. The robotic arm controller 4106 may transmit the sensor data to the processor 4102 for determining movement information.

The robotic arm controller 4106 receives movement instructions from the processor 4102 and determines, through Jacobian, forward, and/or inverse kinematics, which motors and joints should be activated, how fast and how far, and in what direction. The robotic arm controller 4106 then sends the appropriate command signals to motor power amplifiers in the motor controller 4124 to drive the joint motors in the robotic arm 506.

The example robotic arm 506 receives appropriate motor power signals and moves accordingly. Sensors and brakes in the arm 506 react to the various operations and feedback information from the robotic arm controller 4106. In some embodiments, the robotic arm 506 is mechanically and communicatively connected to the coupling plate 3304, which transmits coupler status and orientation information to the robotic arm controller 4106.

In some embodiments, the example robotic arm 506 of FIG. 41 includes a coupler controller 4130. The example coupler controller 4130 is configured to bypass the robotic processor 4106 and relay control information between the processor 4102 and the coupling plate 3304. The coupler controller 4130 may receive messages from the processor 4102 and correspondingly cause joints R7 to R9 rotate on the coupling plate 3304. The coupler controller 4130 may also receive sensor information regarding joint position and/or speed and transmit one or more messages to the processor 4102 indicative of the joint position and/or speed. In these embodiments, the processor 4102 may transmit messages for controlling the robotic arm 506 and separate messages for the coupling plate 3304.

In some embodiments, the robotic arm controller 4106 is configured to determine how joints R7 to R9 are to move. However, if the coupling plate 3304 is not communicatively coupled directly to the robotic arm 506, the robotic processor 4106 may transmit the movement signals to the coupler controller 4130 via the processor 4102. In instances where at least some operators of the robotic processor 4106 are located with the processor 4102, the coupler controller 4130 receives movement commands or signals from the processor 4102 in conjunction with the robotic arm 506 receiving movement commands or signals from the processor 4102.

In the illustrated embodiment of FIG. 41, the example stereoscopic visualization camera 300, the processor 4102, the coupling plate 3304, the robotic arm 506, the robotic arm controller 4106, and/or the input devices 1410 receive power via an input power module 4140. The example module 4140 includes a power supply (such as power from a wall outlet) and/or an isolation transformer to prevent powerline anomalies from disrupting system performance. In some instances, the power supply can include a battery power supply.

The stereoscopic visualization platform 516 may also include an emergency stop switch 4142 that is configured to immediately cut off power. The switch 4142 may only cutoff power to the robotic arm 506 and/or the coupling plate 3304. The processor 4106 may detect activation of the emergency stop switch 4142 and cause joint brakes to engage to prevent the robotic arm 506 from falling. In some instances, the robotic arm 506 is configured to activate the joint brakes after detecting a loss of power. In some embodiments, joints R1 to R6 of the robotic arm 506 are configured to slip if a force above a threshold is applied, thereby enabling an operator to quickly move the arm out of the way in an emergency, with or without power.

In some embodiments, the example processor 4102 is configured to display one or more graphical representations of the robotic arm 506, the coupling plate 3304, and/or the stereoscopic visualization camera 300. The processor 4102 may cause the graphical representation to be displayed in one or more user interfaces that provide control for the robotic arm 506, the coupling plate 3304, and/or the camera 300. The processor 4102 may position and orient the graphical representation to reflect the current position of the robotic arm 506, the coupling plate 3304, and/or the camera. The processor 4102 uses, for example, feedback messages from the robotic arm controller 4106 to determine which joints in the graphical representation are to be rotated, thereby changing the orientation and/or position of the display device. In some instances, the processor 4102 is configured to receive user input via the graphical representation by, for example, an operator moving the links, joints, or camera 300 in the graphical representation to a desired position. In the case of movement of the stereoscopic visualization camera 300, the processor 4102 may transmit the new coordinates corresponding to where the camera was moved. In the case of moved joints or links, the processor 4102 may transmit to the robotic arm controller 4106 messages indicative of joint rotation and/or positions of links.

In some embodiments, the processor 4102 operates in connection with the robotic arm controller 4106 to adjust one or more lenses of the camera based on or in cooperation with movement of the robotic arm 506 and/or the coupling plate 3304. For example, if the robotic arm 506 is moved toward a surgical site, the processor 4102 operates in connection with the robotic arm controller 4106 to change a working distance or focal point by moving one or more of the lenses of the stereoscopic visualization camera 300 to maintain focus. The processor 4102 operates in connection with the robotic arm controller 4106 to determine, for example, that movement of the robotic arm 506 causes a working distance to decrease. The EPU processor 4102 operates in connection with the robotic arm controller 4106 to determine a new position for the lenses based on the new working distance set by moving the robotic arm 506. This may include moving one or more lenses for adjusting focus. In some embodiments, the processor 4102 may instruct the camera 300 to operate a calibration routine for the new position of the robotic arm 506 to eliminate, for example, spurious parallax.

In some instances, an operator may be changing positions of one or more lenses of the stereoscopic visualization camera 300 and reach a lens travel limit. The position of the lenses is sent from the camera 300 to the processor 4102, which to determine that a limit has been reached. After detecting that a limit has been reached, the processor 4102 may cause the robotic arm 506 to move (via the controller 4106) based on input from the operator, thereby extending their command from lens movement to arm movement to reach a desired magnification or target area. As such, the processor 4102 operating in connection with the robotic arm controller 4106 enables an operator to use only one user interface rather than changing between an interface for the robotic arm and the camera. It should be appreciated that the processor 4102 and/or the controller 4106 may check desired movement against any predetermined movement limits to ensure the movement will not cause the camera 300 or robotic arm 506 to enter into restricted patient or operator space. If a limit violation is detected, the processor 4102 in connection with the robotic arm controller 4106 may display an alert to the operator (via a user interface displayed on the touchscreen input device 1410*a* and/or the display monitor 512) indicative of the limit to indicate a reason the robotic arm 506 was stopped.

C. Robotic Arm and Stereoscopic Camera Calibration Embodiment

As discussed above, the example stereoscopic visualization camera 300 is configured to provide high-resolution stereoscopic video images of a target surgical site at different magnifications. As part of the stereoscopic visualization platform 516, the stereoscopic visualization camera 300 operates in connection with the robotic arm 506 and/or the coupling plate 3304 for precise and clear changes to image focus, working distance, magnification, etc. To accomplish the image acquisition flexibility, the stereoscopic visualization platform 516 is configured to operate one or more calibration, initialization, and/or reset routines. In some embodiments, the stereoscopic visualization camera 300, the robotic arm 506, the coupling plate 3304, or more generally, the stereoscopic visualization platform 516 is calibrated during manufacture and/or after installation. Calibration of the camera 300 with the robotic arm 506 provides positioning information of the camera 300 relative to the robotic arm 506 and operator space. After power-up of the stereoscopic visualization platform 516, in some embodiments, the camera 300 and/or the robotic arm 506 is configured to perform further calibration/initialization to measure and verify a location and orientation of the camera 300 at that time.

The example processor 4102 is configured to store results from the calibration (e.g., calibration data), in for example, the memory 1570 and/or the memory 4120 of FIG. 41. The calibration results may be stored to calibration registers and/or lookup tables ("LUTs") in the memories 1570 and/or 4120. The stored calibration data relates or maps optical, functional, and/or performance characteristics to attributes of the camera 300, the robotic arm 506, and/or the coupling plate 3304 that are adjustable, measurable, and/or verifiable by an operator or by the processor 4102. For example, a working distance actuator motor encoder position for the main objective assembly 702 (of FIG. 7) is mapped in a LUT to a working distance. In another example a zoom lens axial position along a linear encoder for the zoom lens assembly 716 is mapped in a LUT to the magnification level. For each of these examples, the example processor 4102 is configured to determine the proper level of an encoder characteristic, adjust, and verify that the characteristic provides the specified or desired working distance and/or magnification. In some embodiments, LUTs may be compound, where multiple performance characteristics are mapped to multiple platform 516 attributes for overall control of all relevant aspects of the camera 300, the robotic arm 506, and/or the coupling plate 3304.

The combination of a robotic arm 506 and the example stereoscopic visualization camera 300 provides highly accurate position, direction, and/or orientation information of the target view with respect to a frame of reference of the robotic arm 506. The following sections describe how the stereoscopic visualization camera 300 is calibrated to define a visual tip. After a visual tip is determined, the stereoscopic visualization camera 300 is registered to a frame of reference of the robotic arm 506 and/or the coupling plate 3306. Accordingly, after calibration and registration, a stereoscopic view of a surgical site is unified with the integrated control of the stereoscopic visualization camera 300 combined with the position, direction, and orientation control of the robotic arm 506 and/or coupling plate 3304.

In some embodiments, the example processor 4102 of FIG. 41 is configured to integrate a registration of stereoscopic visualization camera 300, including its visual tip, precisely with a position, direction, and/or orientation calibration of the robotic arm 506 to define a unified position, direction, and/or orientation awareness of acquired stereoscopic images and all points therewithin, with respect to a prescribed coordinate frame. The example processor 4102 is configured to use intrinsic visual imaging data from the stereoscopic visualization camera 300 to coordinate or direct the physical positioning and/or orientating of the robotic arm 506 to provide visualization, as desired by an operator. In addition, such direction and coordination provided by the processor 4102 is provided to maintain preferred characteristics of the visualization such as focus, working distance, pre-defined positioning, orientating, etc.

In some embodiments, calibration of the stereoscopic visualization camera 300, the robotic arm 506, and/or the coupling plate 3304 generally includes (i) determining and/or measuring inaccuracies of functional parameters of the stereoscopic visualization platform 516 that affect stereoscopic images; (ii) calibrating or adjusting, the stereoscopic visualization platform 516 to minimize the inaccuracies in the stereoscopic images at or below a desired level; (iii) verifying that the adjustments have been made within a desired level of calibration accuracy through simultaneous comparisons of the dual channels of the stereoscopic images to each other or calibration templates; and (iv) using the stereoscopic visualization platform 516 in the performance of its tasks, where a level of the accuracy of the calibration is detectable and maintained.

In an alternative embodiment, the robotic arm 506 is provided with one or more fixed calibration fiducials that are used to precisely calibrate a physical relationship of the joint and links of the robotic arm 506 to one another as well as to calibrate a relationship of the visual tip of the camera 300 to the robotic arm 506 and/or an initial pose configuration. The robotic platform fixed calibration fiducials can be used to register or integrate the robotic arm 506 with an external environment, such as an operating room theater or with a patient or target space within an external environment. The fixed calibration fiducials can either include a dedicated attachment to an external portion of a body of the robotic arm 506 or a combination of known external features of the robotic arm 506, such as mounting points, joints, corners, or the like.

1. Calibration of the Stereoscopic Visualization Camera Embodiment

To match a stereoscopic view of a surgical site, the example processor 4102 and/or the stereoscopic visualization camera 300 is configured to perform one or more calibration routines. The example routines may be specified by one or more instructions stored in the memory 1570, that when executed by the processor 4102, cause the processor 4102 to determine lens position corresponding to certain working distances, magnifications (e.g., zoom level), and focus levels. The instructions may also cause the processor 4102 to operate one or more routines for determining a center of projection, stereo optical axis, and/or a ZRP for the stereoscopic visualization camera 300 at different working distances and/or magnifications. Calibration enables, for example, the processor 4102 to retain focus on a target surgical site when magnification and/or working distance is changed.

Figure 42:
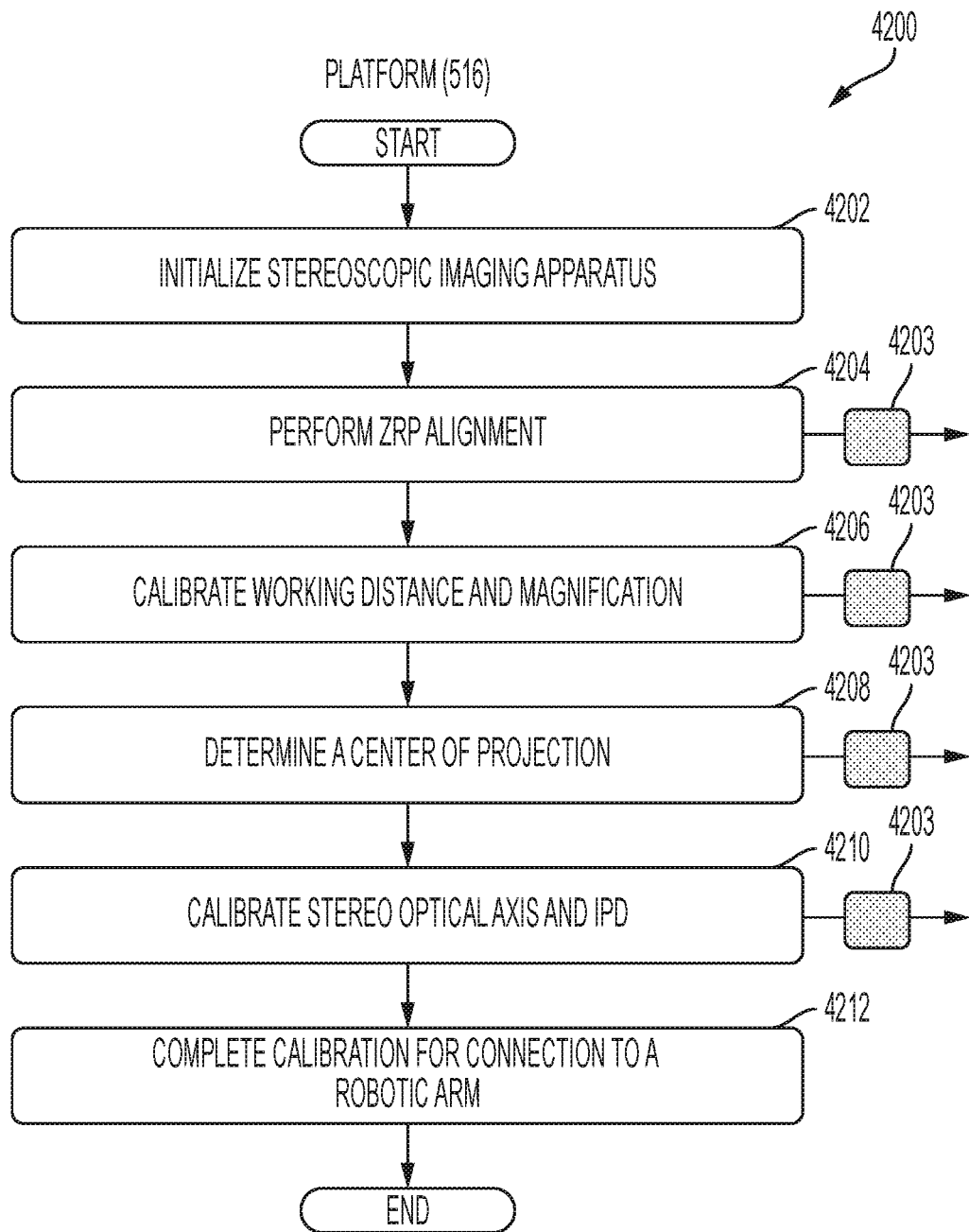
FIG. 42 illustrates an example procedure or routine for calibrating the stereoscopic visualization camera of FIGS. 3 to 33, according to an example embodiment of the present disclosure.

FIG. 42 illustrates an example procedure 4200 or routine for calibrating the stereoscopic visualization camera 300, according to an example embodiment of the present disclosure. Although the procedure 4200 is described with reference to the flow diagram illustrated in FIG. 42, it should be appreciated that many other methods of performing the steps associated with the procedure 4200 may be used. For example, the order of many of the blocks may be changed, certain blocks may be combined with other blocks, and many of the blocks described are optional. Further, the actions described in procedure 4200 may be performed among multiple devices including, for example the optical elements 1402, the image capture module 1404, the motor and lighting module 1406, and/or the information processor module 1408 of the example stereoscopic visualization camera 300. For example, the procedure 4200 may be performed by one of the programs 1560 of the information processor module 1408.

The example procedure 4200 begins when the stereoscopic visualization camera 300 is powered or otherwise initialized (block 4202). The camera 300 may be mounted to the robotic arm 506. Alternatively, the procedure 4200 can be performed when the stereoscopic visualization camera 300 is connected to a fixed mount. The example procedure 4200 next performs ZRP alignment, as discussed above in connection with FIGS. 25 and 26 (block 4204). The example processor 4102 may automatically align the ZRPs, as discussed above, and/or operate in connection with an operator to provide alignment of the left and right optical paths on the image sensors 746, 748. In some examples, the processor 4102 and/or an operator may cause small movements or flexing of a flexure (e.g., the flexure 1300 of FIG. 13) via a motor with sufficient accuracy to make very small adjustments to a tilt of a lens component to move a ZRP into alignment with a pixel grid origin. During semi-manual alignment, the processor 4102 may cause left and right images from the image sensors 746 and 748 to be overlaid on the display monitor 512. An operator may use the input device 1410 to adjust the images, causing pixel sets of the sensors 746 and 748 to be accordingly moved until the ZRPs are properly aligned.

During alignment, the ZRPs are set to be aligned at an image center to avoid spurious parallax. Alignment to within about a single pixel on a display is possible. The degree of alignment from the left and right views to an image center is visible in the overlaid images, including during zooming operations. In an example of a 8° FOV, the use of a 4K image sensor 746, 748 and a corresponding 4K display resolution of the display monitor 512 (comprising about 4000 pixels by about 2000 rows) produces a system resolution of 8°/4000 pixels=7 arc-seconds. However, ZRP alignment can be performed at most any magnification, where the resolution (being the same number of pixels (e.g. 4000)) is divided by a reduced (or increased) angular FOV. For example, an exemplary embodiment of the camera 300 at a high magnification produces an angular FOV of about 2°. An 8K UHD display monitor 512 and sensors 746 and 748 have about 8000 pixels in about 4000 rows. The resolution of this system is 2°/8000 pixels=1 arc-seconds. This is about an order of magnitude, or more, better than known systems in the art, in which the accuracy of assembled, individually-measured components with tolerances that have resolutions measured in arc-minutes. As images sensors and display monitors become higher in density with generally smaller pixels in the same physical sensor or display space, the accuracy of the stereoscopic visualization camera 300 adjustability scales with the smaller pixel size. The enhanced high accuracy alignment of the stereoscopic visualization camera 300 provides for better, more accurate digital effects.

The alignment of the ZRPs is complete when the ZRPs of the left and right images remain at an image center within a desired tolerance range and the images of the target surgical site remain accurate when cycled from low magnification to high magnification. After the ZRPs are aligned throughout the magnification capabilities of the stereoscopic visualization camera 300, the pixel set locations and/or lens locations for each of the magnification levels are stored to, for example, a LUT 4203 or other data structure. In other examples, the processor 4102 writes, to calibration registers, the pixel set locations and/or lens locations for each of the magnification levels.

After the ZRPs are aligned, the example processor 4102 is configured to calibrate for working distance and/or magnification (e.g., zoom) (block 4206). As discussed above in connection with the working distance and zoom examples of FIG. 15, precise knowledge of working distance is important in the camera 300 so that the robotic arm 506 may precisely position the camera relative to desired coordinates. In some instances, an accurate fiducial is used, along with mechanical dimensions of the robotic arm 506, to transform object plane data from an image into a coordinate system respective of the stereoscopic visualization platform 516, referred to herein as robot space.

The example calibration procedure 4200 is performed to map the working distance of the optical system of the stereoscopic visualization camera 300, where the working distance may be calculated or measured in millimeters from a front face of a common mode objective ("CMO") lens assembly (e.g., the front working distance main objective lens 408 of FIGS. 4 and 7) to an object plane. The working distance is mapped to a known measurable parameter, such as for example, a focus motor position, measured in counts of a motor shaft encoding device from a known "home" location such as a physical stop or limit switch trigger position.

Figure 43:
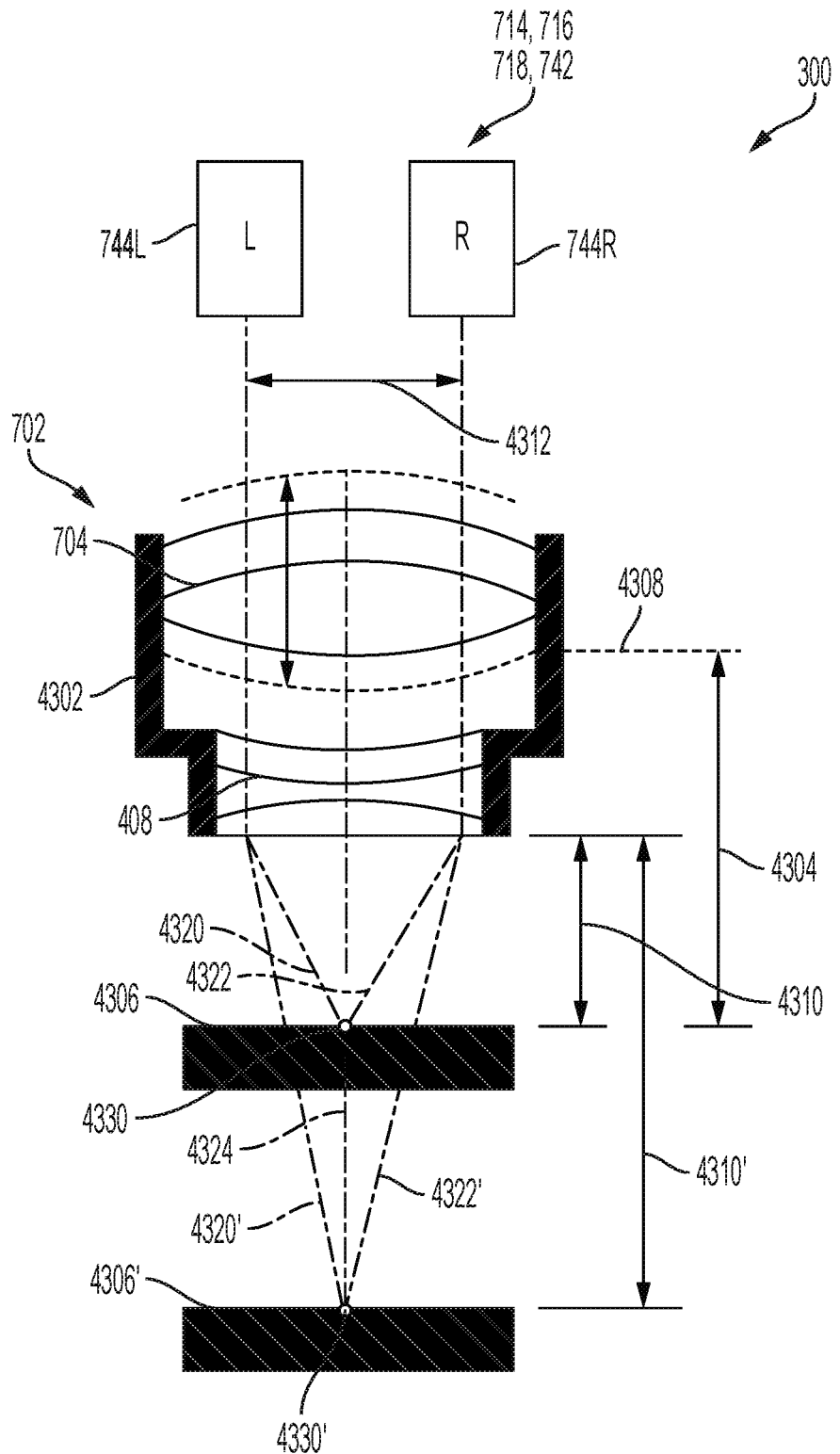
FIG. 43 shows an embodiment of the example stereoscopic visualization camera of FIGS. 3 to 33 and 42 moving an object plane in discrete steps, according to an example embodiment of the present disclosure.

The calibration at block 4206 is performed by the processor 4102 sequentially moving the object plane in discrete steps along the optical axis and re-focusing the image while recording the encoder counts and the working distance, as discussed in more detail in conjunction with FIG. 43. The processor 4102 measures the working distance externally from the front face of the CMO. The mapping of the encoder counts and the working distance is stored to the LUT 4203, or a different LUT and/or calibration registers. This calibration enables the processor 4102 to output an encoder count position to the motor controller, given a desired working distance. Exemplary embodiments of the stereoscopic visualization camera 300 use high-count-per-revolution shaft encoding devices, where resolution of the working distance is on the order of 1 micron per each encoder count. Alternative embodiments may include different encoder resolution to provide higher or lower resolution of working distance, as desired.

FIG. 43 shows an embodiment of the example stereoscopic visualization camera 300 moving an object plane in discrete steps, according to an example embodiment of the present disclosure. The example stereoscopic visualization camera 300 includes the main objective assembly 702 of FIG. 7 (e.g., a single CMO), which is configured to provide left and right views of a target surgical site. In the illustrated example, the main objective assembly 702 is shown as an achromatic refractive assembly with the stationary front working distance lens 408 within a housing 4302 and the movable rear working distance lens 740, which is movable along the z-axis (or other optical axis). Movement of the rear working distance 704 changes the distance to the front working distance lens 408. The spacing between the lenses 408 and 704 determines the overall front focal length 4304 of the main objective assembly 702, and accordingly the location of a front focal plane (or simply "focus plane") 4306. The front focal plane 4306 is located at a distance equal to the focal length 4304 from a principal plane 4308 of the main objective assembly 702. It may be difficult to gauge the location of the principal plane 4308, so a distance from the bottom surface of housing 4302 to the front focal plane is defined as the working distance 4310. The working distance 4310 accordingly accurately sets a plane of the target site or scene that is in focus.

Imaging an object at the front focal plane 4306 develops a conjugate image located at infinity from a back or rear of the main objective assembly 702. Two parallel optical paths comprising optics and sensors 714, 716, 718, 744R, and 744L of the camera 300, transversely separated by an interpupillary distance ("IPD") 4312, generate left and right views along respective left 4320 and right 4322 optical axes in slightly different directions from an optical axis 4324 of the main objective assembly 702. The two optical paths are adjusted such that their respective external converging left and right axes are set to coincide at the center of the FOV of an image 4330. This point 4330 is referred to herein as the "tip" of the stereoscopic visualization camera 300 at the front focal plane 4306.

Adjustment of a position of the rear working distance lens 740 causes a change in the front focal length 4304 main objective assembly 702. As illustrated, a change in the position of the rear working distance lens 740 creates a new working distance 4310' that is located at the position of a new front focal plane 4306'. The movement of the rear working distance lens 740 also causes a realignment of left 4320' and right 4322' optical axes, resulting in a relocated tip 4330' of the camera 300. Visualization of an object with the camera 300 above or below the focus plane 4306 diminishes a focus of the object.

In a manner similar to that for working distance calibration, a similar LUT, or additional columns in a working distance LUT 4203, can be constructed by the processor 4102 varying the magnification while measuring an image height of an object of known size. Magnification can be quantified by determining the counts of the motor shaft encoding device from a known "home" location such as a physical stop or limit switch trigger position. The processor 4102 can measure image height relatively, for example in a number of sensor pixels at each magnification position. Magnification can be characterized by, for example dividing the height in pixels by the height in millimeters.

Returning to FIG. 42, after the working distance and magnification of the stereoscopic visualization camera 300 are calibrated, the example processor 4102 is configured to determine a center of projection (block 4208). The center of projection (e.g., COP) may be determined using one or more routines that model the stereoscopic visualization camera 300, as discussed above in connection with FIG. 15. To match the left and right stereoscopic view of a surgical site, it is often desirable to model the physical camera 300 using a mathematical model implemented in software, firmware, hardware, and/or GPU code for the processor 4102. A perspective of a 3D computer model, such as the MM image of a brain tumor, can often be rendered and viewed from user-adjustable directions and distances (e.g. as if the images are captured by a synthesized stereoscopic camera). The adjustability of the model may be used by the processor 4102 to match a perspective of a live surgical image, which must therefore be known.

Exemplary embodiments of the stereoscopic visualization camera 300 and/or processor 4102 are configured to accurately measure and calculate camera model parameters for each value of magnification and working distance. These values are controlled by separate optics contained within the stereoscopic visualization camera 300. The dual optics are aligned such that the parallax at the center of an image between the left and right channels/views is approximately zero at the focal plane 4330. Additionally, the stereoscopic visualization camera 300 is parfocal across the magnification range, and par central across magnification and working distance ranges because the ZRPs of each left and right channel have been aligned to the centers of their respective pixel grids (described above in block 4202). In other words, changing only the magnification keeps the image in focus in both channels, and trained on the same center point. Similarly, changing only a working distance should cause no vertical parallax in the image, only increased horizontal parallax between the left and right views, if the target and stereoscopic visualization camera 300 remain stationary.

Figure 44:
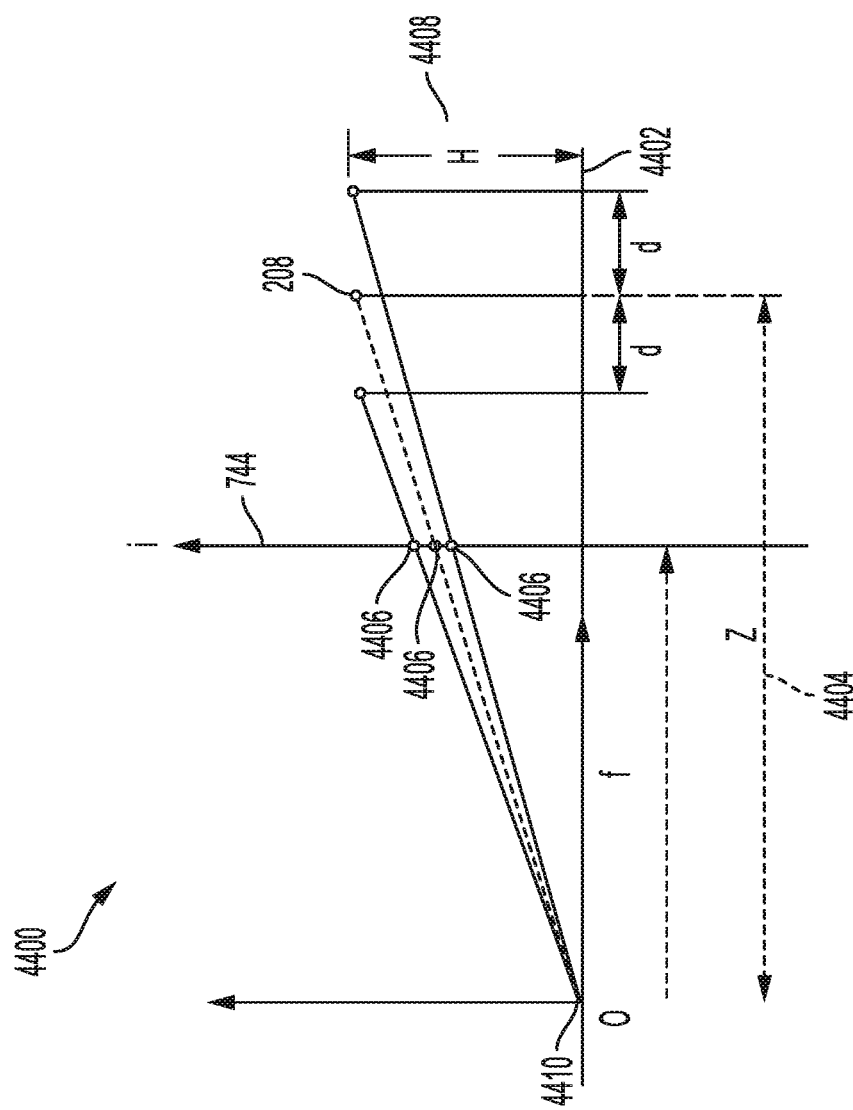
FIG. 44 illustrates a graph illustrative of a routine executable by a processor for determining a center-of-projection of the stereoscopic visualization camera of FIGS. 3 to 33 and 42, according to an example embodiment of the present disclosure.

FIG. 44 illustrates a graph 4400 illustrative of a routine executable by the processor 4102 for determining a COP of the stereoscopic visualization camera 300, according to an example embodiment of the present disclosure. In the illustrated example, a COP of a pinhole or modeled camera 300 is along an optical axis 4402 at the plane of the pinhole (O). To determine the COP for the camera model, a virtual pinhole camera model is used, where the processor 4102 is configured to determine an actual focus distance 4404 from the COP to an object plane. During the calibration routine, the processor 4102 keeps the magnification of the camera 300 fixed while measurements are recorded of an image height 4406, for example in the number of pixels at a plane of the optical image sensor 744, with an object of height 4408 at three different distances along the optical axis 4402: at the object plane, and at a distance "d" less than the object plane distance, and at a distance "d" greater than the object plane distance. The processor 4102 uses routines that include algebra based on similar triangles at the two most extreme positions to determine the focus distance 4404 to a COP 4410. The processor 4102 may determine focus distance at alternative magnifications based on the ratio of the alternative magnification to the magnification used for the calibration.

Returning to FIG. 42, the example processor 4102 is configured to determine COPs for varying working distances and magnifications. The processor 4102 relates motor shaft encoder counts for the lenses to the COP for the varying working distances and magnifications in the LUT 4203, a different LUT, or one or more calibration registers. In some embodiments, the processor 4102 may only store a relation of a COP for one magnification and/or working distance and calculate the other magnifications and/or working distances using the one known COP relation.

After calibrating for a COP, the example processor 4102 is configured to calibrate stereoscopic left and right optical axes and an interpupillary distance ("IPD") between the axes of the stereoscopic visualization camera 300 (block 4210). To characterize the optics of the stereoscopic visualization camera 300, the IPD between the left and right channels/views should be known. In embodiments, the IPD may be designed into the mechanical components holding the sensors and optics shown in FIG. 7. IPD is thus set mechanically. However, the actual optical axis may differ from the mechanical axis of the optical elements and their mounts. Other embodiments enable the IPD to be varied within the stereoscopic visualization camera 300.

In some applications, it is desirable to precisely know the direction of the stereoscopic optical axis with respect to a fiducial or mechanical axis on a frame of the stereoscopic visualization camera 300. This enables, for example, the processor 4102 to aim the stereoscopic visualization camera 300 precisely through mechanical means. The aiming can be characterized by a geometrically-defined view vector, looking out coincidentally with the stereoscopic optical axis, with respect to a frame of reference of the stereoscopic visualization camera 300. In addition, clocking of the left and right channels for the optical sensor 744 is included in a view vector, comprising the stereoscopic visualization camera 300 orientation or pose.

Figure 45:
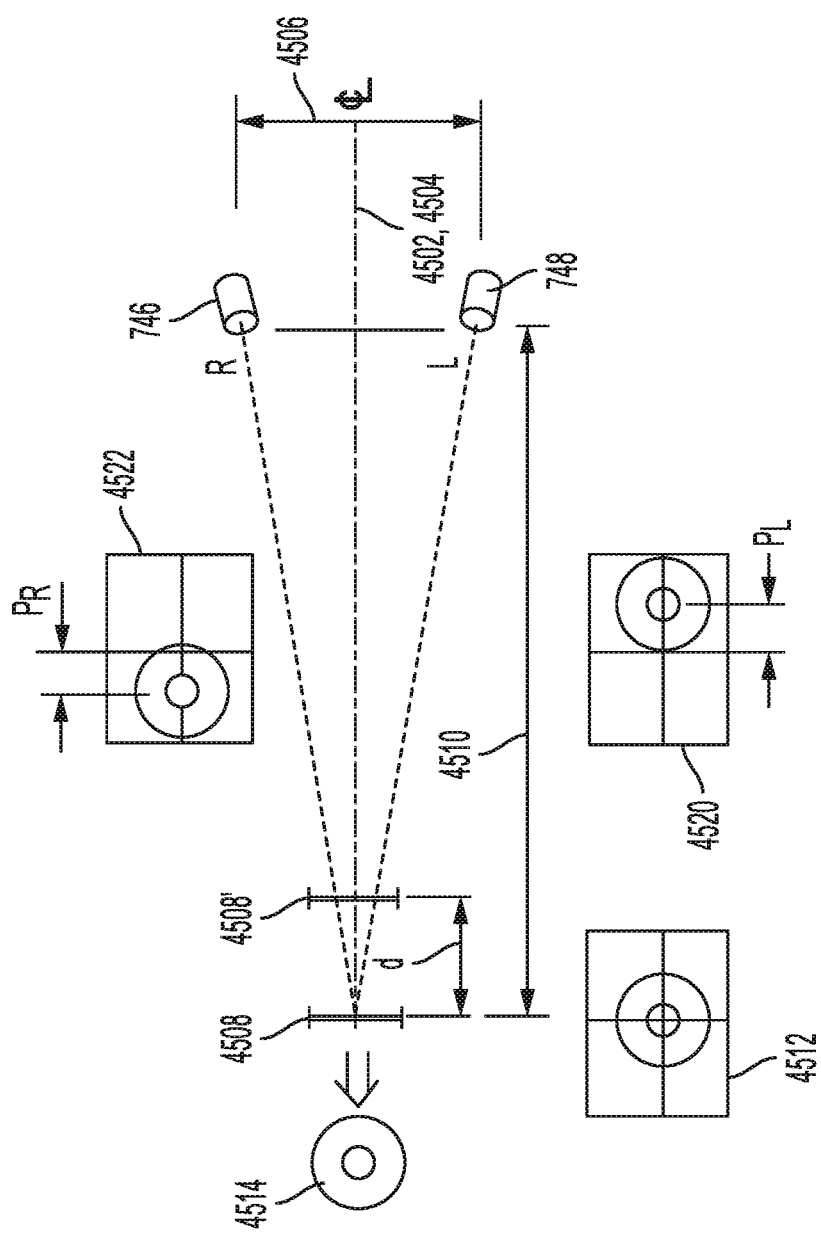
FIG. 45 shows a plan view of an optical schematic that is illustrative of how an interpupillary distance of the stereoscopic visualization camera of FIGS. 3 to 33 is measured and calibrated, according to an example embodiment of the present disclosure.

FIG. 45 shows a plan view of an optical schematic that is illustrative of how the IPD of the stereoscopic visualization camera 300 may be measured and calibrated, according to an example embodiment of the present disclosure. In the illustrated example, an optical axis 4502 is perfectly aligned with a mechanical axis 4504. The right image sensor 746 and the left image sensor 748 (as approximated by one or more camera models) are spaced by an IPD 4506. The sensors 746 and 748 are aligned and focused on an object 4508 (in a target surgical site). The object 4508 is placed at a focus distance 4510 from the sensors 746 and 748 such that parallax at the plane of the object is theoretically zero, as depicted in the display of the left or right view of object at focus plane 4512. In this exemplary example, for clarity the object 4508 is a disc, the front view of which is shown as item 4514.

FIG. 45 also illustrates another example where the object 4508 is displaced along the mechanical axis a distance "d" and is shown as item 4508'. The displacement of the object 4508 generates parallax, which appears in the displays of a left view 4520 as $P_L$ and a right view 4522 as PR. In this example, the mechanical and optical axes are coincident and the parallax magnitudes are equal. The parallax can be measured, for example by counting a number of pixels of disparity between the left and right views 4520 and 4522 and multiplying by a magnification factor pixels/mm that was determined in the COP calibration step. The processor 4102 may calculate the IPD using triangulation. The accuracy of the measurements of the displacement distance d and the parallax of each view contribute to a precise knowledge of the IPD of the stereoscopic visualization camera 300.

Figure 46:
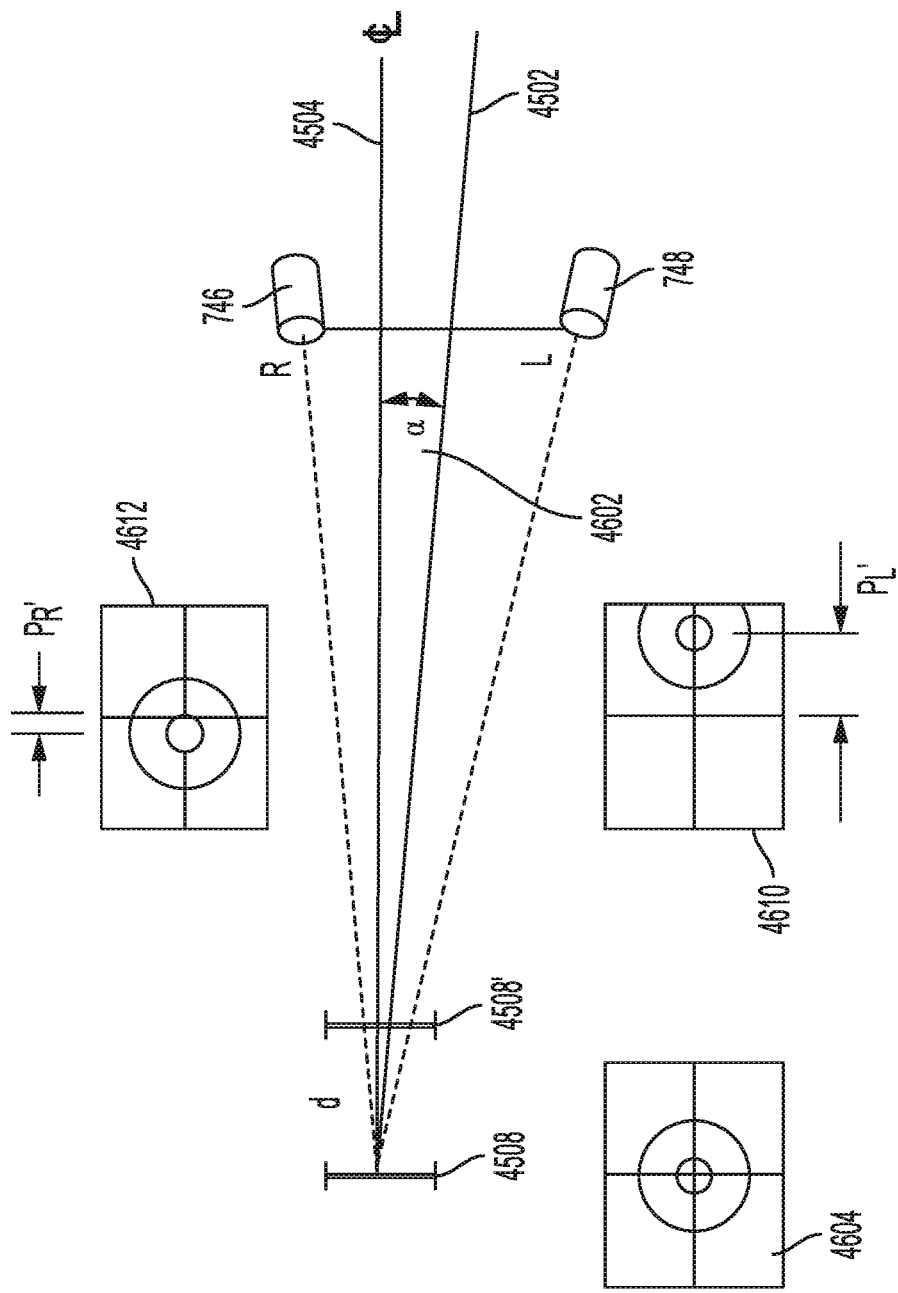
FIG. 46 shows a plan view of an optical schematic that is illustrative of how an optical axis of the stereoscopic visualization camera of FIGS. 3 to 33 may be measured and calibrated, according to an example embodiment of the present disclosure.

FIG. 46 shows a plan view of an optical schematic that is illustrative of how the optical axis of the stereoscopic visualization camera 300 can be measured and calibrated, according to an example embodiment of the present disclosure. In this example, the optical axis 4502 is misaligned from the mechanical axis 4504 by an angle (a), shown as 4602. The right image sensor 746 and the left image sensor 748 (as approximated by one or more camera models) are aligned and focused on an object 4508 (in a target surgical site) that is placed at a focus distance such that parallax at the plane of the object 4508 is theoretically zero, as depicted in the display of the left or right view of object 4508 at focus plane 4604.

FIG. 46 also illustrated another example where the object 4508 is displaced along the mechanical axis the distance "d" and shown as object 4508'. The displacement of the object 4508 generates parallax, which appears in the displays of the left view 4610 as $P_L$ and right view 4612 as PR. In this example where the mechanical axis 4504 and the optical axis 4502 are not coincident, the parallax magnitudes are not equal. The example processor 4102 is configured to calculate the IPD as well as the misalignment angle α (e.g., the stereoscopic optical axis) via triangulation. The accuracy of the measurements of the displacement distance d and the parallax of each view enable the processor 4102 to accurately determine the IPD and the optical axis of the stereoscopic visualization camera 300.

A similar procedure can be employed to measure, for example, misalignment of the mechanical and optical axes in the vertical plane. The combination of misalignment in, for example, the horizontal plane or vertical plane, can be combined such that a view vector can be accurately deduced with respect to the mechanical axis. In some embodiments, the IPD and optical axis parameters may be measured at varying levels of working distance and/or magnification. The relations between IPD, optical axis, working distance, and/or magnification may be stored by the processor 4102 to the LUT 4203, another LUT, and/or calibration registers.

Returning to FIG. 42, after the optical axis and/or IPD of the example stereoscopic visualization camera 300 is calibrated, the example processor 4102 is configured to complete the calibration process to enable the camera 300 to be connected to the robotic arm 506 (block 4212). The procedure 4200 may then end. In some embodiments, at least portions of the example procedure 4200 are repeated if the camera 300 is reinitialized and/or if any of the calibration cannot be verified or validated.

It should be appreciated that the above steps of the procedure 4200 can be performed manually or semi-manually in some embodiments. In other embodiments, the above steps may be performed automatically and continuously by the processor 4200. In some embodiments, measuring can be made through image recognition of a suitable target or any target with a sufficient number of objects comprising sufficient contrast to enable identification in both left and right views. In addition, the processor 4102 may determine or calculate parallax measurements for assessing accurate relative positions of the optical elements of the stereoscopic visualization camera 300. The processor 4102 may perform optical measurement on a real-time basis.

In some embodiments, the use of automated, iterative techniques to perform these or equivalent methods of calibration and measurement can increase the accuracy and reduce the time and/or effort required to calibrate and measure. For example, the working distance (and hence the displacement d) is accurately known by the quantity of encoder counts and the LUT 4203, as described previously. The magnification and its, for example, pixels/mm conversion factor is also accurately known by the quantity of encoder counts and the LUT 4203, as described previously. Counting of pixels in the images for disparity or object size determination can be accurately performed manually or automated, for example, as described previously using template matching. The measurement and storage of these values can be combined such that the stereoscopic camera model parameters and view vector can be accurately deduced in near real-time by the example processor 4102.

Figure 47:
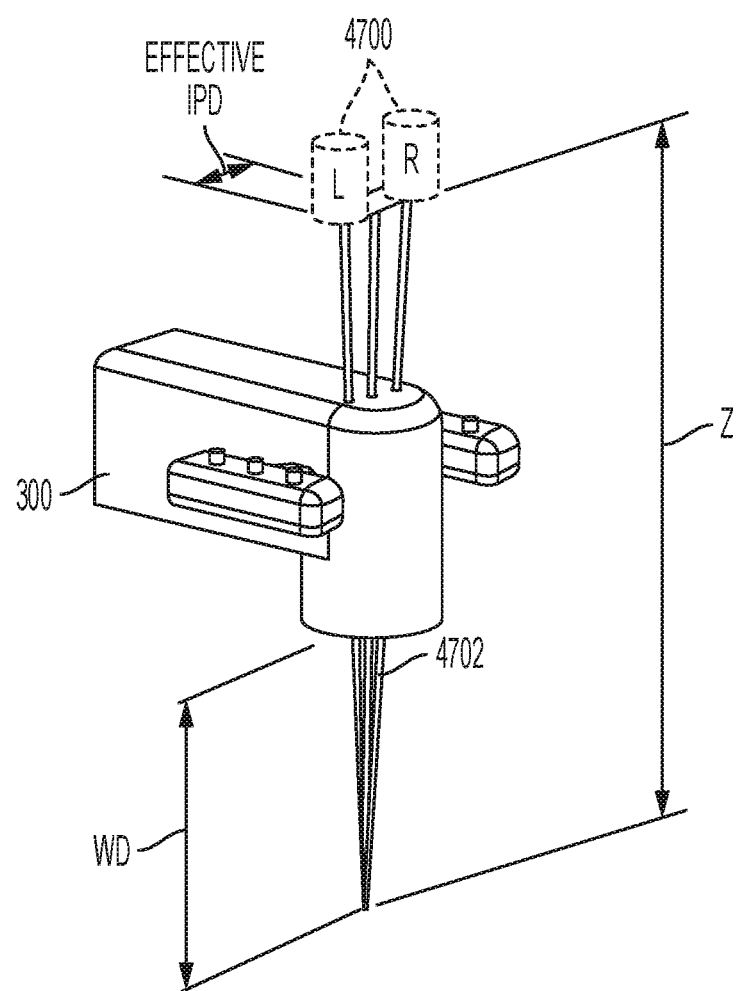
FIG. 47 illustrates a diagram of a calibrated stereoscopic visualization camera in which optical parameters are fully characterized, according to an example embodiment of the present disclosure.

FIG. 47 illustrates a diagram of a calibrated stereoscopic visualization camera 300 in which the optical parameters are fully characterized. In the illustrated embodiment, the left and right optical axes are shown leading to imaginary left and right image sensor positions 4700, as determined via a camera model. FIG. 47 also shows the central stereoscopic optical axis or view vector 4702. The imaginary left and right view components of the camera models are positioned at a focal distance Z. In addition, the left and right view components of the camera models are spaced apart by the measured, effective IPD. In the illustrated example, an object at the focal plane is viewed with similar stereoscopic perspective by the imaginary left and right view components as recorded by the image sensors 746 and 748 within the stereoscopic visualization camera 300.

2. Calibration of the Stereoscopic Visualization Enables Fusion with Additional Images The example processor 4102 is configured to use the calibration parameters/information for not only providing high-resolution clear images, but also to align live stereoscopic images with one or more images/models received from the external devices 4104. The mapping of the calibration data related to camera model parameters in the LUT 4203 and/or calibration registers enables the processor 4102 to create a mathematical model of the stereoscopic visualization camera 300 that is implemented in software, firmware, hardware and/or computer code. In an example, the processor 4102 is configured to receive, determine, or access camera model parameters using, for example, the procedure 4200 discussed in conjunction with FIG. 42. If a calibration has already been performed, the processor 4102 accesses the camera model parameters from one or more memories 1570 and/or 4120. The processor 4102 also receives, from the device 4104, an alternative modality of the image data, such as pre-surgical images, MRI images, a 3D model of the surgical site from MM or CT data, X-ray images, and/or surgical guides/templates. The processor 4102 is configured to render a synthesized stereoscopic image of the alternative modality data using the camera model parameters. The example processor 4102 is also configured to provide the synthesized stereoscopic image for display via the monitor 512. In some examples, the processor 4102 is configured to fuse the synthesized stereoscopic image with the current stereoscopic visualization, where desirable aspects of each modality are visible and/or overlaid in identical perspective as if acquired by a single visualization device.

In some embodiments, the parameters illustrated in FIG. 47 are used by the processor 4102 to match a synthesized stereoscopic image of alternative modality, for example MRI image data, to the stereoscopic perspective of the stereoscopic visualization camera 300. Thus, the example processor 4102 uses the stored optical calibration parameters for stereoscopic image synthesis. In an example, the processor 4102 uses the optical calibration parameters to fuse live stereoscopic images with a three-dimensional model of a brain tumor that was imaged pre-operatively using an MRI device. The example processor 4102 uses the optical calibration parameters to select the corresponding location, size, and or orientation of the three-dimensional model of the brain tumor that matches the stereoscopic images. In other words, the processor 4102 selects a portion of the three-dimensional model that corresponds to the view recorded by the stereoscopic visualization camera 300. The processor 4102 may also change which portion of the model is displayed based on detecting how the working distance, magnification, and/or orientation of the camera 300 changes.

The processor 4102 may cause a graphical representation of the model to be overlaid of the stereoscopic images and/or cause the graphical representation of the model to appear visually fused with the stereoscopic images. The image processing performed by the processor 4102 may include smoothing boundaries between the graphical representation of the model and the live stereoscopic view. The image processing may also include causing at least a portion of the graphical representation of the model to have an increased transparency to enable the underlying live stereoscopic view to also be visible to a surgeon.

In some examples, the processor 4102 is configured to generate and/or render a depth map for every pixel in a stereoscopic image. The processor 4102 may use the calibration parameters to determine, for example, tissue depth in an image. The processor 4102 may use the depth information for image recognition to note tissue of interest and/or identify instrument location to avoid inadvertent contact when the camera 300 is mated with the robotic arm 506. The depth information may be output by the processor 4102 to, for example, robotic suturing devices, diagnostic equipment, procedure monitoring and recording systems, etc. to conduct a coordinated and at least semi-automated surgical procedure.

3. Calibration of the Robotic Arm Embodiment

After the stereoscopic visualization camera 300 is calibrated, as discussed above, it may be connected to the robotic arm 506 and/or the coupling plate 3304. As described below, precise knowledge of the working distance with respect to focal distance Z, provided by the stored calibration parameters, is used by the example processor 4102 and/or the robotic processor 4122 for determining a position and/or orientation for the stereoscopic visualization camera 300. The combination of the stereoscopic visualization camera 300 with the robotic arm is configured to provide seamless transitions of various working distances while holding a focus or view of a target surgical site.

The calibration procedure for the robotic arm 506, described below, may be executed regardless of a robotic arm type. For example, the calibration procedure may be performed for an articulated robotic system that includes mechanical links connected to each other via rotary joints, numbering from simple one or two links and joints, to joint structures comprising six or more joints. The calibration procedure may also be performed for a Cartesian robotic system that comprises a gantry with linear joints, which uses a coordinate system with X, Y and Z directions. A final joint of a Cartesian robotic system may comprise a wrist type swiveling joint. The calibration procedure may further be performed for a cylindrical robotic system that comprises a rotary joint at its base and one or more additional rotary and/or linear joints to form a cylindrical workspace. Moreover, the calibration procedure may be performed for a polar robotic system that comprises an arm connected to a base via a joint that may operate in more than one rotational axis and further comprises one or more linear or wrist joints. The calibration procedure may additionally be performed for a Selective Compliance Assembly Robot Arm ("SCARA") system that comprises a selectively compliant arm operated in a primarily cylindrical fashion, which is used for assembly applications.

Figure 48:
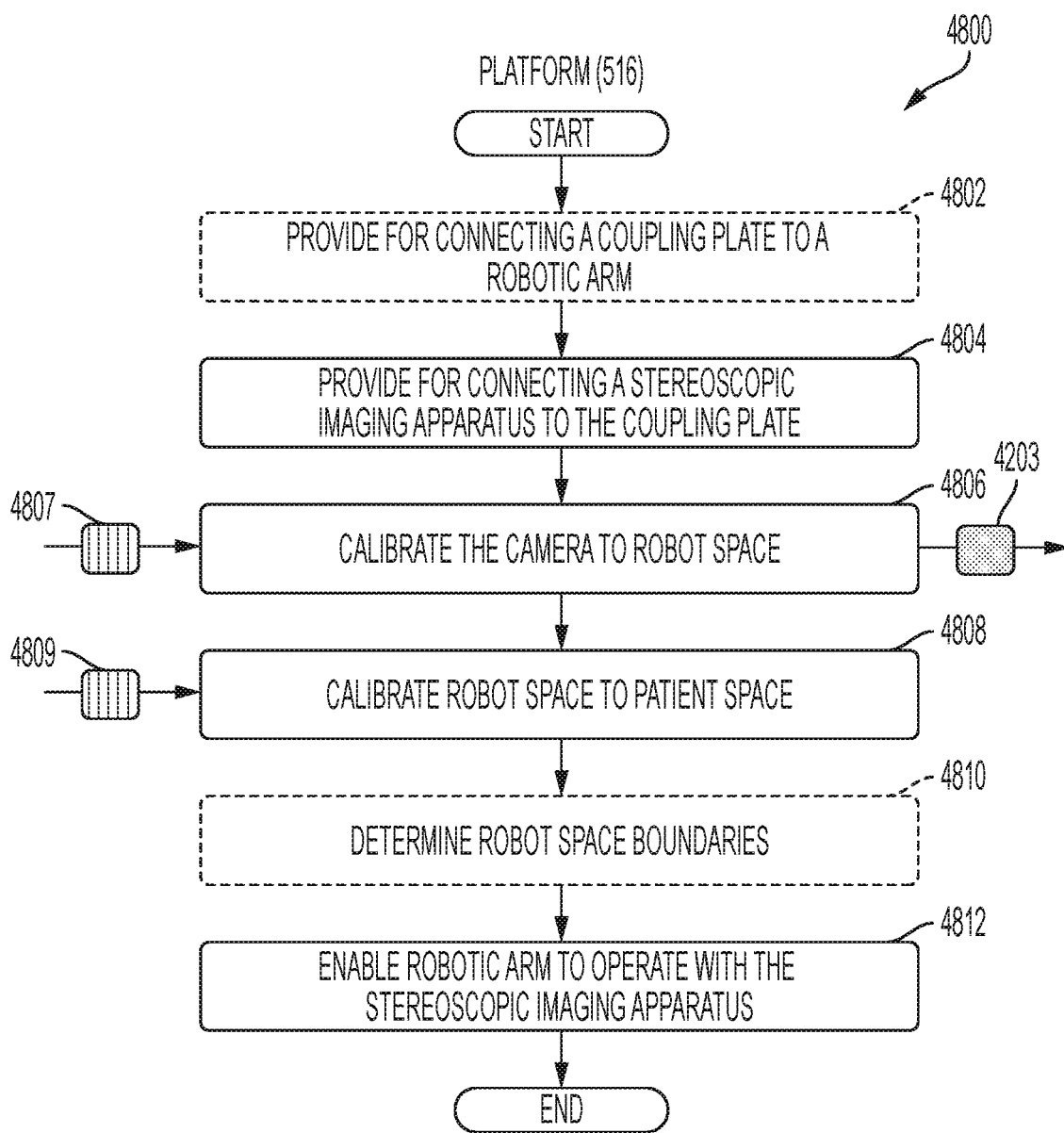
FIG. 48 illustrates an example procedure or routine for calibrating the robotic arm of FIGS. 5 and 33 to 41, according to an example embodiment of the present disclosure.

FIG. 48 illustrates an example procedure 4800 or routine for calibrating the robotic arm 506, according to an example embodiment of the present disclosure. Although the procedure 4800 is described with reference to the flow diagram illustrated in FIG. 48, it should be appreciated that many other methods of performing the steps associated with the procedure 4800 may be used. For example, the order of many of the blocks may be changed, certain blocks may be combined with other blocks, and many of the blocks described are optional. Further, the actions described in procedure 4800 may be performed among multiple devices including, for example the optical elements 1402, the image capture module 1404, the motor and lighting module 1406, the information processor module 1408 of the example stereoscopic visualization camera 300 of FIG. 14 and/or joints R1 to R9 and robotic arm controller 4106 of FIG. 41. For example, the procedure 4800 may be performed by a program stored in the memory 4120 of the robotic arm controller 4106.

In some embodiments, the coupling plate 3304 is connected to the robotic arm 506 (block 4802). If a coupling plate 3304 is not used, the stereoscopic visualization camera 300 is connected directly to the connection or coupling interface 3450 of the robotic arm 506. If the coupling plate 3304 is used, the stereoscopic visualization camera 300 is connected to the coupling plate (block 4804). As discussed above, first end 3702 of the coupling plate 3304 is connected to the robotic arm 506 and the second end 3704 of the coupling plate 3304 is connected to the stereoscopic visualization camera 300.

After the example stereoscopic visualization camera 300 is connected to the robotic arm 506, the example processor 4102 and/or the robotic arm controller 4106 are configured to calibrate the camera and its view vector into a coordinate system originated around the stationary base 3404 of the robotic arm 506 (block 4806). The coordinate system is referred to herein as "robot space" or "robotic space". During this calibration step, known movements to the robotic arm 506 are used by the processor 4102 and/or the robotic arm controller 4106 to determine an orientation and a location of a view vector and object plane of the camera 300 during visualization of a target surgical site.

In some embodiments, the mechanical features of the camera 300, the coupling plate 3304, and the robotic arm 506 exist such that, when mechanically connected together, the relationship between the camera 300, the coupling plate 3304, and the robotic arm 506 is uniquely determined and known. In these embodiments, the processor 4102 and/or the robotic arm controller 4106 determine the position, direction, and/or orientation of the view vector from the known mechanical geometry of the camera 300, the coupling plate 3304, and the robotic arm 506.

In other embodiments where the mechanical features do not exist, the example processor 4102 and/or the robotic arm controller 4106 are configured to perform a routine to accurately determine a spatial relationship between the camera 300 and the robotic arm 506 in robot space. The processor 4102 and/or the robotic arm controller 4106 move the stereoscopic visualization camera 300 to a start position, which may include a stow position, a re-orientation position, or a surgical position. The stereoscopic visualization camera 300 then moves the camera from the start position to a position that approximately visualizes a calibration target located on the stationary base 3404 of the robotic arm 506. The calibration target may be located, for example, at a convenient area of the cart 510 in a position within the motion sphere of the robotic arm 506. Some examples of the calibration target include, for example, small spheres or other uniquely recognizable objects that can be located relative to each other (in two-dimensional or stereoscopic images) in a unique, known orientation. The coordinates of the spheres are fixed and known with respect to the cart 510 and stationary base 3404, and are hence known in robot space. The processor 4102 and/or the robotic arm controller 4106 are configured to store the coordinates to, for example, the memory 4120.

During the calibration, the processor 4102 and/or the robotic arm controller 4106 receive view vector data 4807 regarding working distance, magnification, stereoscopic optical axis, and/or IPD. The stereoscopic visualization camera 300 is set to visualize the spheres at the calibration target simultaneously and determine their position through the use of parallax in the stereoscopic image. The processor 4102 and/or the robotic arm controller 4106 records the positions of the spheres in an initial coordinate system, for example, X, Y, and Z with respect to a fiducial in the camera 300 (i.e. "camera space). The X,Y,Z position may correspond to an origin location, and be defined in a file or LUT as being the origin or having other known coordinate values. The processor 4102 and/or the robotic arm controller 4106 also use output data from joint sensors to determine position and orientation of the joints and links in the robotic arm 506. The processor 4102 and/or the robotic arm controller 4106 also receive position information to determine a position and orientation of the coupling device 3304. Together, the position and orientation of the robotic arm 506 and the coupling device 3304 enable the processor 4102 and/or the robotic arm controller 4106 to determine a pose of the camera 300. The processor 4102 and/or the robotic arm controller 4106 are configured to perform a coordinate transformation between the camera space and robot space based on the positions of the spheres of the calibration target as recorded by the camera, and as the positions of the robotic arm 506 and/or coupling plate 3304. The processor 4102 and/or the robotic arm controller 4106 may store the coordinate transformation to the LUT 4203, a different LUT for the robotic arm 506, and/or one or more calibration registers.

In some embodiments, the camera 300 is moved to record images of multiple calibration targets located either on a cart 510, a ceiling, a wall, and/or within a surgical area. Each of the calibration targets may have a unique orientation that enables it physical X,Y,Z location to be identified. The processor 4102 and/or the robotic arm controller 4106 perform additional coordinate transformations for each of the calibration targets and store the transformations to one or more LUTs and/or registers.

In other embodiments, the processor 4102 and/or the robotic arm controller 4106 may use alternative methods to calibrate the camera 300 to robot space. In this context, "calibration" is taken to mean "registration", where the processor 4102 and/or the robotic arm controller 4106 are configured to calculate registration over a wide space in which the registration may vary. For example, a system can be used where a separate stereoscopic camera is used to observe and locate calibration targets on the cart 510 as well as similar calibration targets which are installed on the camera 300 and/or on a patient or surgical bed. The processor 4102 and/or the robotic arm controller 4106 are configured to model and track the camera 300, which is modeled and tracked as a surgical instrument with a view vector and working distance. The view vector and working distance define parameters for accurately visualizing a target surgical site. In these other embodiments, the other camera determines and reports location and orientation information for the coordinate frame of each such instrument in a reference frame, such as the stereoscopic camera 300. Then, using linear algebra, the poses and/or locations of instruments relative to each other are calculated by the processor 4102 and/or the robotic arm controller 4106, thereby resulting in a calibration of the camera 300 to the robot space.

In some embodiments, the processor 4102 and/or the robotic arm controller 4106 are also configured to calibrate for the coupling plate 3304. In some instances, the coupling plate 3304 includes one or more switches that activate depending on a position of joints R7 to R9. The known position of the switches is used by the processor 4102 and/or the robotic arm controller 4106 as part of the coordinate transformation. Additionally or alternatively, the coupling plate 3304 is calibrated by causing the robotic arm 506 to move while images from the camera 300 are monitored to determine orientation. In an example where the coupling plate 3304 is orientated as shown in FIG. 37, the robotic arm 506 is commanded to move in a direction relative to an assumed orientation (for example, moving the camera 300 along the z-axis). If the assumed orientation is as shown in FIG. 37, wherein the camera 300 is aimed downward, a downward movement of the robotic arm 506 should cause an object in the image to get larger as the camera 300 gets closer. If, for example, the object in the image, instead moves sideways or up/down, then the processor 4102 and/or the robotic arm controller 4106 are configured to detect the motion and determine that the assumed orientation is incorrect. The processor 4102 and/or the robotic arm controller 4106 may generate an error and prompt an operator for the correct orientation and/or determine the correct orientation based on the detected movement in the images. The change in the image from movement of the camera 300 is deciphered automatically through use of, for example, image matching template algorithms, as described previously. In some embodiments, the use of matching template algorithms by the processor 4102 and/or the robotic arm controller 4106 determines joint orientation at the coupling plate 3304, which is stored to a LUT for calibration.

Figure 49:
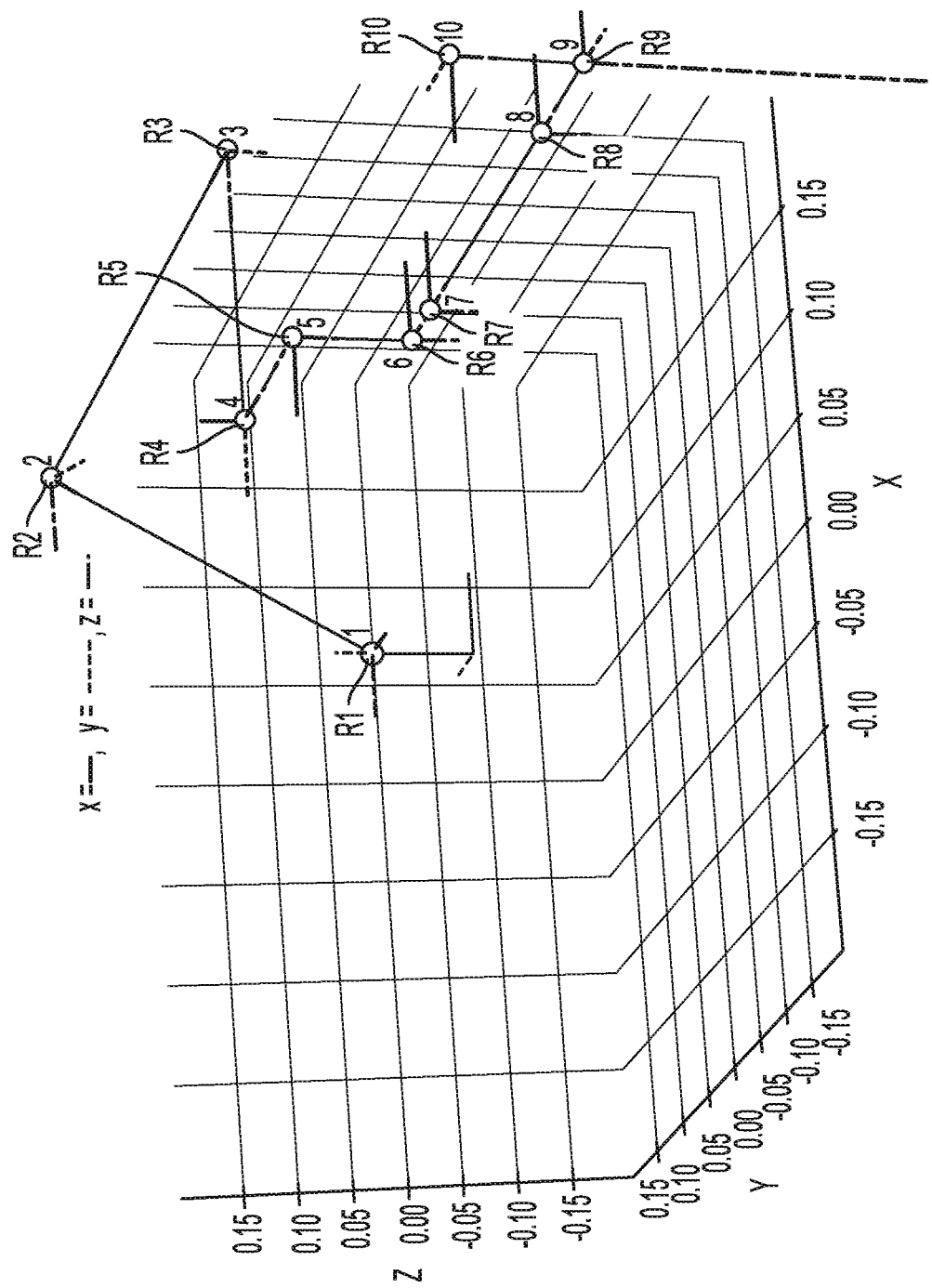
FIG. 49 shows a diagram that is illustrative of how the stereoscopic visualization camera and/or the robotic arm are calibrated to robot space, according to an example embodiment of the present disclosure.

FIG. 49 shows a diagram that is illustrative of how the stereoscopic visualization camera 300 and/or the robotic arm 506 are calibrated to robot space, according to an example embodiment of the present disclosure. In the illustrated embodiment, each of joints R1 to R9 and corresponding links are modeled based on rotational capabilities and/or lengths. The memory 4120 may store the mathematical parameters associated with the model. Further, the processor 4102 and/or the robotic arm controller 4106 may use the mathematical model to determine, for example, a current position of the robotic arm 506 and/or camera 300, which may be used for calculating how joints are to be rotated based on intended movement provided by an operator.

In the illustrated example, joint R1 is provided at a coordinate position of (0,0,0). The lengths between the joints R1 to R9 correspond to a length of the links. In the illustrated example, the stereoscopic visualization camera 300 is modeled as a robot end effector that is connected to nine couplers. The three-dimensional space shown in FIG. 49 is modeled using a sequence of ten homogeneous transformations, which may include matrix multiplications. The first six frames or joints R1 to R6 represent the forward kinematics of the robotic arm 506, and may be calculated using the Denavit-Hartenberg parameters of a robotic arm. The next three frames or joints R7 to R9 represent the transform from the tool-tip of the robotic arm 506 to a tip of the coupling plate 3304. The last frame R10 represents the transform from the tool-tip of the coupling plate 3304 to the control point of the stereoscopic visualization camera 300.

Frame or joint R7 represents the pitch joint of the coupling plate 3304, which, can change between 0° and 90°. Frame or joint R8 represents the yaw joint of the coupling plate 3304, and can change between −90°, 0°, and 90°, depending on the yaw configuration. Joints R7 to R9 of the coupling plate may include a voltage source and a potentiometer. The connector 3450 and/or the coupler controller 4130 of the robotic arm 506 may include an I/O tool-tip connector that is configured to receive a voltage output from the potentiometer. The processor 4102 and/or the robotic arm controller 4106 are configured to receive the output voltage and correspondingly determine pitch and yaw angles of the coupling plate 3304. The processor 4102 and/or the robotic arm controller 4106 combines the pitch and yaw information of the coupling plate with sensor output data from joints R1 to R6 of the robotic arm 506 to calculate position of the frames R1 to R10 to determine the three-dimensional position of the robotic arm 506, the coupling plate 3304, and/or the camera 300.

The control point represents frame 10 at the very end of the kinematic chain, and is fully programmable in terms of position based on which feature is selected. For example, if an operator selects an assisted drive feature, the processor 4102 and/or the robotic arm controller 4106 are configured to set the control point representative of the camera 300 to be inside of the camera along an axis of rotation of the control arms 304. In another example, if an operator selects a lock-to-target feature, the processor 4102 and/or the robotic arm controller 4106 are configured to set the control point of the camera 300 to an origin of an optical axis view vector.

Returning to FIG. 48, the after calibrating the camera 300 to robot space, the processor 4102 and/or the robotic arm controller 4106 are configured to calibrate the robot space to patient space (block 4808). Calibration of patient space is need to enable the stereoscopic visualization platform 516 to make accurate visualizations of a patient, where the orientation between robot system and patient is needed. In some embodiments this orientation is fixed. In other embodiments the orientation, if varying, is sensed and known. In some embodiments a patient is placed in an operating room bed and registered to the bed using one or more fiducials 4809. For example, if a patient is undergoing brain surgery, they are secured to a bed and an external frame is fixed to their skull. The frame is observable by the stereoscopic visualization camera 300 and may comprise fiducials 4809 in an arrangement such as that of the calibration target where two or more non-collinear objects of known locations are visible simultaneously, such that the position and orientation of the frame, and hence the patient's skull, is capable of being determined. Other embodiments may use fiducials 4809 that are implanted into a patient and are visible in MM or similar images. Such fiducials 4809 can be used to accurately track and register a patient's skull as well as the MM image to a coordinate system representative of patient space. Further, other embodiments may use image recognition of features native to the patient themselves. For example, facial or similar recognition using biometric data, in-situ x-ray, or similar alternative modality imaging can be used to precisely locate a position and orientation of the patient. In another example, a model of a surface of a patient's face can be determined using one or more depth map calculations as described above, and surface matching functions performed by the processor 4102 and/or the robotic arm controller 4106.

In an embodiment, a position and orientation of an operating room bed with respect to robot space is fixed and determined. Some embodiments comprise a rigid frame which mechanically registers the bed to, for example, fittings on the cart 510 in a known position and orientation. Alternatively, the bed can be fixed with respect to the robotic arm 506 and fiducials can be used to determine position and orientation. For example, the robotic cart 510 and bed can be anchored to the floor and fixed for the duration of the procedure.

After visualization of the patient's fiducials 4809 by the camera 300, their position and orientation in robot space can be deciphered and stored by the processor 4102 and/or the robotic arm controller 4106, where coordinate system transformations from robot space to patient space are enabled. It is noted that coordinate system transformations from one space to another are generally selectable and reversible. For example, it may be more efficient to transform desired camera motions or poses into robot space to enable the processor 4102 and/or the robotic arm controller 4106 to determine discrete joint motion and orientation. Alternatively, it may be easier and more efficient to present information to a surgeon on the display monitor 512 in patient space. Location of points and vectors can be transformed by the processor 4102 and/or the robotic arm controller 4106 to be respective of most any coordinate system, for example, a cart origin, a patient reference frame, GPS, and/or other coordinate systems as desired.

In some embodiments, the processor 4102 and/or the robotic arm controller 4106 are configured to use automated, iterative techniques to perform these or equivalent methods of robot/patient space calibration and measurement to increase accuracy and reduce calibration time. In exemplary embodiments, the displacement and orientation of the stereoscopic visualization camera 300 with respect to fiducials is accurately known by the processor 4102 and/or the robotic arm controller 4106. Motion of the robotic arm 506 can be accurately performed, and the subsequent images of fiducials can be accurately analyzed. The visualization and knowledge of the calibration parameters can be combined by the processor 4102 and/or the robotic arm controller 4106 such that measurement, and hence calibration can be accurately performed in an automated manner. This is important, for example, to maintain accurate calibrations from one surgical procedure and one patient to the next.

In some examples, the processor 4102 and/or the robotic arm controller 4106 are configured to determine boundaries of the robotic arm 506 and/or camera 300 relative to the patient space and/or robot space. The boundaries represent virtual limits that are implemented in the software to prevent the robotic arm 506 and/or the camera 300 from contacting or escaping defined areas or spaces. In some examples, the limits are defined in one or more LUTs or registers stored in the memory 4120 as scale factors that are applied to joint movement signals by the processor 4102 and/or the robotic arm controller 4106. The magnitude of the scale factor is decreased to zero as the limit to each individual boundary is approached. For example, the joint rotation amount and speed may be determined based on operator input. However, the processor 4102 and/or the robotic arm controller 4106 scales the joint rotation speed by the scale factor before sending the signal(s) to the appropriate joint(s). In addition, the processor 4102 and/or the robotic arm controller 4106 may maintain the rotation amount such that the joint moves the desired amount, but at a reduced speed, until the joint reaches the boundary. It should be appreciated that a joint in a rotation area where a scale factor is applied may not have a scale factor applied if the desired movement is away from the boundary. Thus, the processor 4102 and/or the robotic arm controller 4106 may apply a scale factor to certain joints while applying a scale factor of '1' to other joints based on a current position and estimated desired movement from an operator.

The scale factors are strictly between zero and one, which enables chaining them together and enables the software to support an infinite number of possible boundaries. The scale factors may be lineally decreased as a boundary is approached, which causes a gradually slowing of the rotation of joints R1 to R9 as the robotic arm 506 approaches a boundary. In other examples, the scale factors may decrease exponentially as a boundary is approached.

Generally, operators typically focus their attention on the surgical field or the stereoscopic image on the display monitor 512. As such, the operators are typically unaware of the position of the individual links of the robotic arm 506 and/or the coupling plate 3304. Therefore, it is not always intuitive when the robot arm 506 is about to reach a limit or impact another part of the robot arm 506. The joint limits may therefore always be active and prevent any part of the robot arm 506 from hitting itself or putting the joints in a singular configuration, such as elbow lock. The example processor 4102 and/or the robotic arm controller 4106 are configured to determine the scale factor based on a current position of the robotic arm 506. The processor 4102 and/or the robotic arm controller 4106 may also take into account intended movement instructions provided by an operator to determine which scale factor is to be applied. Based on current and/or anticipated movement, the processor 4102 and/or the robotic arm controller 4106 calculates the scale factors based on distances in joint angle space using, for example, one or more LUTs. The joint angle spacing may define certain combinations of joint angles that are known to cause joint lock or cause the robotic arm 506 to hit itself. As such, the joint angle spacing determination is based on determining and comparing current (and/or anticipated) movements of joints relative to each other.

In addition to the boundaries for the robotic arm 506, the memory 4120 may store boundaries that relate to Cartesian limits that prevent the robotic arm 506 from hitting the cart 510, the robotic arm from hitting the display monitor 512, and/or the camera 300 from hitting the robotic arm 506. The processor 4102 and/or the robotic arm controller 4106 may use, for example, the coordinate system discussed in conjunction with FIG. 49 for determining and/or applying the Cartesian limits. In some examples, the limits may be relative or anchored to a certain link. As such, when the link is moved in the 3D space, the boundary around it moves accordingly. In other examples, the limits are static and fixed to certain coordinate planes or lines within the 3D space shown in FIG. 49. The processor 4102 and/or the robotic arm controller 4106 may apply the limits by calculating or determining scale factors in Cartesian space and applying the forward kinematic transform.

The example processor 4102 and/or the robotic arm controller 4106 may also determine a patient boundary, which defines a virtual place that no point of the robotic arm 506 and/or camera 300 can violate. Patient boundaries may be determined by calculating scale factors in Cartesian space for a distance of each positional joint on the robotic arm 506 and/or the coupling plate 3304 to a location of a boundary plane. The boundary plane, as shown in orientation 5002 of FIG. 50 is implemented as an X,Y plane located at some vertical Z location for non-pitched configurations. For pitched configurations, such as patient semi-sitting shown in orientation 5004 of FIG. 50, the boundary plane is set as a Y,Z plane located at either positive or negative X values depending on the direction the camera 300 faces.

The example boundaries discussed above may be stored to the memory 4120 as default boundaries and/or determined by the processor 4102 and/or the robotic arm controller 4106 prior to a surgical procedure. In some embodiments, certain boundaries may be accessed or determined based on an inputted type of surgical procedure to be performed. For example, patient boundaries may be determined by the camera 300 imaging the patient and determining patient depth using calibration information/parameters. The processor 4102 and/or the robotic arm controller 4106 may then create and apply a boundary to a specified location above or next to the patient. Similar boundaries may be created after detection of monitors, surgical staff, or surgical instruments.

For instance, boundaries can be determined around the use of a specific surgical tool such that tools of larger size or tools that pose certain risks if contacted. The example processor 4102 and/or the robotic arm controller 4106 may receive an input of the tool type and/or detect the tool in the stereoscopic images using image analysis. In other examples, the processor 4102 and/or the robotic arm controller 4106 calculate depth information in relation to a surgical instrument to determine its size, orientation, and/or position. The example processor 4102 and/or the robotic arm controller 4106 translate the image of the surgical instrument into the coordinate system, such as the one discussed in connection with FIG. 49. The processor 4102 and/or the robotic arm controller 4106 also apply scale factors having a value less than '1' to areas that correspond to a location of the surgical instrument, thereby preventing the robotic arm 506 and/or the camera 300 from inadvertently contacting the surgical tool. In some instances, the processor 4102 and/or the robotic arm controller 4106 may track a movement of the surgical tool during a procedure and change the boundary accordingly.

Figure 51:
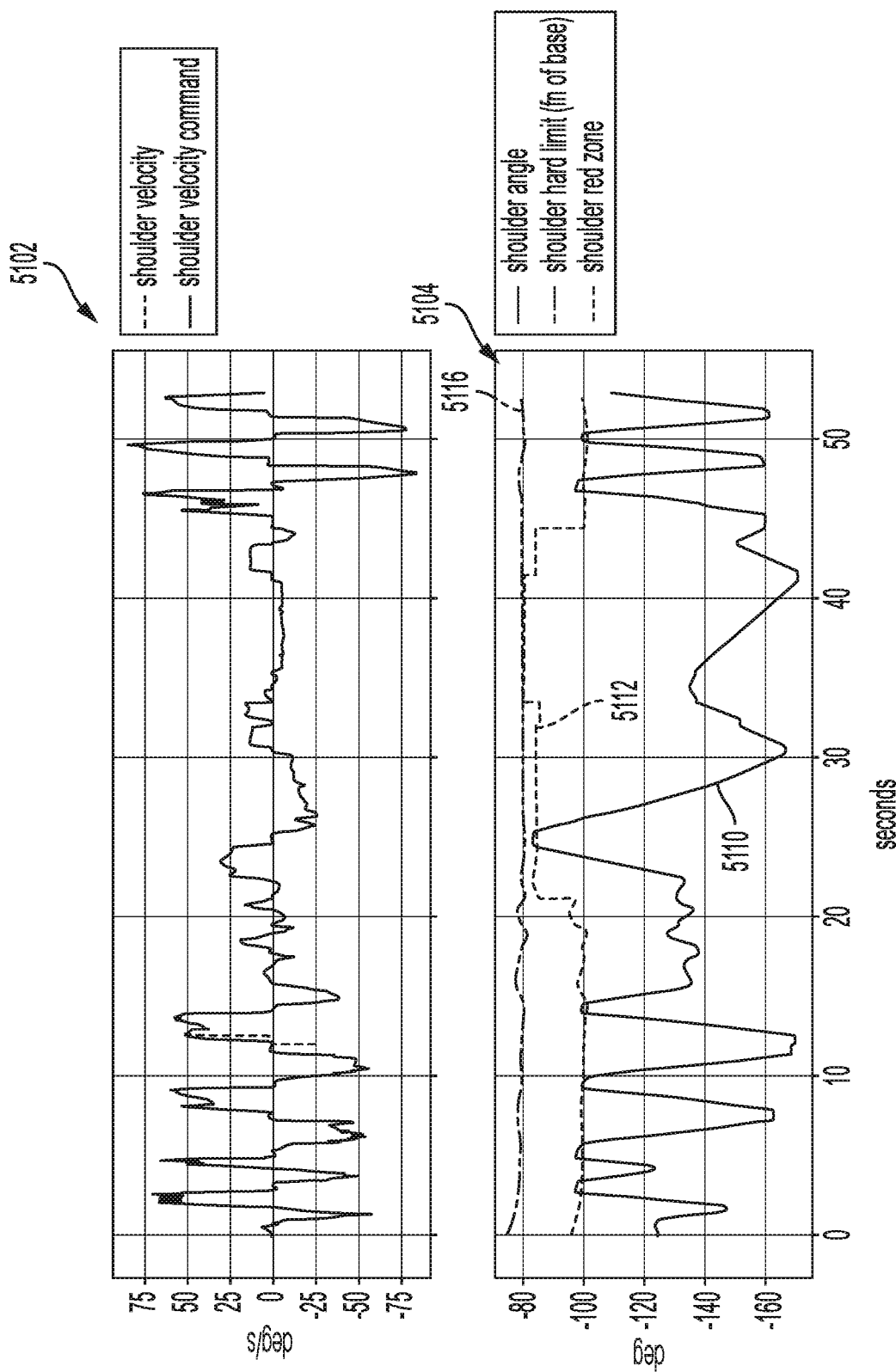
FIG. 51 illustrates an example of how rotational joint speed of the robotic arm and/or the coupling plate is scaled based on distance to a boundary, according to an example embodiment of the present disclosure.

FIG. 51 illustrates an example of how the rotational joint speed of the robotic arm 506 and/or the coupling plate 3304 is scaled based on distance to a boundary, according to an example embodiment of the present disclosure. Graph 5102 shows a velocity of rotation for joint R1 and graph 5104 shows a shoulder angle (e.g., rotation position) 5110 in relation to a first zone 5112 that corresponds to an area close to a boundary where a scale factor is reduced from a value of '1' and a second zone 5114 that corresponds to the boundary where the scale factor is reduced to a value of '0'.

FIG. 51 shows that as the robotic arm 506, and in particular joint R1 causes the at least one link and/or the stereoscopic visualization camera 300 to approach the first zone 5112, the rotational velocity is dynamically scaled with respect to the distance to the second zone 5114. Then, when the at least one link and/or the stereoscopic visualization camera 300 reach the second zone 5114, the scale factor is reduced to a value of '0' and all rotational joint movement toward the boundary is stopped. In other words, as the robotic arm 506 and the stereoscopic visualization camera 300 approach a limit or boundary, the processor 4102 and/or the robotic arm controller 4106 causes a rotational speed of at least some of joints R1 to R9 to decrease and eventually reach a velocity of '0' degrees/second when the second zone 5114 is reached (as shown between 20 and 30 seconds in the graphs 5102 and 5104). The graph also shows that when the at least one link and/or the stereoscopic visualization camera 300 are moved away from the second zone 5114, the processor 4102 and/or the robotic arm controller 4106 use a scale factor value of '1' since the second zone 5114 is not being approached.

In some embodiments, the processor 4102 and/or the robotic arm controller 4106 are configured to cause the display monitor 512 or other user interface to display one or more graphical icons representative of a status of the robotic arm 506. For example, a green icon may be displayed when the robotic arm 506 and/or camera 300 are located in a zone or area where scale factors have a value of '1'. Additionally, a yellow icon may be displayed when the robotic arm 506 and/or camera 300 are located within the first zone 5112 to indicate joint rotational speed is slowed. Further, a red icon may be displayed when the robotic arm 506 reaches the second zone 5114 or a boundary/limit to indicate that no further movement beyond the boundary is possible.

Returning to FIG. 48, after the robot space boundaries are determined, the example processor 4102 and/or the robotic arm controller 4106 are configured to enable the robotic arm 506 for operation with the stereoscopic visualization camera 300 (block 4812). This may include enabling the robotic arm 506 and the stereoscopic visualization camera 300 to be used during a surgical procedure. This may also include enabling features, such as assisted drive and/or lock-to-target. Additionally or alternatively, this may include enabling one or more user controls at one or more of the input devices 1410 of FIG. 41. The example procedure 4800 ends after the robotic arm 506 is enabled with the stereoscopic visualization camera 300. The example procedure 4800 may repeat if the stereoscopic visualization platform 516 is reinitialized, experiences a detected failure, or the calibration cannot be validated.

D. Stereoscopic Visualization Camera and Robotic Arm Operation Embodiments

The example stereoscopic visualization camera 300 is configured to operate in conjunction with the robotic arm 506 and/or the coupling plate 3304 to provide enhanced visualization features. As discussed below in more detail, the enhanced features include an extended focus, automated focal tip positioning, providing a measurement of distances between objects in an image, providing robotic motion with conjoined visualization, sag compensation, image fusion, and storage of visualization positions/orientations. The enhanced visualization features may also include assisted-drive capability of the robotic arm 506 and a lock-to-target capability that enables the camera to be locked onto a specific view while enabling an orientation of the robotic arm 506 and/or the coupling plate 3304 to be changed.

1. Extended Focus Embodiment

In some embodiments, the robotic arm 506 and/or the coupling plate 3304 may provide an extended focus of the camera 300. As discussed above in connection with FIG. 43, the stereoscopic visualization camera 300 includes the main objective assembly 702 for changing a working distance. To focus on an object in the surgical site, the main objective assembly 702 changes a focus distance from just before the object to just past the object. However, in some instances, the main objective assembly 702 reaches a mechanical limit of the front working distance lens 408 before the best focus is achieved.

The example processor 4102 and/or the robotic arm controller 4106 are configured to detect when a mechanical limit is reached and/or determine that a mechanical limit is about to be reached for the lens 408 and accordingly adjust a position of the robotic arm 506 instead. The processor 4102 and/or the robotic arm controller 4106 is configured to use the robotic arm 506 to extend focus by computing a view vector of the camera 300 and causing the robotic arm 506 to be actuated along the optical axis. The processor 4102 and/or the robotic arm controller 4106 determine a distance needed to achieve focus using the above-described calibration parameters of the stereoscopic visualization camera 300. For example, as discussed above, a position of the front working distance lens 408 is mapped to a physical working distance of the main objective assembly 702 to a target object. The distance provides an estimate as to how far a center of the camera 300 is from the target object. Additionally, the calibration parameters may include a mapping between motor or encoder steps for the front working distance lens 408 to working distance to provide an estimation of distance needed to achieve a certain working distance or focus. Accordingly, the processor 4102 and/or the robotic arm controller 4106 may read a current encoder value of the front working distance lens 408 and determine a number in meters that represents a vertical distance from the camera 300 to the target object. In other words, the processor 4102 and/or the robotic arm controller 4106 convert the lens movement (in encoder counts) into a physical distance in the robot space. The processor 4102 and/or the robotic arm controller 4106 then determine joint rotational speeds, directions, and/or durations (e.g., a movement sequence) to that will cause the robotic arm 506 to move the determined distance along the optical axis. The processor 4102 and/or the robotic arm controller 4106 then transmits one or more signals to the appropriate joints corresponding to the movement sequence to cause the robotic arm 506 to provide an extended focus. In some instances, the processor 4102 and/or the robotic arm controller 4106 may apply a scale factor before the signals are transmitted to joints R1 to R9 of the robotic arm 506 and/or the coupling plate 3304.

It should be appreciated that the extension of focus causes an automated movement of the robotic arm 506. In other words, the robotic arm 506 can continue motion of the camera 300 through the point of best focus. In addition, the movement of the robotic arm 506 occurs without inputs from an operator to move the robotic arm, but rather, operator images regarding the changing of a focus. In some instances, the processor 4102 and/or the robotic arm controller 4106 may adjust the focus automatically to maintain a clear image.

In some embodiments, the processor 4102 and/or the robotic arm controller 4106 are configured to move the robotic arm 506 along the camera's working distance in response to a single button press via the input device 1410. This feature enables an operator to fix a motor position of the main objective assembly 702 and obtain focus by moving the robotic arm 506 and/or the coupling plate 3304. This "robot auto focus" feature or procedure is accomplished by the processor 4102 and/or the robotic arm controller 4106 estimating or determining a distance from a front of the main objective assembly 702 to a target, as discussed above in connection with FIG. 43. The processor 4102 and/or the robotic arm controller 4106 is configured to use the determined distance with a feedback law to command a vertical velocity of the robotic arm 506 (or velocity along an optical axis of the camera 300) until the determined distance reaches a value of '0'. The processor 4102 and/or the robotic arm controller 4106 may use this autofocus algorithm anytime during a procedure to bring a target object into focus. In some embodiments, the processor 4102 and/or the robotic arm controller 4106 may use movement of the robotic arm 506 and/or the coupling plate 3304 from the last time autofocus was used as a seed or starting point when searching for a direction of autofocus, thereby improving the speed and accuracy of getting a target object into focus.

It should be appreciated that the example processor 4102 and/or the robotic arm controller 4106 may be configured to cause the robotic arm 506 and/or the coupling plate 3304 to move in addition to or alternatively from moving the front lens set 714, the lens barrel set 718, and/or the final optical set 742, each of which may be movable by a respective motor that has encoder counts mapped to position, focus, working distance, and/or magnification. For example, the processor 4102 and/or the robotic arm controller 4106 may cause the robotic arm 506 to move along an optical axis when any of the front lens set 714, the lens barrel set 718, and/or the final optical set 742 is about to approach a movement limit. In some examples, the processor 4102 and/or the robotic arm controller 4106 may cause the robotic arm 506 to move first to a position that is roughly in focus or near-focus, and then adjust the front lens set 714, the lens barrel set 718, and/or the final optical set 742 to bring the target image into near-ideal focus.

2. Automated Focal Tip Positioning Embodiment

In some embodiments, the robotic arm 506 and/or the coupling plate 3304 may be operated in conjunction with the stereoscopic visualization camera 300 to provide automated focal tip positioning. In these embodiments, the processor 4102 and/or the robotic arm controller 4106 is configured to position the camera 300 for visualization of a target surgical site without information or feedback of a specific image and its contents. The processor 4102 and/or the robotic arm controller 4106 may use the calibrated camera model parameters, discussed above in connection with FIGS. 42 and 49 to perform open loop camera positioning. The processor 4102 and/or the robotic arm controller 4106 may cause the robotic arm 506 to position the stereoscopic visualization camera 300 such that a focal point or tip of the camera is in a scene. The stereoscopic visualization camera 300 determines an aiming direction for the camera 300, with respect to a coordinate system, based on calibration information regarding a pose of the robotic arm 506 and/or the coupling plate and optical calibration parameters of the camera 300. The processor 4102 and/or the robotic arm controller 4106 may characterize the aiming by a geometrically-defined view vector, which is aligned coincidentally with the stereoscopic optical axis of the camera 300, with respect to the coordinate system of the robotic arm 506.

In some embodiments, the processor 4102 and/or the robotic arm controller 4106 are configured to execute an initialization routine to align calibration parameters and/or other memory data to an actual physical reference position, which may be used for tip positioning. For example, the processor 4102 and/or the robotic arm controller 4106 may cause the robotic arm 506 and/or the coupling plate to move to a hard stop at "position 0", where all the position data fields are set to 0 (or 0,0,0 in a three-dimensional space). Further motions are made relative to this point and the position data is updated according to, for example, encoder counts of the various joint motors of the robotic arm 506 and/or coupling plate 3304.

In other embodiments, the processor 4102 and/or the robotic arm controller 4106 may determine or set a tip position of the camera 300 based on one or more visualization parameters. For example, the processor 4102 and/or the robotic arm controller 4106 may use a center-of-projection location as a proximal end of a view vector (e.g., a "starting point" for aiming the camera 300). In some surgical systems, this point on a surgical instrument is referred to as the "hind" point, and may be provided in relation to the tip. The processor 4102 and/or the robotic arm controller 4106 calculate a view vector direction from the tip and hind points to determine an aim of the camera 300 with respect to the coordinate system of the robotic arm 506.

Additionally or alternatively, the processor 4102 and/or the robotic arm controller 4106 may determine a focus distance for calculating a range of a focus plane of a stereoscopic image from the center-of-projection. The center of the image at the focus plane is the "tip" point. The processor 4102 and/or the robotic arm controller 4106 may use a calibrated working distance to determine the actual, spatial, physical distance from the camera 300 to the tip point. Further, the processor 4102 and/or the robotic arm controller 4106 may determine the magnification, as discussed above in regards to magnification calibration.

3. Distance Measurement Embodiment

In some embodiments, the robotic arm 506 and/or the coupling plate 3304 may be operated in conjunction with the stereoscopic visualization camera 300 to provide distance measurements and/or depth measurements between objects in a stereoscopic image. For example, the processor 4102 may determine dimensionally a center of a focal point or tip of the camera 300 with respect the coordinate system of the robotic arm 506 using optical calibration parameters transformed to robot space. As discussed above in connection with FIGS. 45 and 46, a view vector and left/right parallax information of any point in an image can be used by the processor 4102 to calculate its position in three-dimensions through triangulation with respect to the tip, or to any other point in the image. This triangulation enables the processor 4102 to map any point in an image to the robotic coordinate system. As such, the processor 4102 can calculate locations and/or depths of multiple objects and/or locations of different portions of an object with respect to the same coordinate space of the robotic arm 506, which enables a distance measurement and/or depth measurement to be determined between the objects.

The processor 4102 may cause the distance and/or depth measurement information to be displayed visually over and/or in conjunction with the stereoscopic image. In some instances, an operator may use the input device 1410 to select two or more objects by selecting the objects on a screen or pointing directly to the actual objects in the patient using a finger or surgical instrument. The processor 4102 receives the indication of the selection and accordingly determines the coordinates of the objects and the distances therebetween. The processor 4102 may then display a ruler graphic and/or values indicative of the distances (and/or an indication of the selected objects) in conjunction with the stereoscopic images.

Further, the tracking of objects enables locations of other objects that were previously imaged (or are provided in other images) to be stored and later compared. For instance, the camera 300 may move to a location where at least some of the objects are outside of the current FOV. However, an operator can instruct the processor 4102 to determine a distance between an object within the FOV and a previously imaged object that is currently outside the FOV.

In some embodiments, the processor 4102 may use the coordinates of objects for fusing digital images or models from alternate modality visualizations, such as Mill images, X-ray images, surgical templates or guidelines, pre-operative images, etc. The example processor 4102 is configured to use object locations in the coordinate plane as well as depth information to properly scale, orientate, and position the alternate modality visualization. The processor 4102 may select at least a portion of the alternate modality visualization that has identical features (e.g., objects) in a displayed stereoscopic image. For instance, the processor 4102 may use an image analysis routine to locate, in a stereoscopic image, a blood vessel pattern, a scar, a deformity, or other viewable physical structure or object. The processor 4102 then locates the identical features in the alternate modality visualization. The processor 4102 selects a portion of the alternate modality visualization that includes the identical features. The processor 4102 may then use coordinates, depths, and/or distances between the features in the stereoscopic image for scaling, rotating, and/or orientating the selected portion of the alternate modality visualization. The processor may then fuse the adjusted portion of the alternate modality visualization with the stereoscopic image(s). The processor 4102 may track how the identifiable objects move relative to each other and/or relative to the FOV to determine how the fused image is to be accordingly updated. For example, movement of the camera 300 to another surgical location may cause the processor 4102 to select another portion of the pre-surgical image for fusion with the stereoscopic images of the other surgical location.

In some instances, the processor 4102 and/or the robotic arm controller 4106 may cause the robotic arm 506 to move to track a movement of an object in the FOV. The processor 4102 uses the coordinate position of the object to detect movement or obfuscation. In response to the detected movement or obfuscation, the processor 4102 and/or the robotic arm controller 4106 are configured to determine how the robotic arm 506 and/or the coupling plate 3304 are to be moved to track the movement of the object or overcome the obfuscation. For example, the processor 4102 and/or the robotic arm controller 4106 may move the robotic arm 506 in a circular path to visualize a point on a patient's retina from multiple directions to avoid reflections or obfuscation from tools.

4. Image Fusion Embodiments

As discussed above, the processor 4102 is configured to fuse an image from an alternate modality to live stereoscopic images. For example, if a surgeon is operating on a patient with a deep brain tumor, the surgeon can instruct that the processor 4102 visualize an MRI image of the brain tumor in the proper location and at the proper depth and stereoscopic perspective as their live image from the camera 300 on the display monitor 512. In some embodiments, the processor 4102 is configured to use distance and/or depth measurement information of one or more objects in the FOV for fusing with the alternate modality view. The processor 4102 may also provide for imaging fusion using the stereoscopic optical axis (e.g., view vector), the IPD, and/or the camera model parameters that were calculated in the calibration steps discussed in connection with FIG. 42 and stored to one or more LUTs. The use of the optical calibration parameters enables the processor 4102 to display an alternate modality image as if the image was acquired by the stereoscopic visualization camera 300. The processor 4102 may use the optical calibration parameters of the camera to model, scale, or modify alternate modality images based on an effective IPD of the camera 300 such that the alternate modality image is viewed at a distance Z from a focus point in the surgical site, given the applied working distance and magnification of the camera 300.

Figure 52:
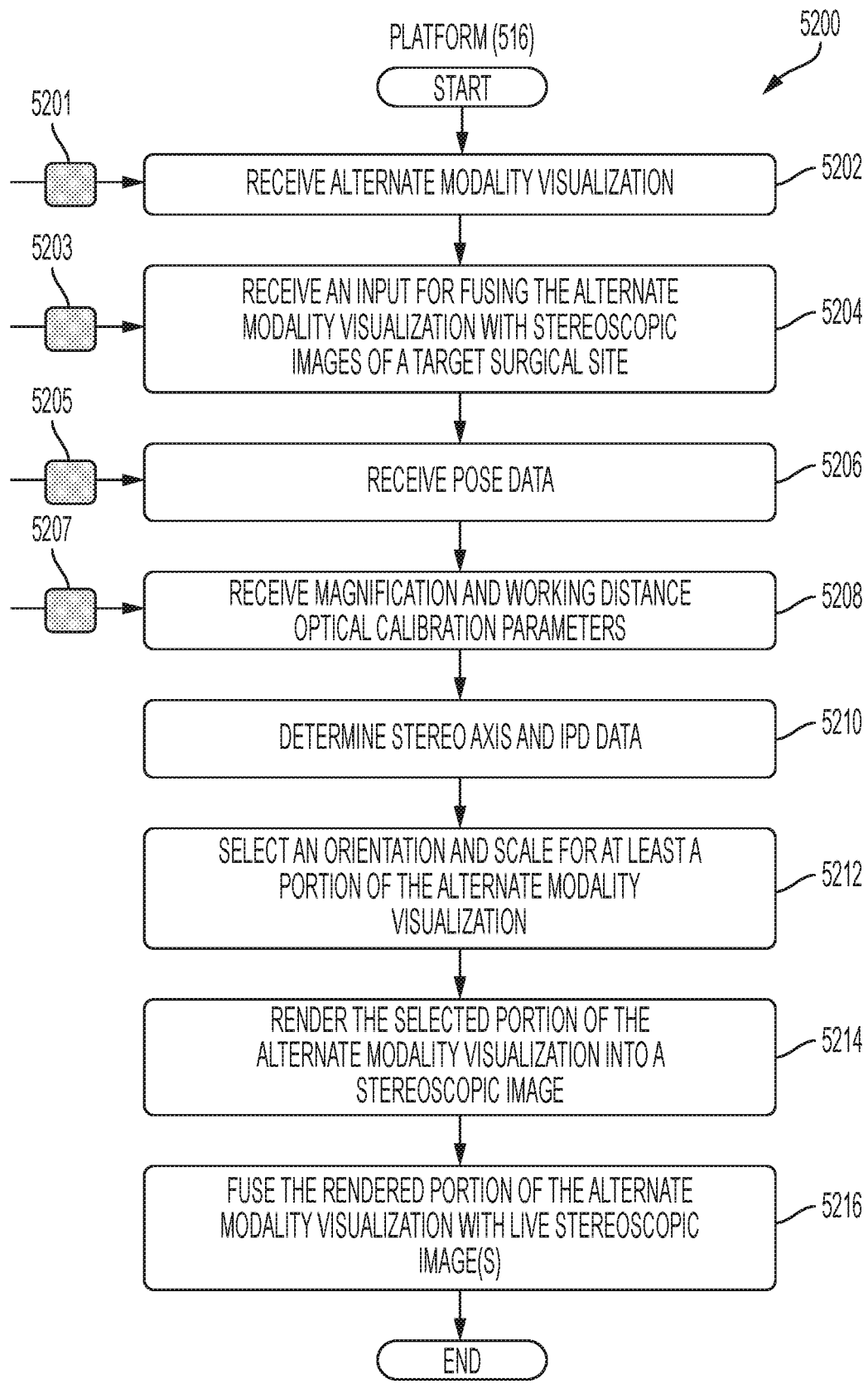
FIG. 52 shows a diagram of an example procedure for fusing an image from an alternate modality visualization with stereoscopic image(s), according to an example embodiment of the present disclosure.

FIG. 52 shows a diagram of an example procedure 5200 for fusing an image from an alternate modality visualization with stereoscopic image(s), according to an example embodiment of the present disclosure. Although the procedure 5200 is described with reference to the flow diagram illustrated in FIG. 52, it should be appreciated that many other methods of performing the steps associated with the procedure 5200 may be used. For example, the order of many of the blocks may be changed, certain blocks may be combined with other blocks, and many of the blocks described are optional. Further, the actions described in procedure 5200 may be performed among multiple devices including, for example the optical elements 1402, the image capture module 1404, the motor and lighting module 1406, the information processor module 1408 of the example stereoscopic visualization camera 300 of FIG. 14 and/or joints R1 to R9 and robotic arm controller 4106 of FIG. 41. For example, the procedure 5200 may be performed by a program stored in the memory 1570 of the processor 4102.

The example processor 4102 of procedure 5200 is configured to use optical calibration parameters to render, for example, previously generated three-dimensional MM data of a patient as a stereoscopic image with proper perspectives as a stereoscopic image recorded by the camera 300. The processor 4102 may receive, for example, an alternate modality visualization, such as the MM data, from device 4104 of FIG. 41 (block 5202). The processor 5202 may also receive an input 5203 via an input device 1410 indicative that the alternate modality visualization is to be fused with stereoscopic images recorded by the stereoscopic visualization camera 300 (block 5204).

During the procedure 5200, when a surgeon positions the camera 300 at a desired orientation and position for a surgical procedure, pose data 5205 is obtained by the processor 4102 (block 5206). The pose data 5201 may include positions of the robotic arm 506, the coupling plate 3304, and/or the stereoscopic visualization camera 300. The processor 4102 also accesses magnification and working distance optical calibration parameters 5207 related to the camera 300 from one or more LUTs, such as the LUTs 4203 of FIG. 42 (block 5208). The processor 4102 uses the pose data 5205 in conjunction with the magnification and working distance optical calibration parameters 5207 to determine a stereoscopic axis and IPD for the camera 300 (block 5210). The processor 4102 applies the pose data, stereoscopic axis data, IPD data, and/or the optical calibration parameters to select at least a portion of the MM data and/or modify, scale, orientate, partition, etc. the selected portion of the Mill data such that the selected portion is provided at a perspective of a view of the patient's brain as viewed by the stereoscopic visualization camera 300 (block 5212). The processor 4102 is configured to apply the stereoscopic optical axis view vector and IPD for rendering the selected portion of Mill data into a stereoscopic image corresponding to the current live view of the camera 300 (block 5114). The processor 4102 may then fuse the stereoscopic Mill image with live stereoscopic image(s) from the camera 300, as discussed herein (block 5216).

As discussed above, the processor 4102 may use an object or feature for positioning or fusing the rendered Mill data with the stereoscopic image(s) from the stereoscopic visualization camera 300. For example, the processor 4102 may use one or more image analysis routines for identifying distinct features or objects in a stereoscopic image, locating the same distinct features in the rendered stereoscopic MM data, and laying the rendered stereoscopic Mill data over the appropriate portion of the camera stereoscopic image(s) such that the features or objects are aligned and have the same scale, size, depth, orientation, etc. The processor 4102 may make the rendered stereoscopic MM data at least partially transparent to enable the live image(s) to also be viewable. Additionally or alternatively, the processor 4102 may adjust a shading at a border of the rendered stereoscopic Mill data to reduce visual contrasts between the rendered stereoscopic Mill data and the camera stereoscopic image(s). The example procedure 5200 of FIG. 52 may then end.

The example procedure 5200 enables the brain tumor to be visualized by the surgeon in an accurate location relative to the stereoscopic images of the camera 300. The surgeon may use this fusion visualization especially partway through a surgical procedure. For example, the surgeon can see the as yet unexposed tumor in a manner best described as "x-ray vision" below a current level of dissection. Control of the transparency of live or rendered stereoscopic MM images may be adjusted via the input device 1410 to optimize clarity of the fused image. The example procedure accordingly enables a safer, more accurate and efficient excision of a tumor.

In some embodiments, the procedure 5200 may be repeated if a FOV, focal point, working distance, and/or magnification changes. In these embodiments, the processor 4102 is configured to use the updated pose information and extract the corresponding stereoscopic axis and IPD from a lookup table to re-render the MM data into an updated, accurate stereoscopic image. The processor 4102 is configured to fuse the newly rendered MM data into the current stereoscopic images such that the live view and the corresponding MM data are located in the proper position, depth, and orientation.

Figure 53:
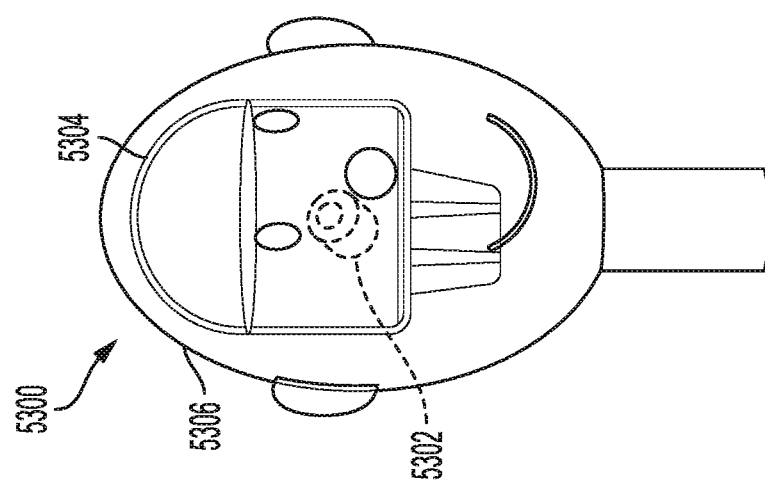

In some embodiments, the example processor 4102 is configured to operate with the stereoscopic visualization camera 300, the robotic arm 506, and/or the coupling plate 3304 to generate live cross-sectional fused visualizations. A cross-section visualization of a surgical site provides a surgeon a significantly improved viewpoint that is not otherwise available. FIG. 53 shows a diagram of a patient 5300 with a glioblastoma 5302, which is illustrated in phantom inside of a patient's head. Specifically, the glioblastoma 5302 may be located in the patient's brain 5304, which is shown in light phantom lines. The diagram of FIG. 53 is typical of pre-operative diagnostic images, for example, from an Mill device, where numerous image slices are stacked and a 3D model of an interior of the patient's cranium 5306 is rendered and visualized.

Figure 54:
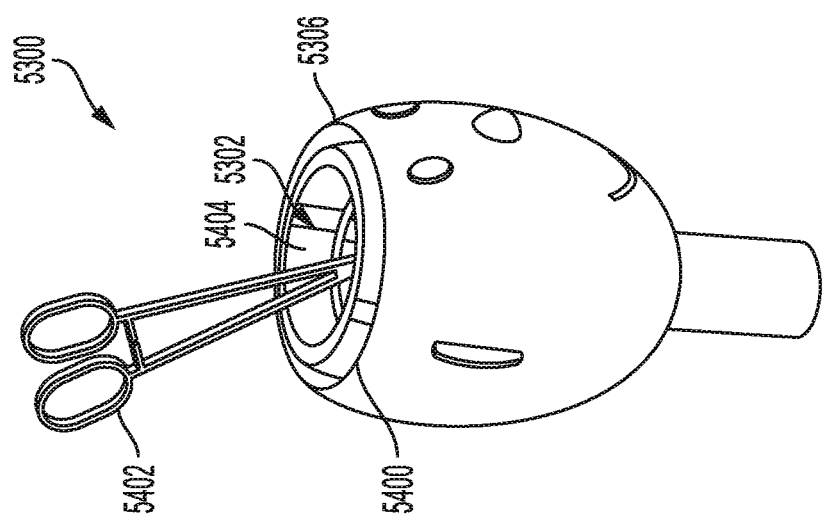
FIGS. 53 to 61 show diagrams illustrative of live cross-sectional fused visualizations generated by the combination of the stereoscopic visualization camera and/or the robotic arm of FIGS. 3 to 52, according to example embodiments of the present disclosure.

In the illustrated example, the glioblastoma 5302 is to be removed through brain surgery. FIG. 54 shows a diagram of a perspective view of the patient 5300 undergoing a craniotomy procedure 5400 to provide access to the cranium 5306. The procedure 5400 also includes brain dissection and retraction using surgical instrument 5402. Generally, a surgical access site 5404 is made in a deep conical shape to access the glioblastoma 5302.

Figure 55:
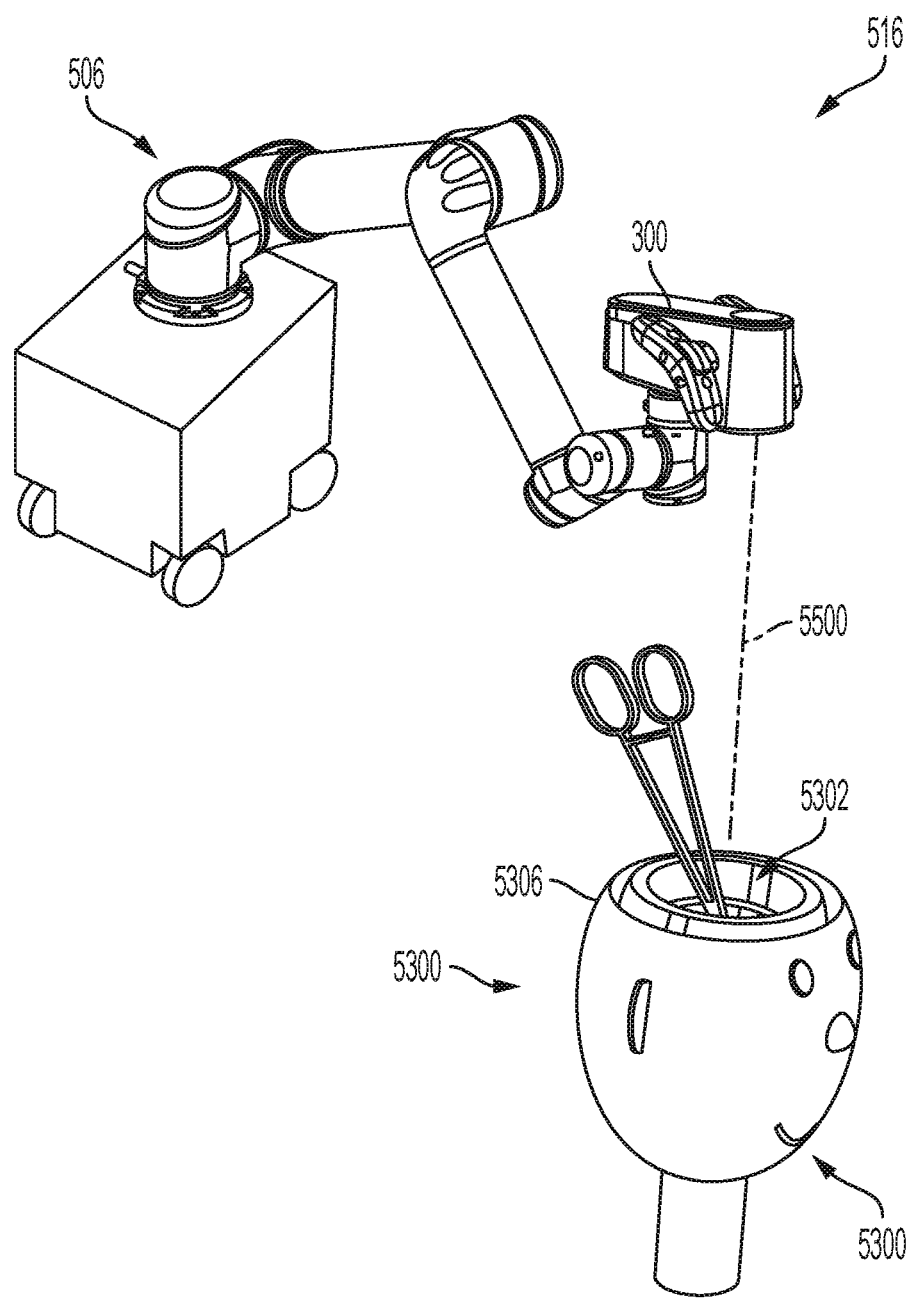
Figure 57:
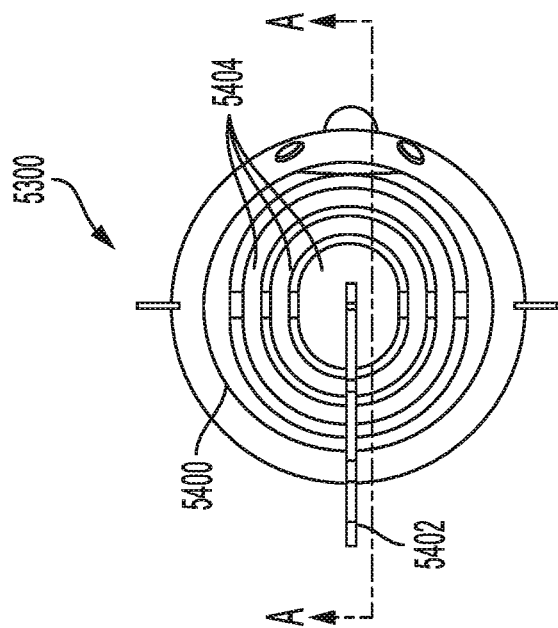

FIG. 55 shows a diagram of the stereoscopic visualization platform 516 including the stereoscopic visualization camera 300 and the robotic arm 506 to visualize the craniotomy procedure 5400, according to an example embodiment of the present disclosure. As illustrated, the craniotomy procedure 5400 is set up such that the robotic arm 506 is positioned to aim the stereoscopic visualization camera 300 through the top of the cranium 5306 along visualization axis 5500 of the conical surgical site 5404. A view of the operating surgeon is generally through the top of the cranium 506, as shown in FIG. 57. As one can appreciate from FIG. 7, the depth of the surgery and, for example, the tip of the surgical instrument 5402 is difficult to see.

The example stereoscopic visualization camera 300, shown in FIG. 55, provides a highly accurate stereoscopic image viewed down the axis 5500 of the conical surgical access site. As discussed above, parallax information between left and right views of the camera 300 for all points common to both views in the access site are used by the processor 4102 to determine a depth of each point from a known reference depth, such as for example, the object plane. In the illustrated example, parallax between the left and right views is equal to a value of '0', which enables the processor 4102 to determine a depth map of each point in the image. The depth map can be re-rendered by the processor 4102 as if the map was viewed from a different angle. Further, the processor 4102 is configured to make at least a portion of the depth map transparent, upon receiving an instruction from a surgeon and/or an operator. In the illustrated example, a portion of the depth map below section plane AA of FIG. 57 can be made transparent by the processor 4102, thereby enabling the processor 4102 to generate a cross-sectional view of the live surgical access site 5404.

Figure 56:
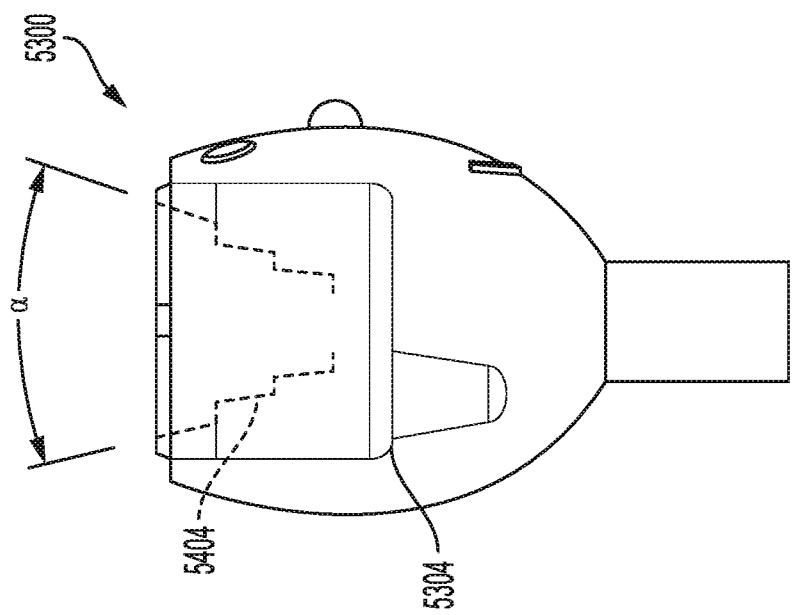

FIG. 56 shows a diagram of a phantom view of the conically shaped surgical access site 5404. The illustrated surgical access site 5404 includes stepped conical segments for clarity in this discussion. In this example a swept cone angle of the site 5404 is designated by angle 'a'.

Figure 58:
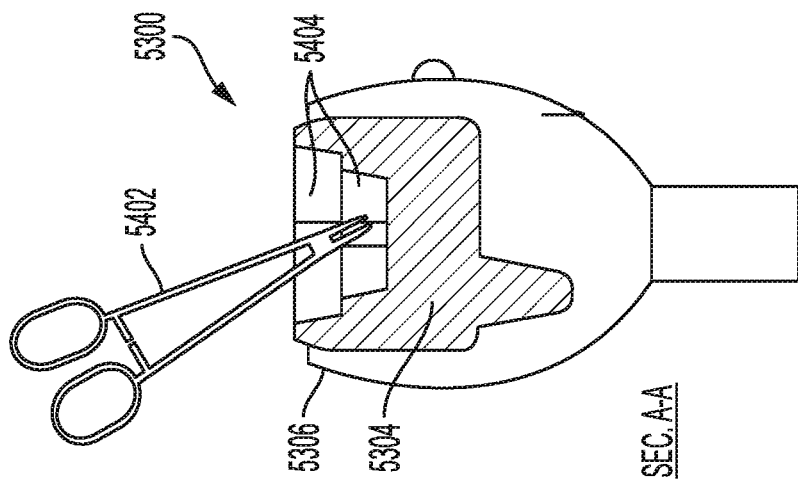

FIG. 58 shows a diagram of the conically shaped surgical access site 5404 for the craniotomy procedure 5400. Prior knowledge of the size and shape of the surgical instrument 5402, along with image recognition of its position, direction, and/or orientation enable the processor 4102 to generate image data for the cross-sectional view shown in FIG. 58. Recognition of the instrument 5402 in the stereoscopic view represented by FIG. 57 enables its precise placement in the cross-sectional view of FIG. 58 and visualization of, for example, the underside of the instrument which is not visible to the surgeon while operating on the patient's brain 5304.

Figure 59:
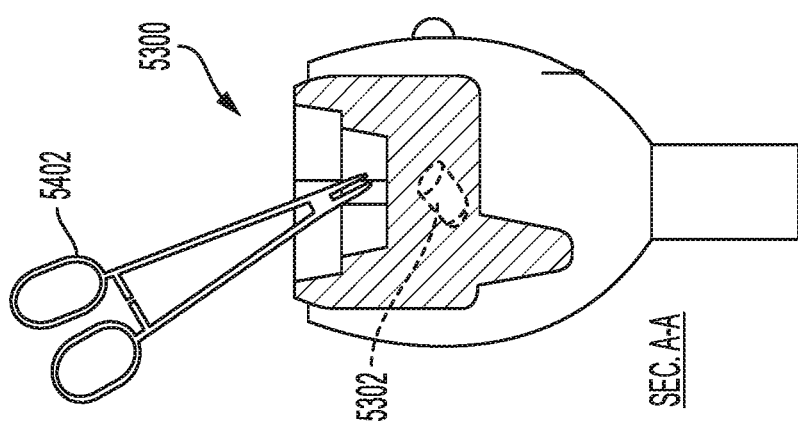

In some embodiments, the processor 4102 is configured to fuse an image of the glioblastoma 5302 with near-live or live stereoscopic image(s). As discussed above, the combination of the robotic arm 506 and the camera 300 provides highly accurate position, direction, and/or orientation information of a view with respect to the robot frame of reference or robot space. After registration or calibration of the robotic arm 506 and the camera 300 to the frame of reference of the patient 5300, accurate position, direction, and/or orientation information of the surgical access site 5404 and its respective position to the patient is generated by the processor 4102. The processor 4102 uses image fusion to superimpose a selection portion of the MRI image of the glioblastoma 5302 on to a cross-sectional view, as shown in FIG. 59. In addition, the image fusion enables the visualization of other relevant MM image data including, for example, brain vasculature or other structure desired to be included in the image. The exemplary surgical procedure proceeds with the surgeon being able to see and understand the depth location of the glioblastoma 5302 in addition to a safe spacing or positioning of the instrument 5402.

Figure 61:
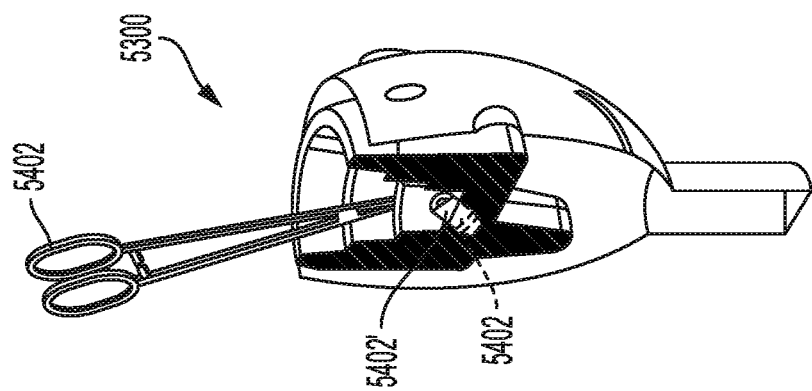
Figure 60:
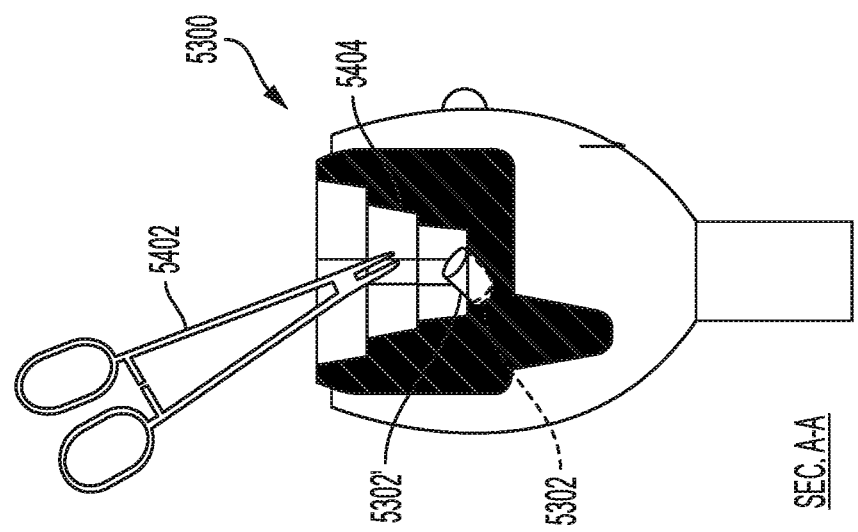

FIG. 59 shows a diagram of a sectional view of the surgical access site 5404. In this example, a portion 5302' of the glioblastoma 5302 is visible to the stereoscopic visualization camera 300. FIG. 60 shows a diagram of a cross-section view orthogonal to plane AA of FIG. 57. The diagram may be illustrative of a cross-sectional view generated by the processor 4102 based on the MM data fused with the live view of the surgical access site 5404. The use of the depth map by the processor 4102 enables rendering of the surgical access site 5404 at various desired section planes and combinations of section planes, as shown in FIG. 61. The rendering enables processor 4102 to display the complete glioblastoma 5302 including the visible portion 5402' and the reminder from the MM data. The processor 4102 may display the visualization from a perspective of the camera 300 or as a cross-sectional view, as shown in FIG. 61.

5. Robotic Motion with Conjoined Visualization Embodiment

In some embodiments, the example processor 4102 operates in connection with the robotic arm controller 4106, the stereoscopic visualization camera 300, the robotic arm 506, and/or the coupling plate 3304 to conjoin visualization with robotic motion. In some examples, the processor 4102 and/or the robotic arm controller 4106 operate in a closed loop to provide conjoined visualization based on robotic motion. In these examples, the processor 4102 and/or the robotic arm controller 4106 are configured to position the robotic arm 506, the coupling plate 3304, and/or the camera 300 for visualization of a surgical site based on a specific image and its contents (e.g., objects, identifiable features, etc.). As discussed above, the robotic arm 506 and camera 300 positions are known by the processor 4102 and/or the robotic arm controller 4106. In addition, image data recorded by the camera is stereoscopic, which provides depth data. As a result, the processor 4102 and/or the robotic arm controller 4106 can determine a location on a patient or in robot three-dimensional space of every visualized point. Thus, when the robotic arm 506 moves the camera 300 in a desired direction from an initial position with an initial image, the desired image change is expected to be seen in a second, post-move image.

Alternatively, the expected post-move image can be calculated by the processor 4102 and/or the robotic arm controller 4106 being configured to apply equations representative of the desired move to the initial image data, which results in a calculated second image. The processor 4102 and/or the robotic arm controller 4106 compare the post-move actual image with the calculated image using a match-template routine or function, as described above. If errors are detected, the processor 4102 and/or the robotic arm controller 4106 can correct the errors by moving the robotic arm 506 and/or the camera 300 accordingly. For example, given an initial image and a desired move "100 pixels to the right" received from an operator, the image data for the theoretical moved image can be calculated as a shift of 100 pixels right by the processor 4102 and/or the robotic arm controller 4106. Then, the physical move is made by performing commands to the various coordinated robot joints, as disclosed, to relocate the robotic arm 506 and/or the camera 300 to the theoretical desired location. A second image is recorded by the camera 300, which is compared by the processor 4102 and/or the robotic arm controller 4106 to the calculated image data using, for example a match template function or its equivalent. If the move is accurate, the data would indicate a 100% correlation at a tip of the camera 300, where both images are perfectly aligned. If, however, the actual image data shows best correlation at another location, for example 101 pixels right and 5 pixels up, then the move could be modified by the processor 4102 and/or the robotic arm controller 4106 to correct the error by physically moving the camera 300, via the robotic arm 506, 1 pixel left and 5 pixels down.

6. Sag Compensation Embodiment

In some embodiments, at least some of joints R1 to R9 of the robotic arm 506 and/or the coupling plate 3304 may experience some sag. The processor 4102 and/or the robotic arm controller 4106 may be configured to provide correction for robotic arm sag. In some instances, the processor 4102 and/or the robotic arm controller 4106 are configured to perform sag compensation on a series of small moves, such that motion accuracy is preserved over a range of motion of the robotic arm 506. For example, to characterize and eliminate sag, sag compensation is performed in motion directions that exercise a particular robotic joint to isolate error as a function of actual robot joint rotational position. By comparing the error to torque moments calculated by multiplying camera 300 load weight by moment arm (or link) length, the compliance of that joint can be determined. Alternatively, joint compliance may be calculated using analytical techniques, for example Finite Element Analysis ("FEA").

Using and storing the above-compliance characterization for all the joints in all rotational positions, the processor 4102 and/or the robotic arm controller 4106 may calculate the overall sag for a particular camera position. The processor 4102 and/or the robotic arm controller 4106 may determine a sag correction factor for each camera position to a LUT and/or calibration registers. Further, the processor 4102 and/or the robotic arm controller 4106 may apply the sag correction factor to robotic arm move commands or a movement sequence (before or after scale factors are applied) such that sag compensation is incorporated into movement commands/signals. The correction factor may be calculated in an ongoing motion procedure, thereby enabling accurate tracking and following of the camera 300. This correction factor further eliminates a need for a second camera for calibration/positioning of the stereoscopic visualization platform 516, and eliminates the need to have fiducial targets on the camera 300, and hence eliminates a problem of drape interference.

7. Storage of Visualization Positions/Orientations Embodiment

In some embodiments, the example processor 4102 is configured to save visualization parameters to return to a certain orientation and/or position of the stereoscopic visualization camera 300. The visualization parameters may include a view vector, location, magnification, working distance, focus, position, and/or orientation of the stereoscopic visualization camera 300, the robotic arm 506 and/or the coupling plate 3304.

In an example, a surgeon may wish to have a highly-magnified visualization of a small suture during an anastomosis of a portion of a blood vessel under visual illumination. The surgeon may then zoom-out to a wider view of the entire vessel under infrared illumination to check for patency. The surgeon may then return to the magnified visualization to complete the suture. In this example, the processor 4102 is configured to save the visualization parameters at each of the positions. The processor 4102 may store positions corresponding to locations that have been continuously viewed for a time period, such as two seconds, five seconds, thirty seconds, etc. The processor 4102 may also store a position after receiving an instruction from the surgeon via the input device 1410.

The processor 4102 may display a list of stored locations and/or waypoints. Selection of a stored location causes the processor 4102 and/or the robotic arm controller 4106 to move the robotic arm and/or the coupling plate 3304 to the previous location and adjust optical parameters, including light illumination and filtering, as set previously. Such a configuration enables a surgeon to seamlessly view all stored locations in sequence without removing their eyes from a displayed image of the procedure or removing their hands and their instruments from the site.

In some embodiments, the processor 4102 may be configured to enable an operator to create waypoints or positions/orientations prior to a surgical procedure. The waypoints may be provided in a sequence, which enables the processor 4102 to progress through the specified waypoints during the procedure after receiving an input from an operator to progress. The processor 4102 may provide a three-dimensional representation of the robotic arm 506, the coupling plate 3304, and/or the camera 300 via the touch-screen input device 1410a to enable an operator to virtually position the stereoscopic visualization platform 516. This may include providing for a magnification, working distance, and/or focus in relation to a virtualized patient and/or based on alternate modality visualizations of the patient. The processor 4102 is configured to store the visualization parameters to, for example, the memory 1570 and/or the memory 4120 for each waypoint.

In some embodiments, the processor 4102 is configured to perform certain visualizations that are particular to certain procedures. For example, image recognition functionality in the processor 4102 is used to automatically align the camera 300 with an object of interest. The image of the surgical site is compared by the processor 4102 to a previous image or image of the target object to provide for recognition of a desired object and its position and orientation within a stereoscopic image. The processor 4102 and/or the robotic arm controller 4106 are configured to, for example, move the robotic arm 506 toward the object and zoom the camera 300 towards the object and set the desired image view attributes for the particular object and procedure. For instance, in ophthalmology, a live retinal image can be compared to a saved image such that, for example, the optic nerve head of the patient's retina can be located from the image recognition. The processor 4102 and/or the robotic arm controller 4106 then automatically move the robotic arm 506 and/or the coupling plate 3304 and focus and/or change a magnification of the camera 300 such that the tip of the camera 300 is pointed at the nerve head for diagnosis. The processor 4102 may then set the camera 300 and/or the monitor 512 for image display without red coloration to enable features of the retina to be more easily distinguished from surrounding tissue.

In addition to saving and returning to stored visualizations, paths of motion from one view to another can also be saved by the example processor. In the anastomosis example discussed above, the processor 4102 and/or the robotic arm controller 4106 may cause the robotic arm 506 and/or the camera 300 to follow an entire length of a blood vessel under high magnification to check for aneurysms or other conditions. The processor 4102 may be configured to recognize and follow the continuous vessel, as desired. The processor 4102 may perform a match template routine on a limited set of pixels to actively determine the direction of motion of the robotic arm 506 and/or the camera 300.

The example processor 4102 may also program and store a path of motion within a visualization of an object, made from different viewing angles. For example, an ophthalmological gonioscopy of a patient's eye can be performed by programming the processor 4102 and/or the robotic arm controller 4106 to pivot about a point inside the eye. In this example, the robotic arm 506 sweeps the camera 300 in a generally conical motion such that the patient's eye is viewed from a plethora of viewing angles. Such motion of surgical site visualizations can be used to select the best angle to preclude spurious reflections from illumination or to see around obstructions in alternative viewing angles.

In some embodiments, the processor 4102 is configured to reduce occlusions in depth map calculations. Occlusions are inherent in depth map calculations due to the parallax of the two views of a stereoscopic image, where a first view sees some portion of a site different from the other view. As a result, each view does not see some part of the other view. By moving the robotic arm 506 among various places and recalculating the depth map while using knowledge of the three-dimensional locations of the image pixels, occlusion is reduced. The depth map may be made more accurate by iteratively calculating the map after known motion steps are performed, anticipated map changes are calculated, errors are determined by the difference, and an average map is constructed.

E. Assisted Drive Embodiments

In some embodiments, the processor 4102 and/or the robotic arm controller 4106 are configured to execute one or more algorithms, routines, etc. defined by instructions stored in the memory 1570 and/or 4120 to enable the robotic arm 506 and/or the coupling plate 3304 to provide powered joint movement based on detected forces applied by an operator for moving the stereoscopic visualization camera 300. In these embodiments, the assisted drive feature enables the robotic arm 506 to operate as an extension of a surgeon by moving the stereoscopic visualization camera 300 to a desired location and/or orientation. As described below, the processor 4102 and/or the robotic arm controller 4106 are configured to monitor force/torque/movement imparted by an operator and positions of arm joints to infer an operator's intent and accordingly move the robotic arm 506 and/or the coupling plate 3304.

Figure 62:
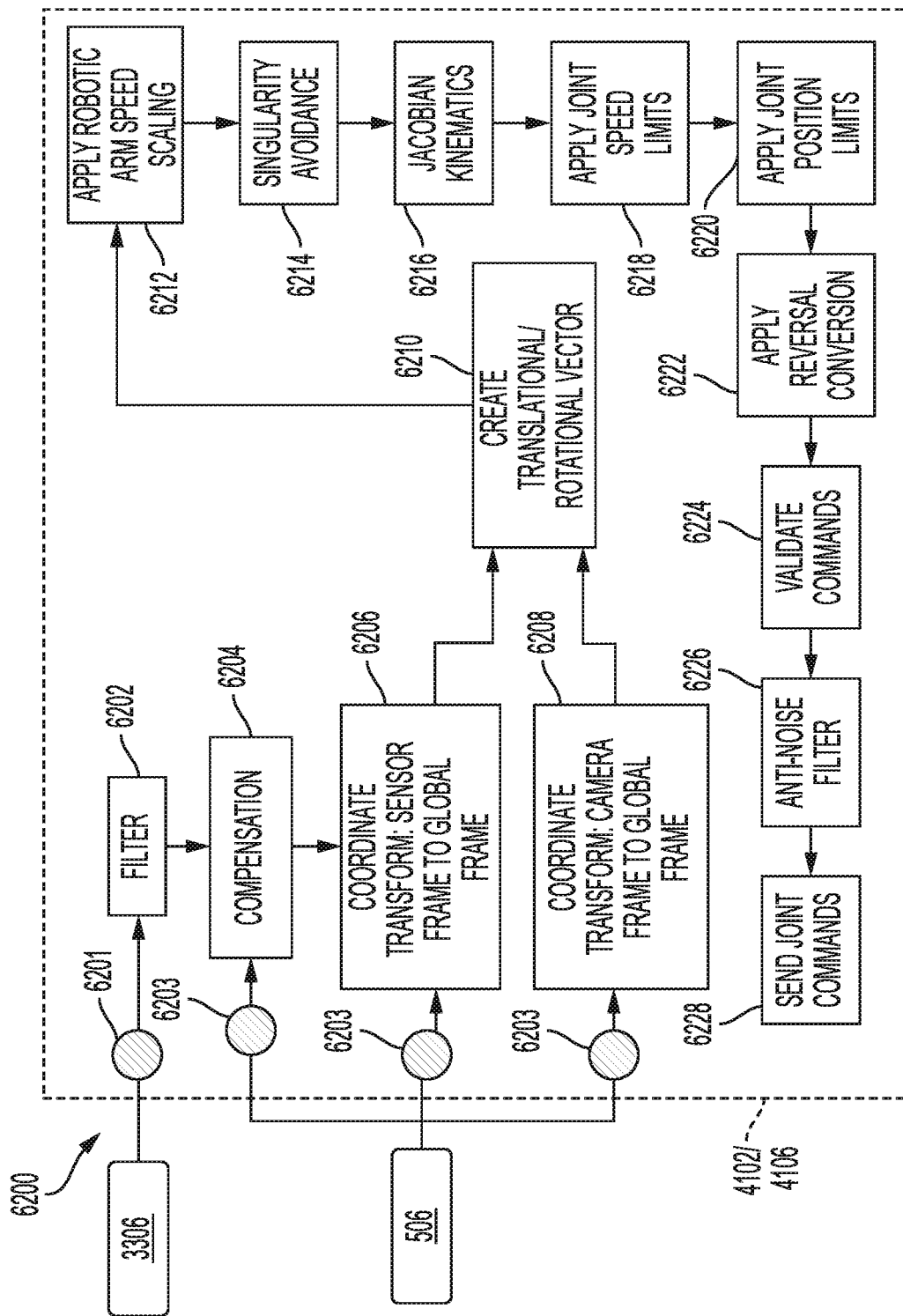
FIG. 62 shows a diagram that is illustrative of a procedure for providing assisted drive of the stereoscopic visualization camera of FIGS. 3 to 52, according to an example embodiment of the present disclosure.

FIG. 62 shows a diagram that is illustrative of an algorithm, routine, or procedure 6200 for providing assisted drive of the stereoscopic visualization camera 300, according to an example embodiment of the present disclosure. Although the procedure 6200 is described with reference to the flow diagram illustrated in FIG. 62, it should be appreciated that many other methods of performing the steps associated with the procedure 6200 may be used. For example, the order of many of the blocks may be changed, certain blocks may be combined with other blocks, and many of the blocks described are optional. Further, the actions described in procedure 6200 may be performed among multiple devices including, for example the information processor module 1408 of the example stereoscopic visualization camera 300 of FIG. 14 and/or joints R1 to R9 and robotic arm controller 4106 of FIG. 41. In some examples, the procedure 6200 may be performed by a program stored in the memory 4120 of the robotic arm controller 4106. The example procedure 6200 may be executed periodically as force is applied to the camera 300. For example, the procedure 6200 may sample force/torque data every update cycle, which may be 1 ("ms"), 5 ms, 8 ms, 20 ms, 50 ms, etc.

In the illustrated embodiment, the processor 4102 and/or the robotic arm controller 4106 receive force/torque output data 6201 from the sensor 3306 related to force imparted by an operator on the camera 300. The processor 4102 and/or the robotic arm controller 4106 are configured to filter the received output data 6201 (block 6202). The output data may include a force and/or torque vector. The filtering may include applying a first low-pass filter, a second low pass filter, and/or a notch filter that targets cart vibrations. In other examples, a single low-pass filter and a notch filter may be used by the processor 4102 and/or the robotic arm controller 4106.

The example processor 4102 and/or the robotic arm controller 4106 also receive joint position data 6203 from one or more joint sensors in the robotic arm 506 and/or the coupling plate 3304. The processor 4102 and/or the robotic arm controller 4106 use the joint position data 6203 to provide compensation for the filtered force/torque output data (block 6204). The compensation may include gravity compensation and/or force-application point compensation. For gravity compensation, the effects of Earth's gravity are removed from the filtered data. For force-application point compensation, the processor 4102 and/or the robotic arm controller 4106 provide compensation to the filtered data (and/or gravity compensated data) based on a point where the force was applied to the camera 300 (e.g., the control arms 304). As discussed above in connection with FIG. 35, the sensor 3306 is located some offset distance away at an angle from the control arms 304. The offset distance and angle cause the force applied at the control arms 304 to be slightly shifted by direction and angle when detected in the sensor 3306. The force-application compensation adjusts the force values as though the force was applied directly to the sensor 3306 instead of the control arms 304. The force-application compensation may be pre-determined based on a known angle and/or distance between the sensor 3306 and the control arms 304. Together, the gravity compensation and the force-application point compensation modify the filtered force/torque data to create a force/torque vector that is proportional to the force/torque provided by an operator at the control arms 304 of the camera.

The example processor 4102 and/or the robotic arm controller 4106 also use the joint position data 6203 in conjunction with the compensated, filtered force/torque output data to perform a coordinate transform between force/torque frame to a global frame or robot space (block 6206). The transform may include one or more predefined equations or relations based on the known robot space and the orientation of the sensor 3306. The example processor 4102 and/or the robotic arm controller 4106 also use the joint position data 6203 to perform a coordinate transform between a camera frame of the stereoscopic visualization camera 300 and the global frame or robot space (block 6208). The coordinate transform for the camera frame may be based on the optical calibration parameters mapped to robot space of the robotic arm 506, as described above.

After performing the coordinate transforms, the example processor 4102 and/or the robotic arm controller 4106 are configured to convert the force/torque vector(s) into one or more translational/rotational vectors using at least one sigmoid function (block 6210). The creation of the translational/rotational vector(s) produces an inference of an intended direction of the operator. The translational and rotational information is used to determine how joints of the robotic arm 506 are to be rotated to mirror, match, and/or approximate the operator's intended movement.

In some examples, the example processor 4102 and/or the robotic arm controller 4106 are configured to apply robot speed scaling to the translational/rotational vector(s) (block 6212). The speed scaling may be based, for example, on operating conditions of robotic arm 506. For example, speed scaling may be applied based, for example, once a surgical procedure has started to prevent the arm from accidently striking operating room staff, instruments, and/or the patient at a relatively high rate of speed. When a procedure has not yet begun, the example processor 4102 and/or the robotic arm controller 4106 may apply less speed scaling for calibration or setting of the robotic arm 506 when a patient is not present.

The example processor 4102 and/or the robotic arm controller 4106 determine potential movement sequences of joints of the robotic arm 506 based on the scaled translational/rotational vector(s). While evaluating possible sequences, the processor 4102 and/or the robotic arm controller 4106 identify joint singularities for avoidance, thereby ruling out the corresponding movement operations of the robotic arm 506 (block 6214). As discussed above, singularities may include elbow lock or other positions that may be prone to hysteresis and backlash. The processor 4102 and/or the robotic arm controller 4106 are configured to select a movement sequence, after movement singularities are eliminated using, for example, Jacobian kinematics (e.g., an inversion of a Jacobian matrix) (block 6216). The Jacobian kinematic equations define how certain joints of the robotic arm 506 and/or the coupling plate 506 are to be moved based on the scaled translational/rotational vector(s). The Jacobian kinematics provide for velocity control while inverse kinematics, discussed below, provide for positional control. In some embodiments, the processor 4102 and/or the robotic arm controller 4106 may instead use inverse kinematics or other robotic arm control routines. The processor 4102 and/or the robotic arm controller 4106 determine a movement sequence that specifies how certain joints of the robotic arm and/or coupling plate 3304 are to move in a coordinated manner and specifies, for example, joint rotation speed, joint rotational direction, and/or joint rotational duration. The movement sequence may also specify a sequence in which joints of the robotic arm 506 and/or the coupling plate 3304 are to be rotated. Any of joints R1 to R9 of the robotic arm and/or coupling plate 3304 may rotate individually or have overlapping movement depending on the movement sequence.

After a movement sequence is determined, the processor 4102 and/or the robotic arm controller 4106 are configured to perform collision avoidance using joint speed scaling and/or boundaries. For example, the processor 4102 and/or the robotic arm controller 4106 are configured to determine if the movement sequence will cause one or more joints and/or links of the robotic arm 506 and/or the coupling plate 3304 to approach a boundary or other defined Cartesian limit, such as space around a patient or instrument. As discussed above in connection with FIG. 49, the processor 4102 and/or the robotic arm controller 4106 may compare estimates of positions of the links and/or joints in the robot space from the movement sequence to one or more defined boundaries and/or angle limits. Based on a distance from a boundary, the processor 4102 and/or the robotic arm controller 4106 applies one or more joint speed limits via a scale value (block 6218). The processor 4102 and/or the robotic arm controller 4106 may also apply one or more joint position limits (block 6220) that prevent, for example, links of the robotic arm 506 from striking each other and/or prevent the robotic arm 506, the coupling plate 3304, and/or the camera 300 from extending past a boundary. Locations just before position limits (e.g., 1 centimeter ("cm") 2 cm, 10 cm, etc. before a position limit) and/or locations at the position limits may correspond to locations in Cartesian robot space where a value of the scale factor is '0'.

In some examples, the processor 4102 and/or the robotic arm controller 4106 may perform Jacobean kinematics with the boundaries provided as an input to the equations, where movement through areas close to a boundary are provided a higher cost factor. The use of boundary cost factors causes the processor 4102 and/or the robotic arm controller 4106 to avoid locations close to boundaries, if possible, when determining a movement sequence. The cost factor may include inversely proportional to a decrease in a scale factor associated with a particular location in robot space. The scale factor may apply to each joint/link, or separate scale factors may exist for each joint for the same location in robot space.

After providing for collision avoidance, the example processor 4102 and/or the robotic arm controller 4106 are configured to provide for correction for relatively fast reversals of the robotic arm 506 (block 6222). The processor 4102 and/or the robotic arm controller 4106 may implement a zero phase delay algorithm to reject directional impulses that quickly cause one or more joints to change rotational direction. The zero phase delay algorithm may be implemented by a filter that prevents, for example, the robotic arm from bucking or rocking if an operator reverses direction too quickly.

As illustrated in FIG. 62, the example processor 4102 and/or the robotic arm controller 4106 are configured to validate commands of the movement sequence (block 6224). The processor 4102 and/or the robotic arm controller 4106 may validate a command to ensure that a command (or signal indicative of a command) is within operating parameters (e.g., duration, rotational speed, etc.) of a joint motor. The processor 4102 and/or the robotic arm controller 4106 may also validate a command by comparing the command to current thresholds to ensure the robotic arm 506 will not draw excess current during any phase of the movement sequence.

The example processor 4102 and/or the robotic arm controller 4106 may also apply one or more anti-noise filters to the movement commands or signals indicative of the movement commands (block 6226). The filter may include a high frequency low-pass filter that removes high frequency noise components, which may induce transient signals in a joint motor. After any filtering, the processor 4102 and/or the robotic arm controller 4106 transmit the one or more commands via one or more signals or messages to the appropriate joint motor of the robotic arm 506 and/or the coupling plate 3304 according to the movement sequence (block 6228). The transmitted commands cause motors at the respective joints to move the robotic arm 506 and/or the coupling plate 3304, thereby causing the camera 300 to move as intended by the operator. The example procedure 6200 may repeat as long as an operator applies force to the camera 300.

Figure 63:
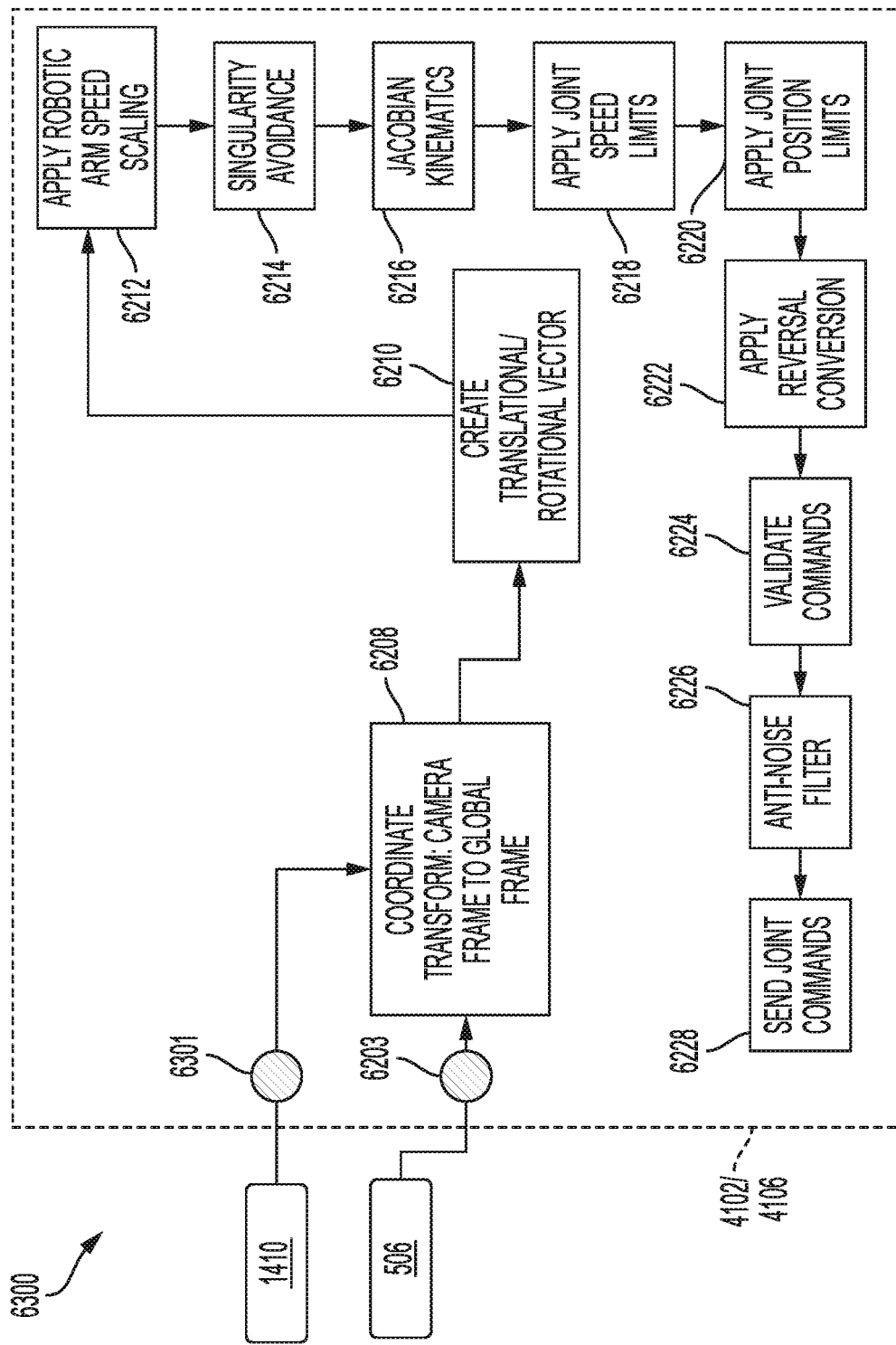
FIG. 63 shows a diagram of an example procedure for moving the example visualization camera of FIGS. 3 to 52 using an input device, according to an example embodiment of the present disclosure.

FIG. 63 shows a diagram of an example procedure 6300 for moving the example visualization camera 300 using an input device 1410, according to an example embodiment of the present disclosure. The example procedure 6300 is nearly identical to the procedure 6200 of FIG. 62, except blocks 6202 to 6206 related to the sensor 3306 are removed. In the illustrated example, a control input 6301 is received from an input device 1410, such as buttons on the control arm 304, a foot pedal, joystick, touchscreen interface, etc. The control input 6301 is indicative of directional movement of the camera in the Cartesian robot space of the robotic arm 506.

As illustrated in FIG. 63, the control input 6301 is combined with the joint position data 6203 from one or more joint sensors in the robotic arm 506 and/or the coupling plate 3304 for performing a coordinate transform from a camera frame to a global frame and/or robot space (block 6208). The example procedure 6300 then continues in the same manner as discussed for procedure 6200. The processor 4102 and/or the robotic arm controller 4106 accordingly cause the robotic arm 506, the coupling plate 3304, and/or the camera 300 to move to a desired location and/or orientation based on the control input 6301 received from the input device 1410.

F. Lock-to-Target Embodiments

In some embodiments, the processor 4102 and/or the robotic arm controller 4106 are configured to execute one or more algorithms, routines, etc. defined by instructions stored in the memory 1570 and/or 4120 to enable the robotic arm 506 and/or the coupling plate 3304 to provide a lock-to-target feature. In these embodiments, the lock-to-target feature enables the robotic arm 506 to operate as an extension of a surgeon by enabling the stereoscopic visualization camera 300 to be re-oriented while being locked onto a target surgical site. As described below, the processor 4102 and/or the robotic arm controller 4106 are configured to monitor force/torque/movement imparted by an operator and positions of arm joints to infer an operator's intent and accordingly re-orientate the robotic arm 506 and/or the coupling plate 3304 such that the focal point of the camera 300 remains locked or stationary.

The lock-to-target feature enables the camera 300 to be reoriented by causing all motion to be constrained to the surface of a virtual sphere. The tip of the camera 300 is located at an outer surface of the virtual sphere (e.g., a top hemisphere of the virtual sphere) and a focal point of the camera 300 or target surgical site constitutes a center of the virtual sphere. The example processor 4102 and/or the robotic arm controller 4106 enable an operator to move the camera 300 over an outer surface of the virtual sphere while keeping the camera 300 pointed at the center of the sphere, thereby keeping the target surgical site in focus during the movement. The lock-to-target feature enables an operator to easily and quickly obtain significantly different views of the same target site.

Figure 64:
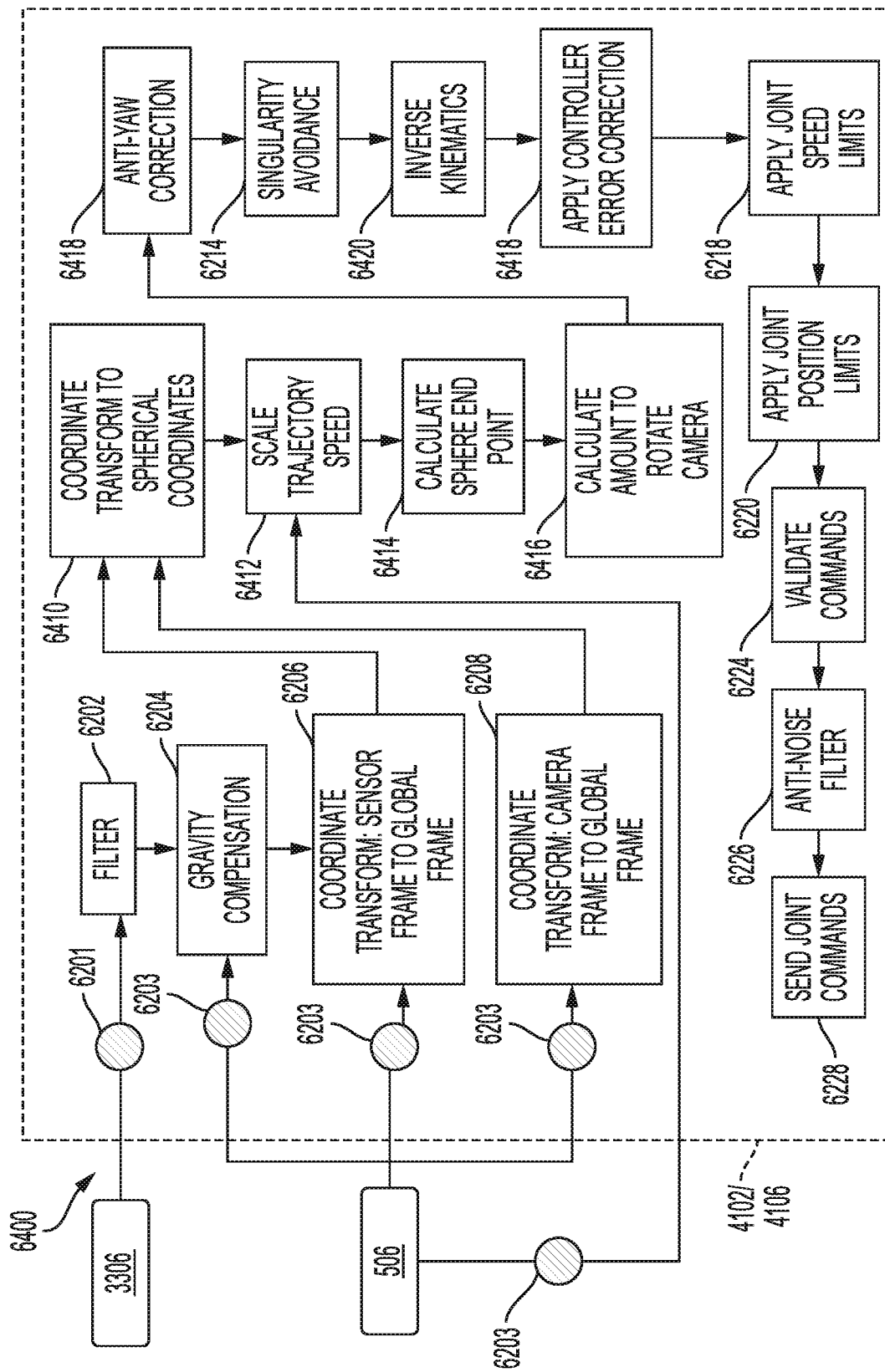
FIG. 64 shows a diagram that is illustrative of an algorithm, routine, or procedure for providing a lock-to-target for the stereoscopic visualization camera, according to an example embodiment of the present disclosure.

FIG. 64 shows a diagram that is illustrative of an algorithm, routine, or procedure 6400 for providing a lock-to-target for the stereoscopic visualization camera 300, according to an example embodiment of the present disclosure. Although the procedure 6400 is described with reference to the flow diagram illustrated in FIG. 64, it should be appreciated that many other methods of performing the steps associated with the procedure 6400 may be used. For example, the order of many of the blocks may be changed, certain blocks may be combined with other blocks, and many of the blocks described are optional. Further, the actions described in procedure 6400 may be performed among multiple devices including, for example the information processor module 1408 of the example stereoscopic visualization camera 300 of FIG. 14 and/or joints R1 to R9 and robotic arm controller 4106 of FIG. 41. In some examples, the procedure 6400 may be performed by a program stored in the memory 4120 of the robotic arm controller 4106.

The example procedure 6400 is similar to the assisted drive procedure 6200. However, the procedure 6400 provides for the commanding of joint positions to retain a focal point of the camera 300 while the example procedure 6200 provides for the calculation of joint velocities. The example procedure 6400 determines a desired force/movement vector input by an operator and calculates a rotational transform such that the focal point of the camera 300 remains stationary while one or more joints of the robotic arm 506 and/or the coupling plate 3304 are moved to re-orient the camera 300. The reorientation of the camera 300 enables a target surgical site to be imaged from different angles. The reorientation may be needed when a first view path is blocked by, for example, an instrument, and the surgeon desires to maintain the current focal point.

The example procedure 6400 begins when an operator selects lock-to-target button on the input device 1410, which causes an instruction message or signal to be transmitted to the processor 4102 and/or the robotic arm controller 4106. After receiving the message, the processor 4102 and/or the robotic arm controller 4106 operate in a lock-to-target mode where the working distance and/or focal point is held stationary while enabling an operator to change an orientation of the camera 300, which causes one or more joints of the robotic arm and/or coupling plate 3304 to provide assisted movement. When an instruction is received, the example processor 4102 and/or the robotic arm controller 4106 may record the current working distance, magnification, focus, and/or other optical parameters of the camera 300. The processor 4102 and/or the robotic arm controller 4106 may also record a current image of the FOV.

After the procedure 6400 begins, the processor 4102 and/or the robotic arm controller 4106 receive force/torque output data 6201 from the sensor 3306 related to force imparted by an operator on the camera 300. As discussed in connection with FIG. 62, the processor 4102 and/or the robotic arm controller 4106 filter and provide gravity/force-application compensation for the data 6102 (blocks 6202 and 6204). Also similar to FIG. 62, the processor 4102 and/or the robotic arm controller 4106 use the joint position data 6203 in conjunction with the compensated, filtered force/torque output data to perform a coordinate transform between force/torque frame to a global frame or robot space (block 6206). The example processor 4102 and/or the robotic arm controller 4106 also use the joint position data 6203 to perform a coordinate transform between a camera frame of the stereoscopic visualization camera 300 and the global frame or robot space (block 6208). The example processor 4102 and/or the robotic arm controller 4106 also perform a transform from the global frame or robot space to spherical coordinates that correspond to a virtual sphere (block 6410).

After the coordinate transforms, the example processor 4102 and/or the robotic arm controller 4106 are configured to scale trajectory speed based, for example, on an operation mode of the camera 300 (block 6412). The scaling may be similar to the scaling performed at block 6212 of FIG. 62. The example procedure 6400 of FIG. 64 continues by the processor 4102 and/or the robotic arm controller 4106 calculating a sphere end point (block 6414). Calculation of the sphere end point provides an inference about the operator's desired movement direction and determines how far the camera 300 is to be moved over the virtual sphere without rotating the sphere.

Figure 65:
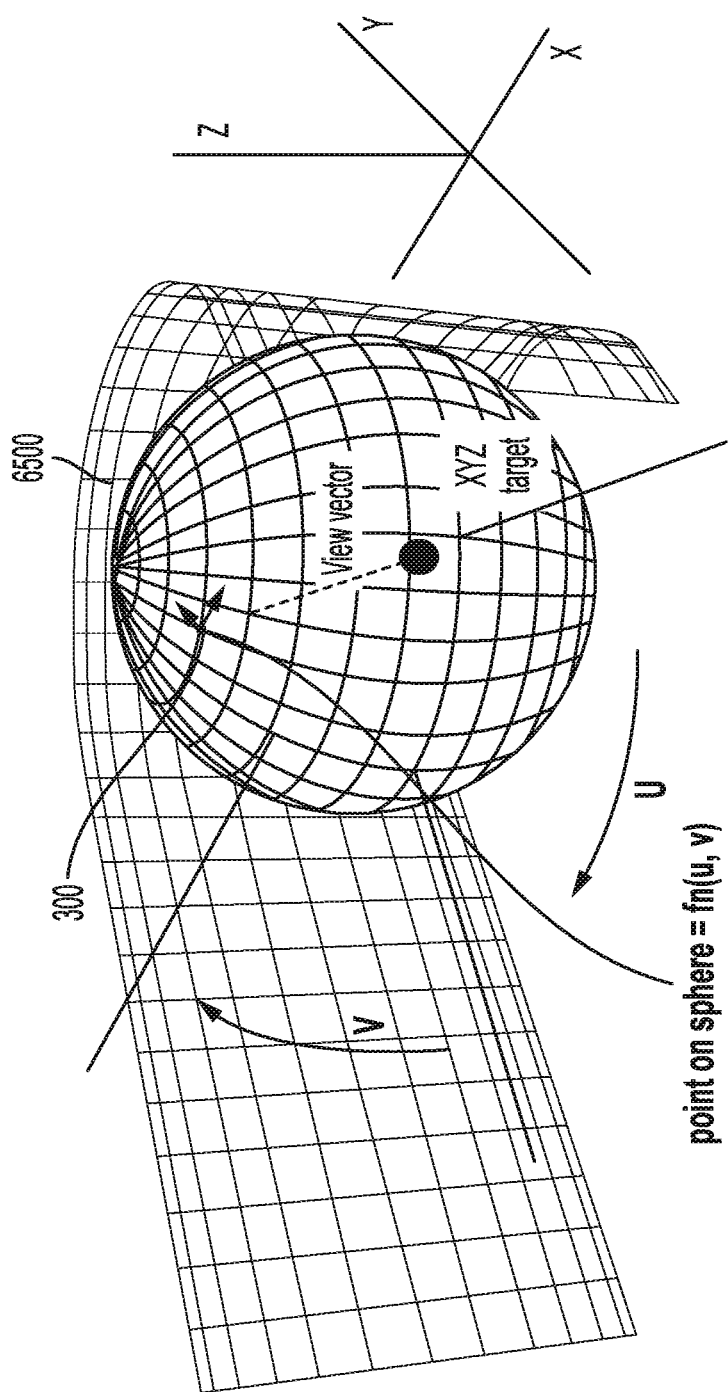
FIG. 65 shows a diagram that is illustrative of a virtual sphere for the lock-to-target feature of FIG. 64, according to an example embodiment of the present disclosure.

FIG. 65 shows a diagram that is illustrative of a virtual sphere 6500 for the lock-to-target feature, according to an example embodiment of the present disclosure. As shown in FIG. 65, the stereoscopic visualization camera 300 is virtually placed on the sphere 6500 based on a current position, as determined from the joint position data 6203. A view vector of the camera 300 points to a tip, designated as the xyz target, which is located in a center of the sphere 6500. The processor 4102 and/or the robotic arm controller 4106 are configured to use the transformed force/torque data to determine how the camera 300 on the sphere is to move along a surface of the sphere 6500 while maintaining the view vector pointed at the xyz target, where any given point on the sphere is given by an equation that is a function of rotational sphere angles v' and 'u'. When the force/torque data is used, the processor 4102 and/or the robotic arm controller 4106 use an 'x' and 'y' component corresponding to the translational force for directly determining how the camera 300 is to move on the virtual sphere 6500 to determine the sphere end point.

The processor 4102 and/or the robotic arm controller 4106 may determine the sphere end point differently for different inputs. For example, if an input is received via the input device 1410, as shown in FIG. 63, the processor 4102 and/or the robotic arm controller 4106 converts 'up', 'down', 'left', and 'right' from camera coordinates to robot space coordinates, which are provided as x,y vectors. Similar to the force/torque data, the x,y vectors are used by the processor 4102 and/or the robotic arm controller 4106 for directly determining how the camera 300 is to move on the virtual sphere 6500 to determine the sphere end point. It should be appreciated that in instances where inputs are received via the input device, the operations discussed in conjunction with blocks 6202 to 6206 may be omitted, as shown in FIG. 63.

In some examples, the processor 4102 and/or the robotic arm controller 4106 are configured to receive orbit input data. In these examples, the processor 4102 and/or the robotic arm controller 4106 hold the sphere angle constant while iterating movement along sphere angle 'u' of the virtual sphere 6500. The iterative movement along sphere angle 'u' enables the sphere end point to be determined for the orbit input. It should be appreciated that while the inputs are applied to the virtual sphere 6500, in other examples, the inputs may be applied to other shapes. For example, the virtual sphere 6500 instead may be defined as a virtual cylinder, an ellipsoid, an egg-shape, a pyramid/frustum, etc.

In other examples, the processor 4102 and/or the robotic arm controller 4106 are configured to receive level scope input data. In these examples, the processor 4102 and/or the robotic arm controller 4106 hold the sphere angle 'u' constant while iterating movement along sphere angle 'v' of the virtual sphere 6500. The iterative movement along sphere angle 'v' causes the camera 300 to be moved to a top of the virtual sphere 6500.

Returning to FIG. 64, after the sphere end point is determined, the processor 4102 and/or the robotic arm controller 4106 are configured to calculate an amount of rotation needed for the camera 300 to maintain the lock at the x,y,z target after the camera 300 has been moved along the virtual sphere to the determined end point (block 6416). The processor 4102 and/or the robotic arm controller 4106 may also provide anti-yaw correction during this calculation (block 6418). In other words, the processor 4102 and/or the robotic arm controller 4106 are configured to determine how the camera 300 is to be orientated given its new position on the virtual sphere 6500 such that the view vector or tip of the camera 300 is provided at the same x,y,z target, which is pointed at a center of the virtual sphere 6500, which corresponds to a target surgical site or focal point.

During this step, the processor 4102 and/or the robotic arm controller 4106 determine the joint angles of the robotic arm 506 and/or the coupling plate 3304 needed to achieve the desired orientation. After the x,y,z sphere end point is calculated in block 6414, the processor 4102 and/or the robotic arm controller 4106 determine roll and pitch amounts for the camera 300. In some embodiments, the calculation is a two-step process. First, the processor 4102 and/or the robotic arm controller 4106 calculate an initial 4×4 transform matrix T that provides movement of the camera 300 without rotation given the x,y,z sphere end point. Then, the processor 4102 and/or the robotic arm controller 4106 calculate local roll and pitch amounts such that the camera 300 remains locked at a target located at x,y,z (and/or positioned at the x,y,z sphere end point) for subsequent cycles of joint rotations. The processor 4102 and/or the robotic arm controller 4106 may use Equations (4) and (5) below to calculate roll and pitch amounts, where T next corresponds to a 4×4 transform matrix. The calculations can be performed at each update cycle (e.g., 8 ms).

$$T_{next} = T \begin{pmatrix} R & 0 \\ 0 & 1 \end{pmatrix} \quad (4)$$

such that:

$x_{target\_next} = x_{target}$
$y_{target\_next} = y_{target}$
$z_{target\_next} = z_{target}$ $$R = \begin{bmatrix} \cos\check{l}_{\prime} & 0 & \sin\check{l}_{\prime} \\ 0 & 1 & 0 \\ -\sin\check{l}_{\prime} & 0 & \cos\check{l}_{\prime} \end{bmatrix} \begin{bmatrix} 1 & 0 & 0 \\ 0 & \cos\check{l}_{\prime} & -\sin\check{l}_{\prime} \\ 0 & \sin\check{l}_{\prime} & \cos\check{l}_{\prime} \end{bmatrix} \quad (5)$$

In Equation (4) above, $x_{taregt\_next}$, $y_{taregt\_next}$, and $z_{taregt\_next}$ are constraints on the $T_{next}$ matrix. The above-constraints specify that the roll and pitch angles are chosen such that the x,y,z equations above are valid. In other words, the x,y,z location of a target at a next update cycle of joint rotations has to be equal to the x,y,z location of the target in the current cycle. The constraints enable the camera 300 to be rotated via roll and pitch angles but remained locked relative to the x,y,z location.

Further, $-\sin\theta$ on the bottom row of the first matrix of Equation (5) corresponds to a pitch angle while $\sin\theta$ on the bottom row of the second matrix corresponds to a roll angle. A closed form expression for pitch may exist given function cos(roll). The processor 4102 and/or the robotic arm controller 4106 may use an iterative method to estimate roll, calculated as function cos(roll), with pitch equal to fn(cos(roll)) to generate a correct roll/pitch solution pair for the equations above.

After the roll and pitch amounts are calculated from the operations described in connection with blocks 6416 and 6418, the example processor 4102 and/or the robotic arm controller 4106 are configured to provide singularity avoidance and calculate inverse kinematics to determine joint rotation to achieve the roll and pitch amounts in addition to the new x,y,z position of the camera 300 along the virtual sphere 6500 (blocks 6214 and 6420). The calculation of the inverse kinematics enables the processor 4102 and/or the robotic arm controller 4106 to determine a movement sequence for joints of the robotic arm 506 and/or the coupling plate 3304.

The example processor 4102 and/or the robotic arm controller 4106 may apply error correction for the movement sequence in addition to joint speed limits and/or position limits (blocks 6418, 6218, 6220). As discussed above in connection with FIG. 62, the limits and error correction may prevent the robotic arm 506, the camera 300, and/or coupling plate 3304 from hitting themselves, exceeding one or more boundaries, and/or being within acceptable joint positions. The processor 4102 and/or the robotic arm controller 4106 may also validate commands for the joints of the movement sequence provide anti-noise filtering before sending the commands (or signals indicative of the commands) to one or more joints R1 to R9 of the robotic arm 506 and/or the coupling plate 3304 based on the movement sequence (blocks 6224, 6226, 6228). The example procedure 6400 may then end if no other movement is detected. Otherwise, the procedure 6400 is repeated at periodic intervals (e.g., 10 ms, 20 ms, etc.) as operator inputs are received.

In some embodiments, the processor 4102 and/or the robotic arm controller 4106 may provide lock-to-target tracking for instruments. In these examples, the xyz target of a center of the virtual sphere 6500 is replaced with a dynamic trajectory that corresponds to a moving target. Such a feature may enable a tracking of spinal tools, for example. In these embodiments, an instrument may include one or more fiducials and/or other markers. The example stereoscopic visualization camera 300 records images that include the fiducials. The processor 4102 and/or the robotic arm controller 4106 may perform a coordinate transform from the camera frame space to robot space to determine how the instrument is being moved along the x,y,z axes. The example processor 4102 and/or the robotic arm controller 4106 track how the fiducials move in the image and determine the corresponding x,y,z movement vectors. In some instances, the x,y,z vectors may be input into the sphere end point calculation of block 6414 of FIG. 64 to change the location of a center of the virtual sphere 6500. In response to a movement of the sphere 6500, the processor 4102 and/or the robotic arm controller 4106 determine how the robotic arm 506 is to be positioned to maintain the same working distance and/or orientation with the new target location. The processor 4102 and/or the robotic arm controller 4106 may then apply inverse kinematics to determine joint rotations of the robotic arm 506 and/or the coupling plate to track the movement of the target. Similar to the procedures 6200 and 6400, the processor 4102 and/or the robotic arm controller 4106 may apply error correction, joint limits, filters, and/or validation before sending commends to joints as specified in a determined movement sequence.

CONCLUSION

It will be appreciated that each of the systems, structures, methods and procedures described herein may be implemented using one or more computer programs or components. These programs and components may be provided as a series of computer instructions on any conventional computer-readable medium, including random access memory ("RAM"), read only memory ("ROM"), flash memory, magnetic or optical disks, optical memory, or other storage media, and combinations and derivatives thereof. The instructions may be configured to be executed by a processor, which when executing the series of computer instructions performs or facilitates the performance of all or part of the disclosed methods and procedures.

It should be understood that various changes and modifications to the example embodiments described herein will be apparent to those skilled in the art. Such changes and modifications can be made without departing from the spirit and scope of the present subject matter and without diminishing its intended advantages. It is therefore intended that such changes and modifications be covered by the appended claims. Moreover, consistent with current U.S. law, it should be appreciated that 35 U.S.C. 112(f) or pre-AIA 35 U.S.C. 112, paragraph 6 is not intended to be invoked unless the terms "means" or "step" are explicitly recited in the claims. Accordingly, the claims are not meant to be limited to the corresponding structure, material, or actions described in the specification or equivalents thereof The invention is claimed as follows:

1. A robotic imaging apparatus comprising:
   a base section configured for connection to a secure structure or a cart;
   a robotic arm including
   a first end connected to the base section,
   a second end including a coupling interface, and
   a plurality of joints and links connecting the first end to the second end, each joint including a motor configured to rotate the joint around an axis and a joint sensor configured to transmit a position of the respective joint;
   a stereoscopic camera connected to the robotic arm at the coupling interface, the stereoscopic camera configured to record left and right images of a target surgical site for producing a stream of stereoscopic images of the target surgical site;
   a sensor positioned at the coupling interface and configured to detect translational and rotational force imparted on the stereoscopic camera by an operator and to transmit output data that is indicative of the detected force;
   a memory storing at least one algorithm defined by one or more instructions and/or data structures that specify a rotation direction, speed, and duration of movement for each of the joints of the robotic arm based at least on a current position of the robotic arm and the detected force; and at least one processor communicatively coupled to the sensor and the robotic arm, the at least one processor configured to:
receive the output data from the sensor that is indicative of the detected force,
determine, using the at least one algorithm in the memory, a movement sequence for the robotic arm based on a current position of the robotic arm and the output data from the sensor, and
cause at least one of the joints of the robotic arm to rotate based on the determined movement sequence via one or more motor control signals provided to the at least one joint,
wherein the rotation of the at least one joint provides power-assisted movement of the robotic arm based on the detected force imparted on the stereoscopic camera by the operator.

2. The apparatus of claim 1, wherein the at least one processor is configured to determine the current position of the robotic arm based on output data from the joint sensors of the plurality of joints.

3. The apparatus of claim 1, wherein the sensor includes a six-degrees-of-freedom force-sensing device configured to detect translational force in an x-axis, a y-axis and a z-axis and rotational force around a yaw-axis, a pitch-axis and a roll-axis.

4. The apparatus of claim 1, wherein the stereoscopic camera includes at least one control arm having a release button to enable the power-assisted movement, and
wherein the at least one processor is configured to:
receive an input message indicative that the release button was selected; and
determine the movement sequence using the output data from the sensor after receiving the input message related to the release button.

5. The apparatus of claim 1, further comprising a coupling plate with a first end configured to connect to the coupling interface of the robotic arm and a second end including a second coupling interface configured to connect to the stereoscopic camera,
wherein the coupling plate includes at least one joint including a joint sensor configured to transmit a position of the respective joint and a motor that is controllable by the at least one processor according to the movement sequence.

6. The apparatus of claim 5, wherein the sensor is located at the coupling interface or the second coupling interface.

7. The apparatus of claim 5, wherein the coupling plate includes a second joint that enables the stereoscopic camera to be manually rotated by an operator between a horizontal orientation and a vertical orientation, wherein the second joint includes a joint sensor configured to transmit a position of the second joint.

8. The apparatus of claim 1, wherein the stereoscopic camera includes a housing including a bottom side that is configured to connect to the robotic arm at the coupling interface.

9. The apparatus of claim 1, wherein the processor is configured to:
determine a least one scale factor based on at least one of the current position of the robotic arm or a future position of the robotic arm based on the movement sequence; and
apply the scale factor to at least one joint speed of the movement sequence.

10. The apparatus of claim 9, wherein the at least one scale factor is configured based on a distance of the robotic arm or the stereoscopic camera from a virtual boundary, and wherein the at least one scale factor decreases to a value of '0' as the virtual boundary is approached.

11. The apparatus of claim 10, wherein the processor is configured to cause a display device to display an icon indicative that the at least one scale factor has been applied to the movement sequence.

12. The apparatus of claim 1, wherein the processor is configured to:
determine a least one scale factor based on joint angles between joints of the robotic arm or joint limits; and
apply the scale factor to at least one joint speed of the movement sequence.

13. The apparatus of claim 1, wherein the processor is configured to:
provide gravity compensation for the output data; and
provide force-application compensation for the output data to compensate for an offset between a location of the sensor and a location of the stereoscopic camera upon which the detected force is imparted by the operator.

14. The apparatus of claim 1, wherein the processor is configured to:
determine or identify joint singularities for the plurality of joints of the robotic arm for control of hysteresis and backlash; and
determine the movement sequence based on the at least one algorithm while avoiding robotic arm movement through the joint singularities.

15. The apparatus of claim 1, wherein the processor is configured to cause at least one of the joints of the robotic arm to rotate by transmitting one or more command signals to the motor of the respective joint indicative of the rotation direction, the speed, and the duration of movement as specified by the movement sequence.

16. The apparatus of claim 1, wherein the processor is configured to compare images recorded by the stereoscopic camera as the robotic arm is being moved during the movement sequence to confirm the robotic arm is being moved as determined during the movement sequence.

17. The apparatus of claim 1, wherein the at least one algorithm includes use of at least one of inverse kinematics and Jacobean kinematics.

18. A robotic imaging apparatus comprising:
a robotic arm including
a first end configured for connection to a secure structure,
a second end including a coupling interface, and
a plurality of joints and links connecting the first end to the second end, each joint including a motor configured to rotate the joint around an axis and a joint sensor configured to transmit a position of the respective joint;
a stereoscopic camera connected to the robotic arm at the coupling interface, the stereoscopic camera configured to record left and right images of a target surgical site for producing a stream of stereoscopic images of the target surgical site;
a sensor positioned at the coupling interface and configured to detect translational and rotational force imparted on the stereoscopic camera by an operator and to transmit output data that is indicative of the detected force;
a memory storing at least one algorithm defined by one or more instructions and/or data structures that specify a rotation direction, speed, and duration of movement for each of the joints of the robotic arm based at least on a current position of the robotic arm and the detected force; and at least one processor communicatively coupled to the sensor and the robotic arm, the at least one processor configured to:
- receive the output data from the sensor that is indicative of the detected force,
- determine, using the at least one algorithm in the memory, a movement sequence for the robotic arm based on a current position of the robotic arm and the output data from the sensor, and
- cause at least one of the joints of the robotic arm to rotate based on the determined movement sequence via one or more motor control signals provided to the at least one joint.

19. The apparatus of claim 18, wherein the rotation of the at least one joint provides power-assisted movement of the robotic arm based on the detected translational and/or rotational forces imparted on the stereoscopic camera by the operator.

20. A robotic imaging apparatus comprising:
a robotic arm including
- a first end configured for connection to a secure structure,
- a second end including a coupling interface, and
- a plurality of joints and links connecting the first end to the second end, each joint including a motor configured to rotate the joint around an axis and a joint sensor configured to transmit a position of the respective joint;

a stereoscopic camera connected to the robotic arm at the coupling interface, the stereoscopic camera configured to record left and right images of a target surgical site for producing a stream of stereoscopic images of the target surgical site;

a sensor positioned at the coupling interface and configured to detect translational and rotational force imparted on the stereoscopic camera by an operator and to transmit output data that is indicative of the detected force; and at least one processor communicatively coupled to the sensor and the robotic arm, the at least one processor configured to:
- receive the output data from the sensor that is indicative of the detected force,
- determine, using at least one algorithm defined by one or more instructions and/or data structures stored in a memory, a movement sequence of rotation direction, speed and duration for each of the joints of the robotic arm based on a current position of the robotic arm and the output data from the sensor, and
- cause at least one of the joints of the robotic arm to rotate based on the determined movement sequence via one or more motor control signals provided to the at least one joint.

* * * * *